US010493251B2

(12) United States Patent
Ha et al.

(10) Patent No.: US 10,493,251 B2
(45) Date of Patent: Dec. 3, 2019

(54) HANDLE WITH FEATURES TO COUPLE CATHETER ASSEMBLY WITH ENDOSCOPE AND ACTUATE CATHETER

(71) Applicant: Acclarent, Inc., Menlo Park, CA (US)

(72) Inventors: Hung V. Ha, San Jose, CA (US);
Ketan P. Muni, San Jose, CA (US);
Darius D. Eghbal, Oakland, CA (US);
James G. Lee, Cincinnati, OH (US);
Gregory W. Johnson, Milford, OH (US); Lawrence D. Wasicek, San Jose, CA (US)

(73) Assignee: Acclarent, Inc., Irvine, CA (US)

( * ) Notice: Subject to any disclaimer, the term of this patent is extended or adjusted under 35 U.S.C. 154(b) by 942 days.

(21) Appl. No.: 14/827,920

(22) Filed: Aug. 17, 2015

(65) Prior Publication Data

US 2016/0287851 A1    Oct. 6, 2016

Related U.S. Application Data

(60) Provisional application No. 62/140,082, filed on Mar. 30, 2015.

(51) Int. Cl.
*A61M 29/02* (2006.01)
*A61B 17/24* (2006.01)
(Continued)

(52) U.S. Cl.
CPC ............ *A61M 29/02* (2013.01); *A61B 1/0014* (2013.01); *A61B 17/24* (2013.01);
(Continued)

(58) Field of Classification Search
CPC ............ A61M 29/02; A61M 25/10181; A61M 2029/025; A61M 2210/0681;
(Continued)

(56) References Cited

U.S. PATENT DOCUMENTS 6,716,813 B2    4/2004  Lim et al.
7,630,676 B2    12/2009 Pirwitz
(Continued)

OTHER PUBLICATIONS

U.S. Appl. No. 62/139,941, filed Mar. 30, 2015.
(Continued)

*Primary Examiner* — Anh T Dang
(74) *Attorney, Agent, or Firm* — Frost Brown Todd LLC

(57) ABSTRACT

A dilation system includes a handle, a guide member, a balloon dilation member, an actuator, and an endoscope. The handle is configured to provide single-handed use to a user. The guide member is coupled with a distal end of the handle and extends distally therefrom. The balloon dilation member is slidably disposed within the body and the guide member and includes an expandable balloon. The actuator is configured to translate and/or rotate to thereby cause translation and/or rotation of the balloon dilation member. The handle may include a guide member actuator configured to cause translation of the guide member. The handle may further include a rotation mechanism configured to impart rotation upon the guide member. The handle may also include a housing configured to receive and selectively retain the endoscope. The housing is configured to translate and/or rotate to thereby cause translation and/or rotation of the endoscope.

18 Claims, 90 Drawing Sheets

(51) Int. Cl.
*A61M 25/10* (2013.01)
*A61B 1/00* (2006.01)
*A61B 17/00* (2006.01)
*A61B 90/57* (2016.01)

(52) U.S. Cl.
CPC ........ *A61M 25/10181* (2013.11); *A61B 90/57* (2016.02); *A61B 2017/0042* (2013.01); *A61B 2017/00296* (2013.01); *A61B 2017/00464* (2013.01); *A61M 2029/025* (2013.01); *A61M 2210/0675* (2013.01); *A61M 2210/0681* (2013.01)

(58) Field of Classification Search
CPC .................. A61B 1/0014; A61B 17/24; A61B 2017/0042; A61B 2017/00464; A61B 2017/00296
See application file for complete search history.

(56) References Cited

U.S. PATENT DOCUMENTS

| | | |
|---|---|---|
| 9,155,492 B2 | 10/2015 | Jenkins et al. |
| 2008/0097154 A1* | 4/2008 | Makower ........... A61B 1/00135 600/114 |
| 2008/0183128 A1 | 7/2008 | Morriss et al. |
| 2010/0030031 A1 | 2/2010 | Goldfarb et al. |
| 2010/0274188 A1 | 10/2010 | Chang et al. |
| 2011/0004057 A1 | 1/2011 | Goldfarb et al. |
| 2012/0071856 A1* | 3/2012 | Goldfarb ................ A61B 17/24 604/514 |

OTHER PUBLICATIONS

U.S. Appl. No. 62/140,082, filed Mar. 30, 2015.
St. Croix, B. et al., "Genes Expressed in Human Tumor Endothelium", Science, Aug. 18, 2000, 289:1197-1202, 6 pgs.

* cited by examiner

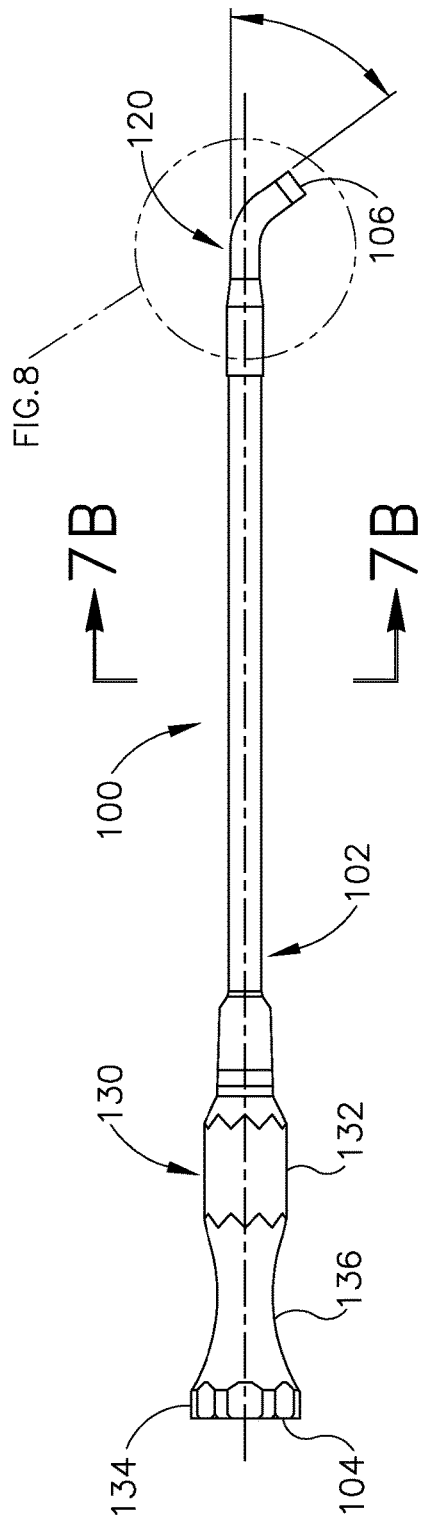
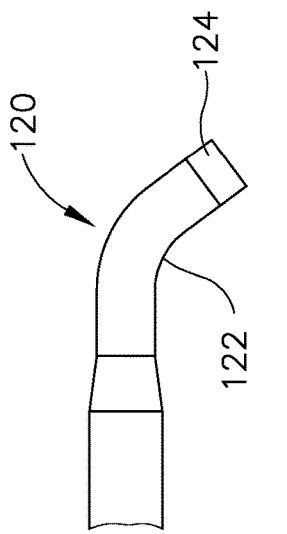
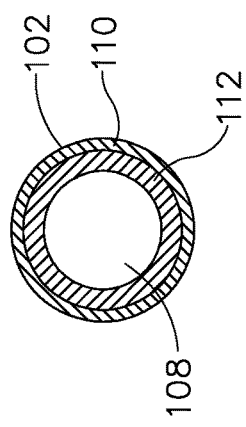
Fig. 7A
Fig. 7B
Fig. 8

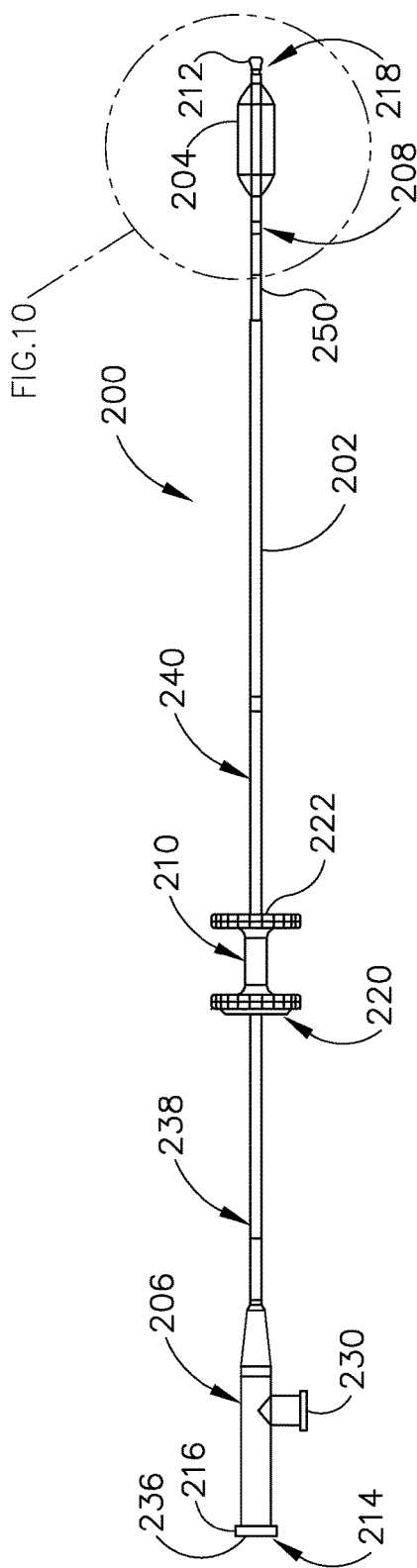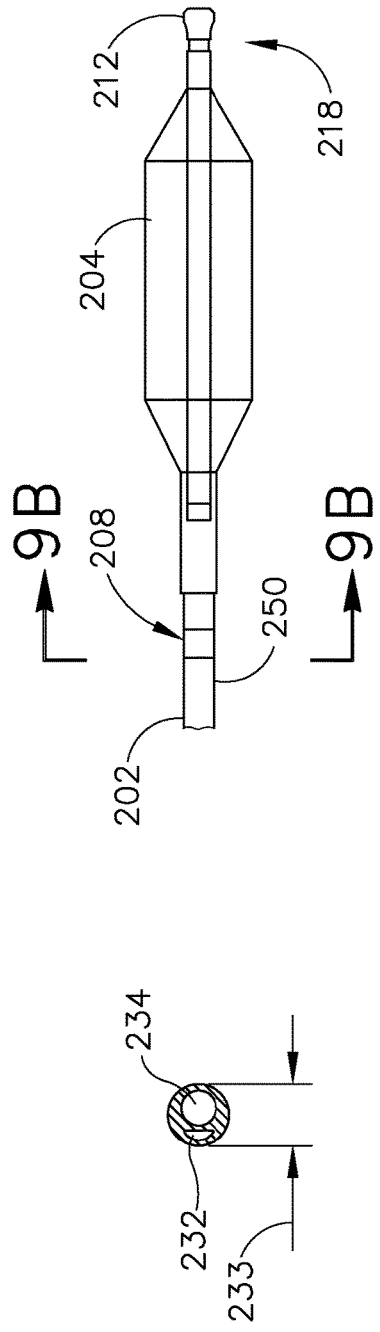
Fig.9A
Fig.9B
Fig.10

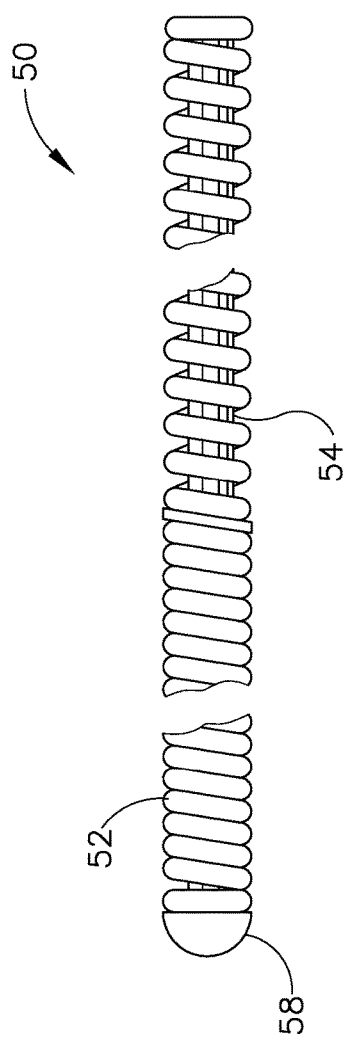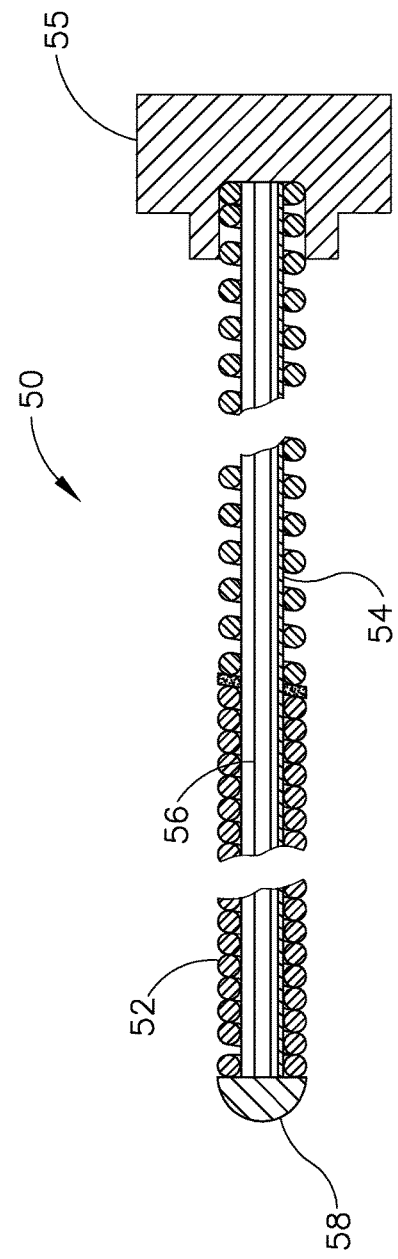
Fig.13
Fig.14

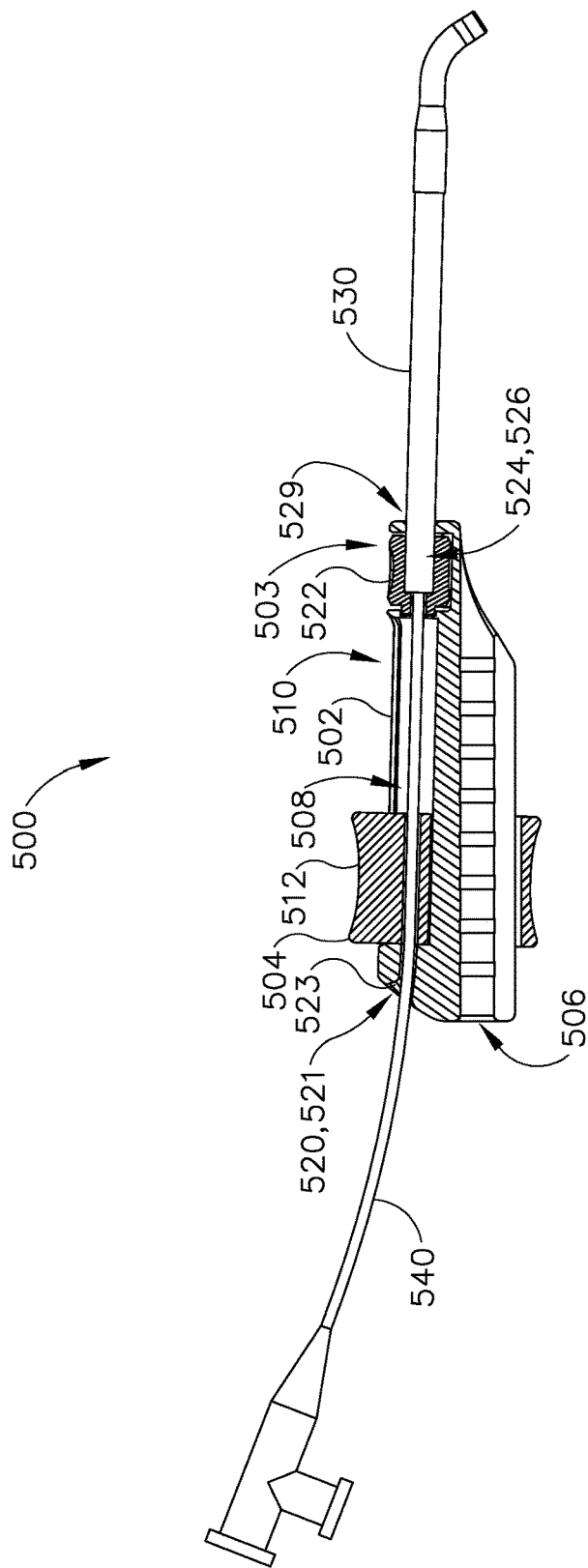

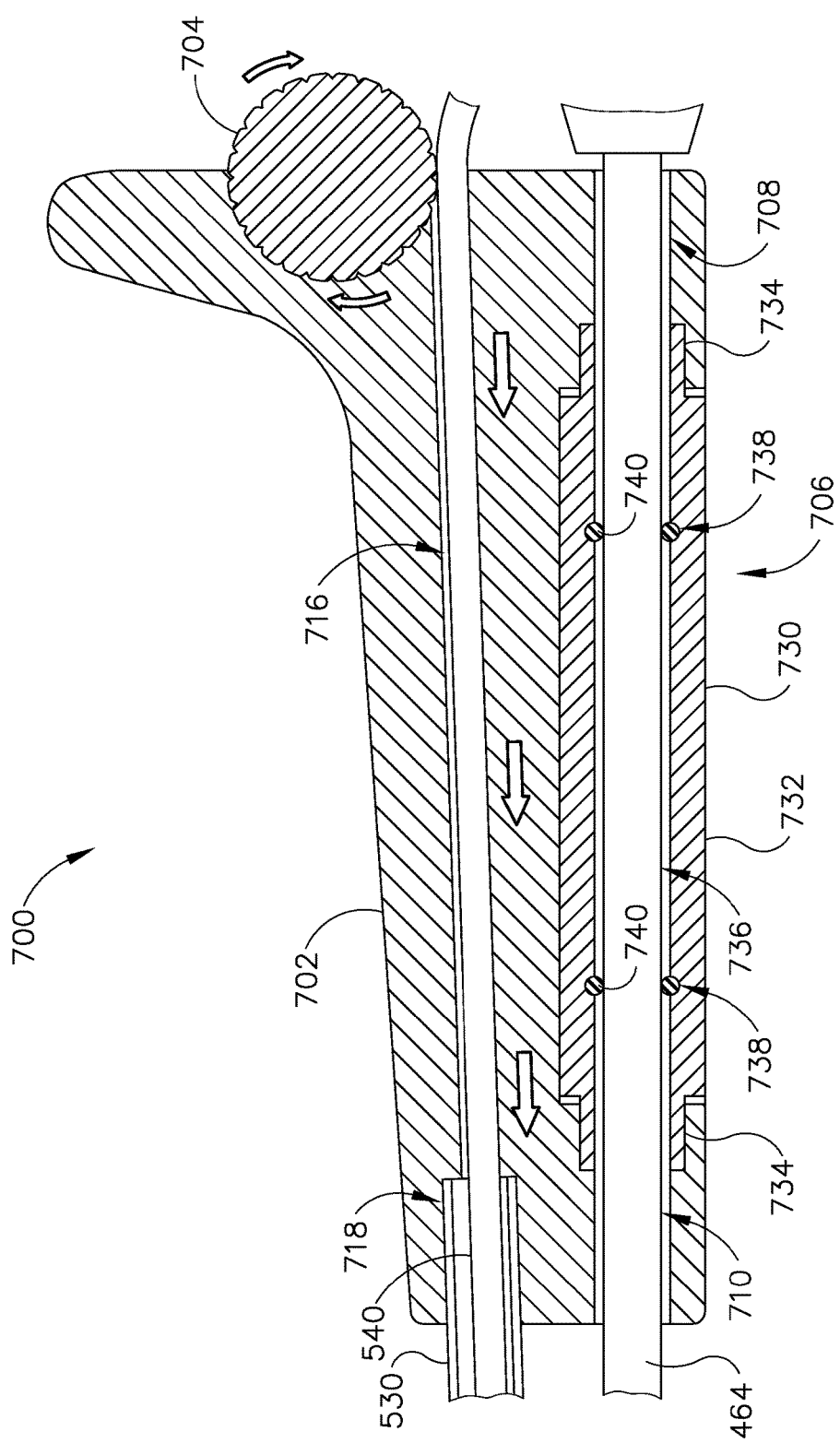

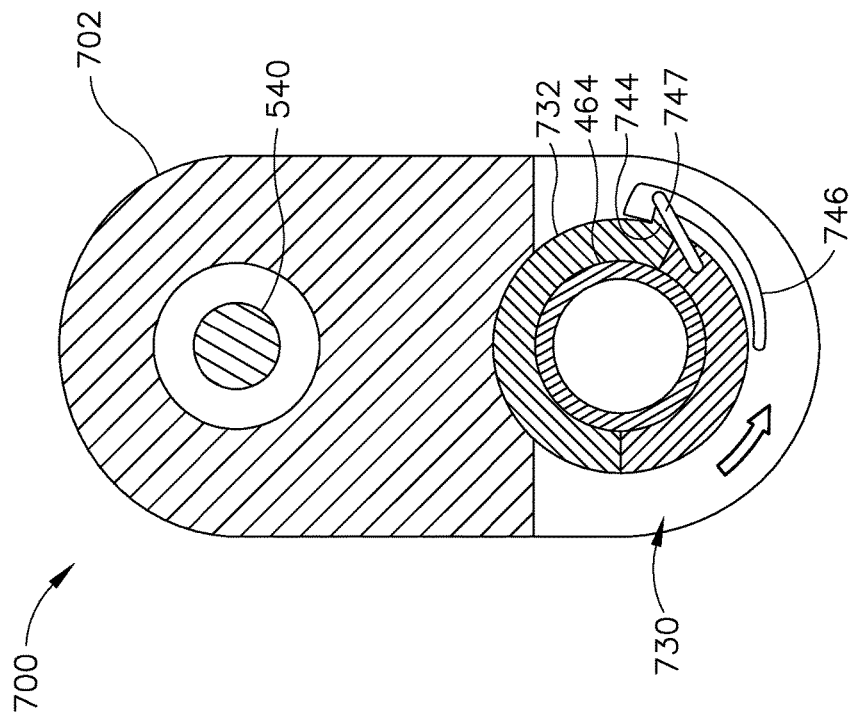
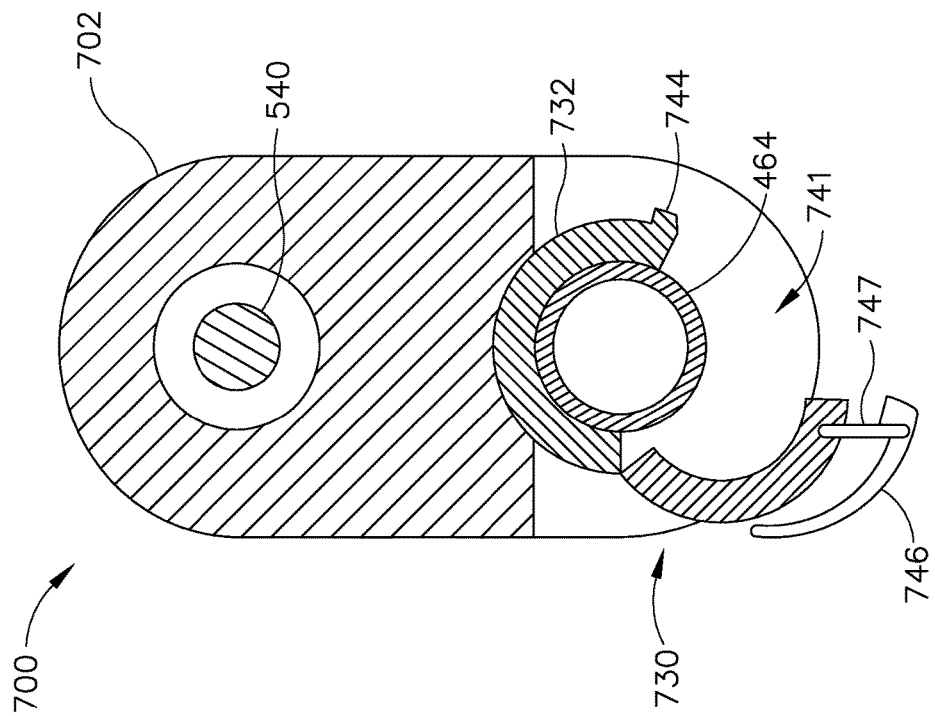

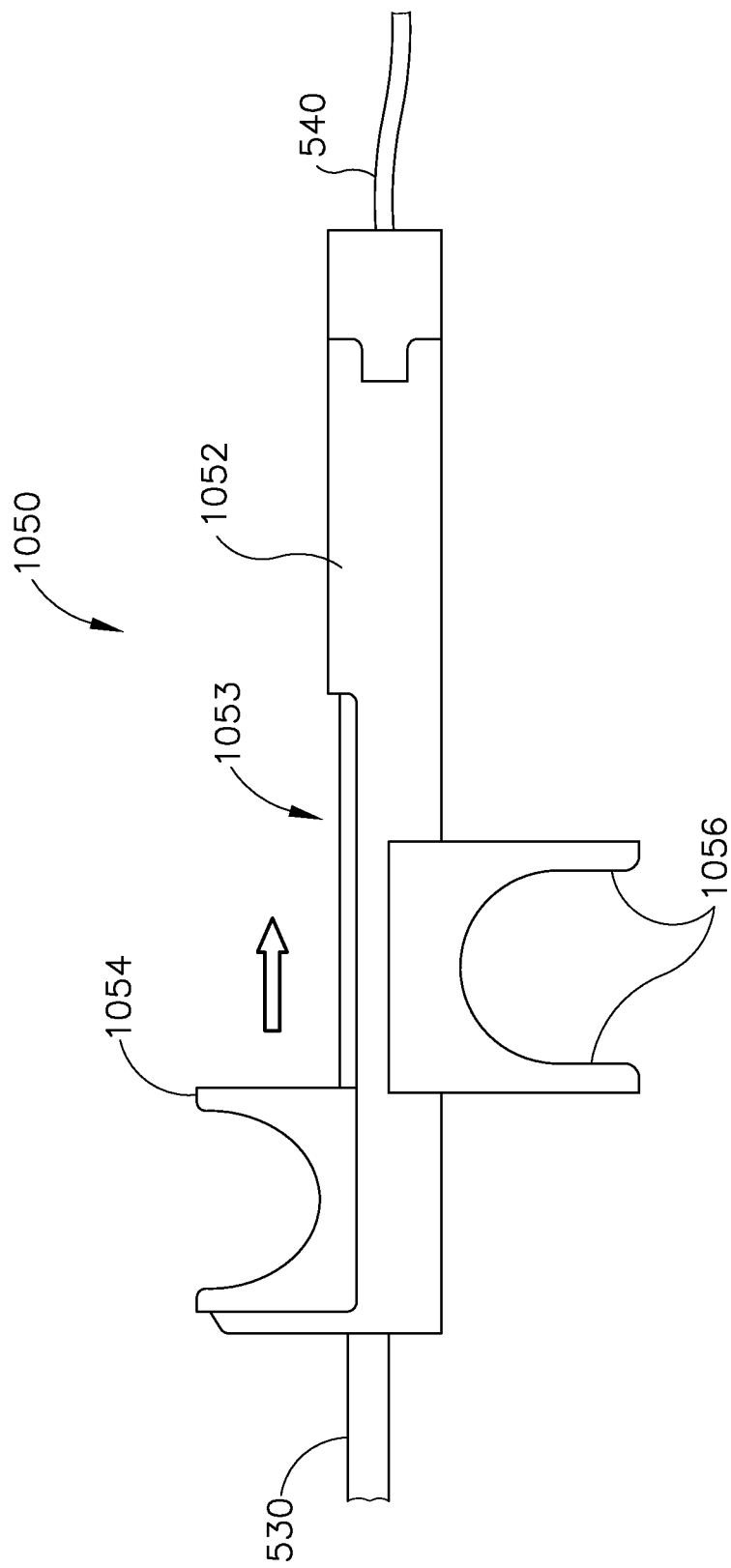

HANDLE WITH FEATURES TO COUPLE CATHETER ASSEMBLY WITH ENDOSCOPE AND ACTUATE CATHETER

PRIORITY

This application claims priority to U.S. Provisional Pat. App. No. 62/140,082, entitled "Handle with Features to Couple Catheter Assembly with Endoscope and Actuate Catheter," filed Mar. 30, 2015, the disclosure of which is incorporated by reference herein.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guidewire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pat. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Menlo Park, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, now abandoned, the disclosure of which is incorporated by reference herein. An example of such an endoscope is the Acclarent Cyclops™ Multi-Angle Endoscope by Acclarent, Inc. of Menlo Park, Calif.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pub. No. 2012/0078118, entitled "Sinus Illumination Lightwire Device," published Mar. 29, 2012, issued as U.S. Pat. No. 9,155,492 on Oct. 13, 2015, the disclosure of which is incorporated by reference herein. An example of such an illuminating guidewire is the Relieva Luma Sentry™ Sinus Illumination System by Acclarent, Inc. of Menlo Park, Calif.

It may be desirable to provide easily controlled inflation/deflation of a balloon in dilation procedures, including procedures that will be performed only by a single operator. While several systems and methods have been made and used to inflate an inflatable member such as a dilation balloon, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 7A depicts a side elevational view of an exemplary guide catheter;

FIG. 7B depicts a cross-sectional front view of the guide catheter of FIG. 7A taken through line 7B-7B of FIG. 7A;

FIG. 8 depicts a detailed side elevational view of a distal end of the guide catheter of FIG. 7A;

FIG. 9A depicts a side elevational view of an exemplary balloon dilation catheter;

FIG. 9B depicts a cross-sectional front view of the balloon dilation catheter of FIG. 9A taken through line 9B-9B of FIG. 10;

FIG. 10 depicts a detailed side elevational view of a distal end of the balloon dilation catheter of FIG. 9A;

FIG. 13 depicts a side elevational view of an exemplary illuminating guidewire suitable for use with the dilation catheter system of FIG. 12;

FIG. 14 depicts a cross-sectional side view of the illuminating guidewire of FIG. 13;

FIG. 21A depicts a cross-sectional side view of the handle of FIG. 17 taken along line 21-21 of FIG. 19, with the guide catheter of FIG. 7A and an exemplary balloon dilation catheter positioned therein;

FIG. 40B depicts a cross-sectional side view of the handle of FIG. 38 taken along line 40-40 of FIG. 38, with the guide catheter of FIG. 7A, the balloon dilation catheter of FIG. 38, and the endoscope of FIG. 15 positioned therein, and with the balloon dilation catheter translated distally by rotation of an actuator of the handle;

FIG. 42A depicts a cross-sectional rear view of the handle of FIG. 38 taken along line 42-42 of FIG. 38, with the guide catheter of FIG. 7A, the balloon dilation catheter of FIG. 38, and the endoscope of FIG. 15 positioned therein, with the locking cover of FIG. 41A in the first, unlocked, rotational position;

FIG. 42B depicts a cross-sectional rear view of the handle of FIG. 38 taken along line 42-42 of FIG. 38, with the guide catheter of FIG. 7A, the balloon dilation catheter of FIG. 38, and the endoscope of FIG. 15 positioned therein, with the locking cover of FIG. 41A rotated into a second, locked, rotational position;

FIG. 69 depicts a side elevational view of another exemplary handle suitable for use with the dilation catheter system of FIG. 12, with the guide catheter of FIG. 7A, an exemplary balloon dilation catheter, and the endoscope of FIG. 15 positioned therein.

Figure 1:
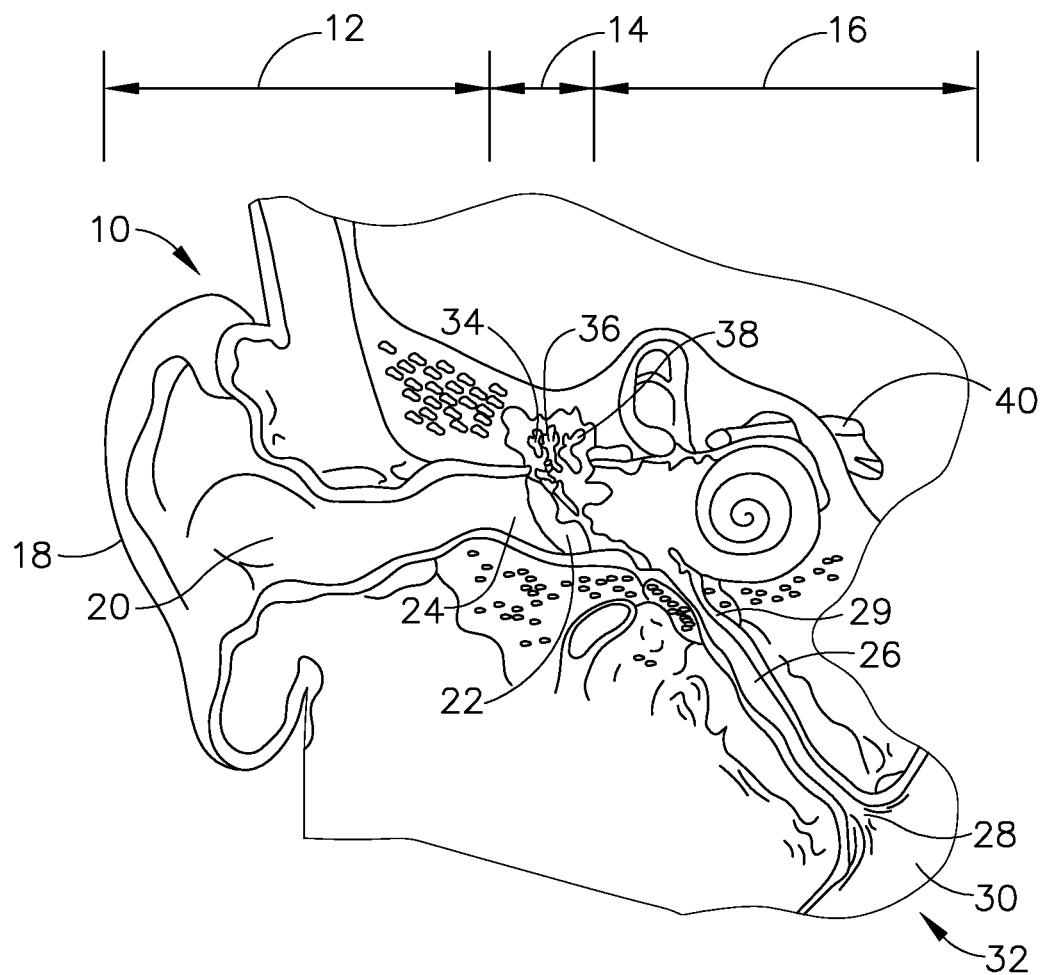
FIG. 1 depicts a cross-sectional front view of a human ear showing the inner, middle, and outer ear portions and the Eustachian tube connecting the middle ear with the nasopharynx region of the throat via a pharyngeal ostium thereof.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Methods of Treating the Middle Ear and Eustachian Tube

Figure 2:
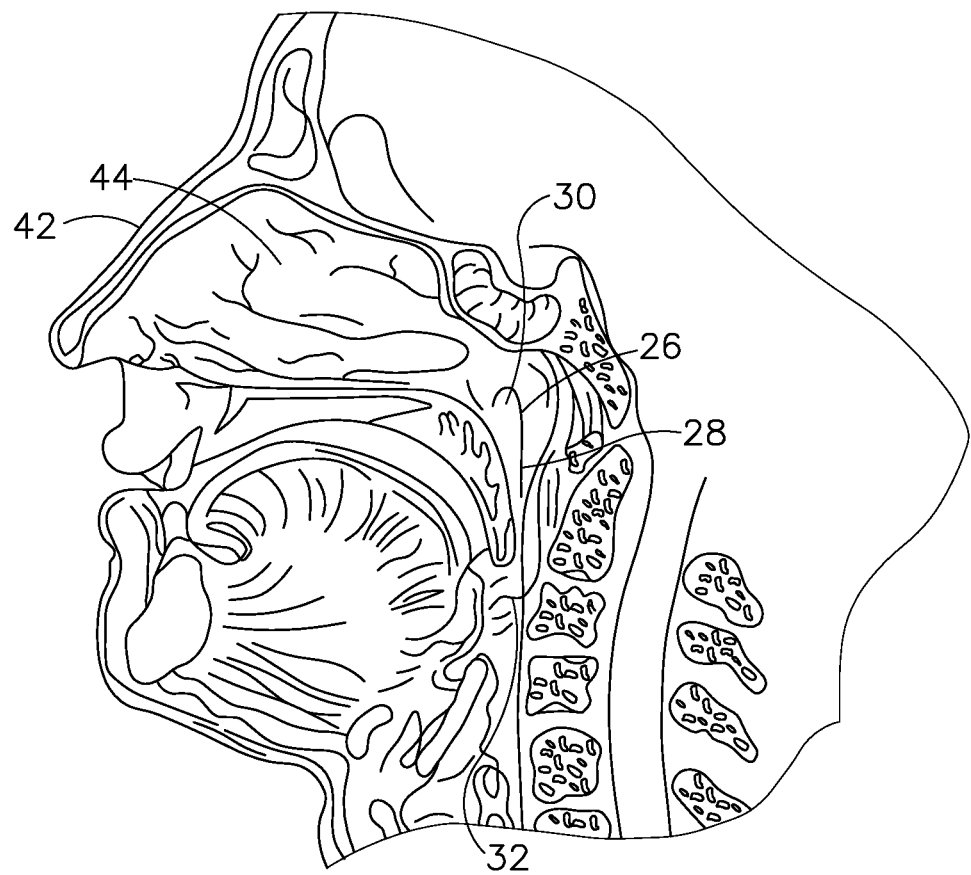
FIG. 2 depicts a cross-sectional side view of a human head showing the nasopharynx region of the throat illustrated in FIG. 1 containing the pharyngeal ostium of the Eustachian tube illustrated in FIG. 1.

Referring to FIGS. 1 and 2, an ear (10) is divided into three parts: an external ear (12), a middle ear (14), and an inner ear (16). The external ear (12) consists of an auricle (18) and ear canal (20) that gather sound and direct it toward a tympanic membrane (22) (also referred to as the eardrum) located at an inner end (24) of the ear canal (20). The middle ear (14) lies between the external ear (12) and the inner ear

(16) and is connected to the back of the throat (32) by a Eustachian tube (26), which serves as a pressure equalizing valve between the ear (10) and the sinuses. The Eustachian tube (26) terminates in a pharyngeal ostium or ostium (28) in the nasopharynx region (30) of the throat (32). In addition to the tympanic membrane (22), the middle ear (14) also consists of three small ear bones (also referred to as the ossicles or auditory ossicles): the malleus (34) (also referred to as the hammer), the incus (36) (also referred to as the anvil), and the stapes (38) (also referred to as the stirrup). These middle ear bones (34, 36, 38) transmit sound vibrations to the inner ear (16) and thereby act as a transformer, converting sound vibrations in the ear canal (20) of the external ear (12) into fluid waves in the inner ear (16). These fluid waves stimulate several nerve endings (40) that, in turn, transmit sound energy to the brain where it is interpreted.

The Eustachian tube (26) is a narrow, two to two-and-a-half centimeter long channel, measured from the ostium (28) to the bony isthmus (29), connecting the middle ear (14) with the nasopharynx region (30), the upper throat area just above the palate, in back of the nose (42). The Eustachian tube (26) functions as a pressure equalizing valve for the middle ear (14), which is normally filled with air. When functioning properly, the Eustachian tube (26) opens for a fraction of a second periodically (about once every three minutes) in response to swallowing or yawning. In so doing, it allows air into the middle ear (14) to replace air that has been absorbed by the middle ear lining (mucous membrane) or to equalize pressure changes occurring on altitude changes. Anything that interferes with this periodic opening and closing of the Eustachian tube (26) may result in hearing impairment or other ear symptoms.

Obstruction or blockage of the Eustachian tube (26) results in a negative middle ear pressure (14), with retraction, or sucking in, of the tympanic membrane (22). In adults, this is usually accompanied by some ear discomfort, a fullness or pressure feeling, and may result in a mild hearing impairment and head noise (commonly referred to as tinnitus). There may be no symptoms in children. If the obstruction is prolonged, fluid may be drawn from the mucous membrane of the middle ear (14), creating a condition referred to as serous otitis media—i.e., fluid in the middle ear (14). This may occur frequently in children in connection with an upper respiratory infection and account for the hearing impairment associated with this condition.

A lining membrane (mucous membrane) of the middle ear (14) and the Eustachian tube (26) is connected with, and is the same as, the membrane of the nose (42), the sinuses (44), and the throat (32). Infection of these areas results in mucous membrane swelling, which in turn may result in obstruction of the Eustachian tube (26). This is referred to as serous otitis media, i.e., essentially a collection of fluid in the middle ear (14) that can be acute or chronic, and may be the result of blockage of the ostium (28) of the Eustachian tube (26), which allows fluid to accumulate in the middle ear (14). In the presence of bacteria, this fluid may become infected, leading to an acute suppurative otitis media—i.e., an infected or abscessed middle ear (14). When infection does not develop, the fluid remains until the Eustachian tube (26) again begins to function normally, at which time the fluid is absorbed or drains down the Eustachian tube (26) into the throat (32) through the ostium (28) of the Eustachian tube (26).

Chronic serous otitis media may result from longstanding blockage of the Eustachian tube (26), or from thickening of the fluid so that it cannot be absorbed or drained down the Eustachian tube (26). This chronic condition may be associated with hearing impairment. There may be recurrent ear pain, especially when the individual catches a cold. Fortunately, serous otitis media may persist for many years without producing any permanent damage to the middle ear (14). The presence of fluid in the middle ear (14), however, may make it very susceptible to recurrent acute infections. These recurrent infections may result in damage to the middle ear (14).

When the Eustachian tube (26) contains a build-up of fluid, a number of things may occur. First, the body absorbs the air from the middle ear (14), causing a vacuum to form, which tends to pull the lining membrane and tympanic membrane (22) inwardly, causing pain. Next, the body replaces the vacuum with more fluid, which tends to relieve the pain, but the patient can experience a fullness sensation in the ear (10). Treatment of this condition with antihistamines and decongestants can take many weeks to be fully effective. Finally, the fluid can become infected, which is painful and makes the patient feel ill and which may cause the patient not to be able to hear well. If the inner ear (14) is affected, the patient may feel a spinning or turning sensation (e.g., vertigo). The infection may be treated with antibiotics.

However, even if antihistamines, decongestants, and antibiotics are used to treat an infection or other cause of fluid build-up in the middle ear (14), these treatments might not immediately resolve the pain and discomfort caused by the buildup of fluid in the middle ear (14). In some instances, the most immediate relief will be felt by the patient if the fluid can be removed from the Eustachian tube (26).

Antibiotic treatment of middle ear infections may results in normal middle ear function within three to four weeks. During the healing period, the patient can experience varying degrees of ear pressure, popping, clicking, and fluctuation of hearing, occasionally with shooting pain in the ear (10). Resolution of the infection may leave the patient with uninfected fluid in the middle ear (14), localized in the Eustachian tube (26).

Fluid build-up caused by these types of infections may be treated surgically. The primary objective of surgical treatment of chronic serous otitis media is to reestablish ventilation of the middle ear (14), keeping the hearing at a normal level, and preventing recurrent infection that might damage the tympanic membrane (22) the and middle ear bones (34, 36, 38).

Figure 3:
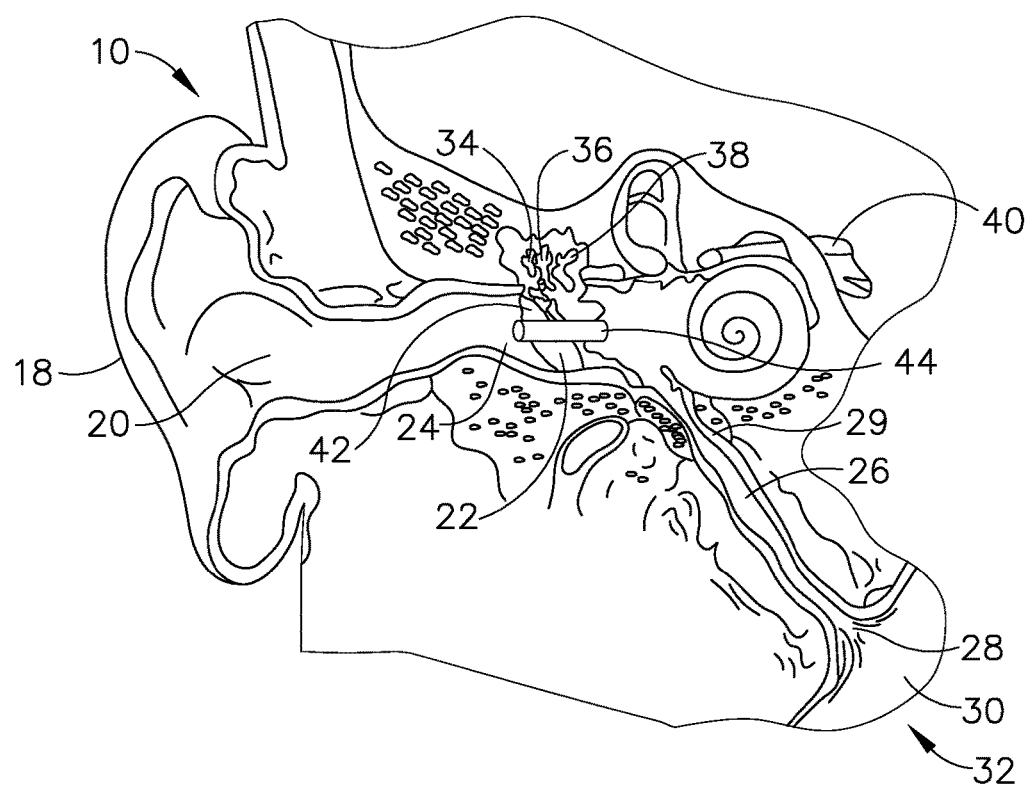
FIG. 3 depicts a cross-sectional front view of a human ear showing a surgical method for relieving fluid in the middle ear in which a ventilation tube is placed within an incision in the tympanic membrane.

For example, as shown in FIG. 3, a myringotomy can be performed to relieve fluid in the middle ear (14). A myringotomy is an incision (42) in the tympanic membrane (22) performed to remove fluid in the middle ear (14). A hollow plastic tube (44), referred to as a ventilation tube, is inserted and lodged in the incision (42) to prevent the incision (42) from healing and to ensure ventilation of the middle ear (14). The ventilation tube (44) temporarily takes the place of the Eustachian tube (26) in equalizing the pressure in the middle ear (14). The ventilation tube (44) may remain in place for three to nine months during which time the Eustachian tube (26) blockage subsides. When the ventilation tube (44) dislodges, the tympanic membrane (22) heals. The Eustachian tube (26) then resumes its normal pressure equalizing function.

Figure 4:
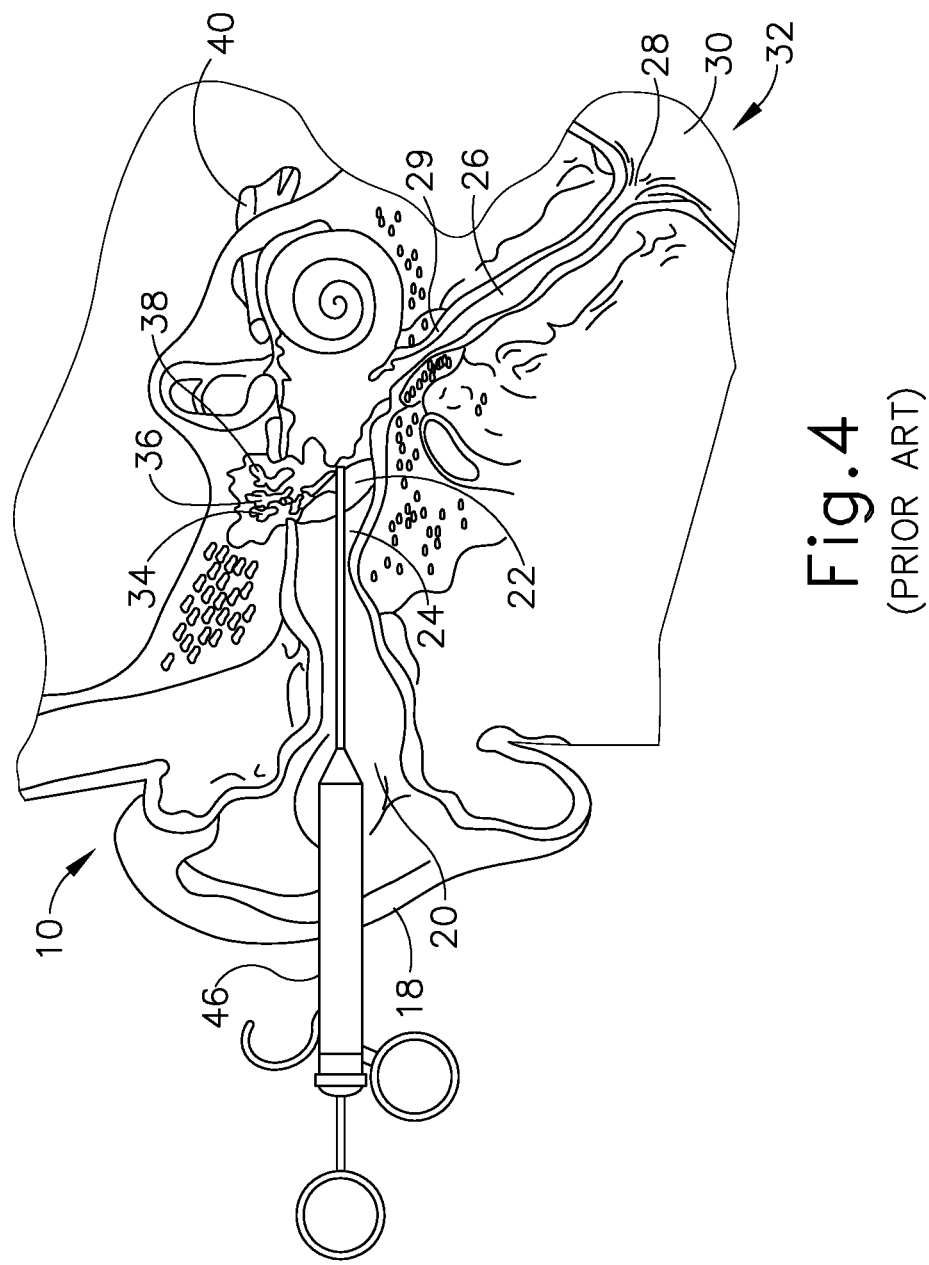
FIG. 4 depicts a cross-sectional front view of a human ear showing another surgical method for relieving fluid in the middle ear in which a syringe is shown having a needle perforating the tympanic membrane.

Another method of relieving the pressure in the middle ear (14) is shown in FIG. 4 in which a hypodermic needle (46) is driven through the tympanic membrane (22) through which any accumulated fluid can be withdrawn (e.g., from the upper portion of the Eustachian tube (26)).

The methods of FIGS. 3 and 4 involve rupturing the tympanic membrane (22) to relieve the fluid accumulation and pressure increase in the middle ear (14). Neither of these methods, in addition to the sometimes permanent puncture created in the tympanic membrane (22), is especially effective in removing all of the fluid in the Eustachian tube (26) since often the ostium (28) of the Eustachian tube (26) is blocked and dammed with fluid.

Figure 5:
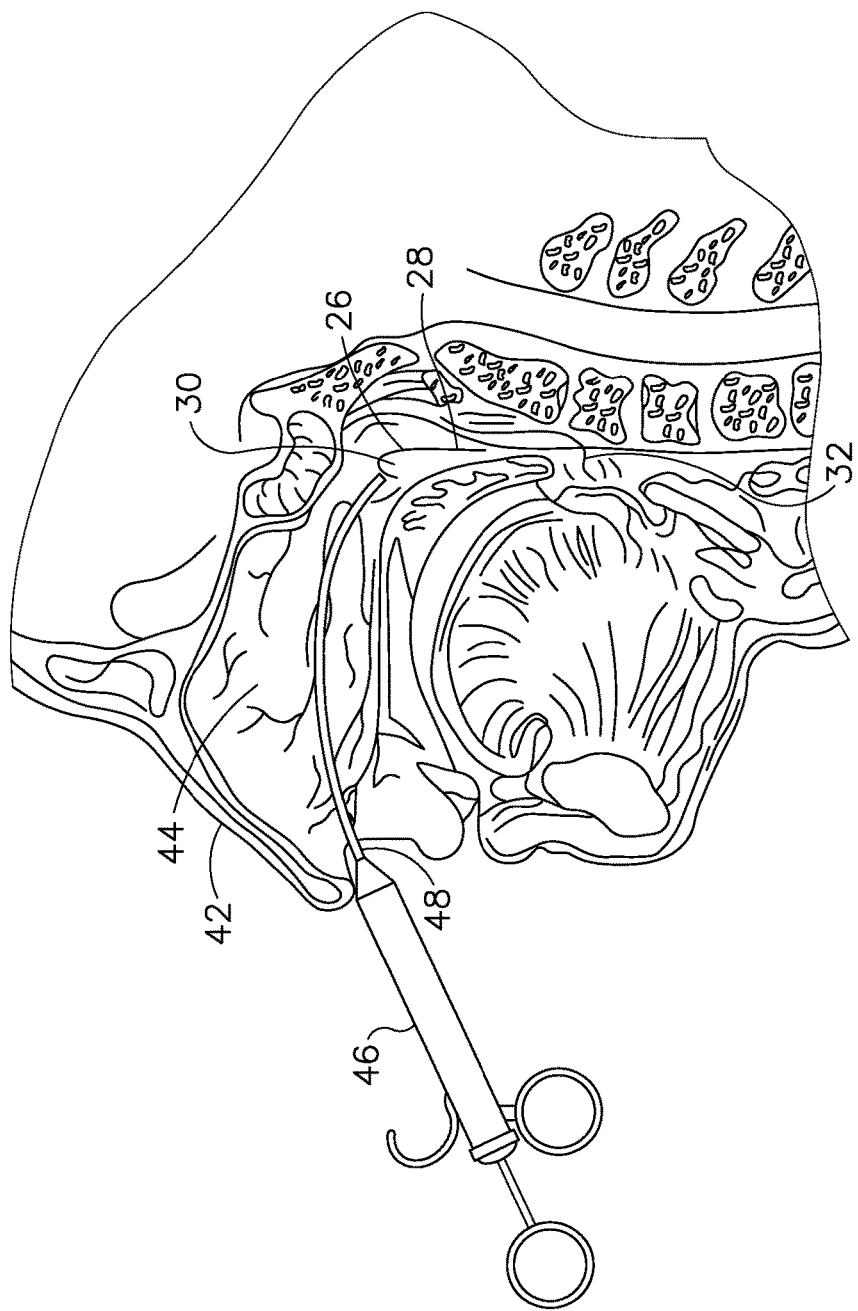
FIG. 5 depicts a cross-sectional side view of a human head showing a politzerization method for relieving fluid in the middle ear in which a syringe is shown having a flexible tip extending into the nose and/or throat area so that the tip abuts the pharyngeal ostium of the Eustachian tube while the nose is plugged.
Figure 6:
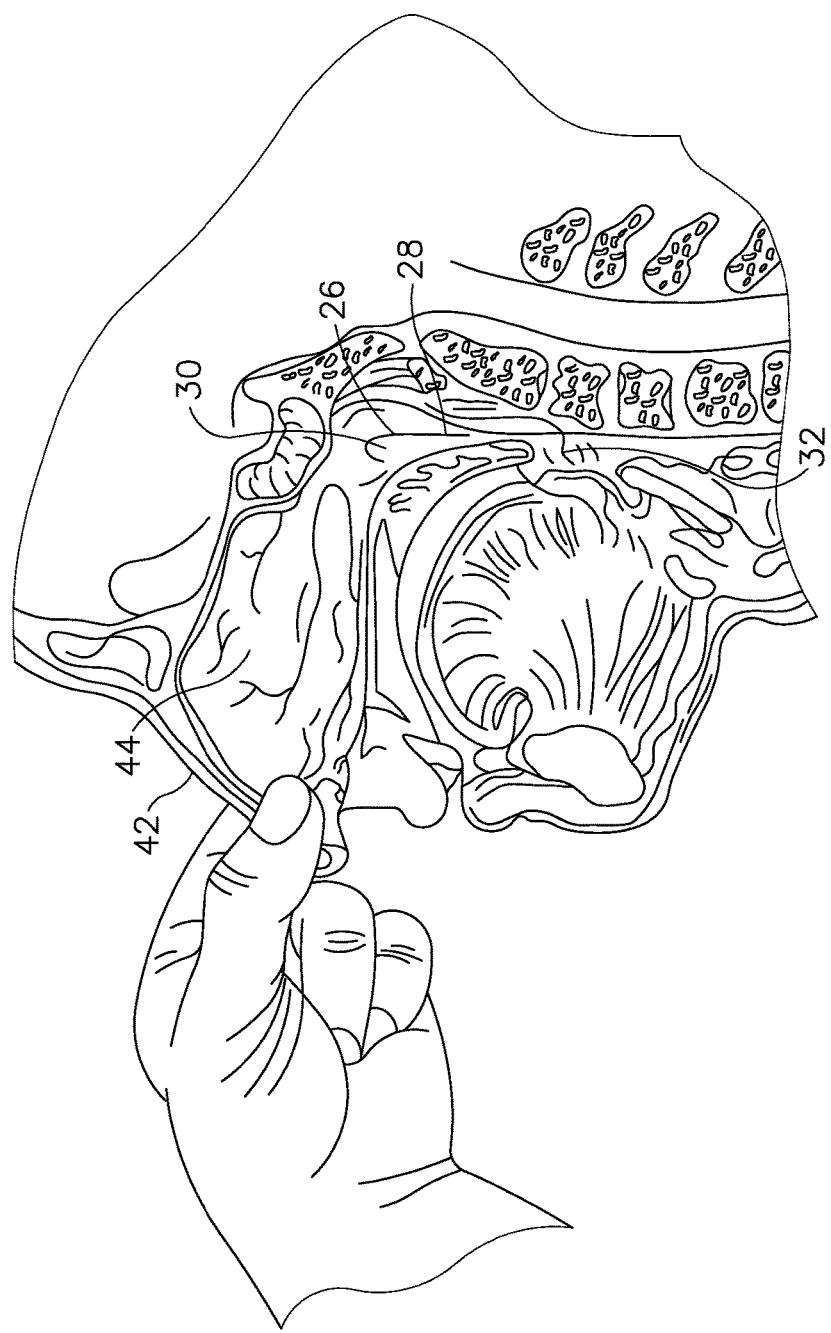
FIG. 6 depicts a cross-sectional side view of a human head showing the politzerization method of FIG. 5 while the nose is plugged.

In connection with the above surgical treatments of FIGS. 3 and 4, Eustachian tube (26) inflation is also employed to relieve the pressure build-up and fluid accumulation as shown in FIG. 5. The hypodermic syringe (47), shown with a flexible tip (48), is inserted into a nostril or into the mouth until the flexible tip (48) is positioned adjacent the ostium (28) of the Eustachian tube (26) in the nasopharynx region (30) of the throat (32). Air is blown through the flexible tip (48) via the syringe (47) into the obstructed Eustachian tube (26) and, thus, into the middle ear (14) to help relieve the congestion and reestablish middle ear ventilation. This procedure is often referred to as politzerization. Politzerization may be most effective when one of the nostrils is pinched shut (as shown in FIG. 6), while the patient simultaneously swallows. This procedure forces air into the Eustachian tube (26) and the middle ear (14). This technique may be good for opening the Eustachian tube (26) but it does not necessarily clear accumulated fluid away.

Another method for clearing the middle ear (14) (at least temporarily) is referred to as the "valsalva" maneuver, accomplished by forcibly blowing air into the middle ear (14) while holding the nose (42), often called "popping the ear." This method may also be good for opening the Eustachian tube (26) but it does not necessarily clear the accumulated fluid away either.

Typical disorders associated with the middle ear (14) and the Eustachian tube (26) may include perforated ear drums, tympanosclerosis, incus erosion, otitis media, cholesteotoma, mastoiditis, patulous Eustachian tube, and conductive hearing loss. To treat some of these disorders, ear surgery may be performed. Most ear surgery is microsurgery, performed with an operating microscope. Types of ear surgery include stapedectomy, tympanoplasty, myringotomy and ear tube surgery.

One of the simplest ear surgeries is the myringotomy or the incision of the tympanic membrane (22). However, ear surgery can also require the removal of the tympanic membrane (22) for the visualization of the middle ear (14). A surgeon may try to preserve the integrity of the tympanic membrane (22) by making incisions in the skin of the ear canal (20) and removing the tympanic membrane (22) as a complete unit. Alternatively, middle ear access may be achieved via the mastoids. This method approaches the middle ear (14) from behind the ear (10) and drills through the mastoid air cells to the middle ear (14). Whether the bony partition between the external ear (12) and the mastoid is removed or not depends on the extent of the disease. "Canal-wall-down" refers to the removal of this bony partition. "Canal-wall-up" refers to keeping this bony partition intact. The term "modified radical mastoidectomy" refers to an operation where this bony partition is removed and the tympanic membrane (22) and the middle ear bones (34, 36, 38) are reconstructed. A radical mastoidectomy is an operation where this bony partition is removed and the tympanic membrane (22), the malleus and the incus bones are permanently removed so that the inner lining of the large cholesteotoma sac can be safely cleaned. This operation is done when an extensive cholesteotoma is encountered or one that is adherent to the inner ear (16) or facial nerve.

Afflictions of the middle ear (14) and the Eustachian tube (26) may cause pain, discomfort and even hearing loss or permanent ear damage. Although a number of treatments have been developed, as described above each of them have shortcomings. Therefore, a need exists for improved methods and systems for accessing, diagnosing and treating target tissue regions within the middle ear (14) and the Eustachian tube (26). Ideally, such methods and systems would be minimally invasive and pose very little risk of damage to healthy ear tissue.

US Pat. Pub. No. 2010/0274188, entitled "Method and System for Treating Target Tissue Within the Eustachian Tube," published Oct. 28, 2010, now abandoned, the disclosure of which is incorporated by reference herein, is directed toward methods and systems for accessing, diagnosing, and treating target tissue regions within the middle ear (14) and the Eustachian tube (26). One particular method described in the publication is for dilating the Eustachian tube (26) of a patient. A guide catheter may be advanced through a nasal passage of the patient to position a distal end of the guide catheter at or near the ostium (28) of the Eustachian tube (26) of the patient. A distal portion of the guide catheter may include a bend having an angle between 30 degrees and 90 degrees. The distal portion may be more flexible than a proximal portion of the guide catheter. A guidewire may be advanced through the guide catheter such that a distal end of the guidewire enters the Eustachian tube (26). A dilation catheter may be advanced over the guidewire to position a dilator of the dilation catheter within the Eustachian tube (26). The dilator may be expanded to dilate the Eustachian tube (26). The dilation catheter and guidewire may then be removed from the patient.

II. Overview of Exemplary Dilation Catheter System

Improvement in the methods devices described above would provide a system for dilation of the Eustachian tube (26) that would be ergonomic and easy to use and would safely and effectively access the Eustachian tube (26). For instance, as shown in FIGS. 7A-10, a guide catheter (100) and a balloon dilation catheter (200), which are together operable by a single hand, may be used to safely and effectively access the Eustachian tube (26).

As shown in FIG. 7A, guide catheter (100) of the present example includes an elongate tubular shaft (102) that has a proximal end (104), a distal end (106), and a lumen (108) therebetween. Guide catheter (100) may have any suitable length, diameter, angle of bend, and location of the bend along the length of guide catheter (100), to facilitate accessing the Eustachian tube (26). In some embodiments, for example, guide catheter (100) may have a length between about 8 cm and about 20 cm, and more preferably between about 10 cm and about 15 cm, and in particular about 11 cm.

FIG. 7B is a cross-sectional view of elongate tubular shaft (102) of guide catheter (100). As can be seen, elongate tubular shaft (102) has an outer shaft tube (110), an inner shaft tube (112), and a lumen (108). Outer shaft tube (110) may be constructed of a stiff material such as stainless steel and inner shaft tube (112) may be constructed of a more flexible material such as a polymeric material including but not limited to nylon and further including a PTFE liner. Lumen (108) has a diameter of between about 2 mm and 3 mm, and preferably between about 2.5 mm and 2.6 mm such that balloon dilation catheter (200) can be easily inserted into lumen (108) for dilation of the Eustachian tube (26). The combination guide catheter (100) and balloon dilation catheter (200) make a compact system that is designed for a one-handed procedure. By compact, it is intended that the length of guide catheter (100) that is distal of a bend (122)

in guide catheter (100) is between about 0.5 cm and 2.0 cm, often between about 1 and 2 cm, and in particular about 1 cm. The compactness may help reduce interference with other instruments, such as an endoscope that may be used to help in visualizing the positioning of the system.

A distal portion (120) of guide catheter (100) is shown in an enlarged view in FIG. 8. Distal portion (120) of guide catheter (100) may have a bend (122) with an angle between about 45 degrees and about 65 degrees, and more preferably between about 50 degrees and about 60 degrees, and in particular about 55 degrees to facilitate access into the Eustachian tube (26). Distal portion (120) of guide catheter (100) is made of a transparent material such as a polymer including but not limited to nylon and PTFE such that balloon dilation catheter (200) is visible within distal portion (120) and is more flexible than elongate shaft (102). A distal tip (124) of distal portion (120) of guide catheter (100) is made of polyether block amides (e.g., PEBAX® by Arkema) such that it provides for atraumatic access to the Eustachian tube (26), and may contain 20% barium sulfate or other similar radiopaque materials for visualizable access.

Referring again to FIG. 7A, a proximal portion (130) of guide catheter (100) includes a proximal hub (132) to aid in insertion of balloon dilation catheter (200) into the Eustachian Tube (26). Hub (132) has a larger diameter proximal end (134) and a smaller diameter middle section (136) to facilitate stabilization of guide catheter (100) in the nose (42), rotation of guide catheter (100) and insertion of balloon dilation catheter (200) as will be described in further detail below. Hub (132) is ergonomically designed for insertion, location and rotation with slight manipulations with one hand.

Figure 11:
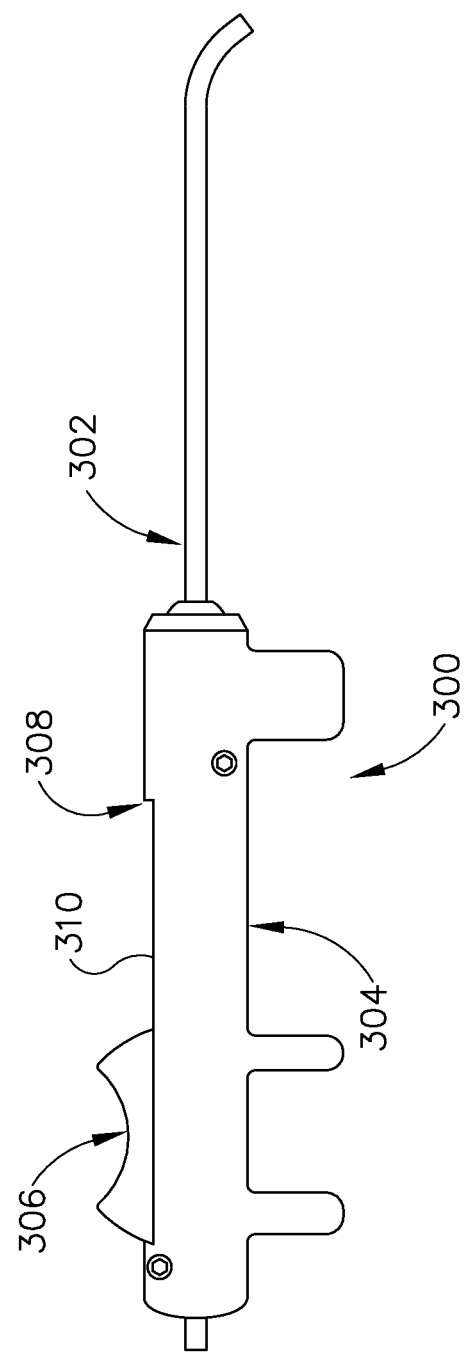
FIG. 11 depicts a side elevational view of another exemplary guide catheter.

Another example of a guide catheter (300) is shown in FIG. 11. In this example, the proximal hub is a handle. Guide catheter (300) comprises an elongate shaft (302) and a handle (304) to aid in insertion of a balloon catheter (not shown) into the Eustachian Tube (26) in a manner similar to that described below with regard to guide catheter (100). In the example shown in FIG. 11, an actuator (306) comprises a slider that is attached to the balloon catheter that is contained within handle (304) and is slidably contained within elongate shaft (302) of guide catheter (300). In use, guide catheter (300) is inserted into the sinus of the patient and the balloon catheter is advanced into the Eustachian tube (26) via thumb or single finger advancement of actuator (306) along the length of a slot (310) formed in the handle (304). The advancement of the balloon catheter is continued until a visual marker indicates that advancement is complete, or until the enlarged tip of the balloon catheter abuts the isthmus of the Eustachian tube (26) or the actuator (306) abuts a distal end (308) of the slot (310) in the handle (304) and is therefore fully deployed.

Balloon dilation catheter (200) is shown in FIG. 9A. Balloon dilation catheter (200) generally includes an elongate shaft (202) having a proximal end (214) and a distal end (218). Balloon dilation catheter (200) further includes a balloon (204) on distal end (218) of elongate shaft (202). Balloon (204) may be a polymer balloon (compliant, semicompliant or non-compliant). In some versions, balloon (204) may be a suitable non-compliant material such as but not limited to polyethylene terepthalate (PET), PEBAX®, nylon, or the like. Balloon dilation catheter (200) may include any size of balloon (204) including but not limited to balloons of 2 mm to 8 mm in diameter, or of between about 5 mm and 6 mm (when inflated) and 12 mm to 24 mm in working length (for example 2 mm×12 mm, 3.5 mm×12 mm, 5 mm×16 mm, 5 mm×24 mm, 6 mm×16 mm, 6 mm×20 mm, 6 mm×24 mm, 7 mm×16 mm and 7 mm×24 mm). Balloon dilation catheter (200) generally includes a proximally located connection (230) for inflating/activating balloon (204).

Balloon (204) may be expanded to dilate the Eustachian tube (26) after it is placed in a desired location therein. For example, the Eustachian tube (26) includes a pharyngeal ostium (28), and balloon dilation catheter (200) may be advanced to position balloon (204) in the pharyngeal ostium (28). An endoscope may be used to assist in positioning balloon dilation catheter (200). The endoscope may be advanced through the nasal passage to view balloon dilation catheter (200). A marker (208) on elongate shaft (202) of balloon dilation catheter (200) can be viewed from the endoscope to approximate a location of balloon (204) relative to the opening of the Eustachian tube (26) based on a distance of marker (208) from a proximal end of balloon (204). Accordingly, balloon dilation catheter (200) can be moved to place marker (208) in a desired location before expansion of balloon (204) in the Eustachian tube (26).

Balloon dilation catheter (200) further includes an actuator (210). Actuator (210) has a proximal side (220) and a distal side (222). In the embodiment shown in FIG. 9A, actuator (210) is secured by an adhesive to elongate shaft (202). A portion (240) of elongate shaft (202) that is distal of actuator (210) is sufficiently stiff to be guided through the nasal cavity and into the Eustachian Tube (26) and is constructed of stainless steel and preferably includes a stainless steel hypotube. A portion (238) of elongate shaft (202) that is proximal of actuator (210) and a portion (250) that is distal of portion (240) is more flexible than portion (240) and is constructed of a polymeric material including but not limited to PEBAX®. In this way, proximal portion (238) of elongate shaft (202) will not interfere with the endoscope described above as it is advanced through the nasal passage such that balloon dilation catheter (200) can be easily viewed. Actuator (210) allows for easy, ergonomic one-handed advancement of balloon dilation catheter (200) through guide catheter (100) and into the Eustachian Tube (26). Actuator (210) may be used to advance or retract in alternative ways including but not limited to use of the thumb, the index finger, or a combination of fingers (i.e. index and middle fingers) or the thumb and the index or middle finger.

Distal end (218) of balloon dilation catheter (200) further includes a tip (212) and a flexible shaft portion (250) that is constructed of a polymeric material including but not limited to PEBAX® that extends from the distal end of elongate shaft (202) to the proximal end of balloon (204). In the embodiment shown in FIG. 9A, tip (212) is a bulbous polymeric blueberry shaped tip that is atraumatic and is about 1.5 mm to 2 mm in length with an outer diameter of between about 2 mm and 3 mm. The smoothness and roundness of tip (212) facilitates advancement of balloon dilation catheter (200) by helping it glide smoothly through the Eustachian Tube (26). Tip (212) further acts as a safety stop. The isthmus (29) of the Eustachian tube (26), shown in FIG. 1 is approximately 1 mm in diameter. The diameter of tip (212) is larger than an outer diameter (233) of elongate shaft (202) shown in cross-section in FIG. 9B such that the size of tip (212) will prevent balloon dilation catheter (200) from passing through the isthmus (29) into the middle ear (14).

Balloon (204) may be held in location while in an expanded state for an extended period of time (e.g. several seconds or minutes). Balloon dilation catheter (200) may also deliver a substance to the Eustachian tube (26), such as one or more of the therapeutic or diagnostic agents described herein. Balloon (204) may also carry an expandable stent for delivery into the Eustachian tube (26) upon expansion of balloon (204). Balloon dilation catheter (200) and guide catheter (100) may be removed from the patient after balloon (204) has been deflated/unexpanded. The Eustachian tube (26) may then resume functioning, normally opening and closing to equalize atmospheric pressure in the middle ear (14) and protect the middle ear (14) from unwanted pressure fluctuations and loud sounds.

In use, guide catheter (100) may be advanced into a nostril and through a nasal cavity to position a distal end of guide catheter (100) at, in or near the ostium (28) of the Eustachian tube (26). In some versions, guide catheter (100) may be passed through a nostril to the Eustachian tube (26) on the ipsilateral (same side) of the head. In some other versions, guide catheter (100) may be passed through a nostril to the Eustachian tube (26) on the contralateral (opposite side) of the head. A guiding element such as a guidewire or illuminating fiber may be used to aid in accessing the Eustachian tube (26).

After guide catheter (100) is in a desired position, balloon catheter (200) is advanced through guide catheter (100) to position balloon (204) of balloon dilation catheter (200) within the Eustachian tube (26). The physician/user may place the index and middle fingers on either side of the smaller diameter middle section (136) of proximal hub (132) of guide catheter (100). The physician/user will then place the thumb on proximal side (220) of actuator (210) or within both sides of actuator (210) and will use the thumb to slide balloon dilation catheter (200) through guide catheter (100) to position balloon (204) within the Eustachian tube (26). Alternatively, the user may grasp proximal hub (132) of guide catheter (100) and use the index finger placed on proximal side (220) of the actuator (210) or in between distal side (222) and proximal side (220) of actuator (210) to advance balloon dilation catheter (200). The larger diameter tip (212) prevents balloon dilation catheter (200) from advancing too far into the middle ear (14). Further, distal side (222) of actuator (210) will bottom out against proximal end (104) of guide catheter (100), such that balloon dilation catheter (200) cannot advance any further. Actuator (210) prevents balloon dilation catheter (200) from reaching too far into the middle ear (14), which can cause damage to structures in the middle ear (14). Further actuator (210) can be positioned at the appropriate distance along elongate shaft (202) such that access to the Eustachian tube (26) may be from the contralateral or the/ ipsilateral side.

In some other instances, balloon catheter (200) is advanced into a nostril of a patient without the use of guide catheter (100). Balloon (204) of balloon dilation catheter (200) is placed within the Eustachian tube (26). The physician/user will advance balloon dilation catheter (200) until proximal side (220) of actuator (210) is adjacent the patient's nostril. Distal side (222) of actuator (210) will bottom out against the patient's nostril, such that balloon dilation catheter (200) cannot advance any further. Actuator (210) prevents balloon dilation catheter (210) from reaching too far into the middle ear (14), which can cause damage to structures in the middle ear (14). Further, actuator (210) can be positioned at the appropriate distance along elongate shaft (202) such that access to the Eustachian tube (26) may be from the contralateral or the ipsilateral side.

Following placement of balloon dilation catheter (200) into the desired position, any number of procedures may be carried out. Elongate shaft (202) contains adjacent dual lumen tubing (see FIG. 9B). By adjacent dual lumen tubing, it is intended that the lumens are next to each other but are spaced apart, one from one another. Inflation lumen (232) is used for inflation of balloon (204) with water, contrast medium, or saline through inflation port (230) to a pressure of between about 3 and 15 atmospheres, or of between about 6 and 12 atmospheres. Injection lumen (234) permits the optional injection of water, medicament, or even the introduction of a guidewire through injection port (236) at proximal end (216) of proximal connector (206). In order to ensure that inflation port (230) is used for balloon inflation only, inflation port (230) and injection port (236) may optionally comprise different type connectors. For example, inflation port (230) may comprise a female connector whereas injection port (236) comprises a male connector or vice versa. Alternatively, injection port (236) may comprise a right-handed thread connected and inflation port (230) may comprise a left-handed thread connector or vice versa. It may be desirable to inject solutions containing contrast agents, pharmaceutically acceptable salt or dosage form of an antimicrobial agent (e.g. antibiotic, antiviral, anti-parasitic, antifungal, etc.), an anesthetic agent with or without a vasoconstriction agent (e.g. Xylocaine with or without epinephrine, Tetracaine with or without epinephrine, etc.), an analgesic agent, a corticosteroid or other anti-inflammatory (e.g. an NSAID), a decongestant (e.g. vasoconstrictor), a mucus thinning agent (e.g. an expectorant or mucolytic), a surfactant, an agent that prevents or modifies an allergic response (e.g. an antihistamine, cytokine inhibitor, leucotriene inhibitor, IgE inhibitor, immunomodulator), an allergen or another substance that causes secretion of mucous by tissues, hemostatic agents to stop bleeding, antiproliferative agents, cytotoxic agents (e.g. alcohol), biological agents such as protein molecules, stem cells, genes or gene therapy preparations, or the like.

Some nonlimiting examples of antimicrobial agents that may be used include acyclovir, amantadine, aminoglycosides (e.g., amikacin, gentamicin and tobramycin), amoxicillin, amoxicillinlclavulanate, amphotericin B, ampicillin, ampicillinlsulbactam, atovaquone, azithromycin, cefazolin, cefepime, cefotaxime, cefotetan, cefpodoxi/me, ceflazidime, ceflizoxime, ceftriaxone, cefuroxime, cefuroxime axetil, cephalexin, chloramphenicol, clotrimazole, ciprofloxacin, clarithromycin, clindamycin, dapsone, dicloxacillin, doxycycline, erythromycin, fluconazole, foscamet, ganciclovir, atifloxacin, imipenemlcilastatin, isoniazid, itraconazole, ketoconazole, metronidazole, nafcillin, nafcillin, nystatin, penicillin, penicillin G, pentamidine, piperacillinitazobactam, rifampin, quinupristindalfopristin, ticarcillinlclavulanate, trimethoprimlsulfamethoxazole, valacyclovir, vancomycin, mafenide, silver sulfadiazine, mupirocin (e.g., Bactroban, Glaxo SmithKline, Research Triangle Park, N.C.), nystatin, triamcinolonelnystatin, clotrimazolelbetamethasone, clotrimazole, ketoconazole, butoconazole, miconazole, tioconazole, detergent-like chemicals that disrupt or disable microbes (e.g., nonoxynol-9, octoxynol-9, benzalkonium chloride, menfegol, and N-docasanol); chemicals that block microbial attachment to target cells and/or inhibits entry of infectious pathogens (e.g., sulphated and sulphonated polymers such as PC-515 (carrageenan), Pro-2000, and Dextrin 2 Sulphate); antiretroviral agents (e.g., PMPA gel) that prevent retroviruses from replicating in the cells; genetically engineered or naturally occurring antibodies that combat pathogens such as anti-viral antibodies genetically engineered from plants known as "plantibodies;" agents which change the condition of the tissue to make it hostile to the pathogen (such as substances which alter mucosal pH (e.g., Buffer Gel and Acid form); non-pathogenic or "friendly" microbes that cause the production of hydrogen peroxide or other substances that kill or inhibit the growth of pathogenic microbes (e.g., *lactobacillus*); antimicrobial proteins or peptides such as those described in U.S. Pat. No. 6,716,813, entitled "Use of Antimicrobial Proteins and Peptides for the Treatment of Otitis Media and Paranasal Sinusitis," issued Apr. 6, 2004, the disclosure of which is incorporated by reference herein, or antimicrobial metals (e.g., colloidal silver).

Additionally or alternatively, in some applications where it is desired to treat or prevent inflammation the substances delivered may include various steroids or other anti-inflammatory agents (e.g., nonsteroidal anti-inflammatory agents or NSAIDS), analgesic agents or antipyretic agents. For example, corticosteroids that have previously administered by intranasal 10 administration may be used, such as beclomethasone (Vancenase® or Beconase), flunisolide (Nasalid®), fluticasone proprionate (Flonase®), triamcinolone acetonide (Nasacort®), budesonide (Rhinocort Aqua®), loterednol etabonate (Locort) and mometasone (Nasonex®). Other salt forms of the aforementioned corticosteroids may also be used. Also, other non-limiting examples of steroids that may be useable include but are not limited to aclometasone, desonide, hydrocortisone, betamethasone, clocortolone, desoximetasone, fluocinolone, flurandrenolide, mometasone, prednicarbate; amcinonide, desoximetasone, diflorasone, fluocinolone, fluocinonide, halcinonide, clobetasol, augmented betamethasone, diflorasone, halobetasol, prednisone, dexarnethasone and methylprednisolone. Other anti-inflammatory, analgesic or antipyretic agents that may be used include the nonselective COX inhibitors (e.g., salicylic acid derivatives, aspirin, sodium salicylate, choline magnesium trisalicylate, salsalate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam) and alkanones such as nabumetone) and Selective COX-2 Inhibitors (e.g., diaryl-substituted furanones such as rofecoxib; diaryl-substituted pyrazoles such as celecoxib; indole acetic acids such as etodolac and sulfonanilides such as mesulide).

Additionally or alternatively, in some applications, such as those where it is desired to treat or prevent an allergic or immune response and/or cellular proliferation, the substances delivered may include: various cytokine inhibitors such as humanized anti-cytokine antibodies, anti-cytokine receptor antibodies, recombinant (new cell resulting from genetic recombination) antagonists, or soluble receptors; various leucotriene modifiers such as zafirlukast, montelukast and zileuton; immunoglobulin E (IgE) inhibitors such as Omalizumab (an anti-IgE monoclonal antibody formerly called rhu Mab-E25) and secretory leukocyte protease inhibitor); and SYK Kinase inhibitors such as an agent designated as "R-112" manufactured by Rigel Pharmaceuticals, Inc, South San Francisco, Calif.

Additionally or alternatively, in some applications, such as those where it is desired to shrink mucosal tissue, cause decongestion, or effect hemostasis, the substances delivered may include various vasoconstrictors for decongestant and or hemostatic purposes including but not limited to pseudoephedrine, xylometazoline, oxymetazoline, phenylephrine, epinephrine, etc.

Additionally or alternatively, in some applications, such as those where it is desired to facilitate the flow of mucous, the substances delivered may include various mucolytics or other agents that modify the viscosity or consistency of mucous or mucoid secretions, including but not limited to acetylcysteine. In one particular embodiment, the substance delivered may comprise a combination of an anti-inflammatory agent (e.g. a steroid or an NSAID) and a mucolytic agent.

Additionally or alternatively, in some applications such as those where it is desired to prevent or deter histamine release, the substances delivered may include various mast cell stabilizers or drugs which prevent the release of histamine such as cromolyn (e.g., Nasal Chroma) and nedocromil.

Additionally or alternatively, in some applications such as those where it is desired to prevent or inhibit the effect of histamine, the substances delivered may include various antihistamines such as azelastine (e.g., Astylin) diphenhydramine, loratidine, etc.

Additionally or alternatively, in some embodiments such as those where it is desired to dissolve, degrade, cut, break or remodel bone or cartilage, the substances delivered may include substances that weaken or modify bone and/or cartilage to facilitate other procedures wherein bone or cartilage is remodeled, reshaped, broken or removed. One example of such an agent would be a calcium chelator such as EDTA that could be injected or delivered in a substance delivery implant next to a region of bone that is to be remodeled or modified. Another example would be a preparation consisting of or containing bone degrading cells such as osteoclasts. Other examples would include various enzymes of material that may soften or break down components of bone or cartilage such as collagenase (CGN), trypsin, trypsinlLEDTA, hyaluronidase, and tosyllysylchloromethane (TLCM).

Additionally or alternatively, in some applications such as those wherein it is desired to treat a tumor or cancerous lesion, the substances delivered may include antitumor agents (e.g., cancer chemotherapeutic agents, biological response modifiers, vascularization inhibitors, hormone receptor blockers, cryotherapeutic agents or other agents that destroy or inhibit neoplasia or tumorigenesis) such as; alkylating agents or other agents which directly kill cancer cells by attacking their DNA (e.g., cyclophosphamide, isophosphamide), nitrosoureas or other agents which kill cancer cells by inhibiting changes necessary for cellular DNA repair (e.g., carmustine (BCNU) and lomustine (CCNU)), antimetabolites and other agents that block cancer cell growth by interfering with certain cell functions, usually DNA synthesis (e.g., 6 mercaptopurine and 5-fluorouracil (5FU), antitumor antibiotics and other compounds that act by binding or intercalating DNA and preventing RNA synthesis (e.g., doxorubicin, daunorubicin, epirubicin, idarubicin, mitomycin-C and bleomycin) plant (*vinca*) alkaloids and other antitumor agents derived from plants (e.g., vincristine and vinblastine), steroid hormones, hormone inhibitors, hormone receptor antagonists and other agents which affect the growth of hormone-responsive cancers (e.g., tamoxifen, herceptin, aromatase inhibitors such as aminoglutethamide and formestane, trriazole inhibitors such as letrozole and anastrazole, steroidal inhibitors such as exemestane), antiangiogenic proteins, small molecules, gene therapies and/or other agents that inhibit angiogenesis or vascularization of tumors (e.g., meth-I, meth-2, thalidomide), bevacizumab (Avastin), squalamine, endostatin, angiostatin, Angiozyme, AE-941 (Neovastat), CC-5013 (Revimid), medi-522 (Vitaxin), 2-methoxyestradiol (2ME2, Panzem), carboxyamidotriazole (CAI), combretastatin A4 prodrug (CA4P), SU6668, SU11248, BMS-275291, COL-3, EMD 121974, 1MC-IC11, 1M862, TNP-470, celecoxib (Celebrex), rofecoxib (Vioxx), interferon alpha, interleukin-12 (IL-12) or any of the compounds identified in Science Vol. 289, Pages 1197-1201 (Aug. 17, 2000) which is expressly incorporated herein by reference, biological response modifiers (e.g., interferon, bacillus calmetteguerin (BCG), monoclonal antibodies, interluken 2, granulocyte colony stimulating factor (GCSF), etc.), PGDF receptor antagonists, herceptin, asparaginase, busulphan, carboplatin, cisplatin, carmustine, chlorambucil, cytarabine, dacarbazine, etoposide, flucarbazine, fluorouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine, streptocin, taxol, taxotere, analogslcongeners and derivatives of such compounds as well as other antitumor agents not listed here.

Additionally or alternatively, in some applications such as those where it is desired to grow new cells or to modify existing cells, the substances delivered may include cells (mucosal cells, fibroblasts, stem cells or genetically engineered cells) as well as genes and gene delivery vehicles like plasmids, adenoviral vectors or naked DNA, mRNA, etc. injected with genes that code for anti-inflammatory substances, etc., and, as mentioned above, osteoclasts that modify or soften bone when so desired, cells that participate in or effect mucogenesis or ciliagenesis, etc.

In some instances, a local anesthetic, such as Lidocaine is injected through injection lumen (234) prior to dilation of the Eustachian tube (26). Injection lumen (234) can be used for venting during dilation so that pressure in the middle ear (14) does not increase or decrease.

Figure 12:
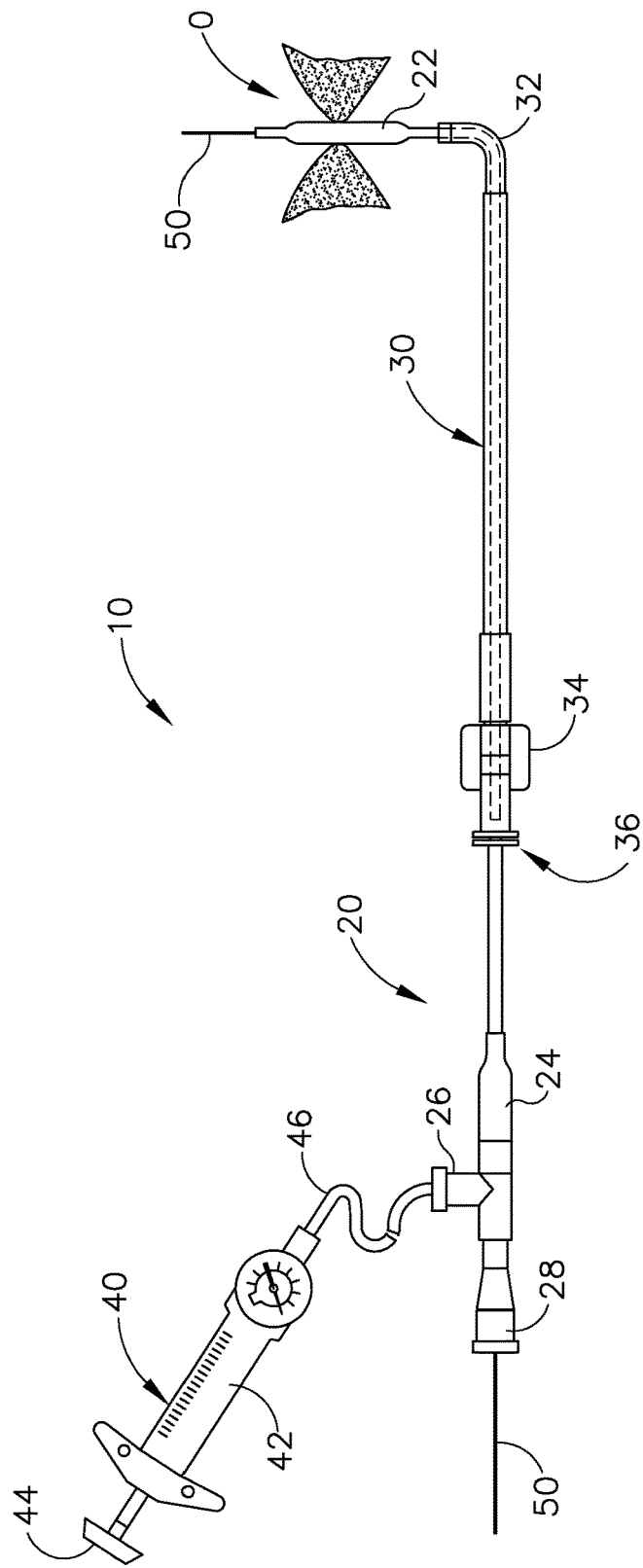
FIG. 12 depicts a side elevational view of an exemplary dilation catheter system.

FIG. 12 shows another exemplary dilation catheter system (410) that may be used to dilate the Eustachian tube (26); or to dilate some other anatomical passageway (e.g., within the ear, nose, or throat, etc.). Dilation catheter system (410) of this example comprises a balloon dilation catheter (420), a guide catheter (430), an inflator (440), and a guidewire (450). It should be understood that dilation catheter (420) may be viewed as a variation of dilation catheter (200) described above. Similarly, guide catheter (430) may be viewed as a variation of guide catheter (100) described above. By way of example only, dilation catheter system (410) may be configured in accordance with at least some of the teachings of U.S. Pat. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. In some versions, at least part of dilation catheter system (410) is configured similar to the Relieva® Spin Balloon Sinuplasty™ System by Acclarent, Inc. of Menlo Park, Calif.

The distal end of balloon dilation catheter (420) includes a balloon (422). The proximal end of balloon dilation catheter (420) includes a grip (424), which has a lateral port (426) and an open proximal end (428). Balloon dilation catheter (420) includes a first lumen (not shown) that provides fluid communication between lateral port (426) and the interior of balloon (422). Balloon dilation catheter (420) also includes a second lumen (not shown) that extends from open proximal end (428) to an open distal end that is distal to balloon (422). This second lumen is configured to slidably receive guidewire (450). The first and second lumens of balloon dilation catheter (420) are fluidly isolated from each other. Thus, balloon (422) may be selectively inflated and deflated by communicating fluid along the first lumen via lateral port (426) while guidewire (450) is positioned within the second lumen. In some versions, balloon dilation catheter (420) is configured similar to the Relieva Ultirra™ Sinus Balloon Catheter by Acclarent, Inc. of Menlo Park, Calif. In some other versions, balloon dilation catheter (420) is configured similar to the Relieva Solo Pro™ Sinus Balloon Catheter by Acclarent, Inc. of Menlo Park, Calif. Other suitable forms that balloon dilation catheter (420) may take will be apparent to those of ordinary skill in the art in view of the teachings herein.

Guide catheter (430) of the present example includes a bent distal end (432) and a grip (434) at its proximal end. Grip (434) has an open proximal end (436). Guide catheter (430) defines a lumen that is configured to slidably receive balloon dilation catheter (420), such that guide catheter (430) may guide balloon (422) out through bent distal end (432). In some versions, guide catheter (430) is configured similar to the Relieva Flex™ Sinus Guide Catheter by Acclarent, Inc. of Menlo Park, Calif. Other suitable forms that guide catheter (430) may take will be apparent to those of ordinary skill in the art in view of the teachings herein.

Inflator (440) of the present example comprises a barrel (442) that is configured to hold fluid and a plunger (444) that is configured to reciprocate relative to barrel (442) to selectively discharge fluid from (or draw fluid into) barrel (442). Barrel (442) is fluidly coupled with lateral port (426) via a flexible tube (446). Thus, inflator (440) is operable to add fluid to balloon (422) or withdraw fluid from balloon (422) by translating plunger (444) relative to barrel (442). In the present example, the fluid communicated by inflator (440) comprises saline, though it should be understood that any other suitable fluid may be used. There are various ways in which inflator (440) may be filled with fluid (e.g., saline, etc.). By way of example only, before flexible tube (446) is coupled with lateral port (426), the distal end of flexible tube (446) may be placed in a reservoir containing the fluid. Plunger (444) may then be retracted from a distal position to a proximal position to draw the fluid into barrel (442). Inflator (440) may then be held in an upright position, with the distal end of barrel (442) pointing upwardly, and plunger (444) may then be advanced to an intermediate or slightly distal position to purge any air from barrel (442). The distal end of flexible tube (446) may then be coupled with lateral port (426).

As best seen in FIGS. 13 and 14, guidewire (450) of the present example comprises a coil (452) positioned about a core wire (454). An illumination fiber (456) extends along the interior of core wire (454) and terminates in an atraumatic lens (458). A connector (455) at the proximal end of guidewire (450) enables optical coupling between illumination fiber (456) and a light source (4 not shown). Illumination fiber (456) may comprise one or more optical fibers. Lens (458) is configured to project light when illumination fiber (456) is illuminated by the light source, such that illumination fiber (456) transmits light from the light source to the lens (458). In some versions, the distal end of guidewire (450) is more flexible than the proximal end of guidewire (450). Guidewire (450) has a length enabling the distal end of guidewire (450) to be positioned distal to balloon (422) while the proximal end of guidewire (450) is positioned proximal to grip (424). Guidewire (450) may include indicia along at least part of its length (4 e.g., the proximal portion) to provide the operator with visual feedback indicating the depth of insertion of guidewire (450) relative to balloon dilation catheter (420). By way of example only, guidewire (450) may be configured in accordance with at least some of the teachings of U.S. Pat. Pub. No. 2012/0078118, entitled "Sinus Illumination Lightwire Device," published Mar. 29, 2012, issued as U.S. Pat. No. 9,155,492 on Oct. 13, 2015, the disclosure of which is incorporated by reference herein. In some versions, guidewire (450) is configured similar to the Relieva Luma Sentry™ Sinus Illumination System by Acclarent, Inc. of Menlo Park, Calif. Other suitable forms that guidewire (450) may take will be apparent to those of ordinary skill in the art in view of the teachings herein.

In an exemplary dilation procedure, guide catheter (430) may first be positioned near the targeted anatomical passageway, such as the ostium (28). Balloon (422) and the distal end of guidewire (450) may be positioned within or proximal to bent distal end (432) of guide catheter (430) at this stage. Guide catheter (430) is initially inserted into the nose of the patient and is advanced to a position that is within or near the ostium (40) to be dilated. This positioning of guide catheter (430) may be performed under visualization provided by an endoscope such as endoscope (460) described below. After guide catheter (430) has been positioned, the operator may advance guidewire (450) distally through guide catheter (430) such that a distal portion of the guidewire (450) passes through the sinus ostium (O) and into the sinus cavity. The operator may illuminate illumination fiber (456) and lens (458), which may provide transcutaneous illumination through the patient's face to enable the operator to visually confirm positioning of the distal end of guidewire (450) with relative ease.

With guide catheter (430) and guidewire (450) suitably positioned, balloon dilation catheter (420) is advanced along guidewire (450) and through bent distal end (432) of guide catheter (430), with balloon (422) in a non-dilated state until balloon (422) is positioned within the ostium (28) (or some other targeted anatomical passageway). After balloon (422) has been positioned within the ostium (O), balloon (422) may be inflated, thereby dilating the ostium. To inflate balloon (422), plunger (444) may be actuated to push saline from barrel (442) of inflator (440) through balloon dilation catheter (420) into balloon (422). The transfer of fluid expands balloon (422) to an expanded state to open or dilate the ostium (O), such as by remodeling the bone, etc., forming ostium (O). By way of example only, balloon (422) may be inflated to a volume sized to achieve about 10 to about 12 atmospheres. Balloon (422) may be held at this volume for a few seconds to sufficiently open the ostium (O) (or other targeted anatomical passageway). Balloon (422) may then be returned to a non-expanded state by reversing plunger (444) of inflator (440) to bring the saline back to inflator (440). Balloon (422) may be repeatedly inflated and deflated in different ostia and/or other targeted anatomical passageways. Thereafter, balloon dilation catheter (420), guidewire (450), and guide catheter (430) may be removed from the patient.

In some instances, it may be desirable to irrigate the sinus and paranasal cavity after balloon dilation catheter (420) has been used to dilate an ostium (O). Such irrigation may be performed to flush out blood, etc. that may be present after the dilation procedure. By way of example only, such irrigation may be carried out in accordance with at least some of the teachings of U.S. Pub. No. 2008/0183128, entitled "Methods, Devices and Systems for Treatment and/or Diagnosis of Disorders of the Ear, Nose and Throat," published on Jul. 31, 2008, the disclosure of which is incorporated by reference herein. An example of an irrigation catheter that may be fed through guide catheter (430) to reach the irrigation site after removal of balloon dilation catheter (420) is the Relieva Vortex® Sinus Irrigation Catheter by Acclarent, Inc. of Menlo Park, Calif. Another example of an irrigation catheter that may be fed through guide catheter (430) to reach the irrigation site after removal of balloon dilation catheter (420) is the Relieva Ultirra® Sinus Irrigation Catheter by Acclarent, Inc. of Menlo Park, Calif. Of course, irrigation may be provided in the absence of a dilation procedure; and a dilation procedure may be completed without also including irrigation.

Figure 15:
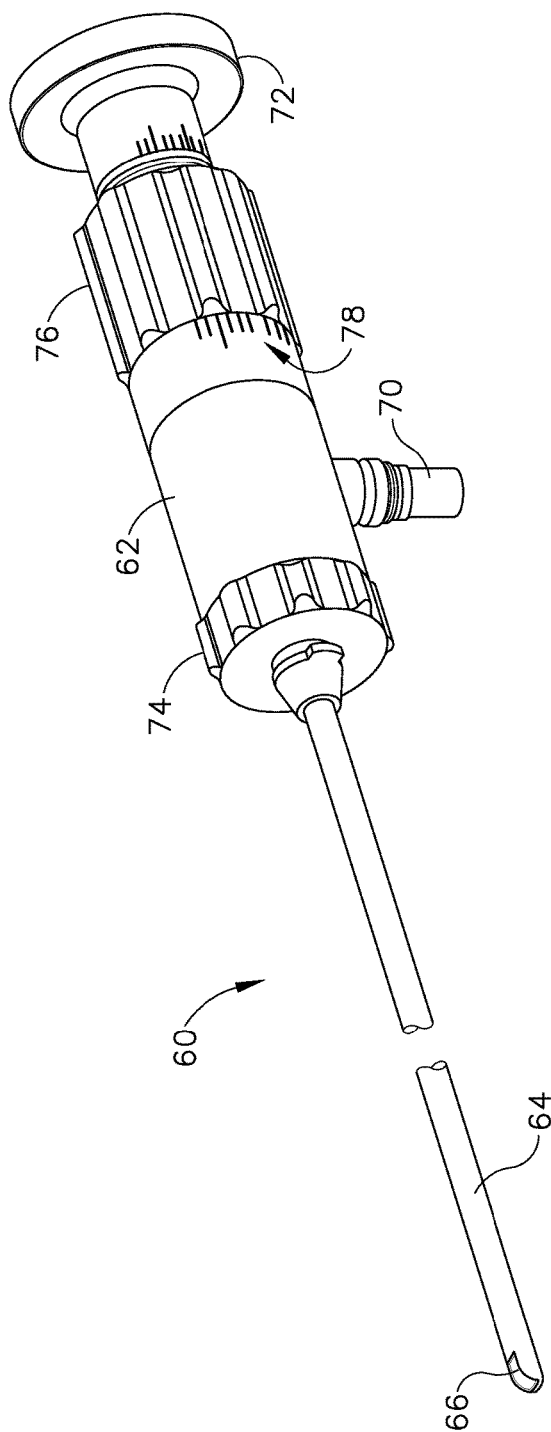
FIG. 15 depicts a perspective view of an exemplary endoscope suitable for use with the dilation catheter system of FIG. 12.
Figure 16:
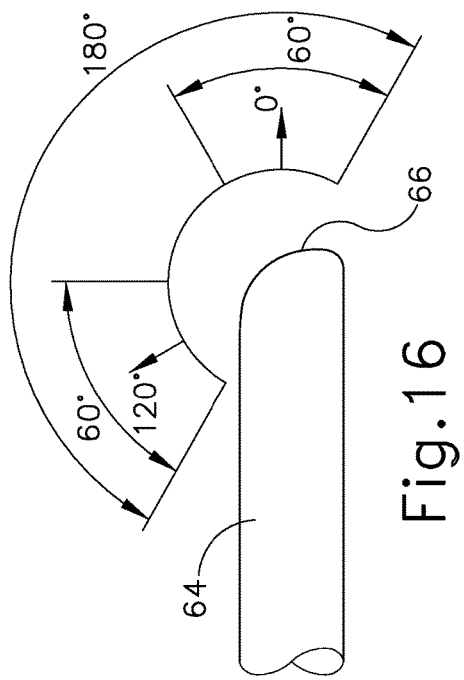
FIG. 16 depicts a side elevational view of the distal end of the endoscope of FIG. 15, showing an exemplary range of viewing angles.
Figure 17:
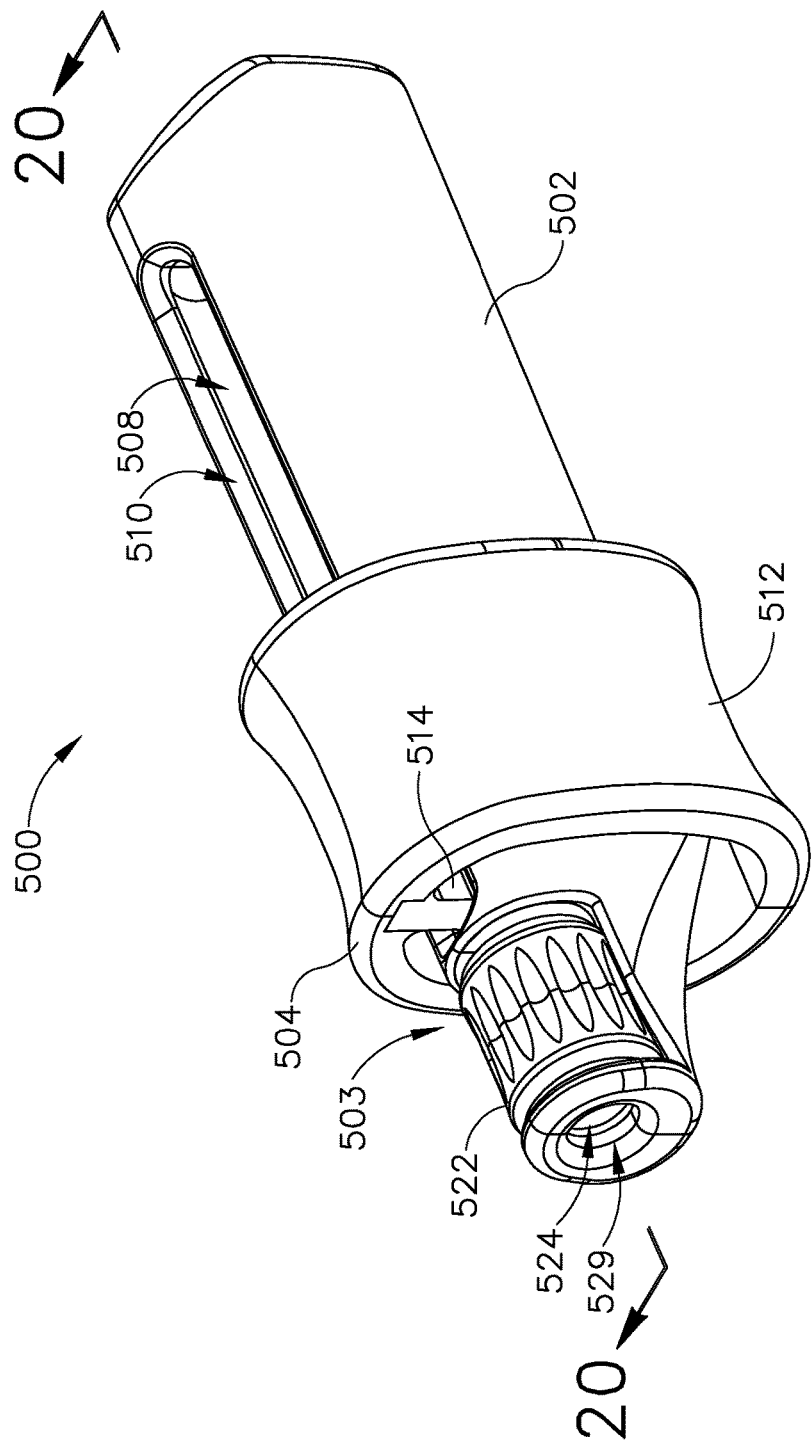
FIG. 17 depicts a perspective view of an exemplary handle suitable for use with the dilation catheter system of FIG. 12.

As noted above, an endoscope (460) may be used to provide visualization within an anatomical passageway (e.g., within the nasal cavity, etc.) during a process of using dilation catheter system (410). As shown in FIGS. 15 and 16, endoscope (460) of the present example comprises a body (462) and a rigid shaft (464) extending distally from body (462). The distal end of shaft (464) includes a curved transparent window (466). A plurality of rod lenses and light transmitting fibers may extend along the length of shaft (464). A lens is positioned at the distal end of the rod lenses and a swing prism is positioned between the lens and window (466). The swing prism is pivotable about an axis that is transverse to the longitudinal axis of shaft (464). The swing prism defines a line of sight that pivots with the swing prism. The line of sight defines a viewing angle relative to the longitudinal axis of shaft (464). This line of sight may pivot from approximately 0 degrees to approximately 120 degrees, from approximately 10 degrees to approximately 90 degrees, or within any other suitable range. The swing prism and window (466) also provide a field of view spanning approximately 60 degrees (4 with the line of sight centered in the field of view). Thus, the field of view enables a viewing range spanning approximately 180 degrees, approximately 140 degrees, or any other range, based on the pivot range of the swing prism. Of course, all of these values are mere examples.

Body (462) of the present example includes a light post (470), an eyepiece (472), a rotation dial (474), and a pivot dial (476). Light post (470) is in communication with the light transmitting fibers in shaft (464) and is configured to couple with a source of light, to thereby illuminate the site in the patient distal to window (466). Eyepiece (472) is configured to provide visualization of the view captured through window (466) via the optics of endoscope (460). It should be understood that a visualization system (e.g., camera and display screen, etc.) may be coupled with eyepiece (472) to provide visualization of the view captured through window (466) via the optics of endoscope (460). Rotation dial (474) is configured to rotate shaft (464) relative to body (462) about the longitudinal axis of shaft (464). It should be understood that such rotation may be carried out even while the swing prism is pivoted such that the line of sight is non-parallel with the longitudinal axis of shaft (464). Pivot dial (476) is coupled with the swing prism and is thereby operable to pivot the swing prism about the transverse pivot axis. Indicia (478) on body (462) provide visual feedback indicating the viewing angle. Various suitable components and arrangements that may be used to couple rotation dial (474) with the swing prism will be apparent to those of ordinary skill in the art in view of the teachings herein. By way of example only, endoscope (460) may be configured in accordance with at least some of the teachings of U.S. Pat. Pub. No. 2010/0030031, entitled "Swing Prism Endoscope," published Feb. 4, 2010, now abandoned, the disclosure of which is incorporated by reference herein. In some versions, endoscope (460) is configured similar to the Acclarent Cyclops™ Multi-Angle Endoscope by Acclarent, Inc. of Menlo Park, Calif. Other suitable forms that endoscope (460) may take will be apparent to those of ordinary skill in the art in view of the teachings herein.

III. Exemplary Single-Hand-Use Handle

As mentioned above, it may be desirable to provide a system for dilation of the Eustachian tube (26) that would be ergonomic and easy to use and would safely and effectively access the Eustachian tube (26). For instance, it may be desirable to provide a handle operable to allow a user to single-handedly operate dilation catheter system (410) described above. In particular, it may be desirable to provide a handle operable to combine guide catheters (100, 300, 430), balloon dilation catheters (200, 420), and/or endoscope (460) in such a manner as to allow a user to maneuver and operate each element using only a single hand. Various examples of such handles will be described in greater detail below; while other examples will be apparent to those of ordinary skill in the art in view of the teachings herein. While the following examples are provided in the context of dilating a Eustachian tube (26) it should be understood that the same examples may be readily applied to the context of dilating ostia of paranasal sinuses, the frontal recess, and/or other anatomical passageways associated with the ear, nose, and throat.

Figure 19:
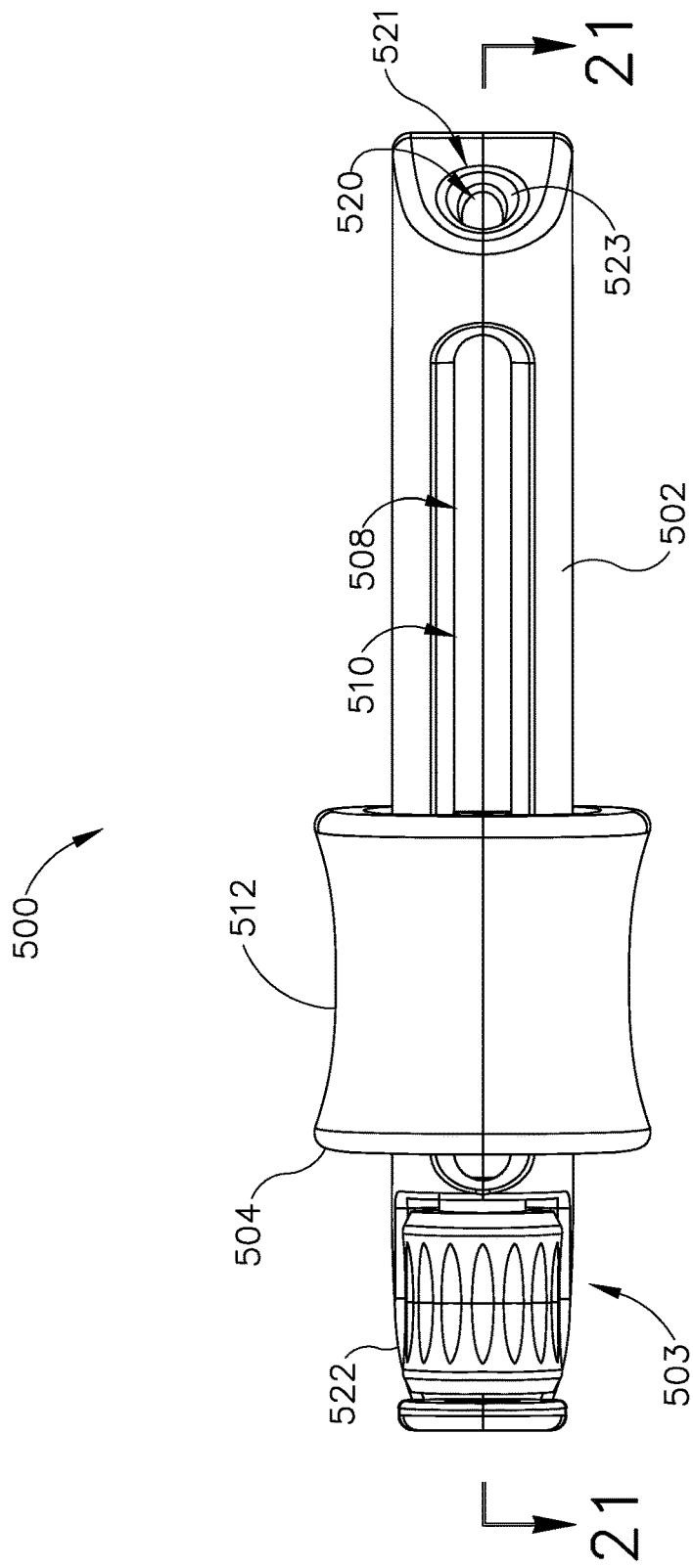
FIG. 19 depicts a top plan view of the handle of FIG. 17.
Figure 20:
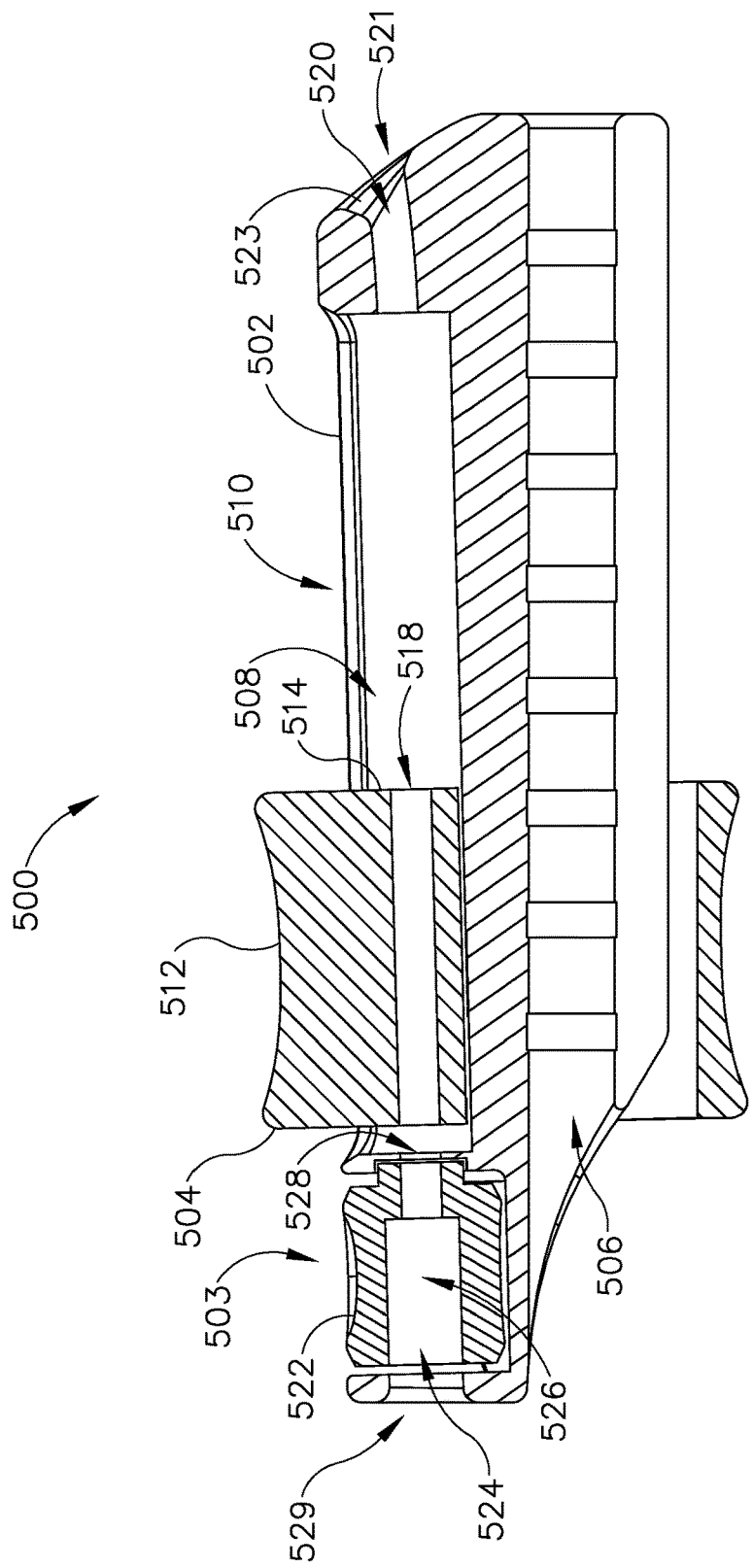
FIG. 20 depicts a cross-sectional front view of the handle of FIG. 17 taken along line 20-20 of FIG. 17.

A. Exemplary Single-Hand-Use Handle with Slidable Actuator and Rotatable Actuator FIGS. 17-21D show an exemplary single-hand-use handle (500). As will be described in more detail below, handle (500) is operable to combine a guide catheter (530), a balloon dilation catheter (540), and endoscope (460) in such a manner as to allow a user to maneuver and operate each element using only a single hand. Handle (500) of the present example comprises a body (502) and an actuator (504). As best seen in FIG. 21, body (502) includes a through-bore (506) formed in a lower portion of body (502). Through-bore (506) extends the length of body (502). As will be described in greater detail below, through-bore (506) is operable to receive and selectively retain shaft (464) of endoscope (460). Body (502) further includes a channel (508) formed in an upper portion of body (502). Channel (508) extends partially the length of body (502). An elongate opening (510) formed in a top surface of body (502) extends substantially the length of channel (508) and provides external access to channel (508). As will be described in more detail below, actuator (504) is slidably coupled within channel (508) of body (502) via elongate opening (510) such that actuator (504) may translate within channel (508) between a proximal longitudinal position and a distal longitudinal position along the length of channel (508). As will also be described in more detail below, actuator (504) is coupled with balloon dilation catheter (540) such that translation of actuator (504) within channel (508) causes concurrent translation of balloon dilation catheter (540) relative to body (502).

Figure 18:
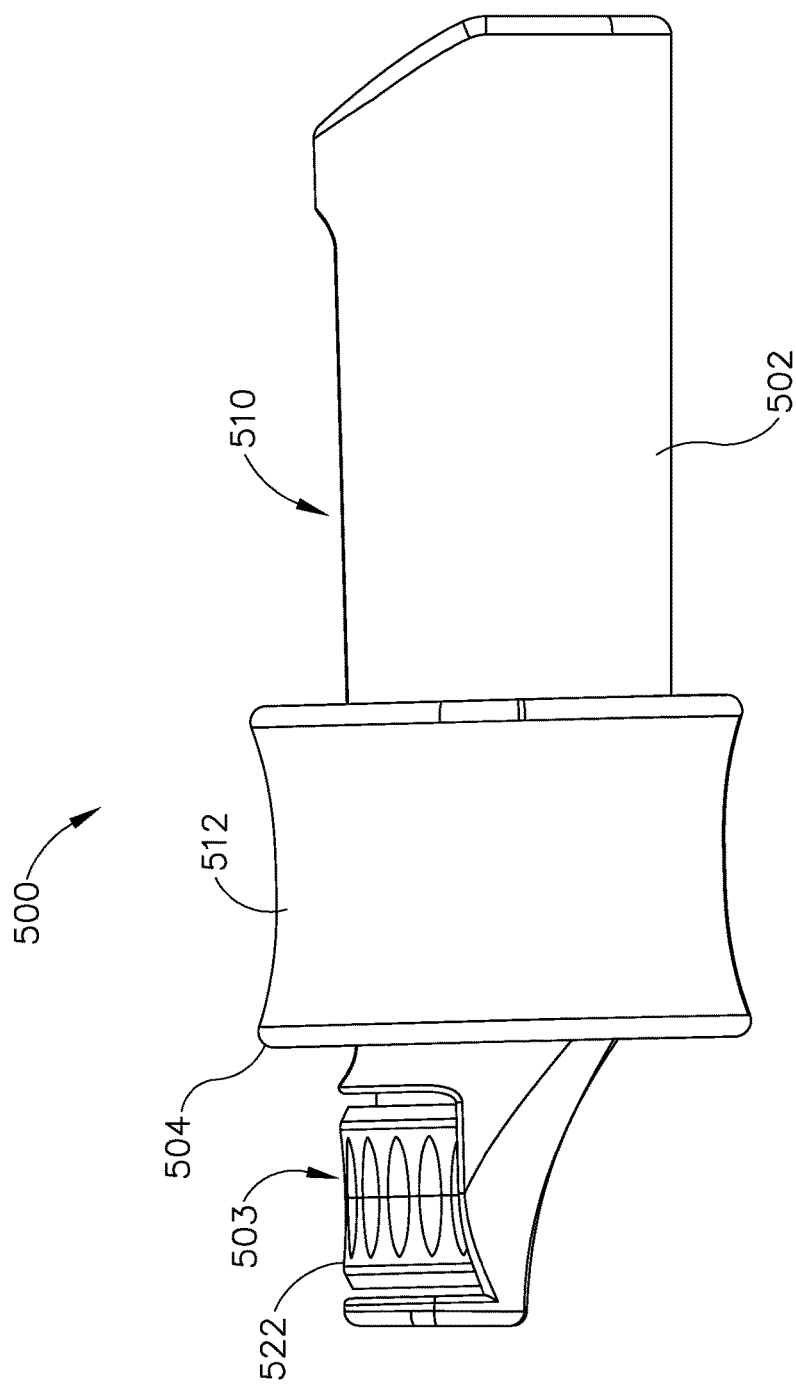
FIG. 18 depicts a side elevational view of the handle of FIG. 17.

Actuator (504) comprises a hollow oval-shaped body (512). Actuator (504) further comprises a protrusion (514) that extends inwardly from an interior surface of body (512). Body (502) is positioned within the hollow interior of body (512) of actuator (504) and protrusion (514) of actuator (504) is positioned within channel (508) so as to slidably couple actuator (504) with body (502). With protrusion (514) positioned within channel (508), actuator (504) is operable to translate along the length of channel (508) between a proximal longitudinal position and a distal longitudinal position. Protrusion (514) comprises a through-bore (518) that is configured to receive and selectively couple balloon dilation catheter (540) with actuator (504). In this way, translation of actuator (504) within channel (508) is communicated to balloon dilation catheter (540). As best seen in FIGS. 18-20, an exterior surface of body (512) of actuator (504) is saddle-shaped. This saddle-shaped exterior surface allows a user to easily locate and maneuver actuator (504) with only a single finger or thumb while holding handle (500).

A rotation knob (522) is rotatably coupled within a channel (503) formed in a distal portion of body (502). Rotation knob (522) is configured to rotate relative to body (502). Rotation knob (522) comprises a through-bore (524). A distal portion (526) of through-bore (524) is sized to receive and selectively retain guide catheter (530) such that guide catheter (530) may be coupled with the distal portion of body (502) and extend distally therefrom as shown in FIG. 21A; and further such that rotation of rotation knob (522) is communicated to guide catheter (530). Guide catheter (530) of the present example is configured to operate substantially similar to guide catheters (100, 300, 430) described above. In particular, guide catheter (530) is operable to direct balloon dilation catheter (540) toward the Eustachian tube (26) (or any other anatomical passageway (e.g., within the ear, nose, or throat, etc.)) such that balloon dilation catheter (540) may safely and effectively access the Eustachian tube (26).

As best seen in FIG. 20, body (502) comprises a proximal bore (520) extending between a proximal end of body (502) and a proximal end of channel (508). A proximal opening (521) of proximal bore (520) includes an edge fillet (523). Edge fillet (523) varies in size/dimension about the circumference of proximal opening (521). Edge fillet (523) provides for a smooth transition of balloon dilation catheter (540) into and out of proximal bore (520) at varying angles relative to body (502) as balloon dilation catheter (540) translates relative to body (502) as will be described in more detail below. Edge fillet (523) is thus configured to prevent wear and tear to balloon dilation catheter (540) as balloon dilation catheter (540) translates into and out of proximal bore (520). Body (502) further comprises a distal bore (528) extending between a proximal end of channel (503) and a distal end of channel (508). Body (502) further comprises a distal bore (529) extending between a distal end of body (502) and a distal end of channel (503). Bores (528, 529) of body (502) are coaxially aligned with through-bore (524) of rotation knob (522).

As also best seen in FIG. 20, proximal bore (520), channel (508), through-bore (518) of actuator (504), bores (528, 529), and through-bore (524) of rotation knob (522) form a continuous passageway through body (502) that leads directly to guide catheter (530) when coupled with rotation knob (522). Balloon dilation catheter (540) is configured to pass through this passageway within body (502) and to further pass though guide catheter (530) when coupled with rotation knob (522). As described above, balloon dilation catheter (540) is selectively coupled with actuator (504) such that translation of actuator (504) within channel (508) is communicated to balloon dilation catheter (540). Thus, it should be understood that translation of actuator (504) within channel (508) causes concurrent translation of balloon dilation catheter (540) within this passageway. In particular, balloon dilation catheter (540) is configured to translate within proximal bore (520), channel (508), through-bore (518) of actuator (504), bores (528, 529), through-bore (524) of rotation knob (522), and guide catheter (530) in response to translation of actuator (504) within channel (508). Balloon dilation catheter (540) of the present example is configured to operate substantially similar to balloon dilation catheters (200, 420) described above. In particular, balloon dilation catheter (540) is operable to safely and effectively access and dilate the Eustachian tube (26) (or any other anatomical passageway (e.g., within the ear, nose, or throat, etc.)).

Figure 21B:
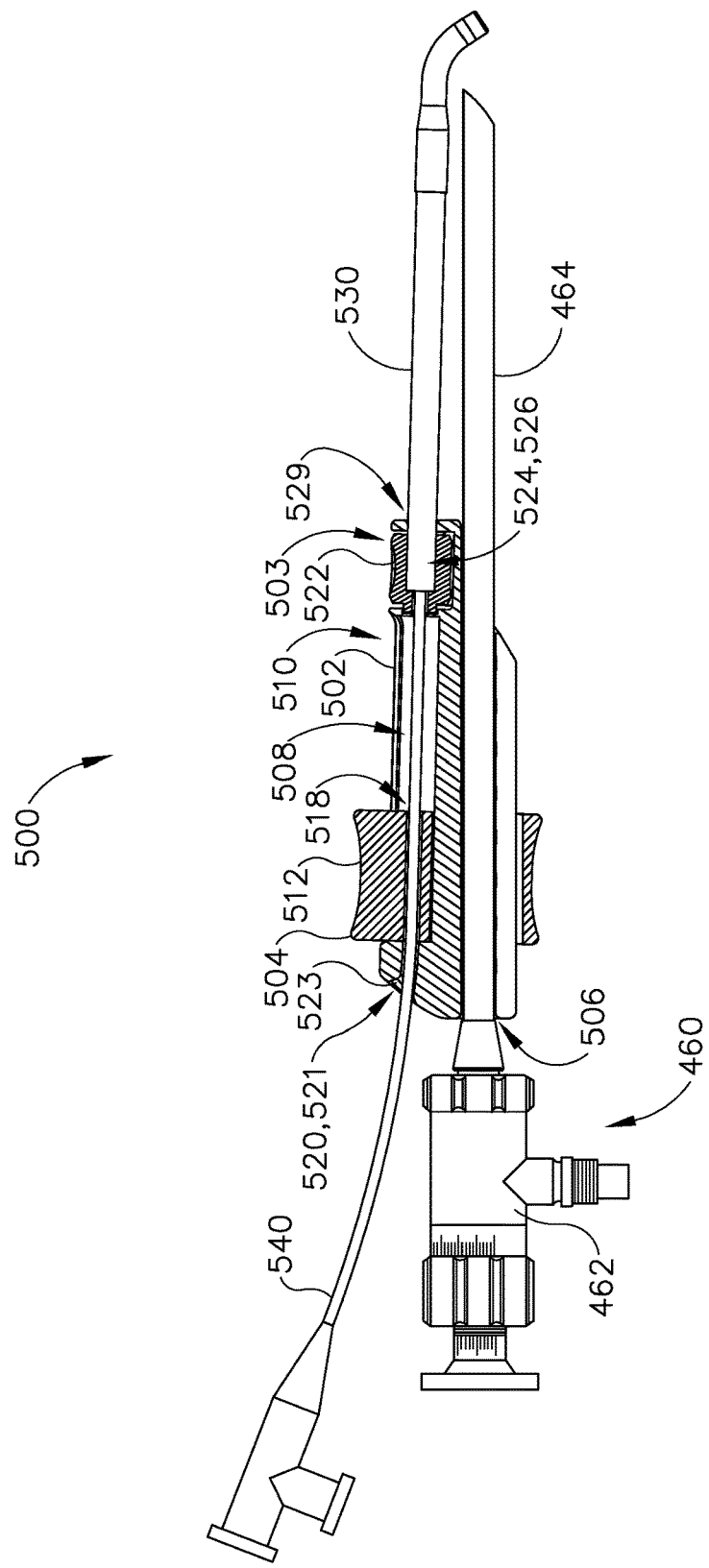
FIG. 21B depicts a cross-sectional side view of the handle of FIG. 17 taken along line 21-21 of FIG. 19, with the endoscope of FIG. 15 positioned therein.
Figure 21C:
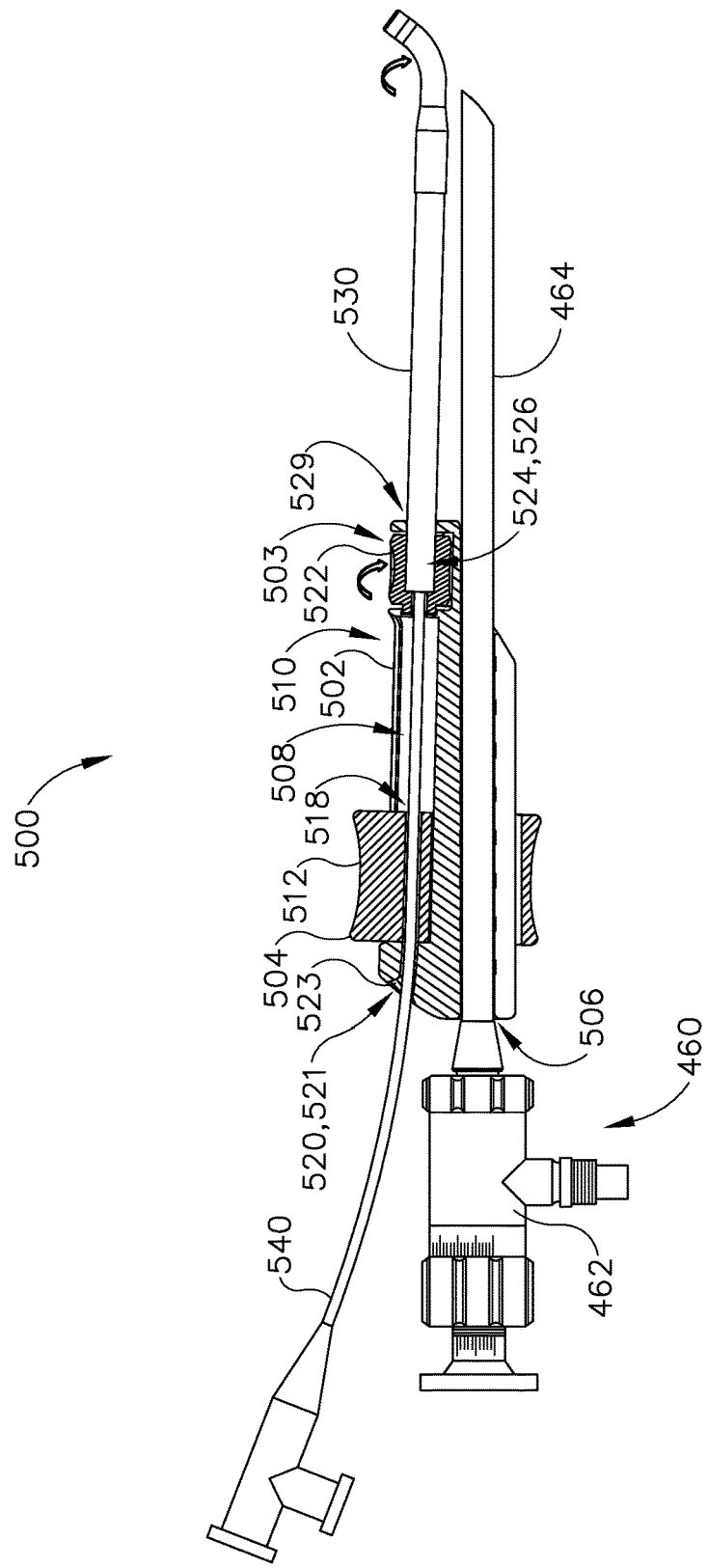
FIG. 21C depicts a cross-sectional side view of the handle of FIG. 17 taken along line 21-21 of FIG. 19, with the guide catheter of FIG. 7A rotated relative to the handle by rotation of a rotation knob.
Figure 21D:
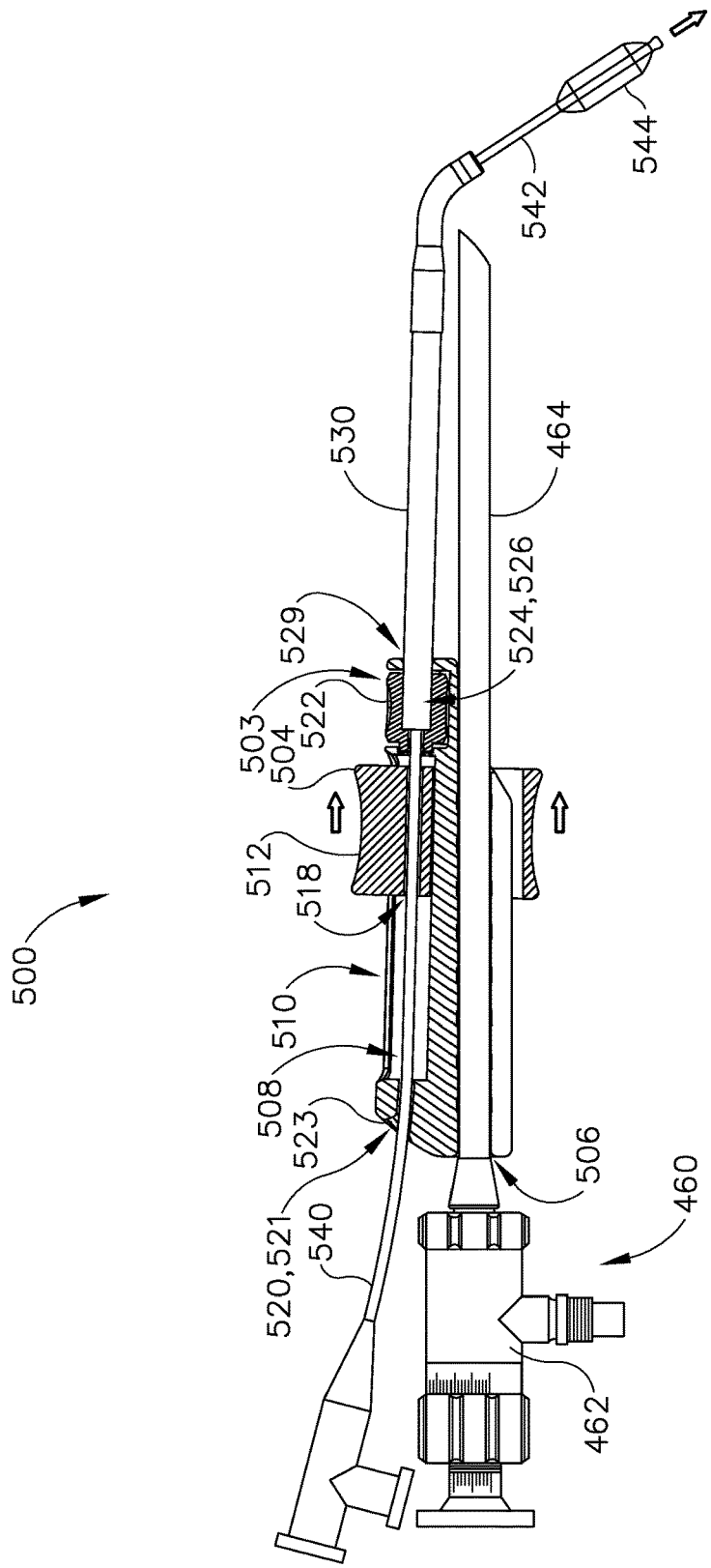
FIG. 21D depicts a cross-sectional side view of the handle of FIG. 17 taken along line 21-21 of FIG. 19, with the balloon dilation catheter of FIG. 21A translated distally by distal translation of an actuator of the handle.
Figure 22:
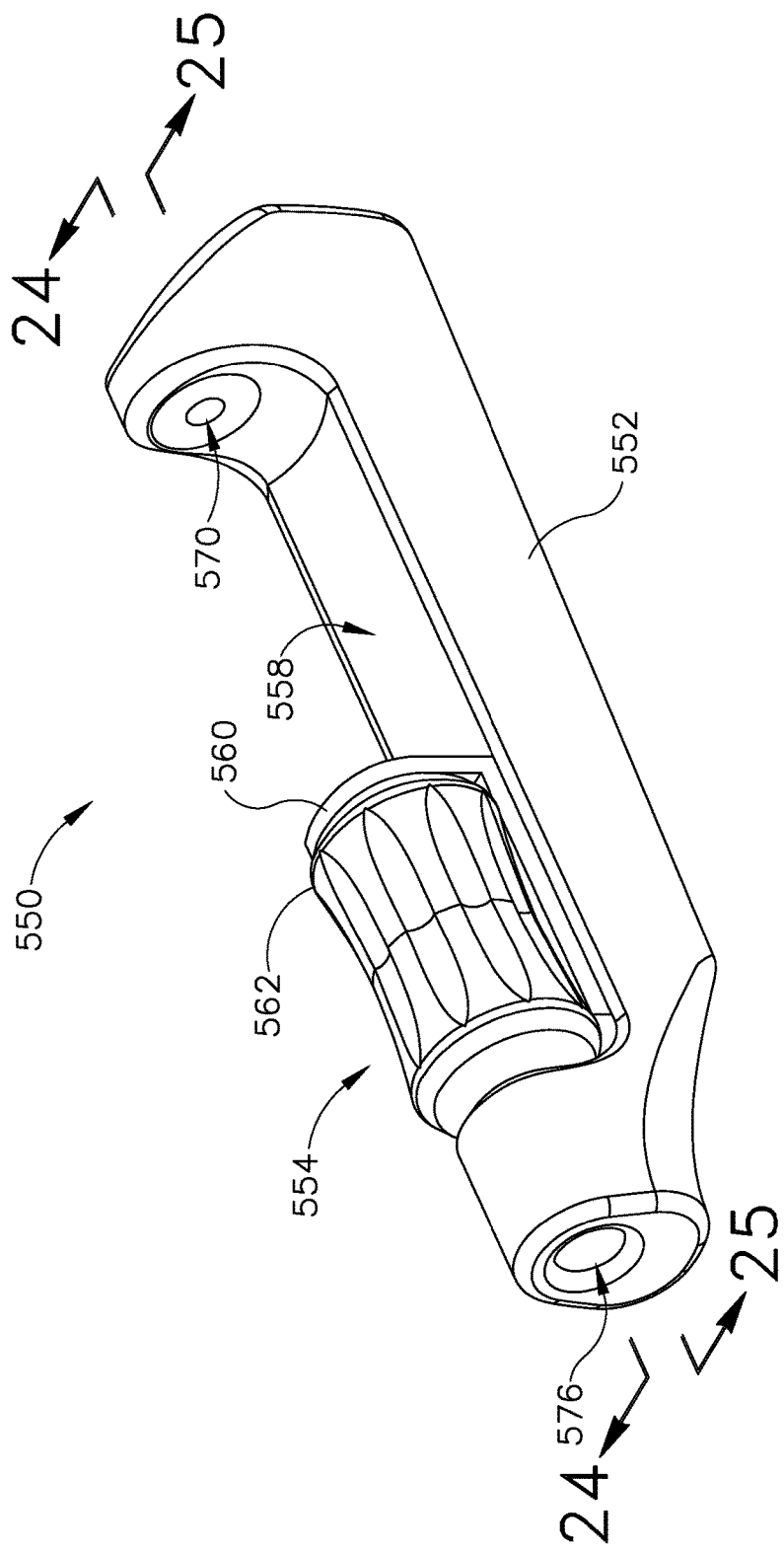
FIG. 22 depicts a perspective view of another exemplary handle suitable for use with the dilation catheter system of FIG. 12.

As shown in FIG. 21B, endoscope (460) may be positioned within through-bore (506) and oriented so as to view the distal end of guide catheter (530). As will be described in more detail below, and as described in U.S. Provisional Pat. App. No. 62/139,941, entitled "Handle with Features to Secure a Catheter Assembly to an Endoscope," filed on even date herewith, the disclosure of which is incorporated by reference herein, body (502) and/or through-bore (506) may comprise a locking feature configured to selectively secure endoscope (460) within through-bore (506). At this point, guide catheter (530) and endoscope (460) may be positioned within the patient adjacent the Eustachian tube (26). Further, to adjust the orientation of guide catheter (530), the user may rotate rotation knob (522) to thereby rotate guide catheter (530) relative to body (502) about the longitudinal axis of guide catheter (530), as shown in FIG. 21C. The user may then translate balloon dilation catheter (540) distally into the Eustachian tube (26) by distally translating actuator (504) as shown in FIG. 21D.

It should be appreciated from the discussion above that handle (500) may be grasped and maneuvered, actuator (504) may be translated, and rotation knob (522) may be rotated, all using a single hand. For instance, while grasping handle (500), the user may use his or her index finger or thumb to translate actuator (504) and/or to rotate rotation knob (522).

B. Exemplary Single-Hand-Use Handle with Rotatable Actuator

Figure 23:
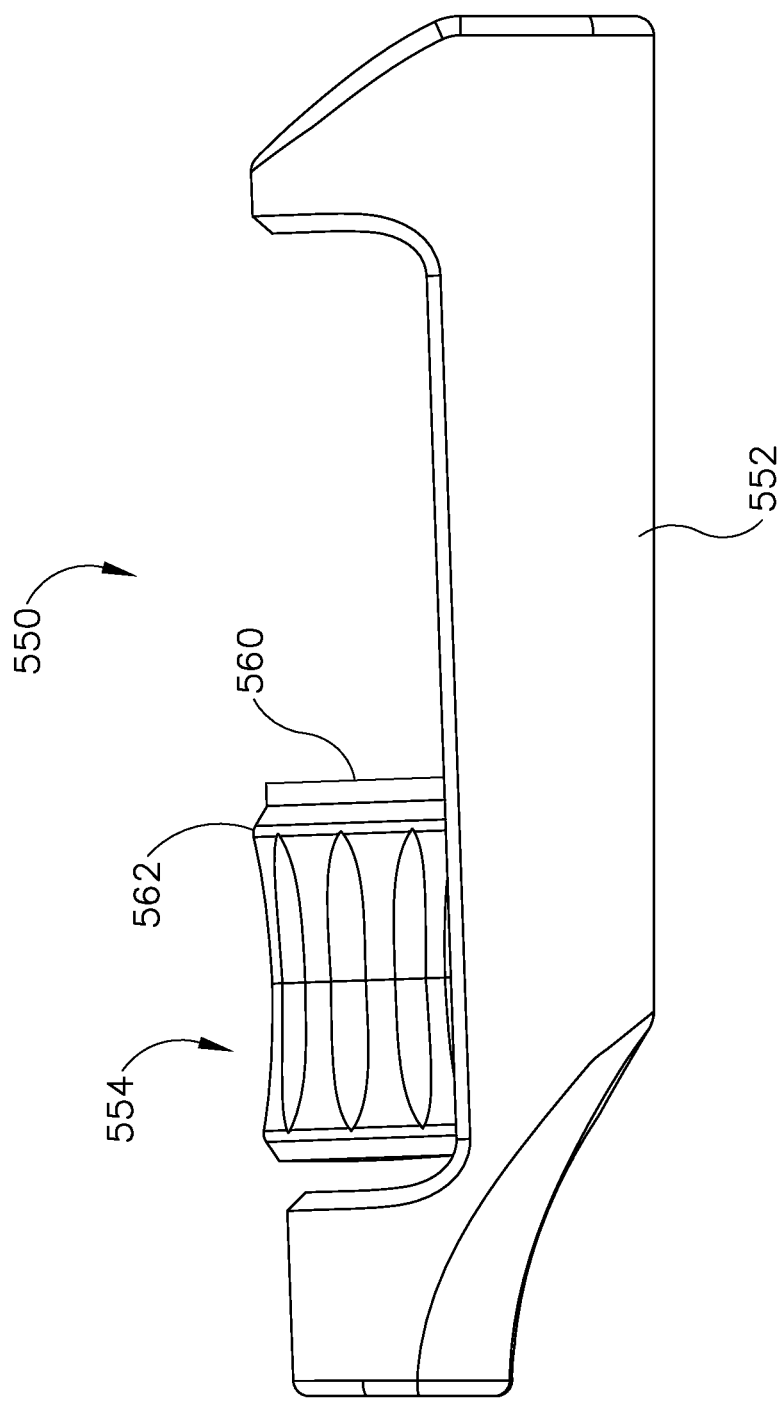
FIG. 23 depicts a side elevational view of the handle of FIG. 22.
Figure 24:
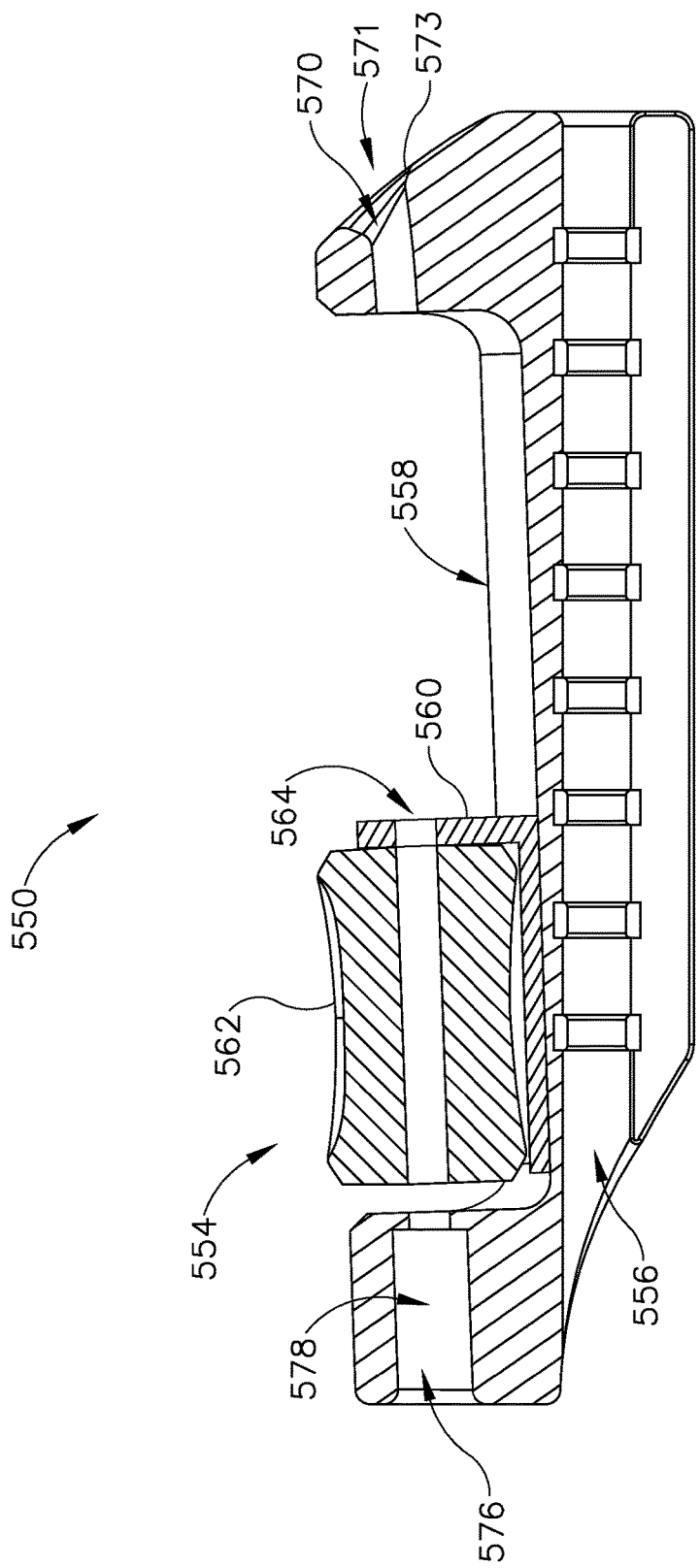
FIG. 24 depicts a cross-sectional side view of the handle of FIG. 22 taken along line 24-24 of FIG. 22.

FIGS. 22-25D show another exemplary single-hand-use handle (550). As will be described in more detail below, handle (550) is operable to combine guide catheter (530), balloon dilation catheter (540), and endoscope (460) in such a manner as to allow a user to maneuver and operate each element using only a single hand. Handle (550) of the present example comprises a body (552) and an actuator (554). As best seen in FIG. 24, body (552) includes a through-bore (556) formed in a lower portion of body (552). Through-bore (556) extends the length of body (552). As will be described in greater detail below, through-bore (556) is operable to receive and selectively retain shaft (464) of endoscope (460). Body (552) further includes a shallow channel (558) formed in an upper portion of body (552). Channel (558) extends partially the length of body (552). As will be described in more detail below, actuator (554) is slidably coupled within channel (558) of body (552) such that actuator (554) may translate within channel (558) between a proximal longitudinal position and a distal longitudinal position along the length of channel (558). As will also be described in more detail below, actuator (554) is coupled with balloon dilation catheter (540) such that translation of actuator (554) within channel (558) causes concurrent translation of balloon dilation catheter (540) relative to body (552).

Actuator (554) comprises a sled (560) and a rotatable member (562). Sled (560) of actuator (554) is positioned within channel (558) so as to slidably couple actuator (554) with body (552). With sled (560) positioned within channel (558), actuator (554) is operable to translate along the length of channel (558) between a proximal longitudinal position and a distal longitudinal position. Rotatable member (562) of actuator (554) is rotatably coupled with sled (560). Rotatable member (562) is configured to rotate relative to sled (560) and body (552). Rotatable member (562) comprises a through-bore (564) that is configured to receive and selectively couple balloon dilation catheter (540) with actuator (554). In this way, rotation of rotatable member (562) and/or translation of actuator (554) within channel (558) is communicated to balloon dilation catheter (540). As best seen in FIGS. 23 and 24, an exterior surface of rotatable member (562) of actuator (554) is saddle-shaped. This saddle-shaped exterior surface allows a user to easily locate and maneuver actuator (554) with only a single finger or thumb while holding handle (550).

Figure 25A:
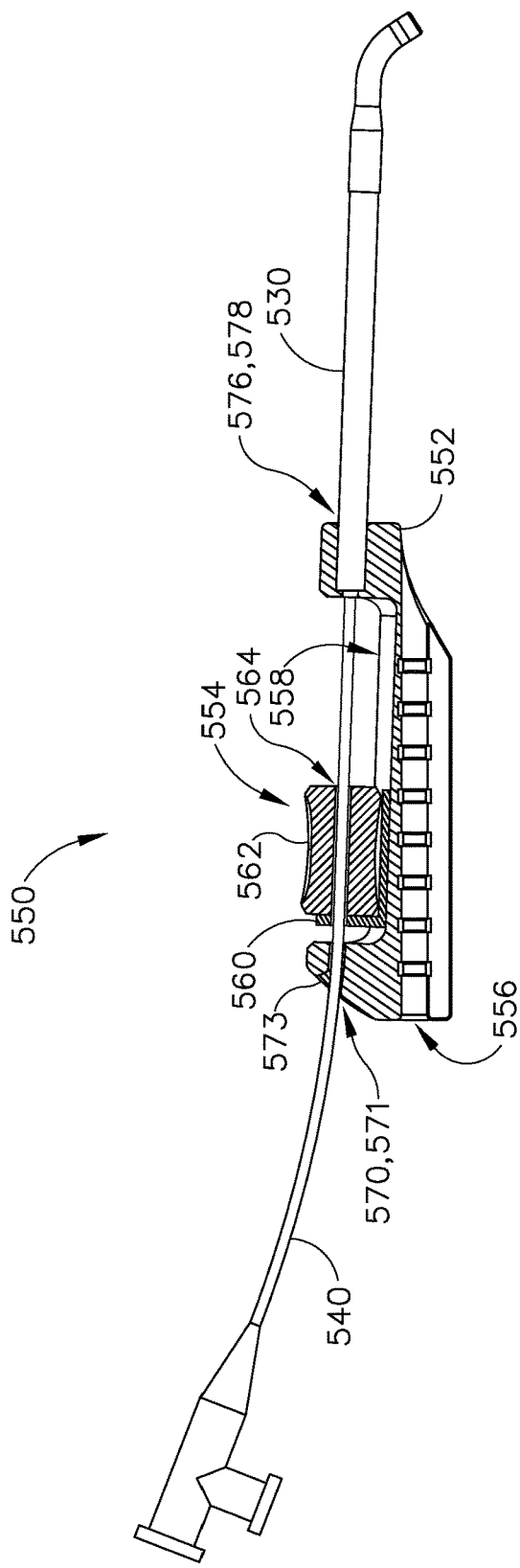
FIG. 25A depicts a cross-sectional side view of the handle of FIG. 22 taken along line 25-25 of FIG. 22, with the guide catheter of FIG. 7A and an exemplary balloon dilation catheter positioned therein.

As best seen in FIG. 24, body (552) comprises a proximal bore (570) extending between a proximal end of body (552) and a proximal end of channel (558). A proximal opening (571) of proximal bore (570) includes an edge fillet (573). Edge fillet (573) varies in size/dimension about the circumference of proximal opening (571). Edge fillet (573) provides for a smooth transition of balloon dilation catheter (540) into and out of proximal bore (570) at varying angles relative to body (552) as balloon dilation catheter (540) translates relative to body (552) as will be described in more detail below. Edge fillet (573) is thus configured to prevent wear and tear to balloon dilation catheter (540) as balloon dilation catheter (540) translates into and out of proximal bore (570). Body (552) further comprises a distal bore (576) extending between a distal end of body (552) and a distal end of channel (558). A distal portion (578) of through-bore (576) is sized to receive and selectively retain guide catheter (530) such that guide catheter (530) may be coupled with the distal portion of body (552) and extend distally therefrom as shown in FIG. 25A.

As also best seen in FIG. 24, proximal bore (570), channel (558), through-bore (564) of actuator (554), and through-bore (576) form a continuous passageway through body (552) that leads directly to guide catheter (530) when coupled with the distal portion of body (552). Balloon dilation catheter (540) is configured to pass through this passageway within body (552) and to further pass though guide catheter (530) when coupled with the distal portion of body (552). As described above, balloon dilation catheter (540) is selectively coupled with rotatable member (562) of actuator (554) such that rotation of rotatable member (562) and/or translation of actuator (554) within channel (558) is communicated to balloon dilation catheter (540). Thus, it should be understood that rotation of rotatable member (562) causes concurrent rotation of balloon dilation catheter (540) within this passageway and that translation of actuator (554) within channel (558) causes concurrent translation of balloon dilation catheter (540) within this passageway. In particular, balloon dilation catheter (540) is configured to rotate and/or translate within proximal bore (570), channel (558), through-bore (564) of actuator (554), through-bore (576), and guide catheter (530) in response to rotation of rotatable member (562) and/or translation of actuator (554) within channel (558) respectively.

Figure 25B:
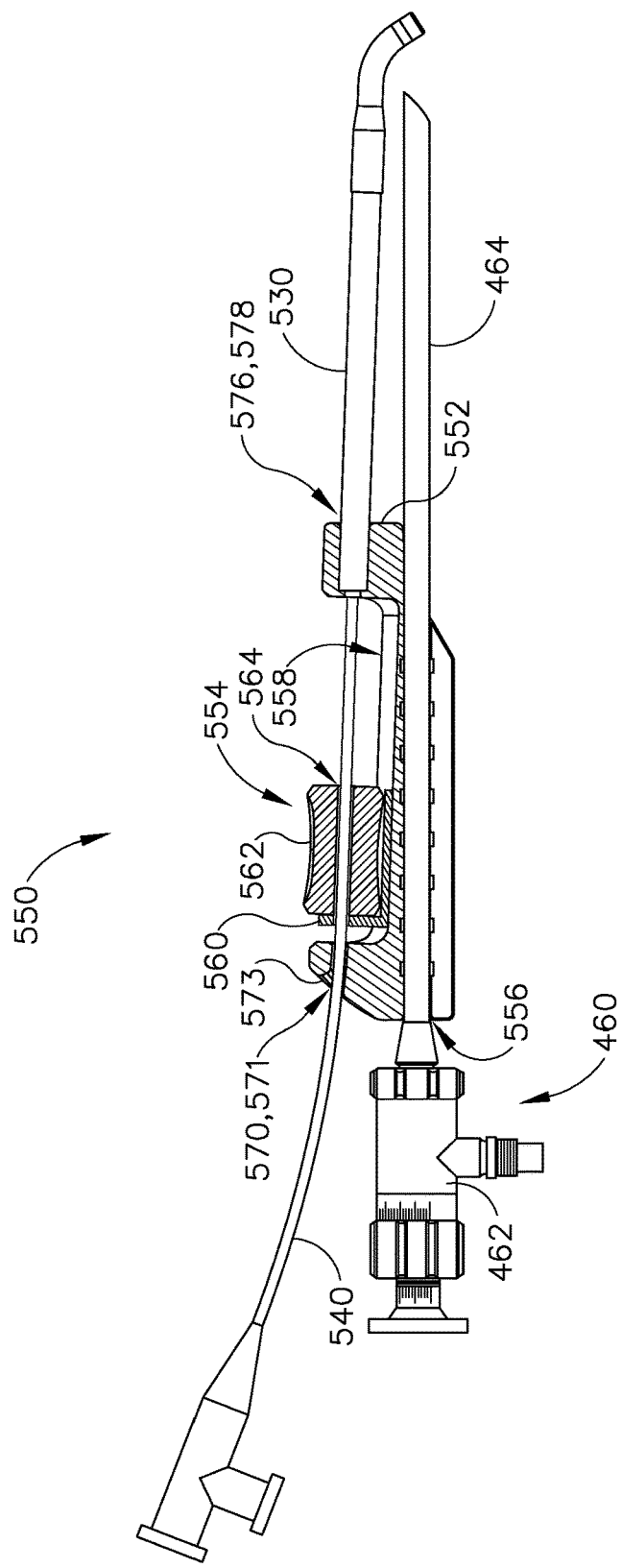
FIG. 25B depicts a cross-sectional side view of the handle of FIG. 22 taken along line 25-25 of FIG. 22, with the endoscope of FIG. 15 positioned therein.
Figure 25C:
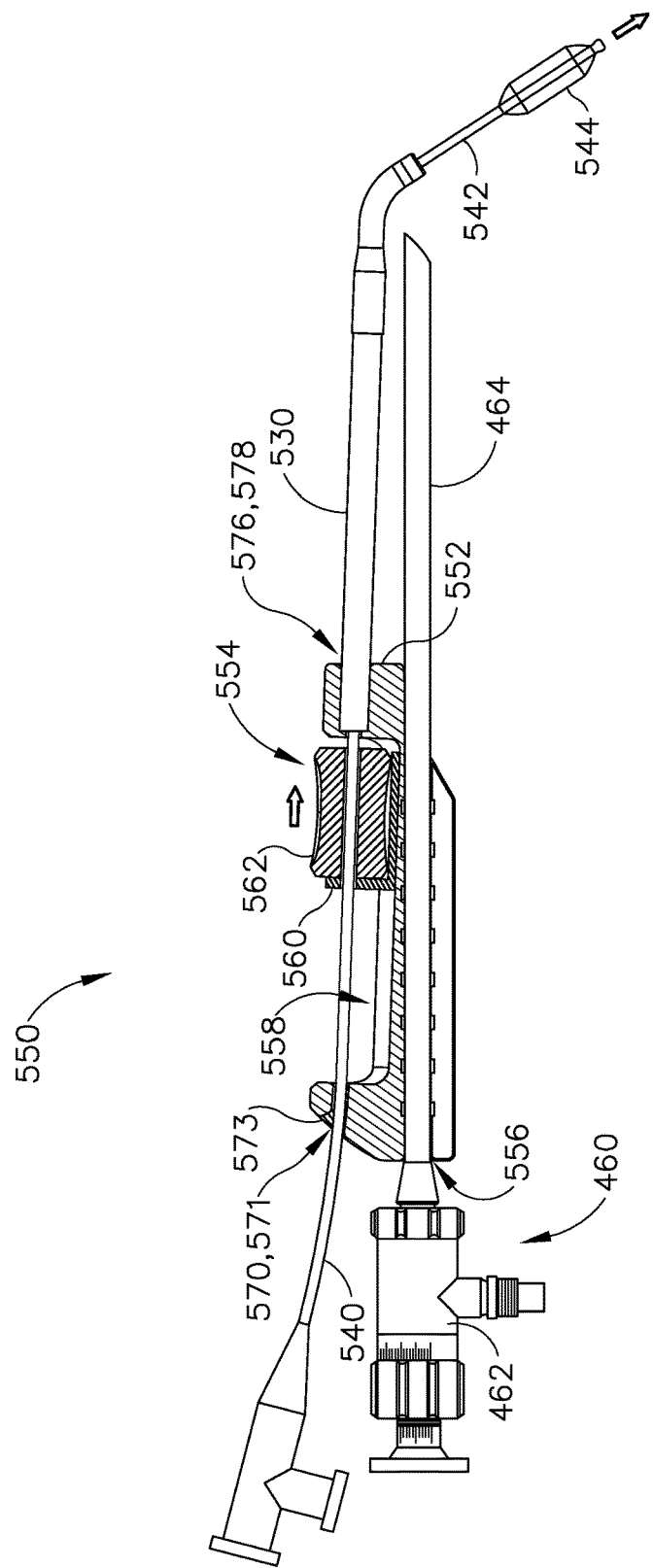
FIG. 25C depicts a cross-sectional side view of the handle of FIG. 22 taken along line 25-25 of FIG. 22, with the balloon dilation catheter of FIG. 25A translated distally by distal translation of an actuator of the handle.
Figure 25D:
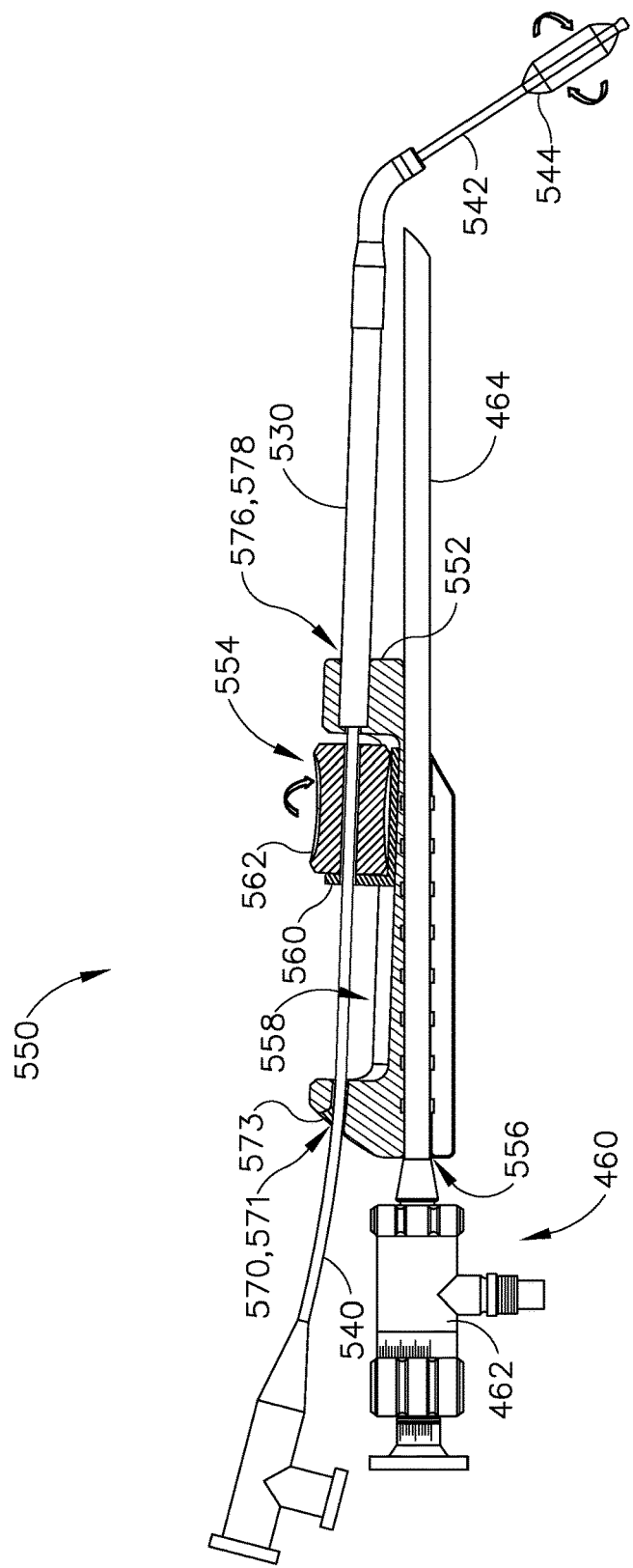
FIG. 25D depicts a cross-sectional side view of the handle of FIG. 22 taken along line 25-25 of FIG. 22, with the balloon dilation catheter of FIG. 25A rotated relative to the handle by rotation of the actuator.
Figure 26:
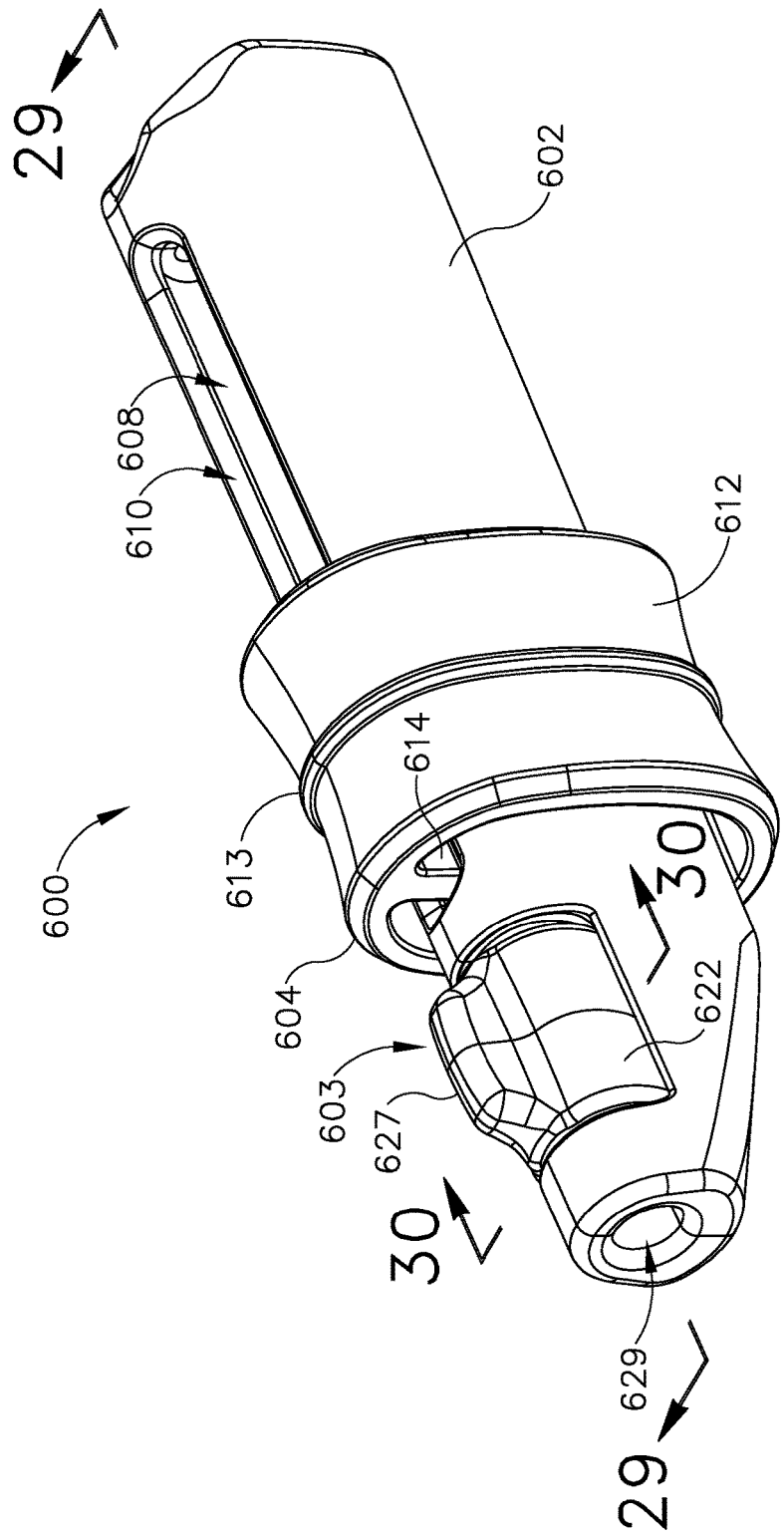
FIG. 26 depicts a perspective view of yet another exemplary handle suitable for use with the dilation catheter system of FIG. 12.

As shown in FIG. 25B, endoscope (460) may be positioned within through-bore (556) and oriented so as to view the distal end of guide catheter (530). As will be described in more detail below, and as described in U.S. Provisional Pat. App. No. 62/139,941, entitled "Handle with Features to Secure a Catheter Assembly to an Endoscope," filed on even date herewith, the disclosure of which is incorporated by reference herein, body (552) and/or through-bore (556) may comprise a locking feature configured to selectively secure endoscope (460) within through-bore (556). At this point, guide catheter (530) and endoscope (460) may be positioned within the patient adjacent the Eustachian tube (26). At this point, the user may translate balloon dilation catheter (540) distally into the Eustachian tube (26) by distally translating actuator (554) as shown in FIG. 25C. Further, to adjust the orientation of balloon dilation catheter (540), the user may rotate balloon dilation catheter (540) by rotating rotatable member (562) as shown in FIG. 25D.

It should be appreciated from the discussion above that handle (550) may be grasped and maneuvered, actuator (554) may be translated, and rotatable member (562) may be rotated, all using a single hand. For instance, while grasping handle (550), the user may use his or her index finger or thumb to translate actuator (554) and/or to rotate rotatable member (562).

C. Exemplary Single-Hand-Use Handle with Rotation Limiting Features

Figure 27:
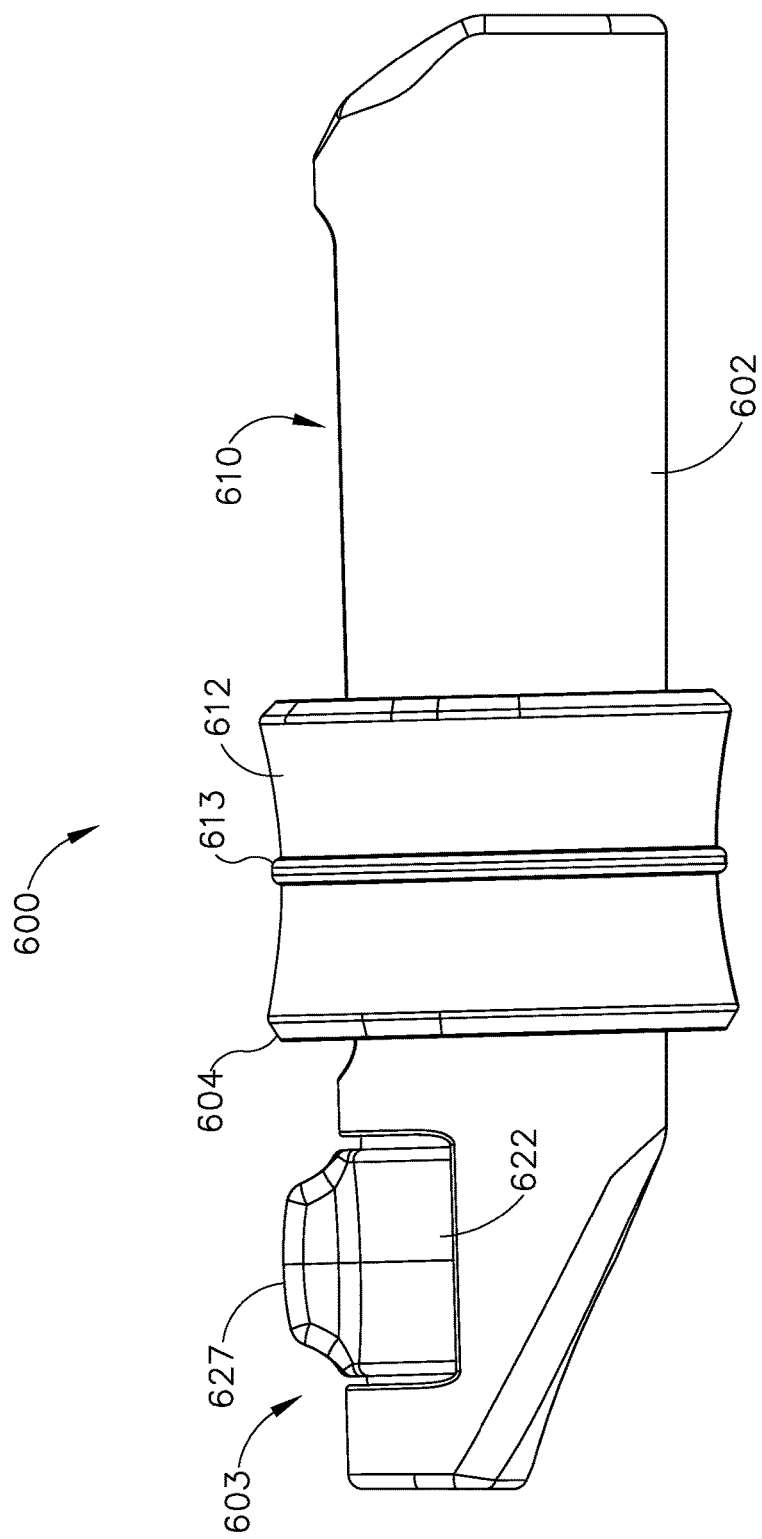
FIG. 27 depicts a side elevational view of the handle of FIG. 26.
Figure 28:
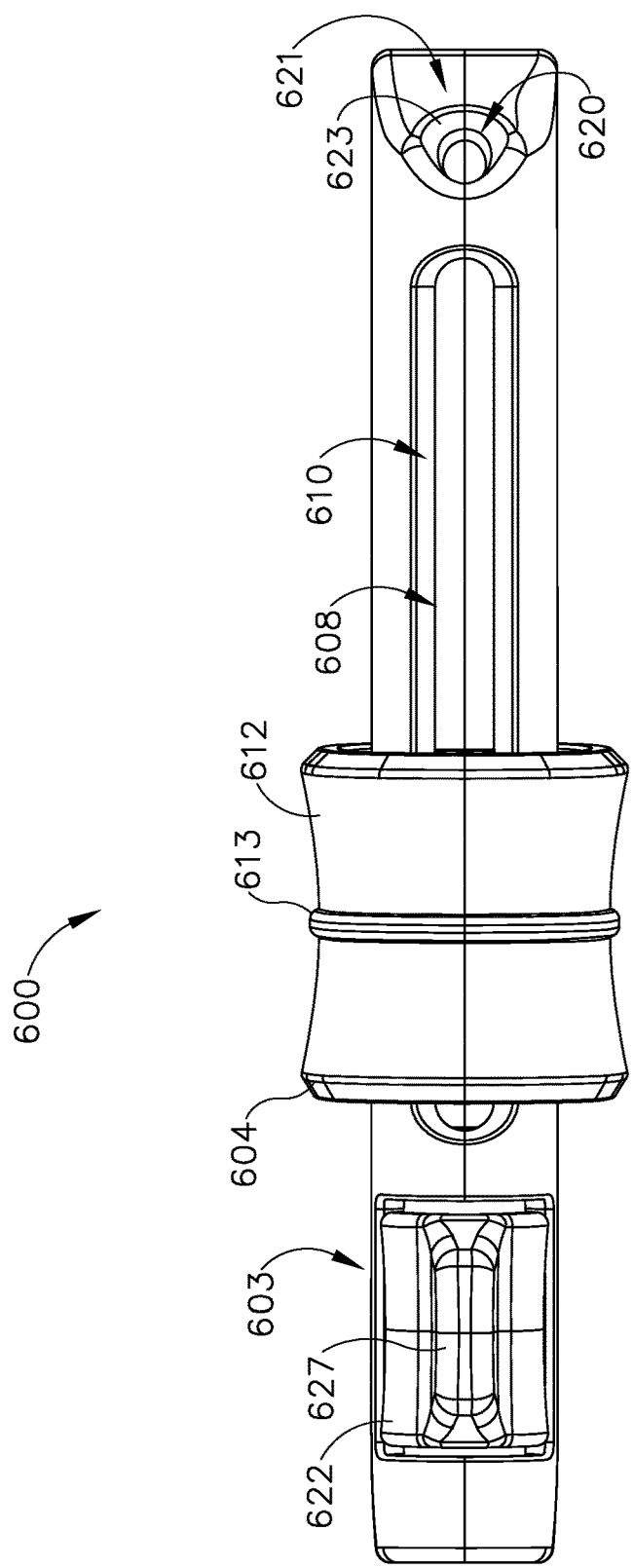
FIG. 28 depicts a top view plan of the handle of FIG. 26.
Figure 29:
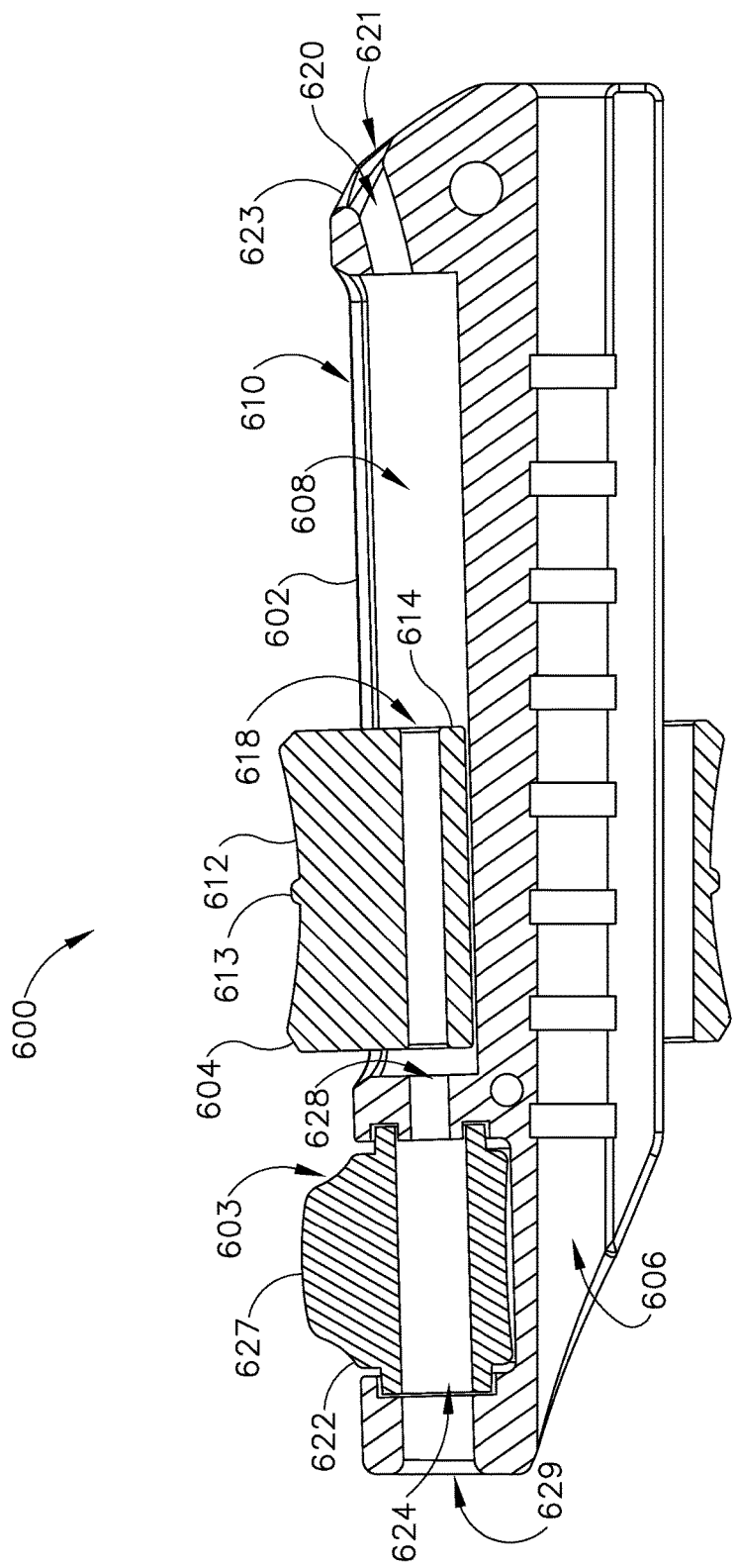
FIG. 29 depicts a cross-sectional side view of the handle of FIG. 26 taken along line 29-29 of FIG. 26.

FIGS. 26-30C show another exemplary single-hand-use handle (600). As will be described in more detail below, handle (600) is operable to combine guide catheter (530), balloon dilation catheter (540), and endoscope (460) in such a manner as to allow a user to maneuver and operate each element using only a single hand. Handle (600) of the present example comprises a body (602) and an actuator (604). As best seen in FIG. 29, body (602) includes a through-bore (606) formed in a lower portion of body (602). Through-bore (606) extends the length of body (602). As will be described in greater detail below, through-bore (606) is operable to receive and selectively retain shaft (464) of endoscope (460). Body (602) further includes a channel (608) formed in an upper portion of body (602). Channel (608) extends partially the length of body (602). An elongate opening (610) formed in a top surface of body (602) extends substantially the length of channel (608) and provides external access to channel (608). As will be described in more detail below, actuator (604) is slidably coupled within channel (608) of body (602) via elongate opening (610) such that actuator (604) may translate within channel (608) between a proximal longitudinal position and a distal longitudinal position along the length of channel (608). As will also be described in more detail below, actuator (604) is coupled with balloon dilation catheter (540) such that translation of actuator (604) within channel (608) causes concurrent translation of balloon dilation catheter (540) relative to body (602).

Actuator (604) comprises a hollow oval-shaped body (612). Actuator (604) further comprises a protrusion (614) that extends inwardly from an interior surface of body (612). Body (602) is positioned within the hollow interior of body (612) of actuator (604) and protrusion (614) of actuator (604) is positioned within channel (608) so as to slidably couple actuator (604) with body (602). With protrusion (614) positioned within channel (608), actuator (604) is operable to translate along the length of channel (608) between a proximal longitudinal position and a distal longitudinal position. Protrusion (614) comprises a through-bore (618) that is configured to receive and selectively couple balloon dilation catheter (540) with actuator (604). In this way, translation of actuator (604) within channel (608) is communicated to balloon dilation catheter (540). As best seen in FIGS. 27-29, an exterior surface of body (612) of actuator (604) is saddle-shaped. In addition, body (612) comprises a projection (613) disposed about the entire exterior circumference of body (612) and extending outwardly therefrom. This saddle-shaped in combination with projection (613) exterior surface allows a user to easily locate and maneuver actuator (604) with only a single finger or thumb while holding handle (600).

Figure 30A:
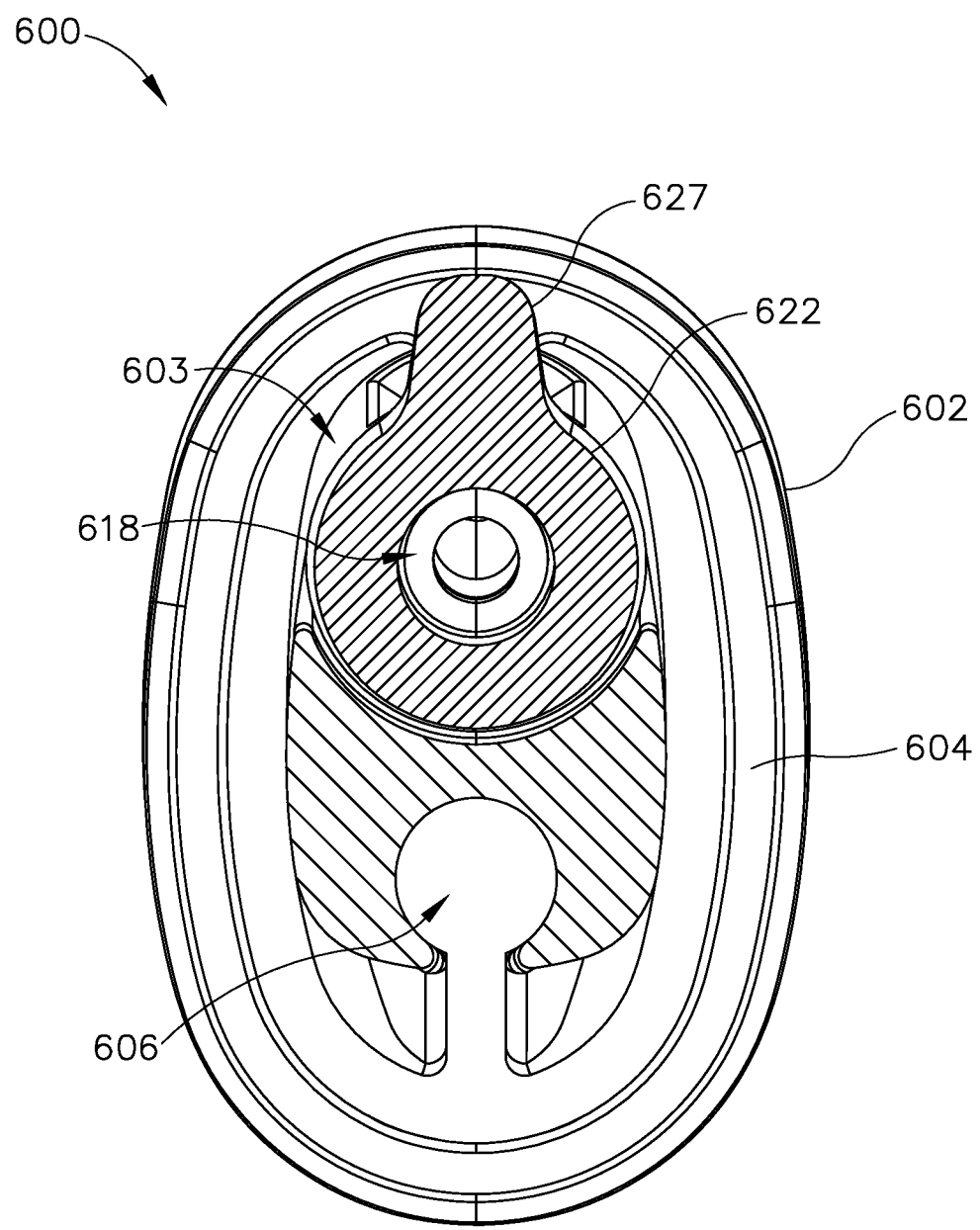
FIG. 30A depicts a cross-sectional front view of the handle of FIG. 26 taken along line 30-30 of FIG. 26, with a rotation knob of the handle in a first rotational portion.
Figure 30B:
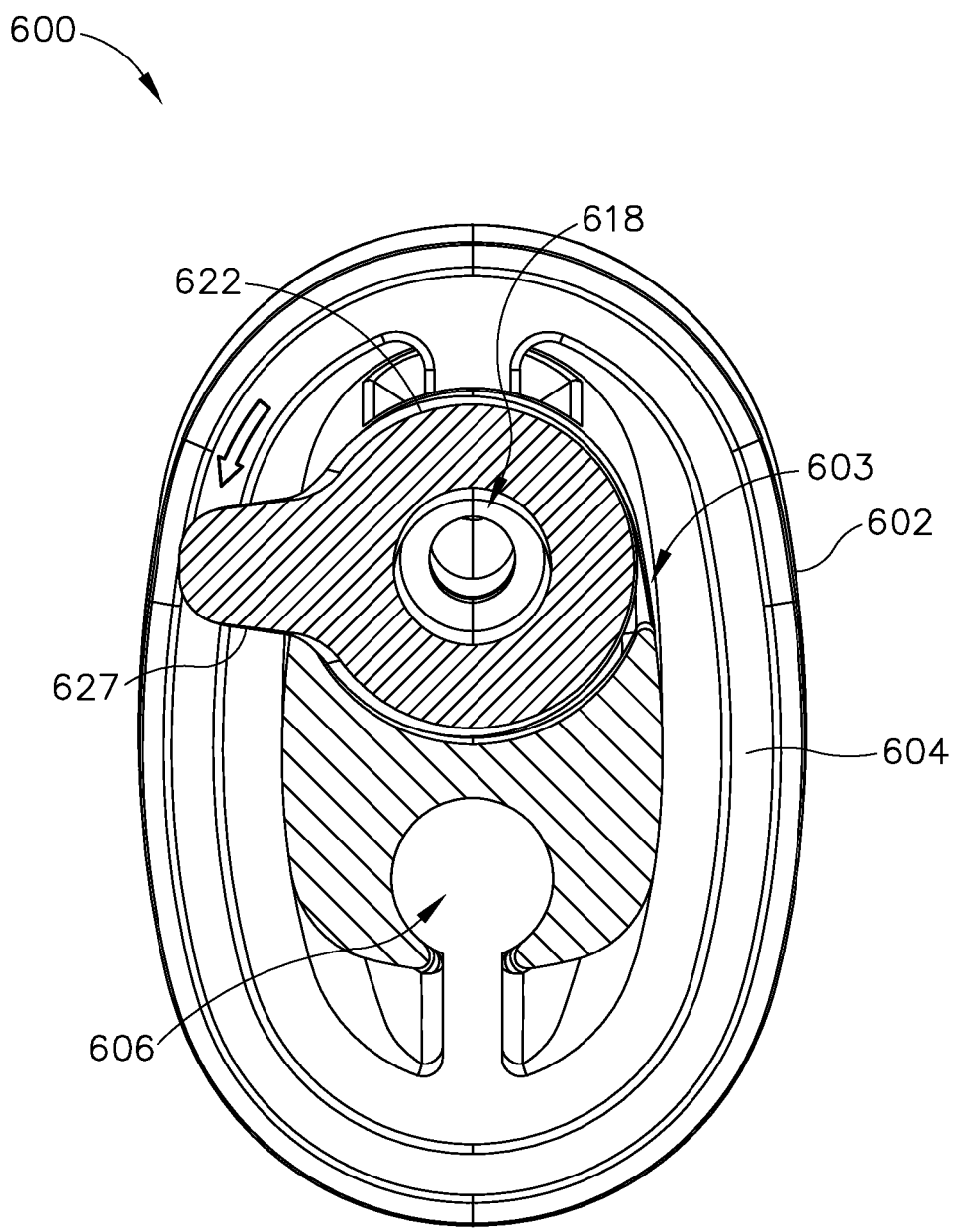
FIG. 30B depicts a cross-sectional front view of the handle of FIG. 26 taken along line 30-30 of FIG. 26, with the rotation knob of FIG. 30A rotated counter-clockwise into a second rotational portion.
Figure 30C:
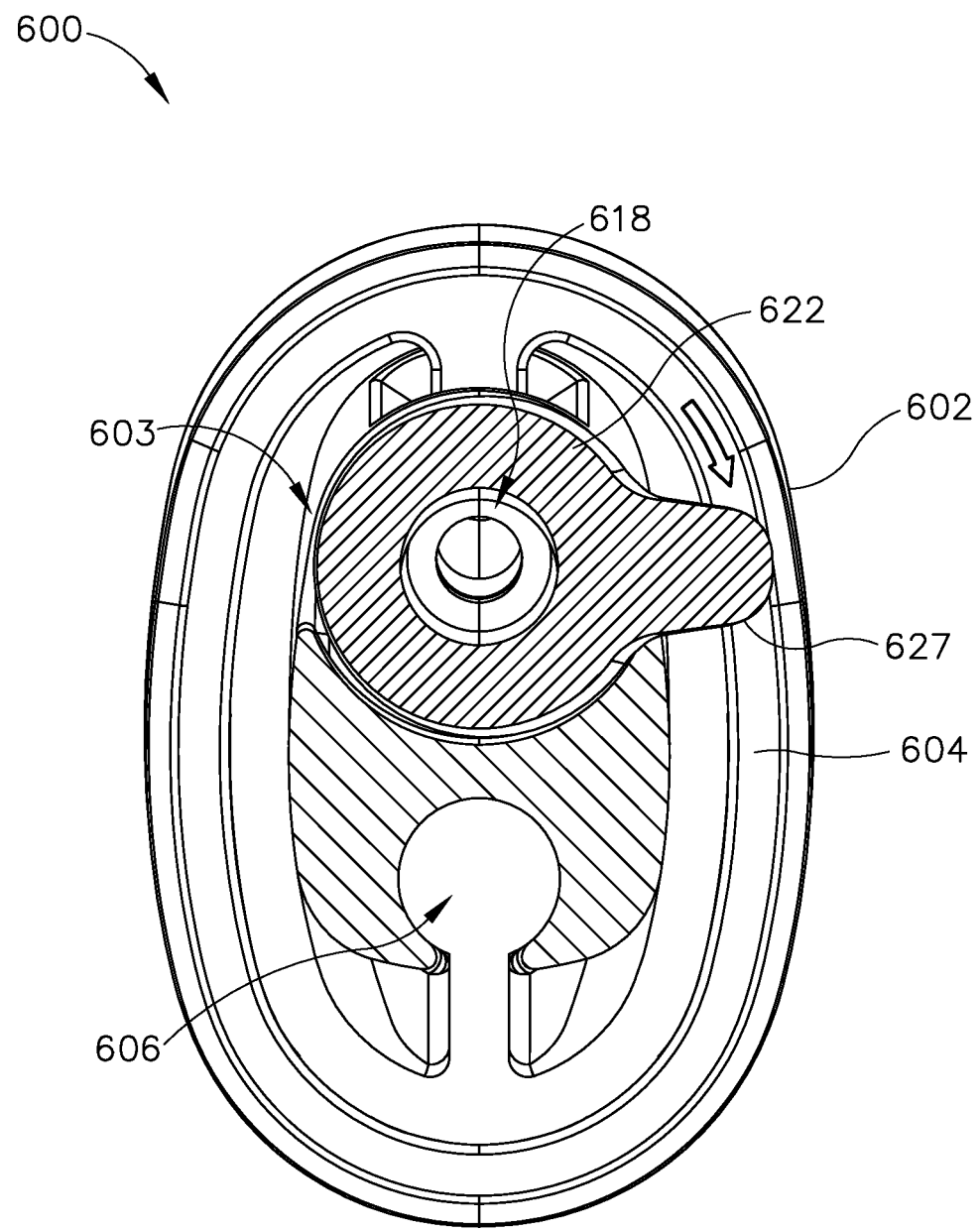
FIG. 30C depicts a cross-sectional front view of the handle of FIG. 26 taken along line 30-30 of FIG. 26, with the rotation knob of FIG. 30A rotated clockwise into a third rotational portion.
Figure 31:
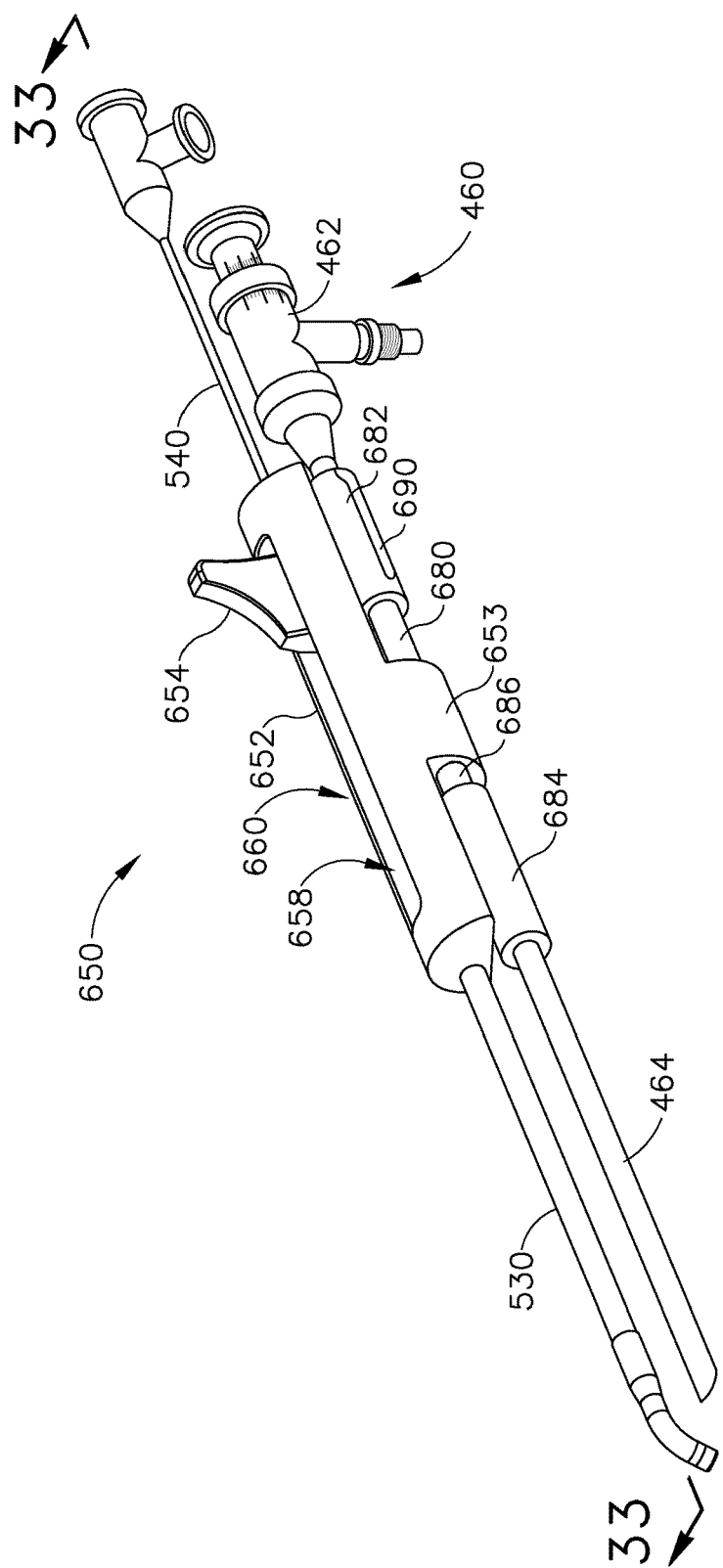
FIG. 31 depicts a perspective view of yet another exemplary handle suitable for use with the dilation catheter system of FIG. 12, with the guide catheter of FIG. 7A, an exemplary balloon dilation catheter, and the endoscope of FIG. 15 positioned therein.

A rotation knob (622) is rotatably coupled within a channel (603) formed in a distal portion of body (602). Rotation knob (622) is configured to rotate relative to body (602). Rotation knob (622) comprises a through-bore (624) sized to receive and selectively retain guide catheter (530) such that guide catheter (530) may be coupled with the distal portion of body (602) and extend distally therefrom; and further such that rotation of rotation knob (622) is communicated to guide catheter (530). Rotation knob (662) comprises a projection (627) configured to limit the amount by which rotation knob (662), and as a result guide catheter (530), may be rotated relative to body (602). As shown in FIGS. 30A-30C, as rotation knob (622) rotates, projection (627) of rotation knob (622) engages top surfaces of channel (603) to thereby limit rotation of rotation knob (622) and as a result guide catheter (530). Channel (603) of the present example encompasses approximately half of rotation knob (622) thereby limiting rotation of rotation knob (622) and guide catheter (530) to approximately 180 degrees. However, channel (603) may alternatively encompass any other appropriate amount of rotation knob (622) to thereby further limit or allow rotation of rotation knob (622) and guide catheter (530).

As best seen in FIG. 29, body (602) comprises a proximal bore (620) extending between a proximal end of body (602) and a proximal end of channel (608). A proximal opening (621) of proximal bore (620) includes an edge fillet (623). Edge fillet (623) varies in size/dimension about the circumference of proximal opening (621). Edge fillet (623) provides for a smooth transition of balloon dilation catheter (540) into and out of proximal bore (620) at varying angles relative to body (602) as balloon dilation catheter (540) translates relative to body (602) as will be described in more detail below. Edge fillet (623) is thus configured to prevent wear and tear to balloon dilation catheter (540) as balloon dilation catheter (540) translates into and out of proximal bore (620). Body (602) further comprises a distal bore (628) extending between a proximal end of channel (603) and a distal end of channel (608). Body (602) further comprises a distal bore (629) extending between a distal end of body (602) and a distal end of channel (603). Bores (628, 629) of body (602) are coaxially aligned with through-bore (624) of rotation knob (622).

As also best seen in FIG. 29, proximal bore (620), channel (608), through-bore (618) of actuator (604), bores (628, 629), and through-bore (624) of rotation knob (622) form a continuous passageway through body (602) that leads directly to guide catheter (530) when coupled with rotation knob (622). Balloon dilation catheter (540) is configured to pass through this passageway within body (602) and to further pass though guide catheter (530) when coupled with rotation knob (622). As described above, balloon dilation catheter (540) is selectively coupled with actuator (604) such that translation of actuator (604) within channel (608) is communicated to balloon dilation catheter (540). Thus, it should be understood that translation of actuator (604) within channel (608) causes concurrent translation of balloon dilation catheter (540) within this passageway. In particular, balloon dilation catheter (540) is configured to translate within proximal bore (620), channel (608), through-bore (618) of actuator (604), bores (628, 529), through-bore (624) of rotation knob (622), and guide catheter (530) in response to translation of actuator (604) within channel (608).

As with handles (500, 550) described above, endoscope (460) may be positioned within through-bore (606) and oriented so as to view the distal end of guide catheter (530).

As will be described in more detail below, and as described in U.S. Provisional Pat. App. No. 62/139,941, entitled "Handle with Features to Secure a Catheter Assembly to an Endoscope," filed on even date herewith, the disclosure of which is incorporated by reference herein, body (602) and/or through-bore (606) may comprise a locking feature configured to selectively secure endoscope (460) within through-bore (606). At this point, guide catheter (530) and endoscope (460) may be positioned within the patient adjacent the Eustachian tube (26). Further, to adjust the orientation of guide catheter (530), the user may rotate rotation knob (622) to thereby rotate guide catheter (530) relative to body (602) about the longitudinal axis of guide catheter (530). The user may then translate balloon dilation catheter (540) distally into the Eustachian tube (26) by distally translating actuator (604).

It should be appreciated from the discussion above that handle (600) may be grasped and maneuvered, actuator (604) may be translated, and rotation knob (622) may be rotated, all using a single hand. For instance, while grasping handle (600), the user may use his or her index finger or thumb to translate actuator (604) and/or to rotate rotation knob (622).

Figure 32:
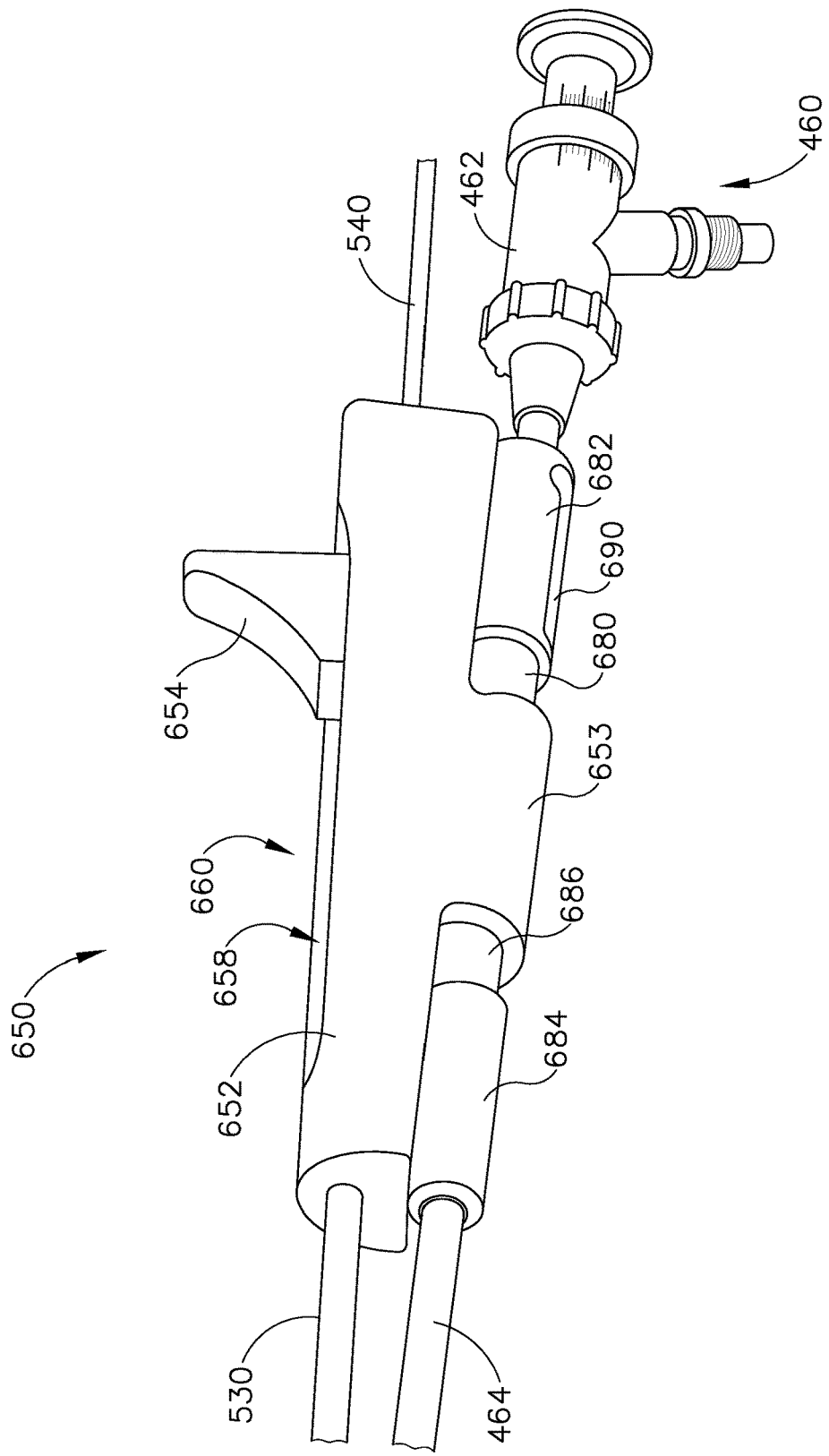
FIG. 32 depicts another perspective view of the handle of FIG. 31, with the guide catheter of FIG. 7A, the balloon dilation catheter of FIG. 31, and the endoscope of FIG. 15 positioned therein.

D. Exemplary Single-Hand-Use Handle with Rotatable Endoscope Housing and Locking Lever FIGS. 31-33F show another exemplary single-hand-use handle (650). As will be described in more detail below, handle (650) is operable to combine guide catheter (530), balloon dilation catheter (540), and endoscope (460) in such a manner as to allow a user to maneuver and operate each element using only a single hand. Handle (650) of the present example comprises a body (652), an actuator (654), and an endoscope housing (680). Endoscope housing (680) comprises a proximal cylindrical portion (682), a distal cylindrical portion (684), and an intermediate cylindrical portion (686) positioned between proximal cylindrical portion (682) and a distal cylindrical portion (684). A diameter of intermediate cylindrical portion (686) is less than a diameter of proximal cylindrical portion (682) and a diameter of distal cylindrical portion (684). As best seen in FIG. 32, body (652) includes a cylindrical knuckle (653) extending from a bottom surface of body (652). Intermediate cylindrical portion (686) is rotatably and slidably disposed within a through-bore (655) of cylindrical knuckle (653) such that endoscope housing (680) is configured to translate and/or rotate relative to body (652). Endoscope housing (680) comprises a through-bore (688) extending the length of endoscope housing (680). As will be described in more detail below, through-bore (688) is operable to receive and selectively retain shaft (464) of endoscope (460) such that translation and/or rotation of endoscope housing (680) is communicated to endoscope (460).

Figure 33A:
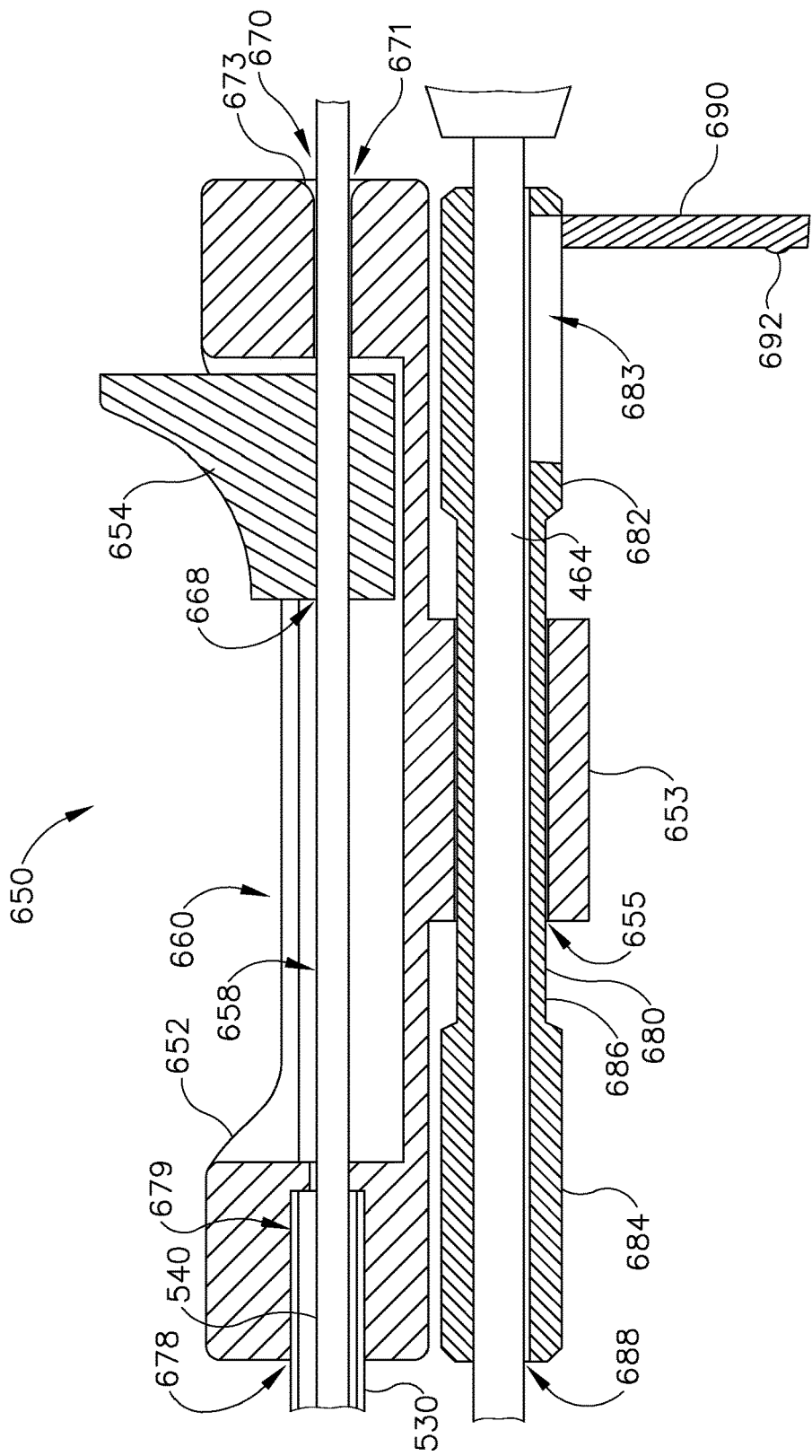
FIG. 33A depicts a cross-sectional side view of the handle of FIG. 31 taken along line 33-33 of FIG. 31, with the guide catheter of FIG. 7A, the balloon dilation catheter of FIG. 31, and the endoscope of FIG. 15 positioned therein, and with a locking member of the handle in a first, unlocked, rotational position.
Figure 33B:
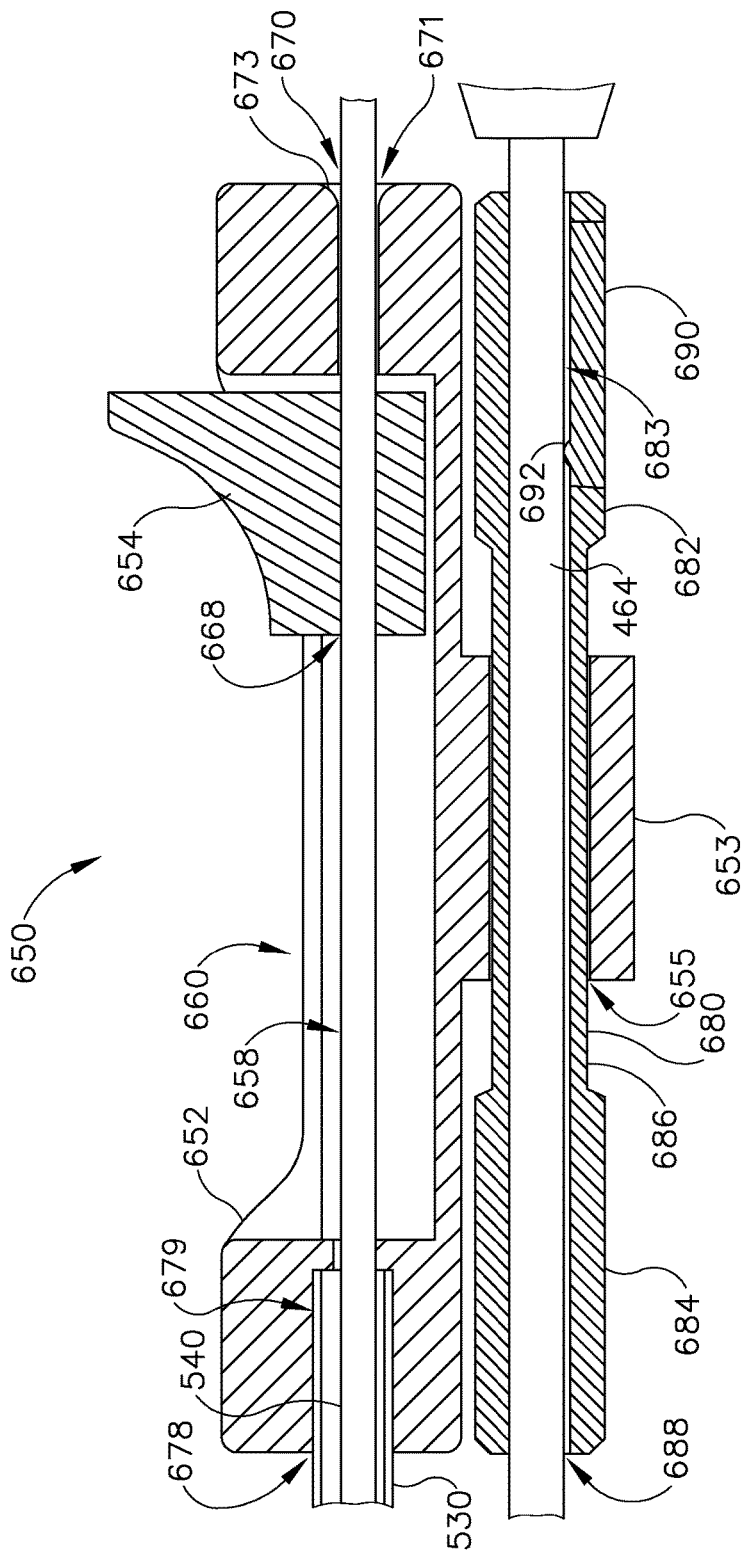
FIG. 33B depicts a cross-sectional side view of the handle of FIG. 31 taken along line 33-33 of FIG. 31, with the guide catheter of FIG. 7A, the balloon dilation catheter of FIG. 31, and the endoscope of FIG. 15 positioned therein, and with the locking member of FIG. 33A rotated into a second, locked, rotational position.

Proximal cylindrical portion (682) of endoscope housing (680) includes an opening (683) formed in a sidewall of proximal cylindrical portion (682). Opening (683) provides external access to through-bore (688). Proximal cylindrical portion (682) of comprises a lever (690) pivotably coupled with proximal cylindrical portion (682) and configured to selectively rotate between a first, unlocked, rotational position (FIG. 33A) and a second, locked, rotational position (FIG. 33B) so as to selectively lock and unlock endoscope (460) within endoscope housing (680). As shown in FIG. 33B, with lever (690) in the locked position, a lateral member (692) of lever (690) is configured to bear against an exterior surface of shaft (464) of endoscope (460) via opening (683) so as to lock endoscope (460) within through-bore (688). It should be appreciated that lever (690) may be rotated from the second, locked, rotational position into the first, unlocked, rotational position in order to enable reorientation or maneuvering of endoscope (460). Various suitable features that may be provided to selectively hold lever (690) in the locked position will be apparent to those of ordinary skill in the art in view of the teachings herein.

Figure 33C:
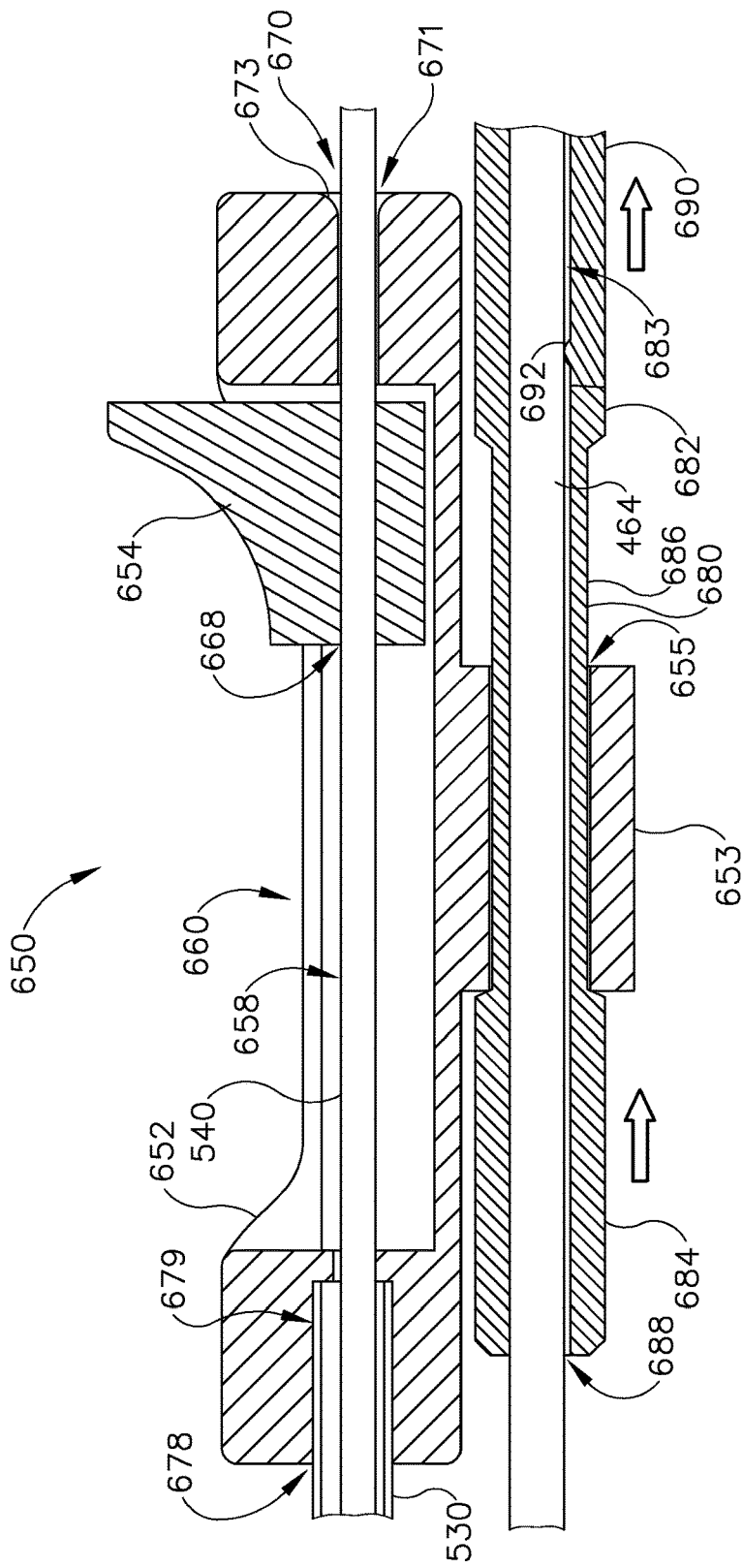
FIG. 33C depicts a cross-sectional side view of the handle of FIG. 31 taken along line 33-33 of FIG. 31, with the guide catheter of FIG. 7A, the balloon dilation catheter of FIG. 31, and the endoscope of FIG. 15 positioned therein, and with the endoscope translated proximally by proximal translation of a endoscope housing of the handle.
Figure 33D:
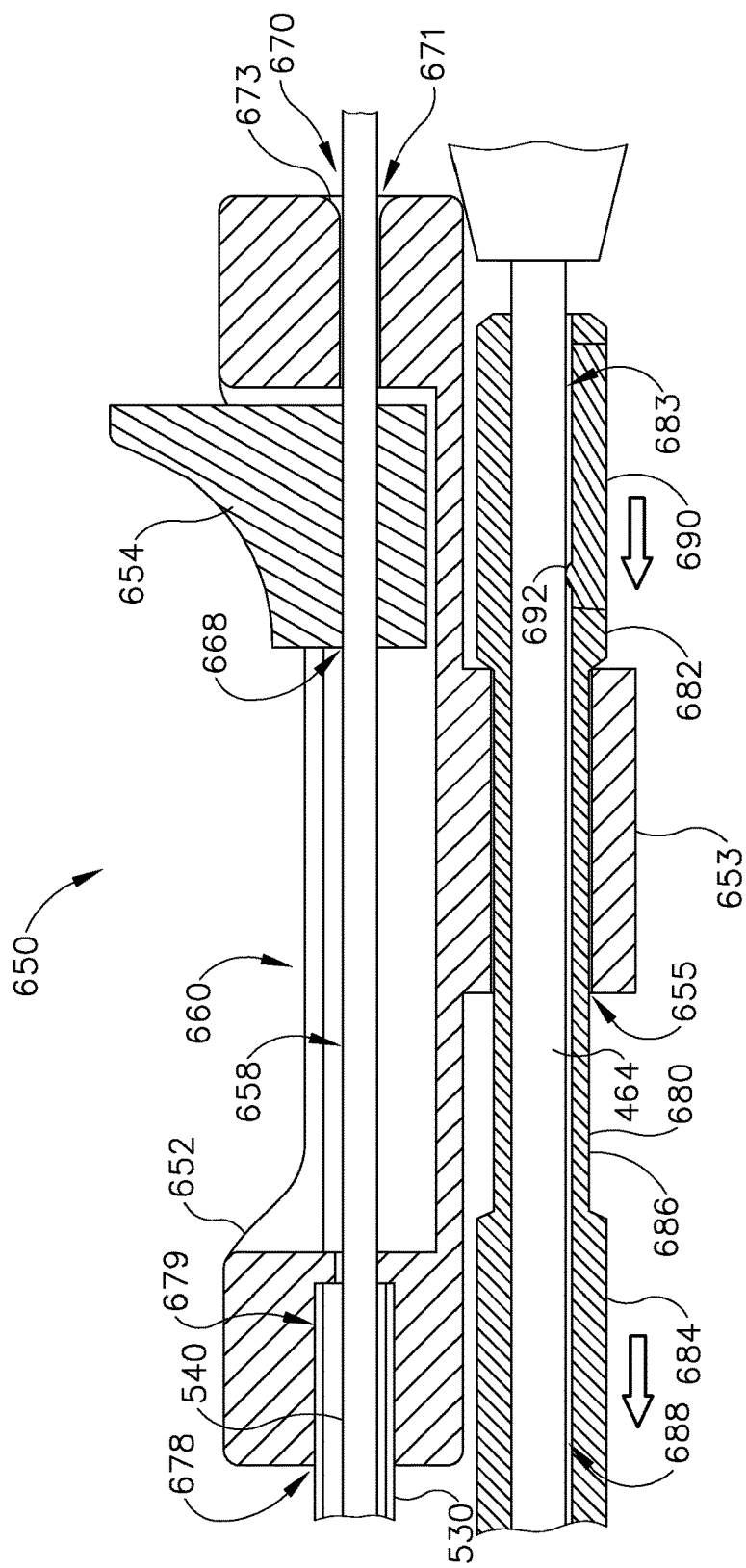
FIG. 33D depicts a cross-sectional side view of the handle of FIG. 31 taken along line 33-33 of FIG. 31, with the guide catheter of FIG. 7A, the balloon dilation catheter of FIG. 31, and the endoscope of FIG. 15 positioned therein, and with the endoscope translated distally by distal translation of the endoscope housing of FIG. 33C.
Figure 33E:
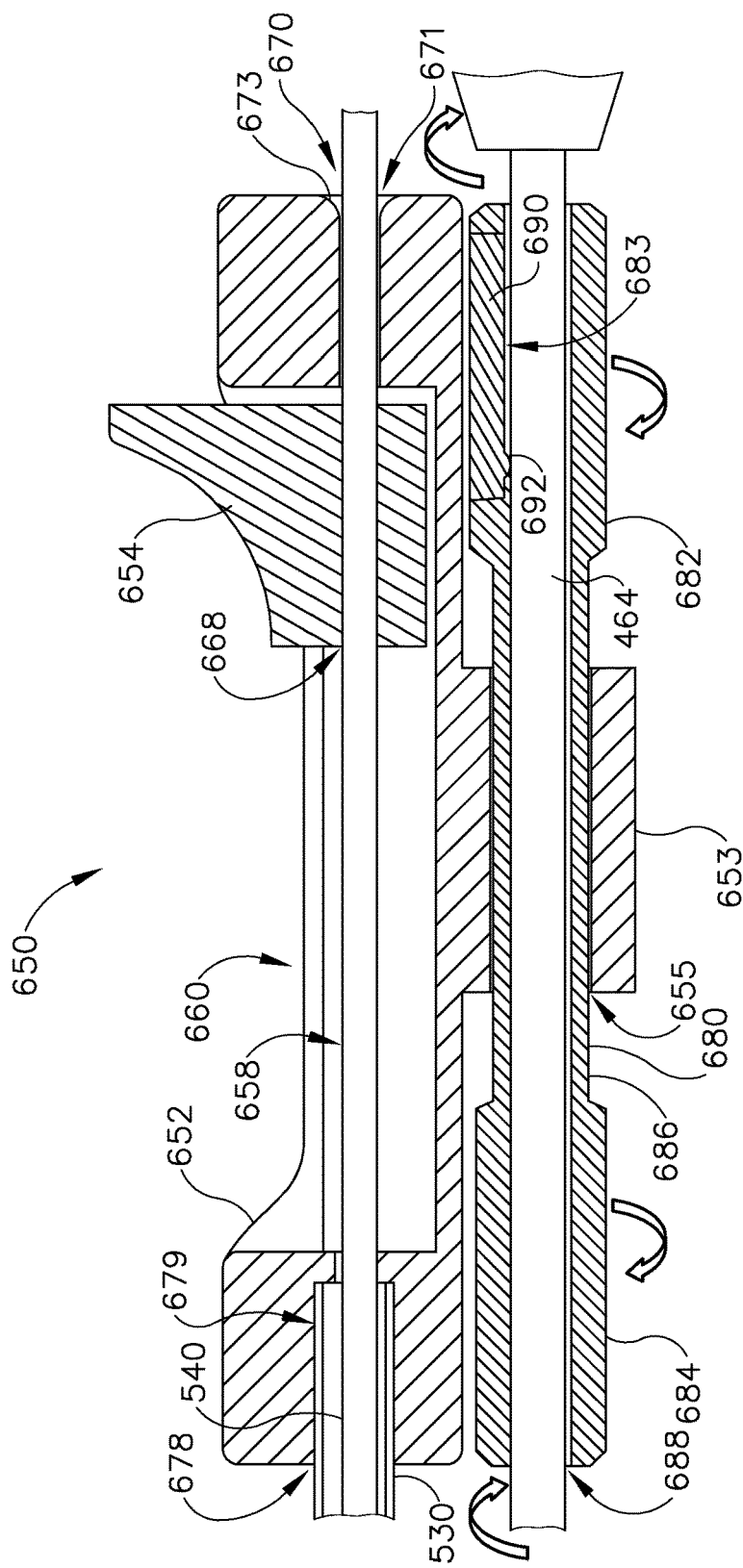
FIG. 33E depicts a cross-sectional side view of the handle of FIG. 31 taken along line 33-33 of FIG. 31, with the guide catheter of FIG. 7A, the balloon dilation catheter of FIG. 31, and the endoscope of FIG. 15 positioned therein, and with the endoscope rotated relative to the handle by rotation of the endoscope housing of FIG. 33C.

With endoscope (460) locked within endoscope housing (680), to adjust the orientation of endoscope (460), a user may translate endoscope housing (680), and thus endoscope (460), proximally (FIG. 33C) and/or distally (FIG. 33D) relative to body (652). As shown in FIG. 33C, a diameter of distal cylindrical portion (684) is greater than a diameter of through-bore (655) of cylindrical knuckle (653) such that distal cylindrical portion (684) limits proximal translation of endoscope housing (680). As shown in FIG. 33D, a diameter of proximal cylindrical portion (382) is greater than the diameter of through-bore (655) of cylindrical knuckle (653) such that proximal cylindrical portion (682) limits distal translation of endoscope housing (680). Additionally or alternatively, to adjust the orientation of endoscope (460), a user may rotate endoscope housing (680), and thus endoscope (460), within cylindrical knuckle (653) relative to body (652) as shown in FIG. 33E. In addition, any alternative locking feature described herein and as described in U.S. Provisional Pat. App. No. 62/139,941, entitled "Handle with Features to Secure a Catheter Assembly to an Endoscope," filed on even date herewith, the disclosure of which is incorporated by reference herein, may be used in addition to or in lieu of lever (690).

Body (652) further includes a channel (658) formed in an upper portion of body (652). Channel (658) extends partially the length of body (652). An elongate opening (660) formed in a top surface of body (652) extends substantially the length of channel (658) and provides external access to channel (658). Actuator (654) is slidably disposed within channel (658) via elongate opening (660) such that actuator (654) is operable to translate along the length of channel (658) between a proximal longitudinal position and a distal longitudinal position along the length of channel (658). Actuator (654) comprises a through-bore (668) that is configured to receive and selectively couple balloon dilation catheter (540) with actuator (654). In this way, translation of actuator (654) within channel (658) is communicated to balloon dilation catheter (540).

As best seen in FIGS. 33A-33F, body (652) comprises a proximal bore (670) extending between a proximal end of body (652) and a proximal end of channel (658). A proximal opening (671) of proximal bore (670) includes an edge fillet (673) about the circumference of proximal opening (671). Edge fillet (673) provides for a smooth transition of balloon dilation catheter (540) into and out of proximal bore (670) at varying angles relative to body (652) as balloon dilation catheter (540) translates relative to body (652) as will be described in more detail below. Edge fillet (673) is thus configured to prevent wear and tear to balloon dilation catheter (540) as balloon dilation catheter (540) translates into and out of proximal bore (670). Body (652) further comprises a distal bore (678) extending between a distal end of body (652) and a distal end of channel (658). A distal portion (679) of distal bore (678) is sized to receive and selectively retain guide catheter (530) such that guide catheter (530) may be coupled with the distal portion of body (652) and extend distally therefrom.

Figure 33F:
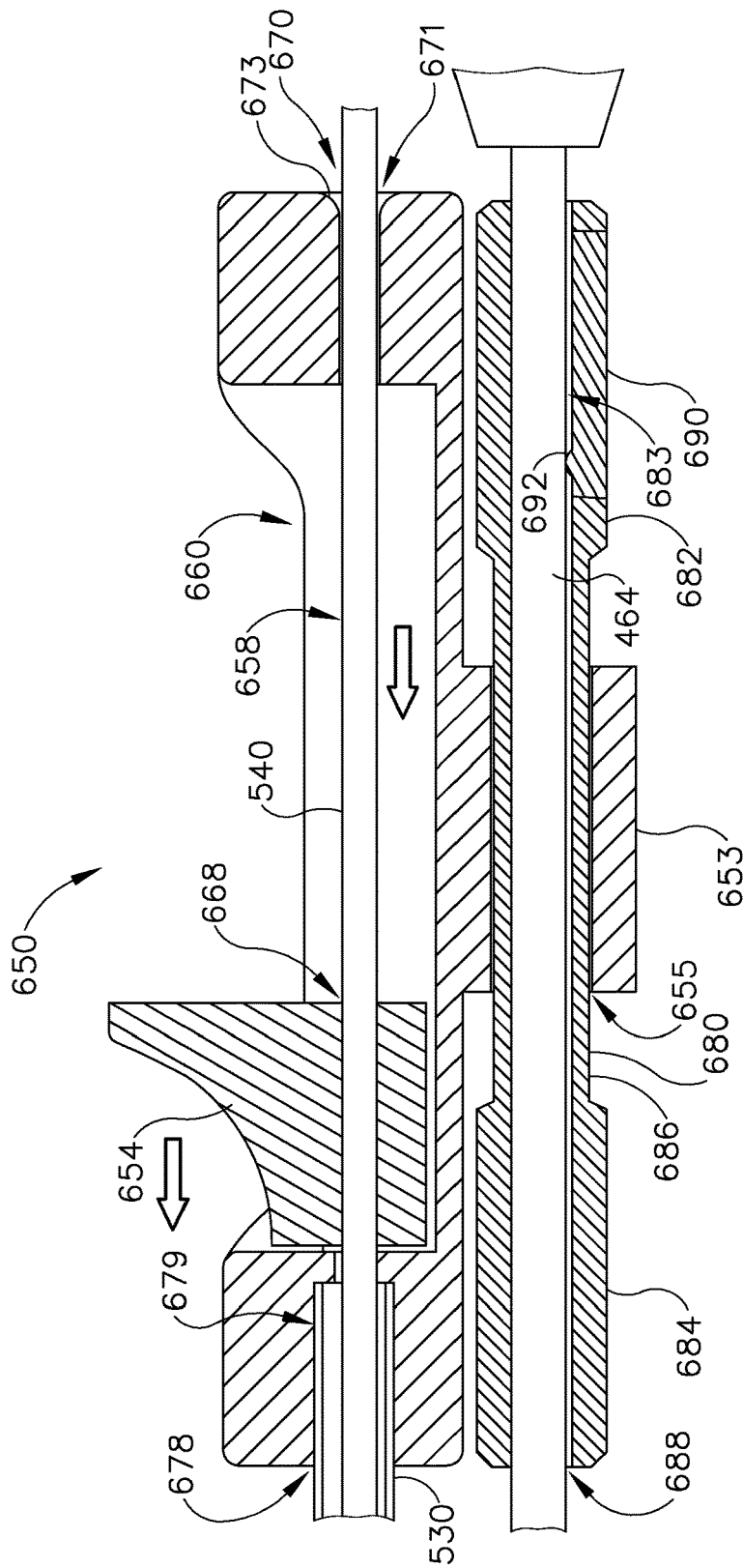
FIG. 33F depicts a cross-sectional side view of the handle of FIG. 31 taken along line 33-33 of FIG. 31, with the guide catheter of FIG. 7A, the balloon dilation catheter of FIG. 31, and the endoscope of FIG. 15 positioned therein, and with the balloon dilation catheter translated distally by distal translation of an actuator of the handle.
Figure 34:
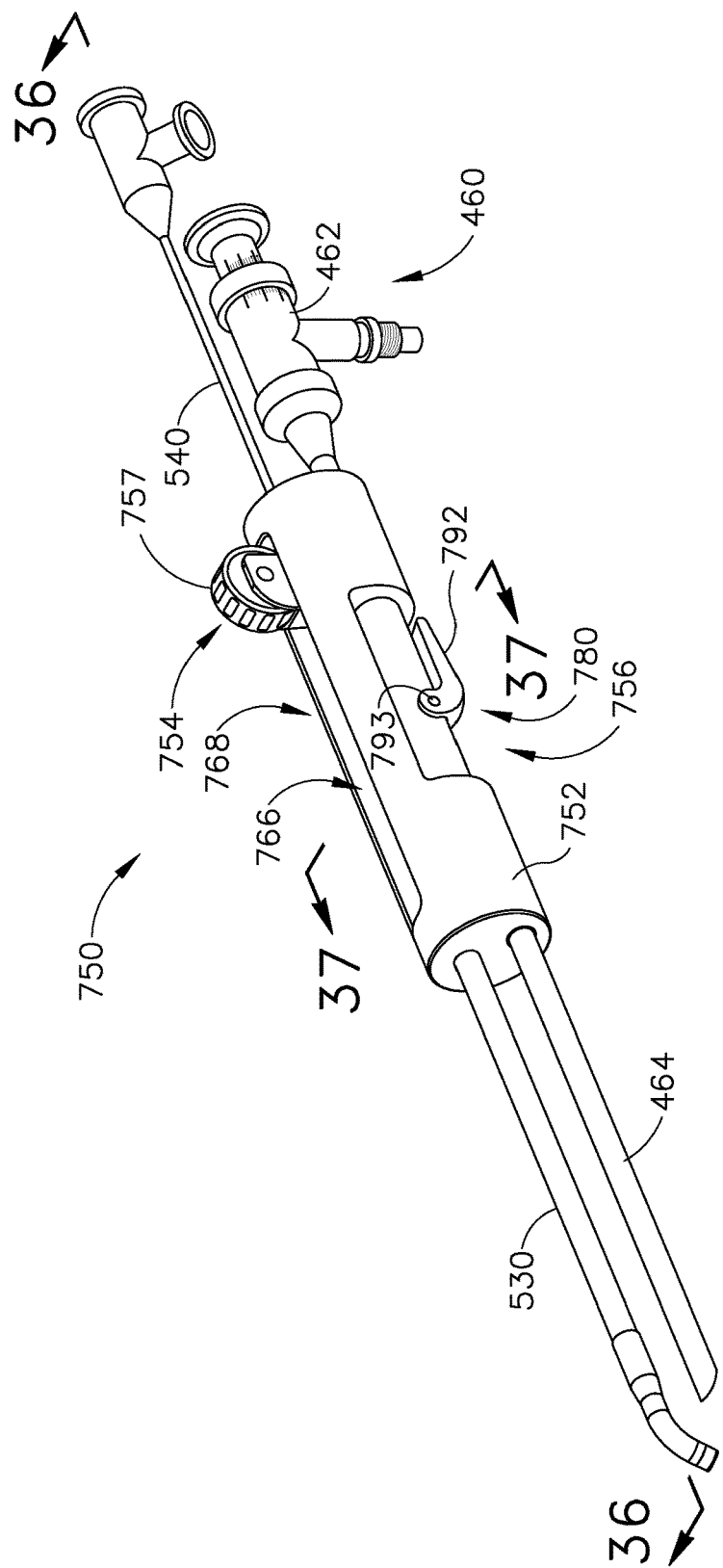
FIG. 34 depicts a perspective view of yet another exemplary handle suitable for use with the dilation catheter system of FIG. 12, with the guide catheter of FIG. 7A, an exemplary balloon dilation catheter, and the endoscope of FIG. 15 positioned therein.
Figure 35:
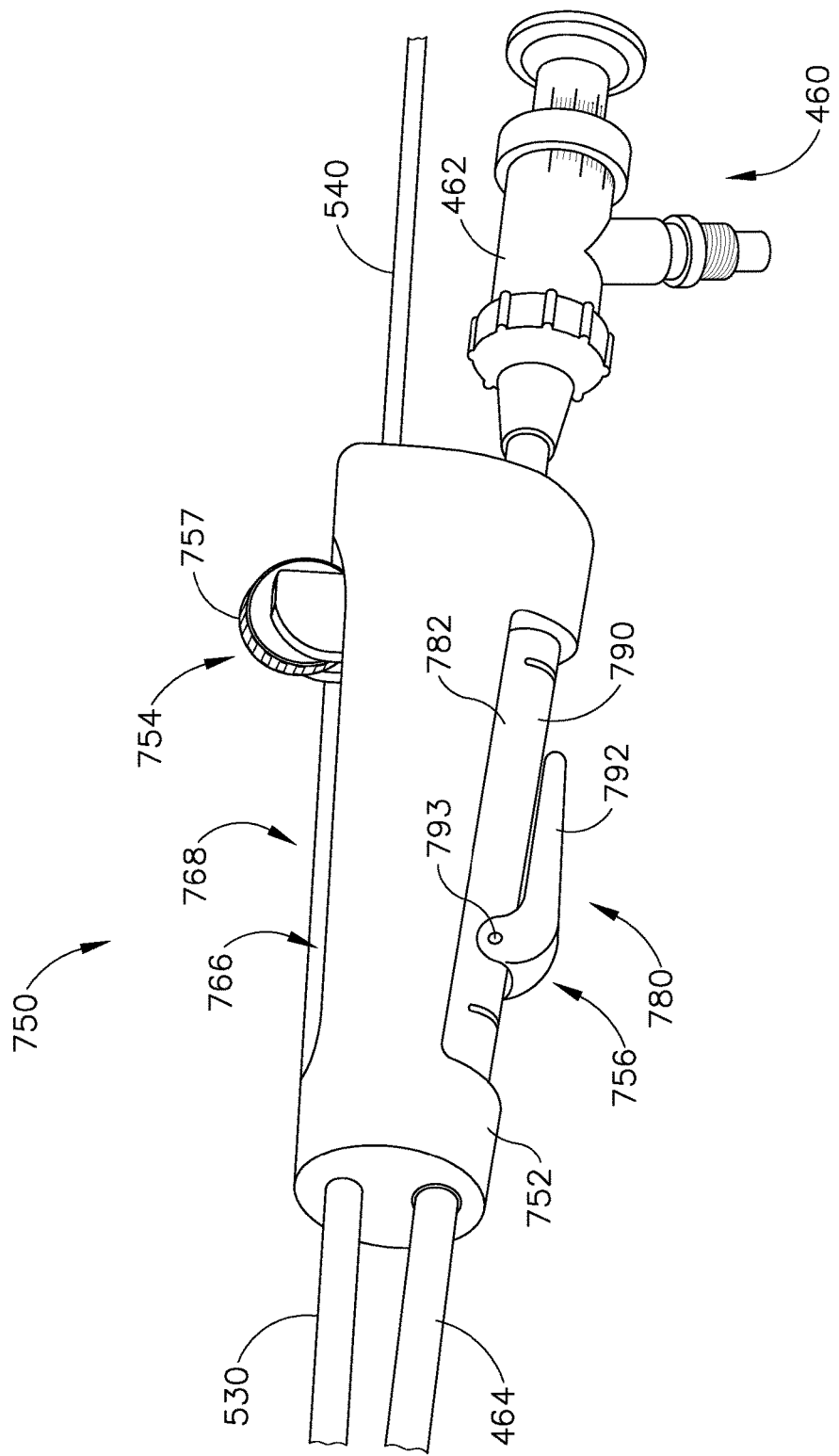
FIG. 35 depicts another perspective view of the handle of FIG. 34, with the guide catheter of FIG. 7A, the balloon dilation catheter of FIG. 34, and the endoscope of FIG. 15 positioned therein.

As also best seen in FIG. 29, proximal bore (670), channel (658), through-bore (668) of actuator (654), and distal bore (678) form a continuous passageway through body (652) that leads directly to guide catheter (530) when coupled with the distal portion of body (652). Balloon dilation catheter (540) is configured to pass through this passageway within body (652) and to further pass though guide catheter (530) when coupled with the distal portion of body (652). As described above, balloon dilation catheter (540) is selectively coupled with actuator (654) such that translation of actuator (654) within channel (658) is communicated to balloon dilation catheter (540). Thus, it should be understood that translation of actuator (654) within channel (658) causes concurrent translation of balloon dilation catheter (540) within this passageway. In particular, and as shown in FIG. 33F, balloon dilation catheter (540) is configured to translate within proximal bore (670), channel (658), through-bore (668) of actuator (654), distal bore (678), and guide catheter (530) in response to translation of actuator (654) within channel (658).

It should be appreciated from the discussion above that handle (650) may be grasped and maneuvered, actuator (654) may be translated, and endoscope housing (680) may be translated and/or rotated, all using a single hand. For instance, while grasping handle (650), the user may use his or her index finger or thumb to translate actuator (654) and/or to translate and/or rotate endoscope housing (680).

E. Exemplary Single-Hand-Use Handle with Rotatable Endoscope Housing and Compression Lever FIGS. 34-37B show another exemplary single-hand-use handle (750). As will be described in more detail below, handle (750) is operable to combine guide catheter (530), balloon dilation catheter (540), and endoscope (460) in such a manner as to allow a user to maneuver and operate each element using only a single hand. Handle (750) of the present example comprises a body (752), an actuator (754), and an endoscope housing (780). Endoscope housing (780) comprises an elongate-tubular body (782). Tubular body (782) includes a pair of annular flanges (784) extending from opposite ends of tubular body (782). Body (752) includes a channel (756) formed in a lower portion of body (752). Channel (756) extends partially the length of body (752). Endoscope housing (780) is rotatably disposed within channel (756). In particular, as best seen in FIGS. 36A-36E, body (752) further includes a proximal bore (758) extending between a proximal end of body (752) and a proximal end of channel (756) and a distal bore (760) extending between a distal end of body (752) and a distal end of channel (756). A distal portion (762) of proximal bore (758) is sized to rotatably receive a first end of tubular body (782) and includes an annular recess (759) formed therein and configured to rotatably receive a first annular flange (784) of tubular body (782) and a proximal portion (764) of distal bore (760) is sized to rotatable receive a second end of tubular body (782) and includes an annular recess (761) formed therein and configured to rotatable receive a second annular flange (784) of tubular body (782) such that endoscope housing (780) is rotatably disposed within channel (756).

Figure 36A:
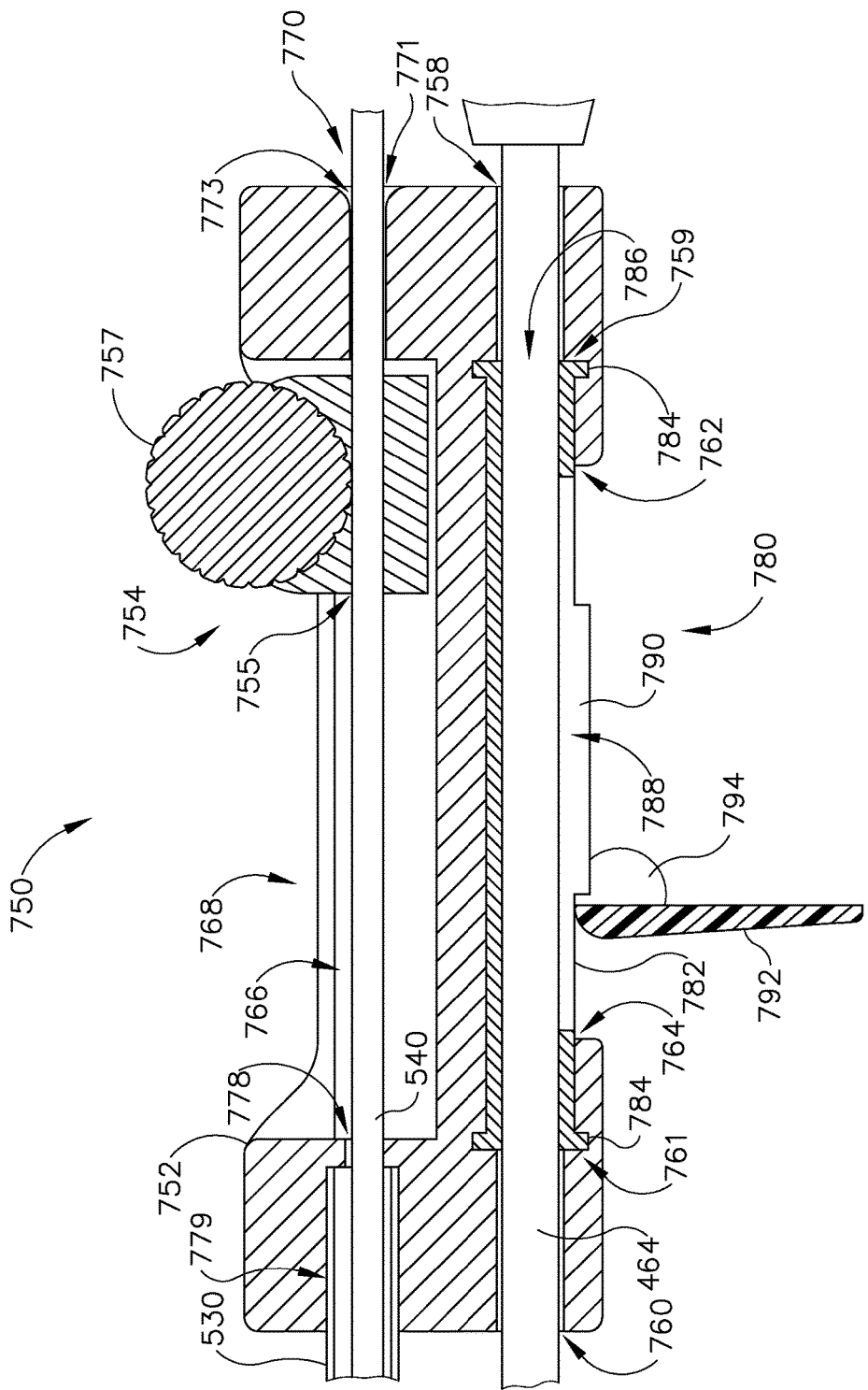
FIG. 36A depicts a cross-sectional side view of the handle of FIG. 34 taken along line 36-36 of FIG. 34, with the guide catheter of FIG. 7A, the balloon dilation catheter of FIG. 34, and the endoscope of FIG. 15 positioned therein, and with a locking member of the handle in a first, unlocked, rotational position.
Figure 36B:
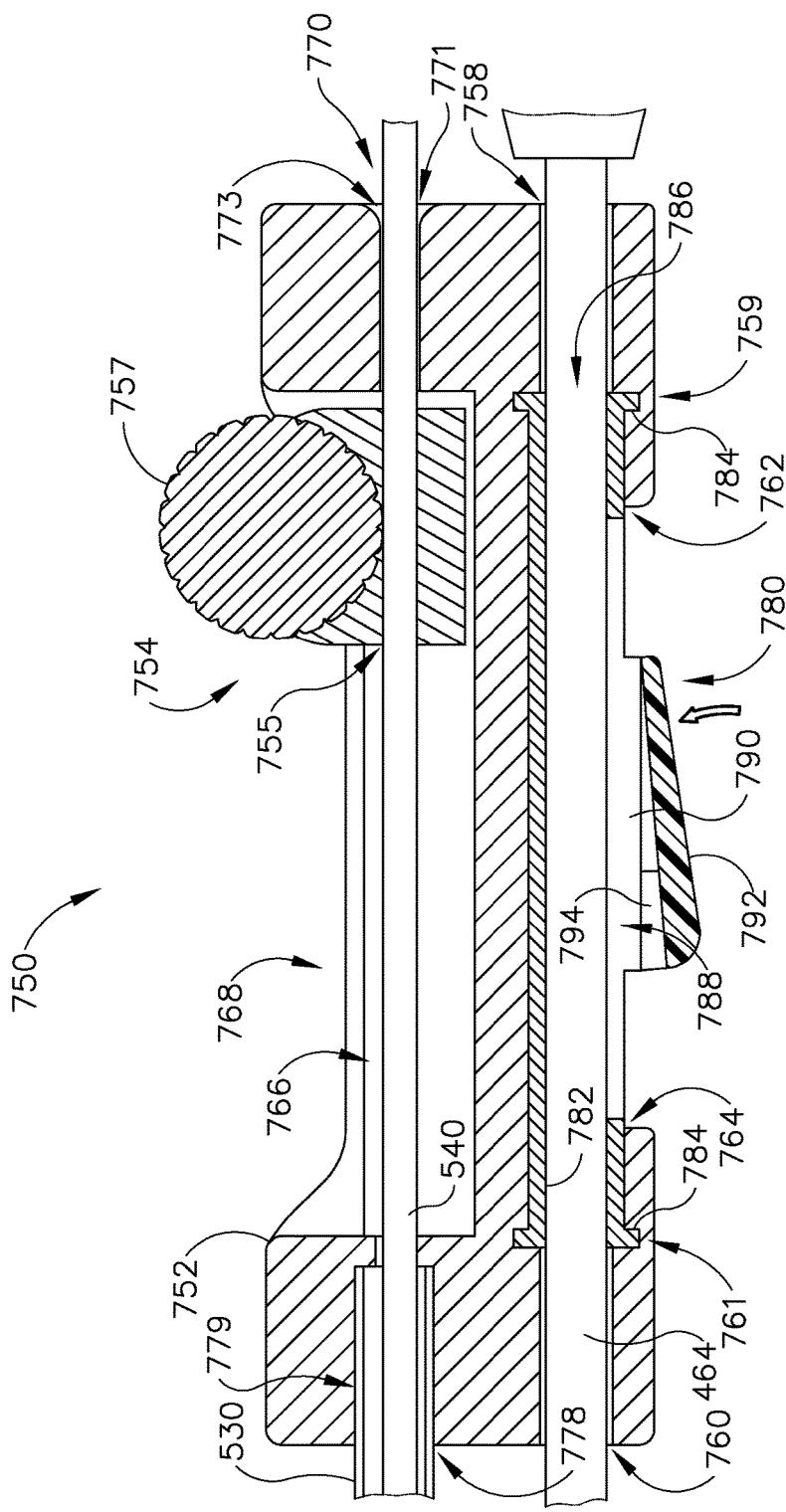
FIG. 36B depicts a cross-sectional side view of the handle of FIG. 34 taken along line 36-36 of FIG. 34, with the guide catheter of FIG. 7A, the balloon dilation catheter of FIG. 34, and the endoscope of FIG. 15 positioned therein, and with the locking member of FIG. 36A rotated into a second, locked, rotational position.

Tubular body (782) includes a through-bore (786) extending the length of tubular body (782). As will be described in more detail below, through-bore (786) is operable to receive and selectively retain shaft (464) of endoscope (460) such that rotation of endoscope housing (780) is communicated to endoscope (460). Tubular body (782) further includes a pair of resilient flanges (790) formed in a sidewall of tubular body (782). A gap (788) is defined between interior surfaces of resilient flanges (790). Resilient flanges (790) are configured to flex toward and away from one another between a first, unlocked, position (FIG. 37A) and a second, locked, position (FIG. 37B). Resilient flanges (790) are resiliently biased toward the first, unlocked, position shown in FIG. 42A. A lever (792) is pivotably coupled with tubular body (782) below through-bore (786) via a pin (793) such that lever (792) is pivotable toward and away from tubular body (782) about pin (793) between a first, unlocked, rotational position (FIG. 36A) and a second, locked, rotational position (FIG. 36B). Lever (792) comprises an angled interior surface (794) such that when in the second, locked, rotational position, angled interior surface (794) of lever (792) is configured to bear against exterior surfaces of resilient flanges (790) so as to drive resilient flanges (790) toward one another. Thus, as best seen in FIG. 37B, with lever (792) in the second, locked, rotational position, angled interior surface (794) of lever (792) is configured to bear against the exterior surfaces of resilient flanges (790) so as to drive resilient flanges (790) toward one another to thereby bear against an exterior surface of endoscope (460) so as to lock endoscope (460) within through-bore (786). Thus, with endoscope (460) locked within endoscope housing (780), to adjust the orientation of endoscope (460), a user may rotate endoscope housing (780), and thus endoscope (460), relative to body (702) and about the longitudinal axis of endoscope (460) as shown in FIG. 36E.

It should be appreciated that lever (792) may be rotated from the second, locked, rotational position into the first, unlocked, rotational position so as to allow resilient flanges (790) to return to the first, unlocked, position in order to enable reorientation or maneuvering of endoscope (460). Various suitable features that may be provided to selectively hold lever (792) in the second, locked, rotational position will be apparent to those of ordinary skill in the art in view of the teachings herein. In addition, any alternative locking feature described herein and as described in U.S. Provisional Pat. App. No. 62/139,941, entitled "Handle with Features to Secure a Catheter Assembly to an Endoscope," filed on even date herewith, the disclosure of which is incorporated by reference herein, may be used in addition to or in lieu of lever (792) and resilient flanges (790).

Body (752) further includes a channel (766) formed in an upper portion of body (752). Channel (766) extends partially the length of body (752). An elongate opening (768) formed in a top surface of body (752) extends substantially the length of channel (766) and provides external access to channel (766). Actuator (754) is slidably disposed within channel (766) via elongate opening (768) such that actuator (754) is operable to translate along the length of channel (766) between a proximal longitudinal position and a distal longitudinal position along the length of channel (766). Actuator (754) comprises a through-bore (755) that is configured to receive and selectively couple balloon dilation catheter (540) with actuator (754). In this way, translation of actuator (754) within channel (766) is communicated to balloon dilation catheter (540).

As best seen in FIGS. 36A-36E, body (752) comprises a proximal bore (770) extending between a proximal end of body (752) and a proximal end of channel (766). A proximal opening (771) of proximal bore (770) includes an edge fillet (773) about the circumference of proximal opening (771). Edge fillet (773) provides for a smooth transition of balloon dilation catheter (540) into and out of proximal bore (770) at varying angles relative to body (752) as balloon dilation catheter (540) translates relative to body (752) as will be described in more detail below. Edge fillet (773) is thus configured to prevent wear and tear to balloon dilation catheter (540) as balloon dilation catheter (540) translates into and out of proximal bore (770). Body (752) further comprises a distal bore comprises a distal bore (778) extending between a distal end of body (752) and a distal end of channel (766). A distal portion (779) of distal bore (778) is sized to receive and selectively retain guide catheter (530) such that guide catheter (530) may be coupled with the distal portion of body (752) and extend distally therefrom.

Actuator (754) comprises a rotatable member (757). Rotatable member (757) is rotatably disposed within actuator (754). A portion of rotatable member (757) is exposed relative to actuator (754) such that rotatable member (757) may be rotated by a user. Another portion of rotatable member (757) extends into through-bore (755) and bears against an exterior surface of balloon dilation catheter (540) such that rotation of rotatable member (757) will cause translation of balloon dilation catheter (540) relative to body (752). Thus, it should be understood that rotation of actuator (754) causes concurrent translation of balloon dilation catheter (540) within through-bore (716) and guide catheter (530) relative to body (732) as shown in FIG. 36C.

Figure 36C:
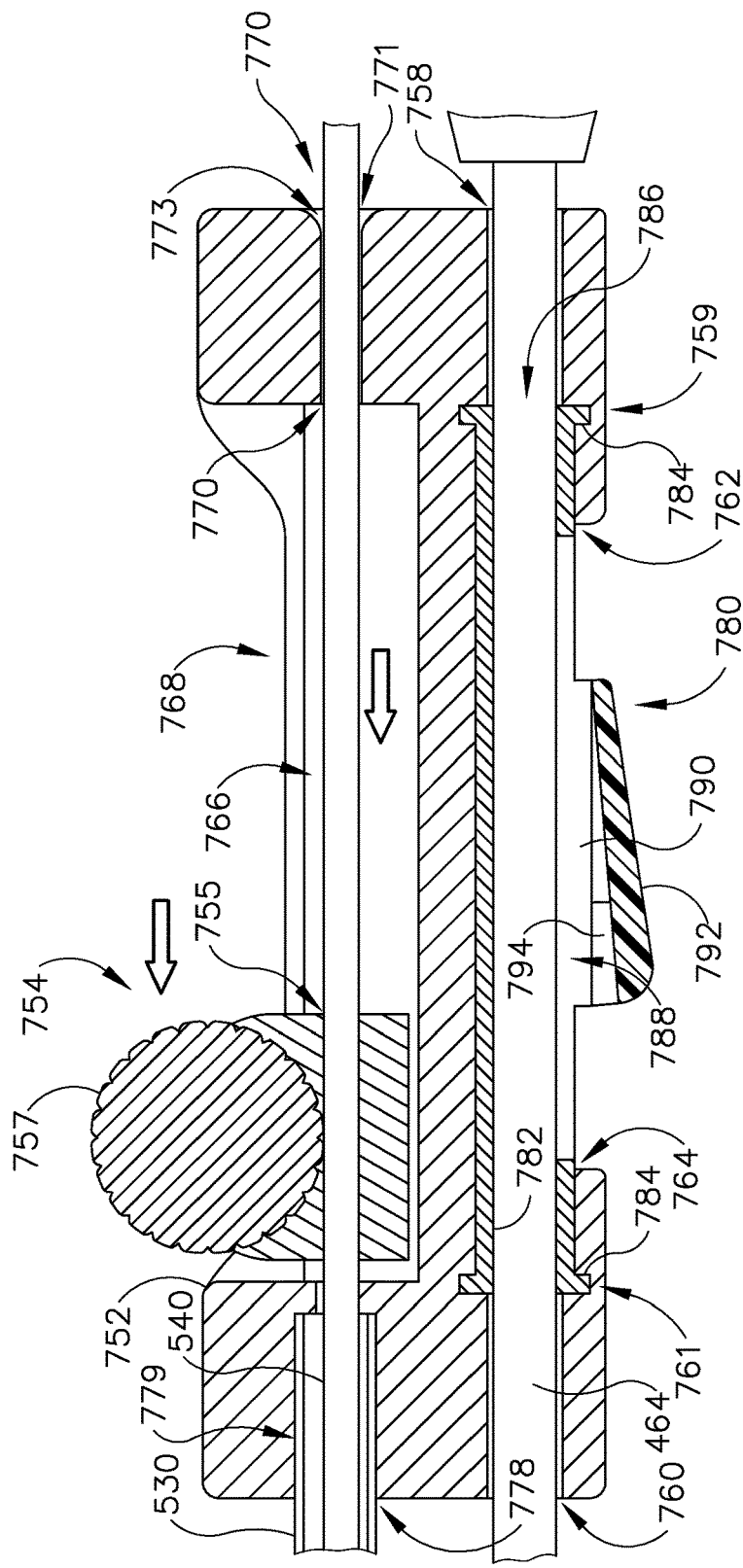
FIG. 36C depicts a cross-sectional side view of the handle of FIG. 34 taken along line 36-36 of FIG. 34, with the guide catheter of FIG. 7A, the balloon dilation catheter of FIG. 34, and the endoscope of FIG. 15 positioned therein, and with the balloon dilation catheter translated distally by distal translation of an actuator of the handle.
Figure 36D:
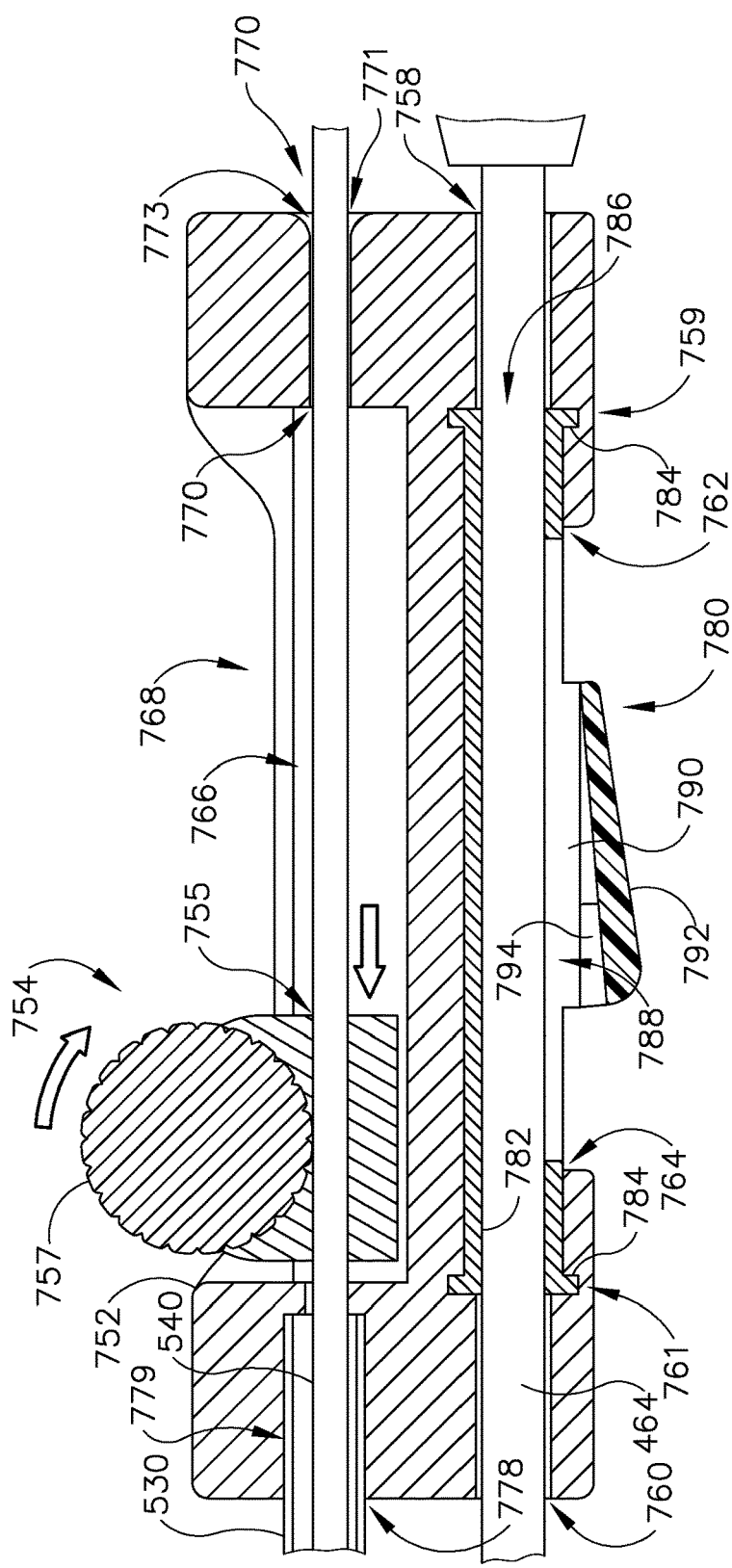
FIG. 36D depicts a cross-sectional side view of the handle of FIG. 34 taken along line 36-36 of FIG. 34, with the guide catheter of FIG. 7A, the balloon dilation catheter of FIG. 34, and the endoscope of FIG. 15 positioned therein, and with the balloon dilation catheter translated further distally by rotation of a rotatable member of the actuator of FIG. 36C.
Figure 36E:
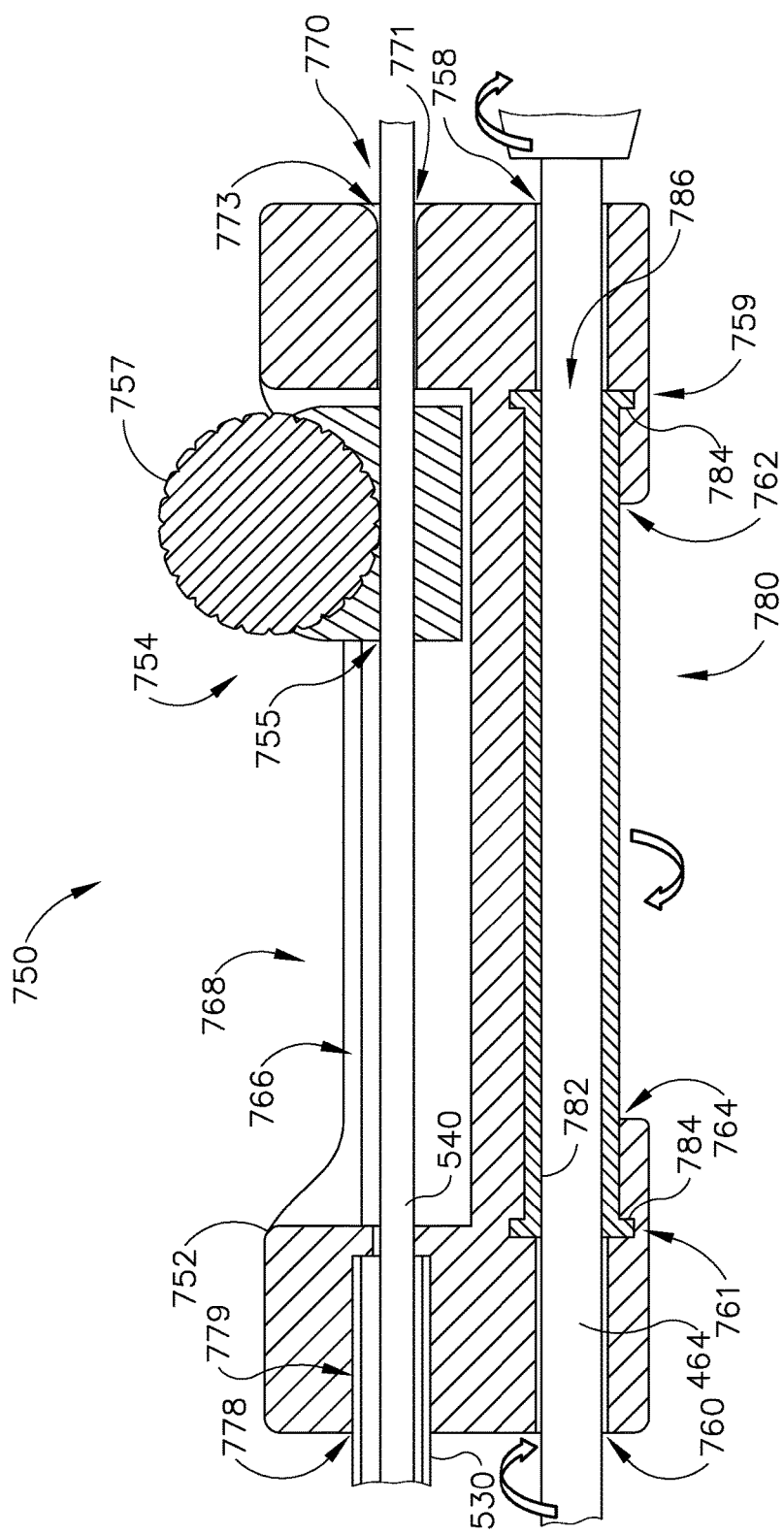
FIG. 36E depicts a cross-sectional side view of the handle of FIG. 34 taken along line 36-36 of FIG. 34, with the guide catheter of FIG. 7A, the balloon dilation catheter of FIG. 34, and the endoscope of FIG. 15 positioned therein, and with the endoscope rotated relative to the handle by rotation of an endoscope housing of the handle.
Figure 37A:
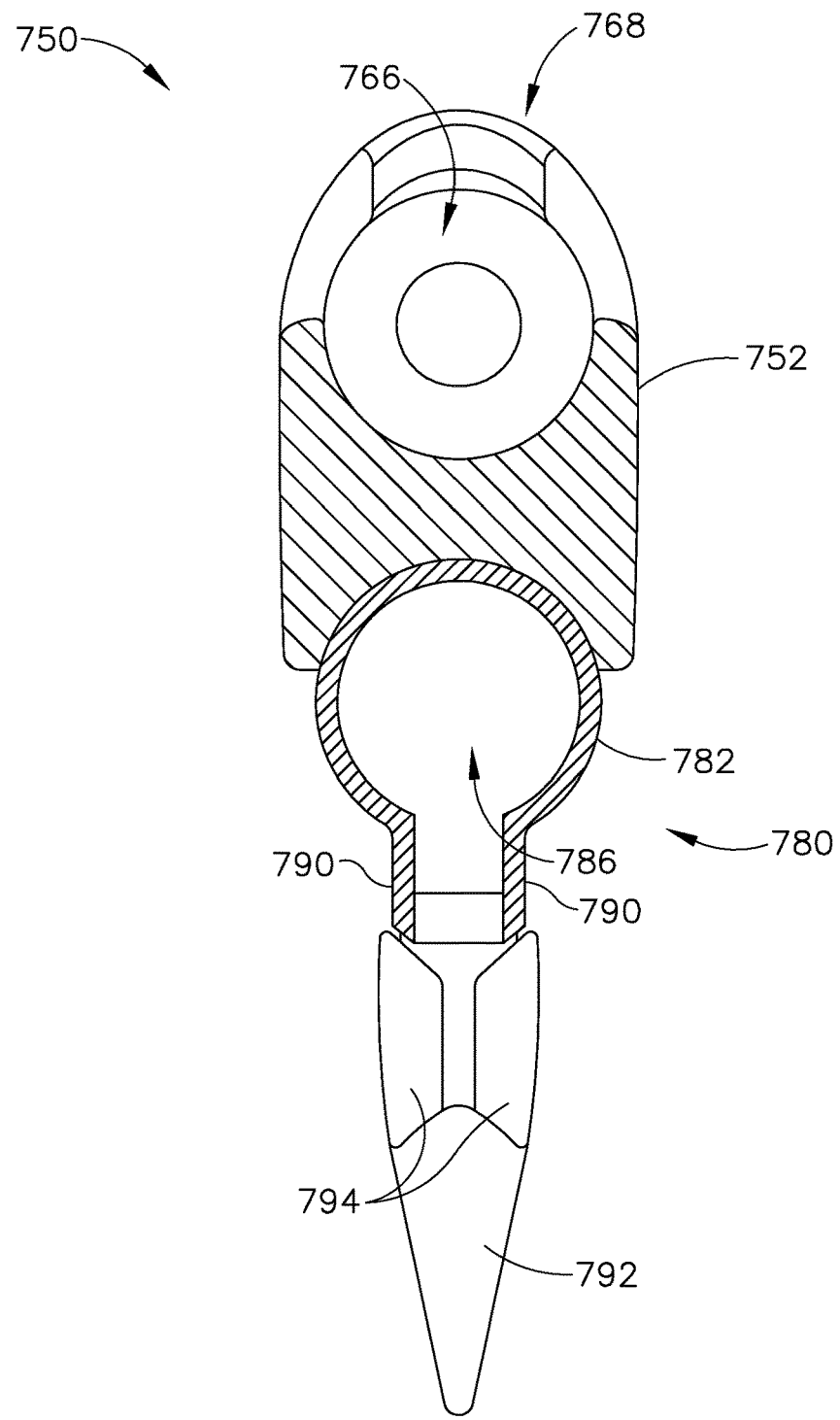
FIG. 37A depicts a cross-sectional end view of the handle of FIG. 34 taken along line 37-37 of FIG. 34, with the guide catheter of FIG. 7A, the balloon dilation catheter of FIG. 34, and the endoscope of FIG. 15 positioned therein, and with the locking member of FIG. 36A in the first, unlocked, rotational position.
Figure 37B:
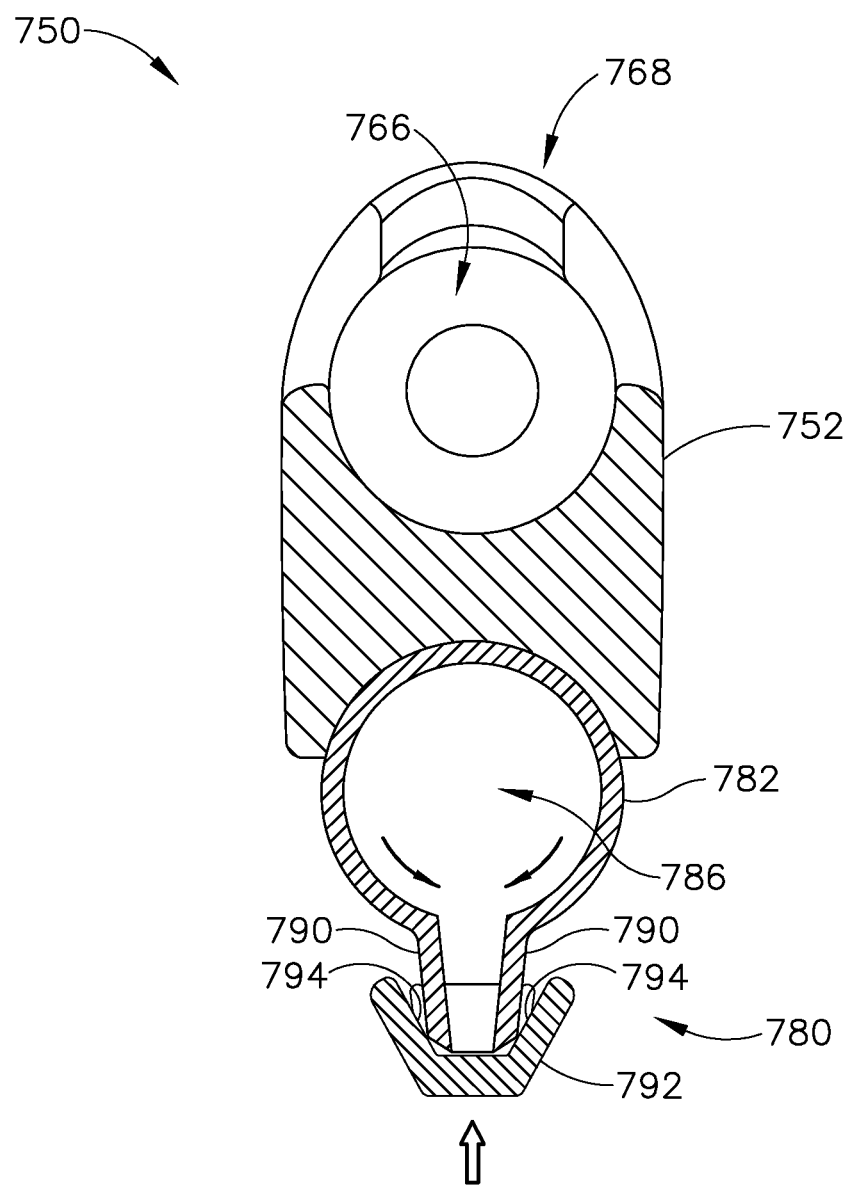
FIG. 37B depicts a cross-sectional end view of the handle of FIG. 34 taken along line 37-37 of FIG. 34, with the guide catheter of FIG. 7A, the balloon dilation catheter of FIG. 34, and the endoscope of FIG. 15 positioned therein, and with the locking member of FIG. 36A rotated into a second, locked, rotational position.
Figure 38:
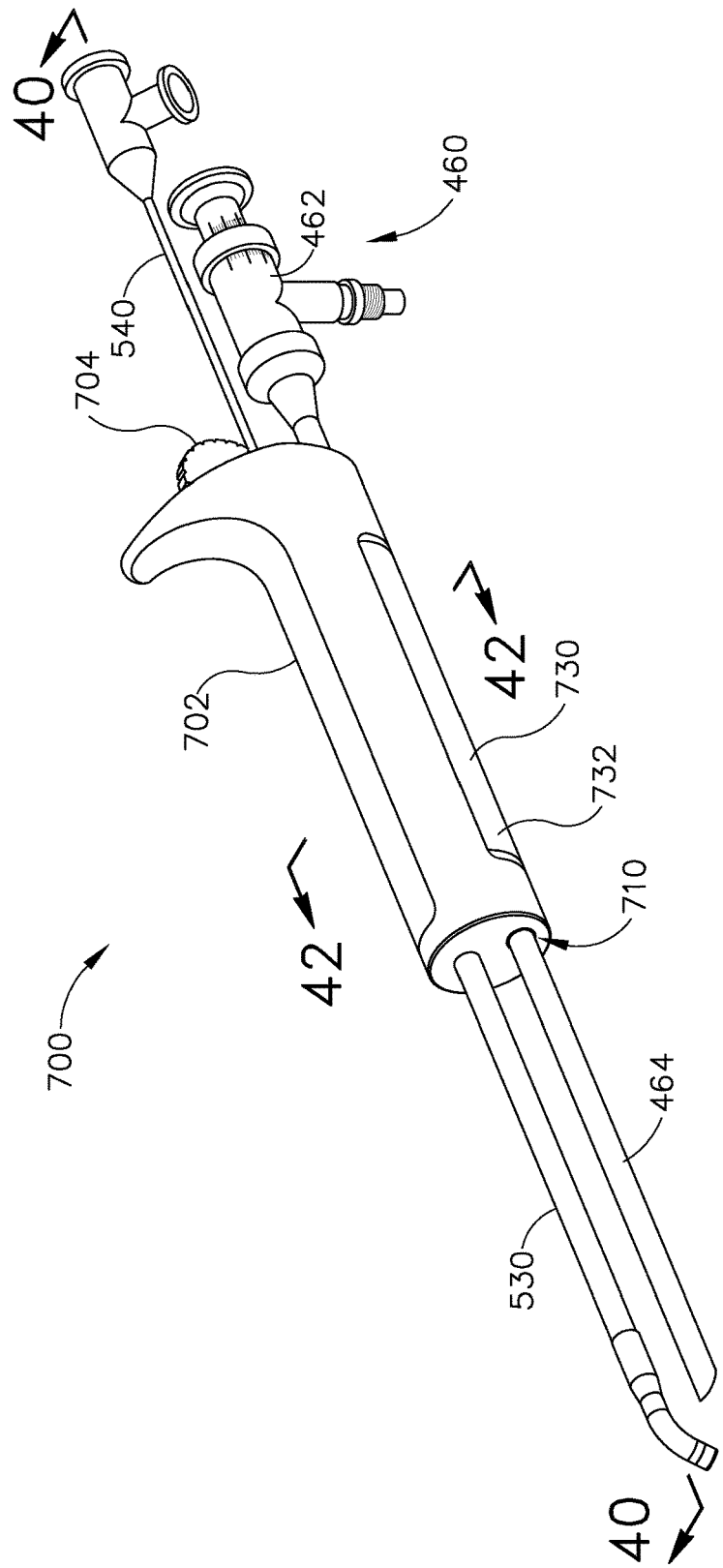
FIG. 38 depicts a perspective view of yet another exemplary handle suitable for use with the dilation catheter system of FIG. 12, with the guide catheter of FIG. 7A, an exemplary balloon dilation catheter, and the endoscope of FIG. 15 positioned therein.
Figure 39:
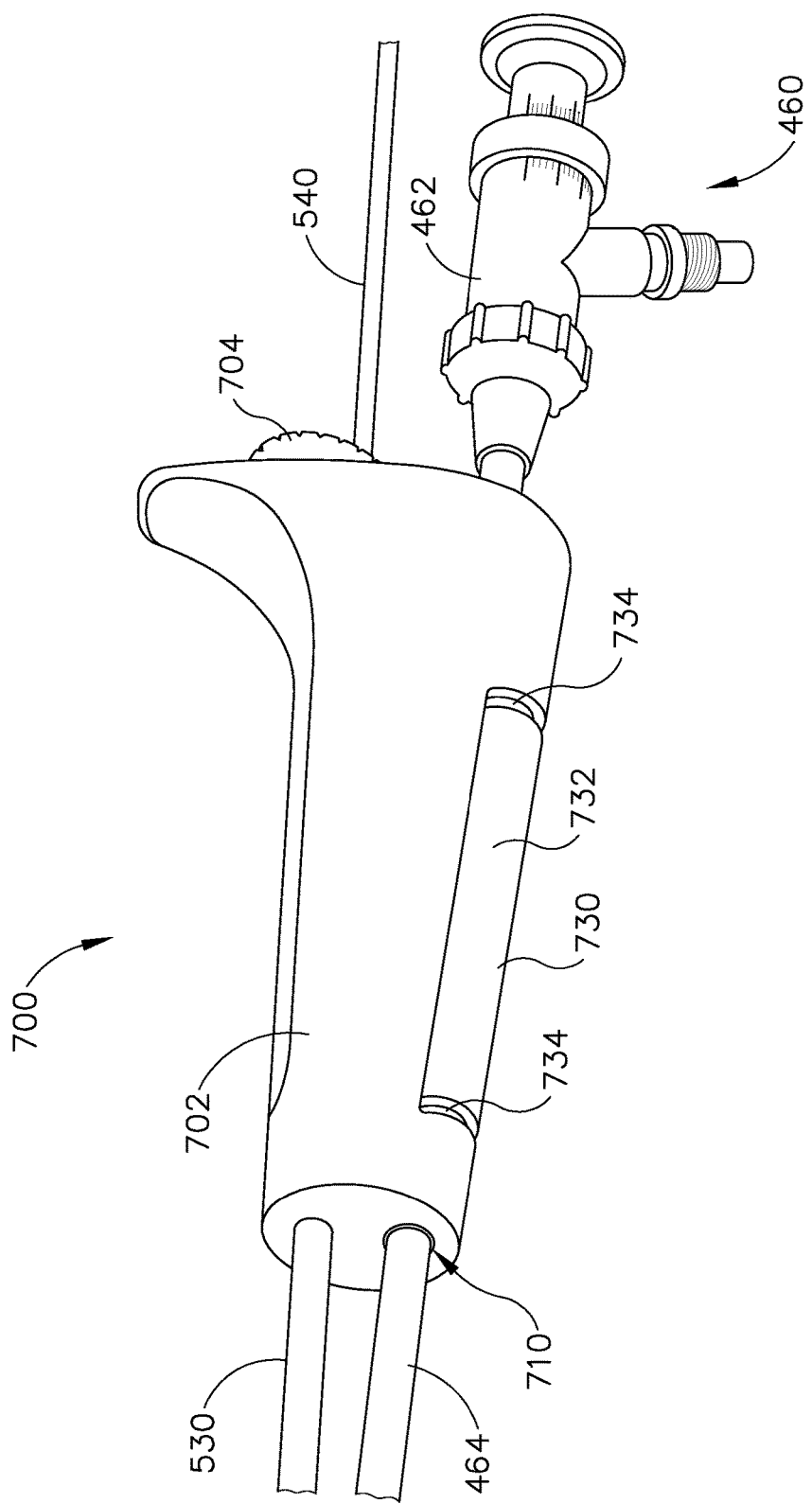
FIG. 39 depicts another perspective view of the handle of FIG. 38, with the guide catheter of FIG. 7A, the balloon dilation catheter of FIG. 38, and the endoscope of FIG. 15 positioned therein.

Also as best seen in FIGS. 36A-36E, proximal bore (770), channel (766), through-bore (755) of actuator (754), and distal bore (778) form a continuous passageway through body (752) that leads directly to guide catheter (530) when coupled with the distal portion of body (752). Balloon dilation catheter (540) is configured to pass through this passageway within body (752) and to further pass though guide catheter (530) when coupled with the distal portion of body (752). As described above, balloon dilation catheter (540) is selectively coupled with actuator (754) such that translation of actuator (754) within channel (766) is communicated to balloon dilation catheter (540). Thus, it should be understood that translation of actuator (754) within channel (766) causes concurrent translation of balloon dilation catheter (540) within this passageway. In particular, and as shown in FIG. 36C, balloon dilation catheter (540) is configured to translate within proximal bore (770), channel (766), through-bore (755) of actuator (754), distal bore (778), and guide catheter (530) in response to translation of actuator (754) within channel (766). As also described above, rotatable member (757) extends into through-bore (755) and bears against an exterior surface of balloon dilation catheter (540) such that rotation of rotatable member (757) causes translation of balloon dilation catheter (540). Thus, it should be understood that rotation of rotatable member (757) causes translation of balloon dilation catheter (540) within the passageway described above. In particular, and as shown in FIG. 36D, balloon dilation catheter (540) is configured to translate within proximal bore (770), channel (766), through-bore (755) of actuator (754), distal bore (778), and guide catheter (530) in response to rotation of rotatable member (757). It should be understood that translation of actuator (754) may be used to achieve more significant or "gross" translation of balloon dilation catheter (540); whereas rotation of rotatable member (757) may be use to achieve more minute or "fine" translation of balloon dilation catheter (540).

It should be appreciated from the discussion above that handle (750) may be grasped and maneuvered, actuator (754) may be translated, rotatable member (757) may be rotated, and endoscope housing (780) may be rotated, all using a single hand. For instance, while grasping handle (750), the user may use his or her index finger or thumb to translate actuator (754), to rotate rotatable member (757), and/or to rotate endoscope housing (780).

Figure 40A:
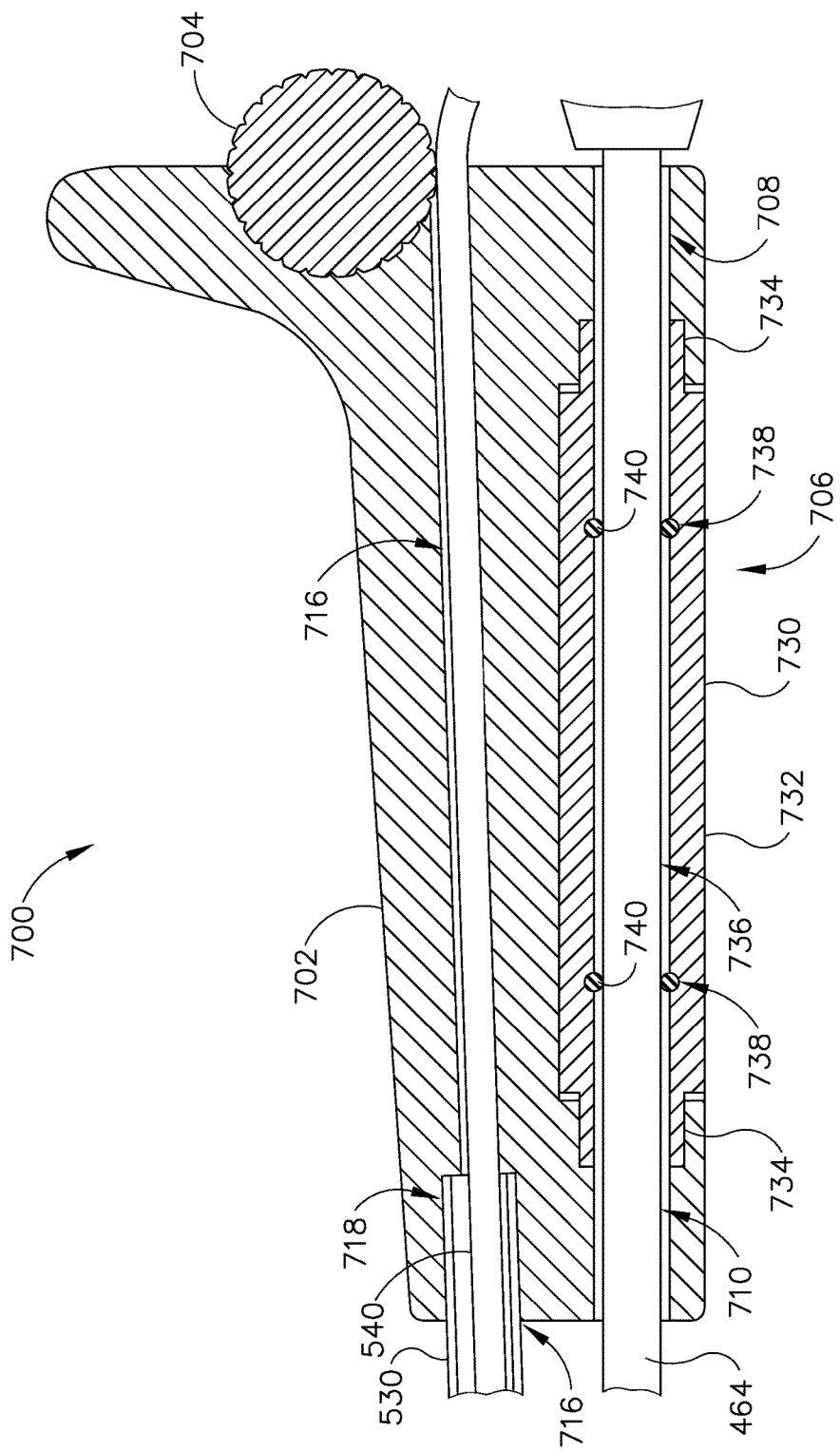
FIG. 40A depicts a cross-sectional side view of the handle of FIG. 38 taken along line 40-40 of FIG. 38, with the guide catheter of FIG. 7A, the balloon dilation catheter of FIG. 38, and the endoscope of FIG. 15 positioned therein.
Figure 40C:
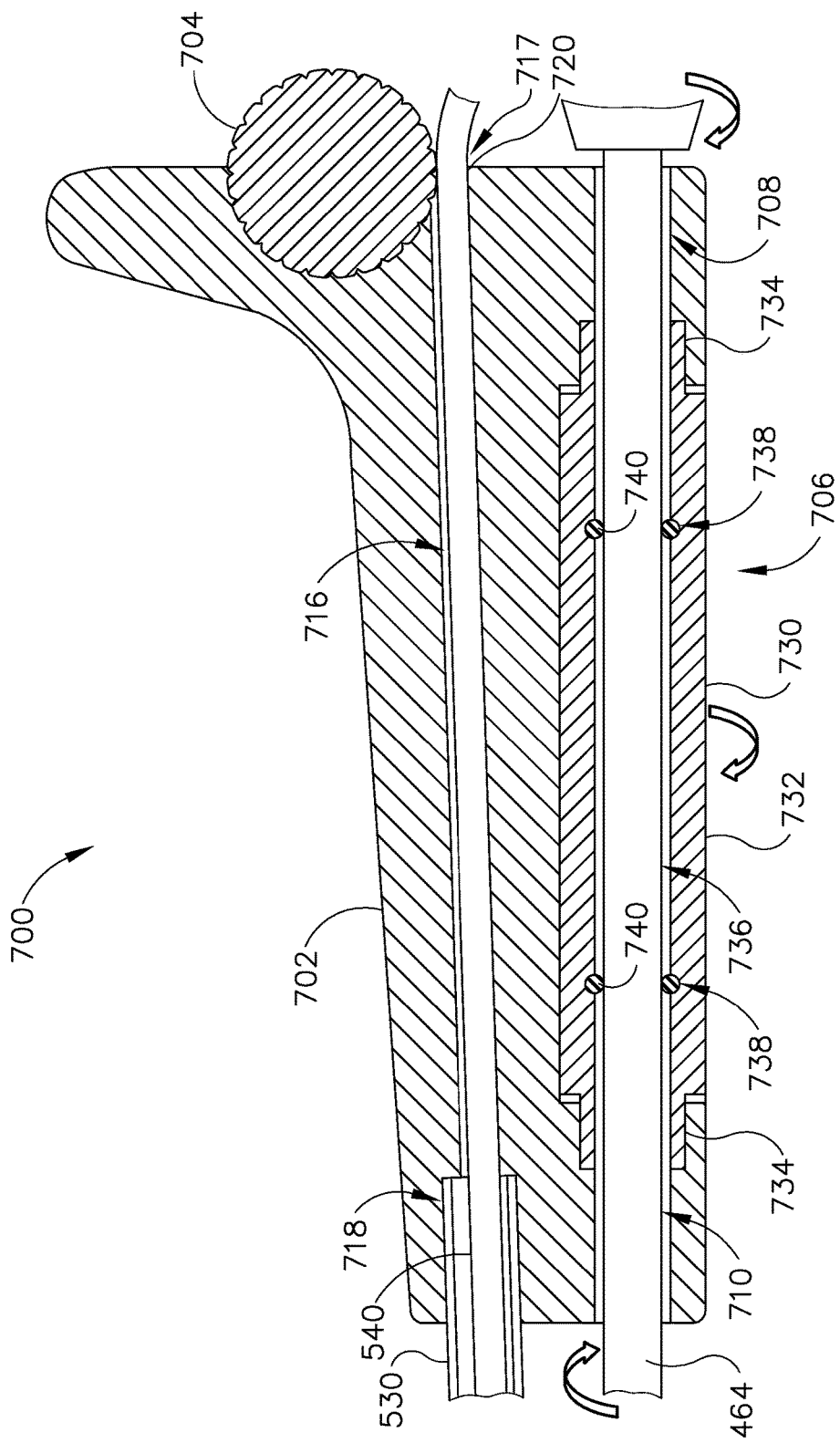
FIG. 40C depicts a cross-sectional side view of the handle of FIG. 38 taken along line 40-40 of FIG. 38, with the guide catheter of FIG. 7A, the balloon dilation catheter of FIG. 38, and the endoscope of FIG. 15 positioned therein, and with the endoscope rotated relative to the handle by rotation of an endoscope housing of the handle.
Figure 41A:
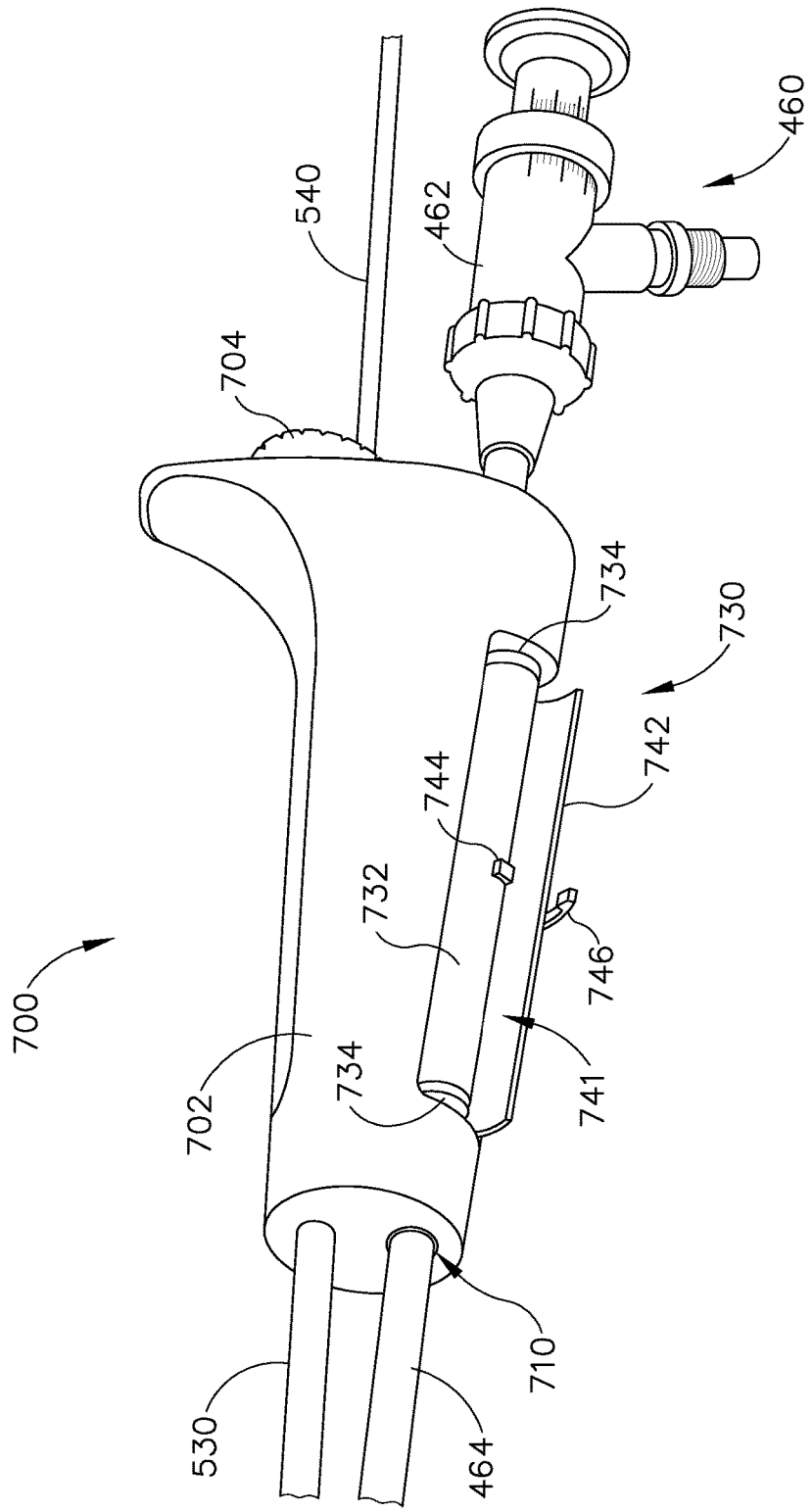
FIG. 41A depicts another perspective view of the handle of FIG. 38, with the guide catheter of FIG. 7A, the balloon dilation catheter of FIG. 38, and the endoscope of FIG. 15 positioned therein, with an exemplary locking cover in a first, unlocked, rotational position.
Figure 41B:
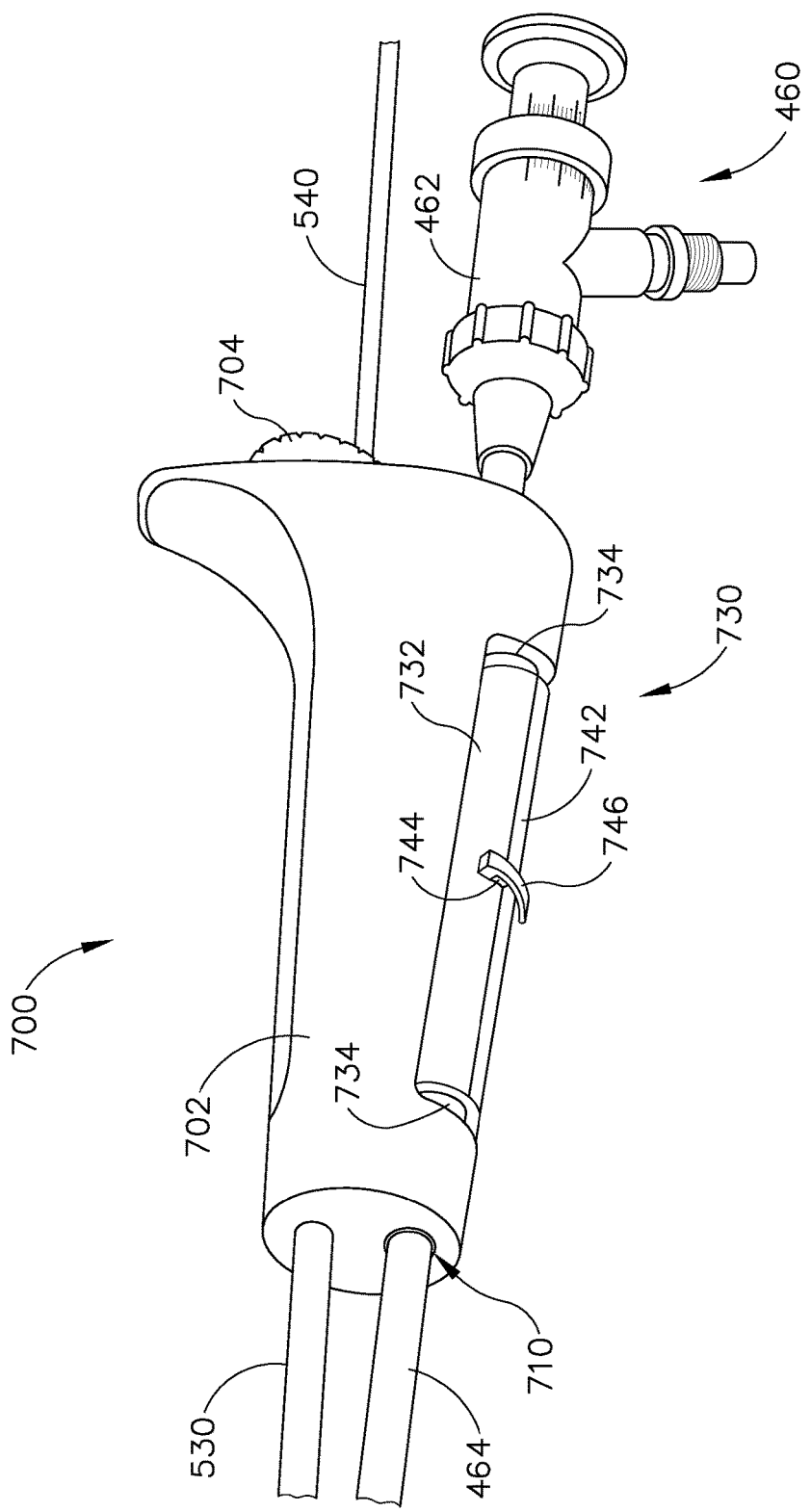
FIG. 41B depicts another perspective view of the handle of FIG. 38, with the guide catheter of FIG. 7A, the balloon dilation catheter of FIG. 38, and the endoscope of FIG. 15 positioned therein, with the locking cover of FIG. 41A rotated into a second, locked, rotational position.

F. Exemplary Single-Hand-Use Handle with Rotatable Endoscope Housing and Rotatable Actuator FIGS. 38-42B show another exemplary single-hand-use handle (700). As will be described in more detail below, handle (700) is operable to combine guide catheter (530), balloon dilation catheter (540), and endoscope (460) in such a manner as to allow a user to maneuver and operate each element using only a single hand. Handle (700) of the present example comprises a body (702), a rotatable actuator (704), and an endoscope housing (730). Endoscope housing (730) comprises an elongate-tubular body (732). Tubular body (732) includes a pair of hollow-cylindrical protrusions (734) extending from opposite ends of tubular body (732). Body (702) includes a channel (706) formed in a lower portion of body (702). Channel (706) extends partially the length of body (702). Endoscope housing (730) is rotatably disposed within channel (706). In particular, as best seen in FIGS. 40A-40C, body (702) further includes a proximal bore (708) extending between a proximal end of body (702) and a proximal end of channel (706) and a distal bore (710) extending between a distal end of body (702) and a distal end of channel (706). A distal portion (712) of proximal bore (708) is sized to rotatably receive a first cylindrical protrusion (734) of tubular body (732) and a proximal portion (714) of distal bore (710) is sized to rotatable receive a second cylindrical protrusion (734) of tubular body (732) such that endoscope housing (730) is rotatably disposed within channel (706). Tubular body (732) further includes a through-bore (736) extending the length of tubular body (732). As will be described in more detail below, through-bore (736) is operable to receive and selectively retain shaft (464) of endoscope (460) such that rotation of endoscope housing (730) is communicated to endoscope (460).

Through-bore (736) of tubular body (732) includes a plurality of annular recesses (738) formed at spaced apart intervals in an interior surface of through-bore (736). Endoscope housing (730) further includes a plurality of friction rings (740) positioned within circular recesses (738) of through-bore (736). By way of example only, friction rings (740) may comprise conventional o-rings, wiper seals, or other elastomeric members. With endoscope (460) positioned within through-bore (736), friction rings (740) are configured to bear against an exterior surface of endoscope (460) so as to selectively lock endoscope (460) within through-bore (736). Thus, with endoscope (460) locked within endoscope housing (730), to adjust the orientation of endoscope (460), a user may rotate endoscope housing (730), and thus endoscope (460) relative to body (702) as shown in FIG. 40C.

As shown in FIGS. 41A-42B, in addition to or in lieu of friction rings (740), tubular body (732) of endoscope housing (730) may comprise an elongate opening (741) formed in a sidewall of tubular body (732). Opening (741) extends substantially the length of tubular body (732) and provides external access to through-bore (736). Tubular body (732) of the present example further comprises a cover (742) that envelops and defines a portion through-bore (736) as best seen in FIGS. 42A and 42B. Cover (742) extends substantially the length of tubular body (732) and is hingedly coupled thereto such that cover (742) is configured to rotate toward and away from tubular body (732) between a first, unlocked, rotational position (FIGS. 41A and 42A) and a second, locked, rotational position (FIGS. 41B and 42B). As best seen in FIG. 42B, with cover (742) in the first, locked, rotational position, cover (742) is configured to bear against an exterior surface of endoscope (460) via opening (741) so as to lock endoscope (460) within through-bore (736). Tubular body (732) comprises a tab (744). Cover (742) comprises a latch (746) pivotably coupled with cover (742) via a linkage (747). Latch (746) is configured to couple about tab (744) of tubular body (732) with cover (742) in the second, locked, rotational position to thereby selectively retain cover (742) in the second, locked, rotational position. It should be appreciated that cover (742) may be unlatched so as to allow cover (742) to return to the first, unlocked, rotational position in order to enable reorientation or maneuvering of endoscope (460). Various suitable features that may be provided to selectively hold cover (742) in the locked position will be apparent to those of ordinary skill in the art in view of the teachings herein. In addition, any alternative locking feature described herein and as described in U.S. Provisional Pat. App. No. 62/139,941, entitled "Handle with Features to Secure a Catheter Assembly to an Endoscope," filed on even date herewith, the disclosure of which is incorporated by reference herein, may be used in addition to or in lieu of friction rings (740) and cover (742).

Body (702) further includes a through-bore (716) formed in an upper portion of body (702). Through-bore (716) extends the length of body (702). As will be described in more detail below, through-bore (716) is configured to slidably receive balloon dilation catheter (540) such that balloon dilation catheter (540) is operable to translate within through-bore (716). A distal portion (718) of through-bore (716) is sized to receive and selectively retain guide catheter (530) such that guide catheter (530) may be coupled with the distal portion of body (702) and extend distally therefrom. Thus, it should be understood that through-bore (716) forms a continuous passageway through body (702) that leads directly to guide catheter (530) when coupled with the distal portion of body (702). Balloon dilation catheter (540) is configured to pass through this passageway within body (702) and to further pass though guide catheter (530) when coupled with the distal portion of body (702). Actuator (704) is rotatably disposed within a proximal portion of body (702). A portion of actuator (704) is exposed relative to body (702) such that actuator (704) may be rotated by a user. Another portion of actuator (704) extends into through-bore (716) and bears against an exterior surface of balloon dilation catheter (540) such that rotation of actuator (704) is configured to cause translation of balloon dilation catheter (540) relative to body (702). Thus, it should be understood that rotation of actuator (704) causes concurrent translation of balloon dilation catheter (540) within through-bore (716) and guide catheter (530) relative to body (732) as shown in FIG. 40B.

A proximal opening (717) of through-bore (716) includes an edge fillet (720) about the circumference of proximal opening (717). Edge fillet (720) provides for a smooth transition of balloon dilation catheter (540) into and out of through-bore (716) at varying angles relative to body (702) as balloon dilation catheter (540) translates relative to body (702) as will be described in more detail below. Edge fillet (720) is thus configured to prevent wear and tear to balloon dilation catheter (540) as balloon dilation catheter (540) translates into and out of through-bore (716).

It should be appreciated from the discussion above that handle (700) may be grasped and maneuvered, actuator (704) may be rotated, and endoscope housing (730) may be rotated, all using a single hand. For instance, while grasping handle (700), the user may use his or her index finger or thumb to rotate actuator (704) and/or to translate rotate endoscope housing (730).

Figure 43:
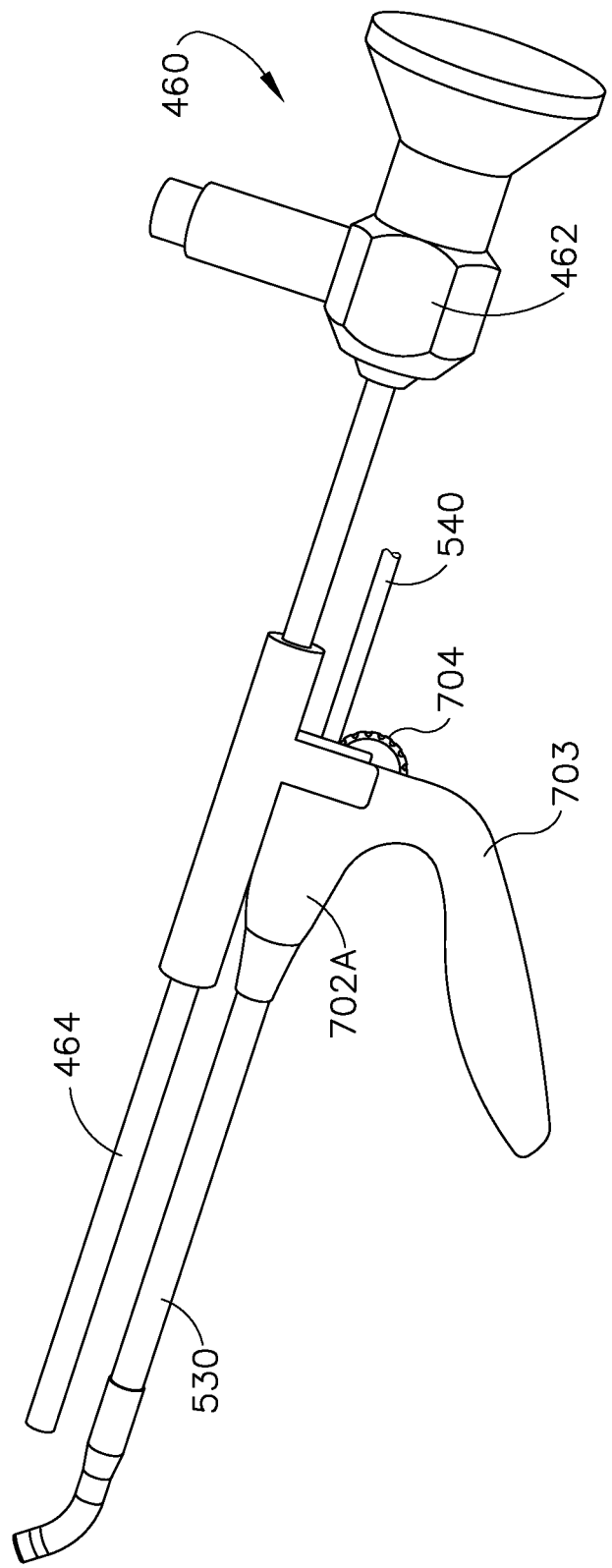
FIG. 43 depicts a perspective view of yet another exemplary handle suitable for use with the dilation catheter system of FIG. 12, with the guide catheter of FIG. 7A, an exemplary balloon dilation catheter, and the endoscope of FIG. 15 positioned therein.
Figure 44:
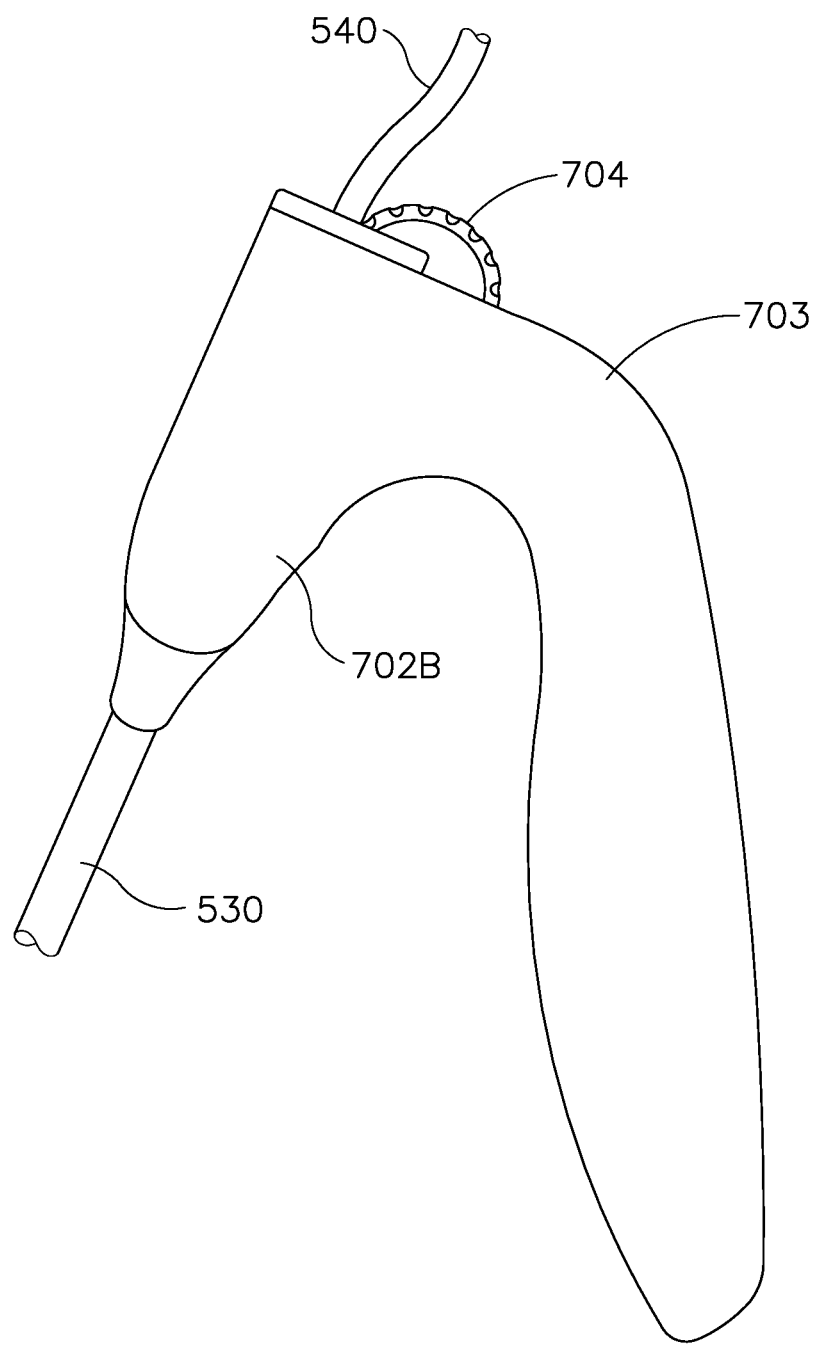
FIG. 44 depicts a perspective view of yet another exemplary handle suitable for use with the dilation catheter system of FIG. 12, with the guide catheter of FIG. 7A and an exemplary balloon dilation catheter positioned therein.
Figure 45:
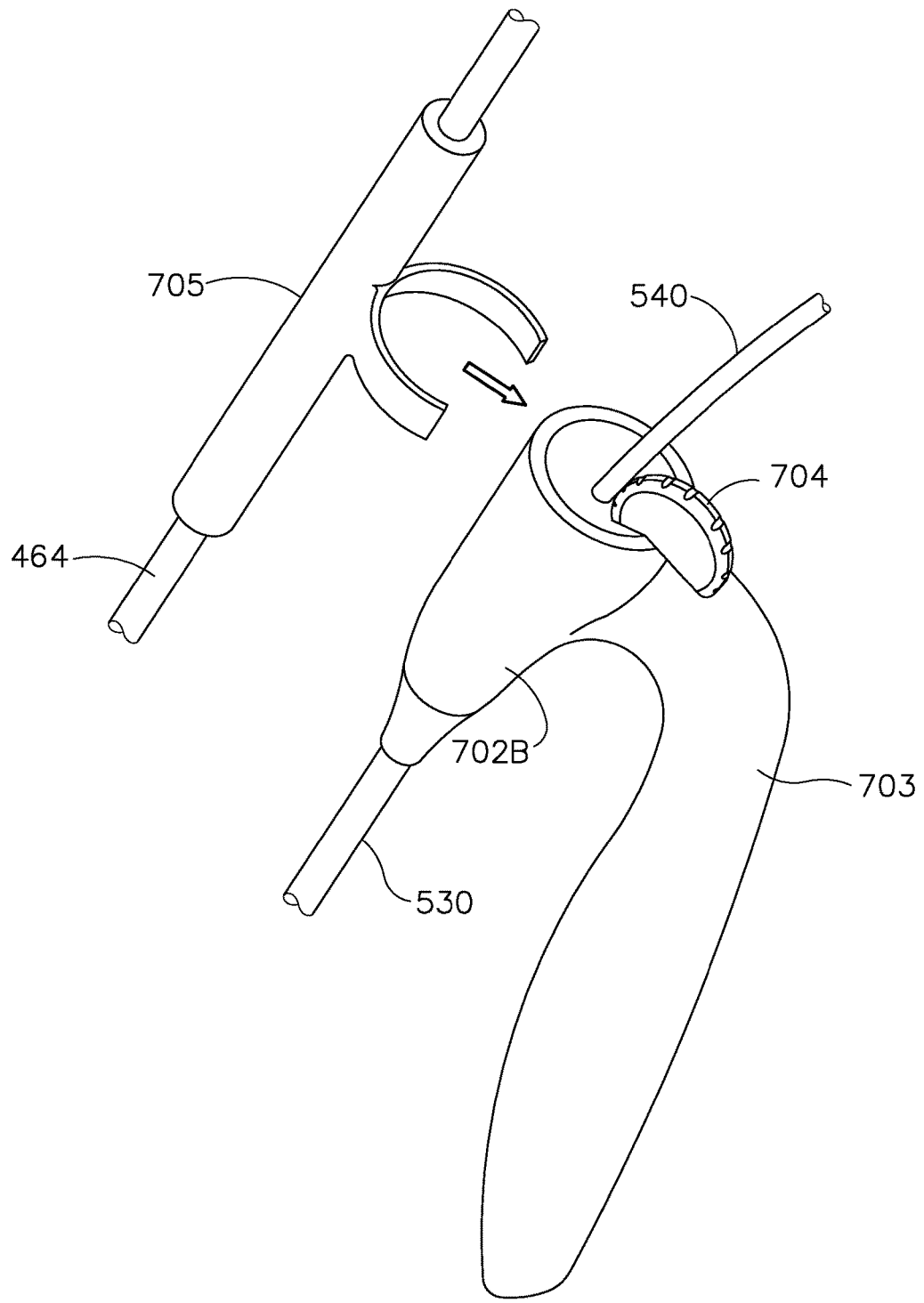
FIG. 45 depicts a perspective view of yet another exemplary handle suitable for use with the dilation catheter system of FIG. 12, with the guide catheter of FIG. 7A, an exemplary balloon dilation catheter, and the endoscope of FIG. 15 positioned therein.

FIGS. 43-45 show exemplary variations of body (702). Body (702A) shown in FIG. 43 comprises an L-shaped handle (703). Handle (703) may be grasped by a user who in turn may use his or her thumb to rotate actuator (704). Body (702B) shown in FIG. 44 comprises an L-shaped handle (703) but omits those portions of body (702) described above related to selectively receiving and retaining endoscope (460). As shown in FIG. 45, however, endoscope (460) may be coupled with body (702B) via a selectively-attachable clip (705) that is configured to selectively receive and retain shaft (464) of endoscope (460) to thereby couple endoscope (460) with body (702B).

G. Exemplary Single-Hand-Use Handle with Translatable Guide Catheter

Figure 46:
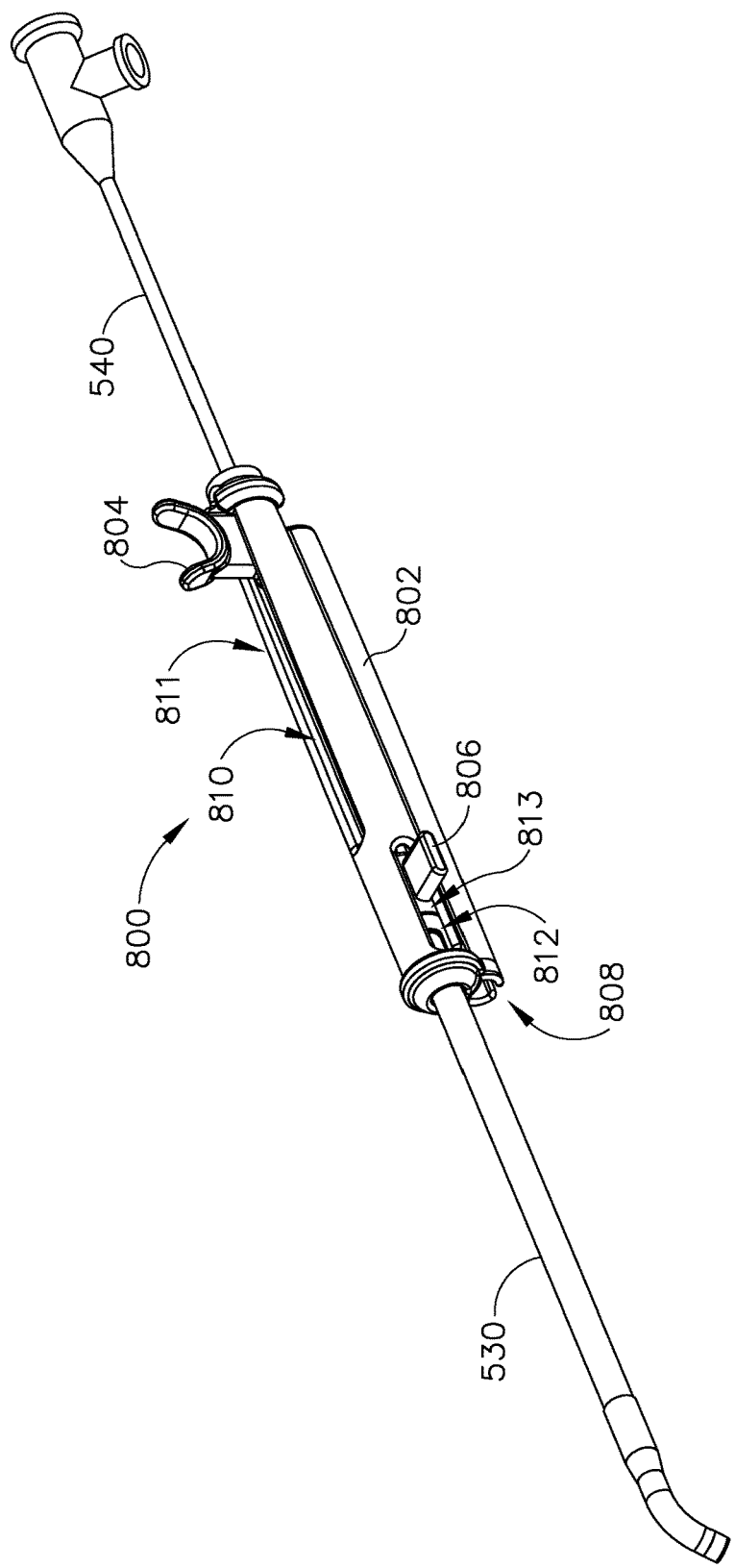
FIG. 46 depicts a perspective view of yet another exemplary handle suitable for use with the dilation catheter system of FIG. 12, with the guide catheter of FIG. 7A and an exemplary balloon dilation catheter positioned therein.
Figure 47A:
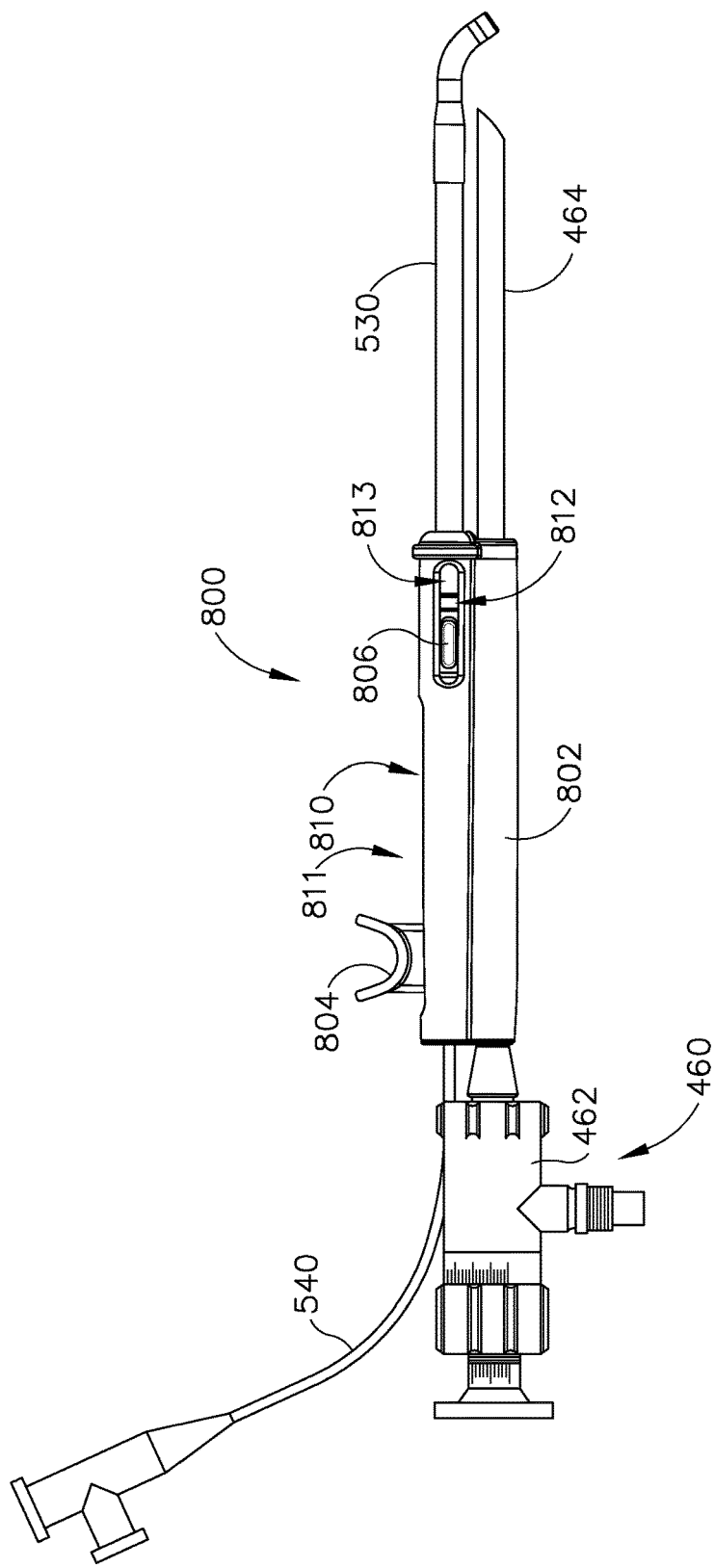
FIG. 47A depicts a side elevational view of the handle of FIG. 46, with the guide catheter of FIG. 7A, the balloon dilation catheter of FIG. 46, and the endoscope of FIG. 15 positioned therein.
Figure 47B:
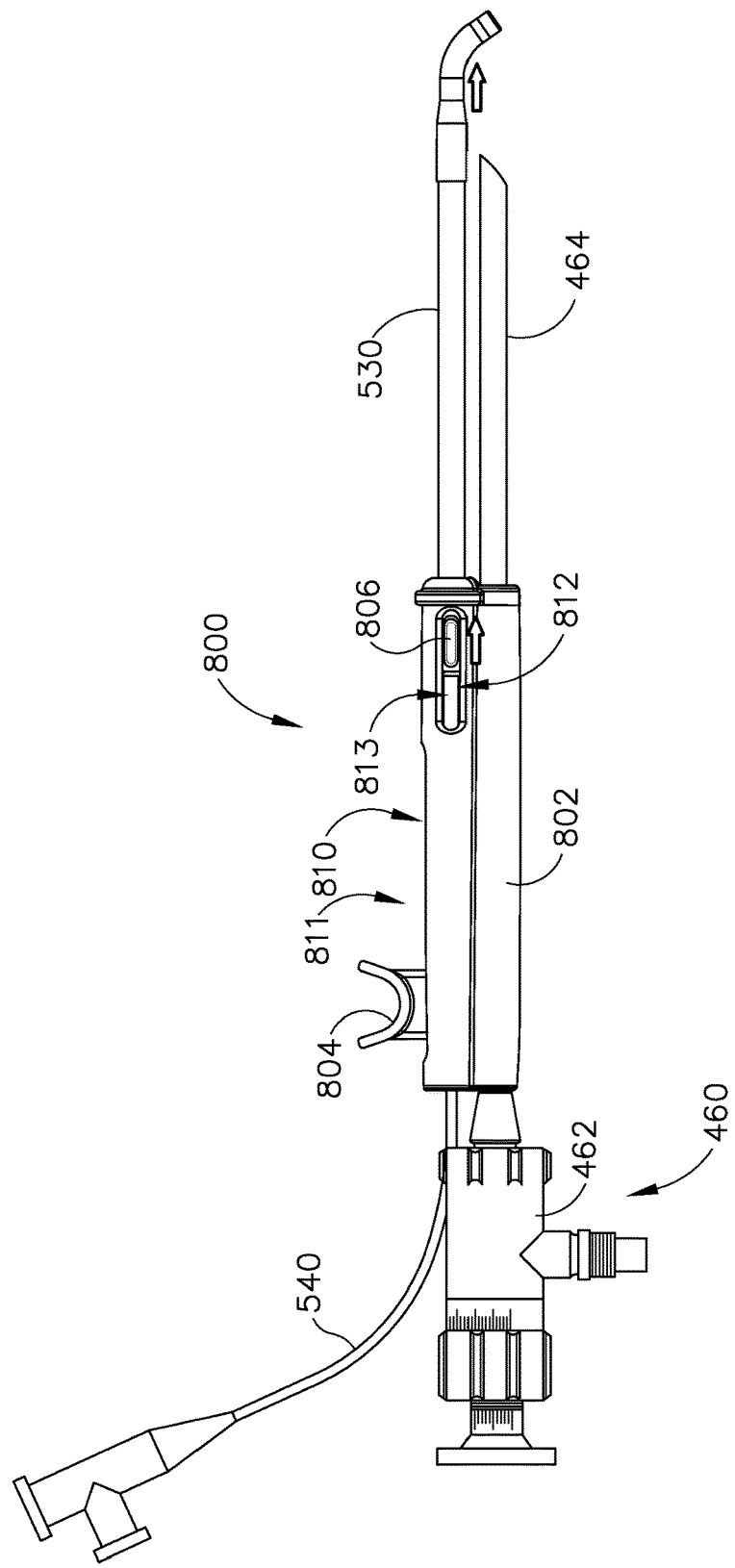
FIG. 47B depicts a side elevational view of the handle of FIG. 46, with the guide catheter of FIG. 7A, the balloon dilation catheter of FIG. 46, and the endoscope of FIG. 15 positioned therein, and with the guide catheter translated distally by distal translation of a first actuator of the handle.
Figure 47C:
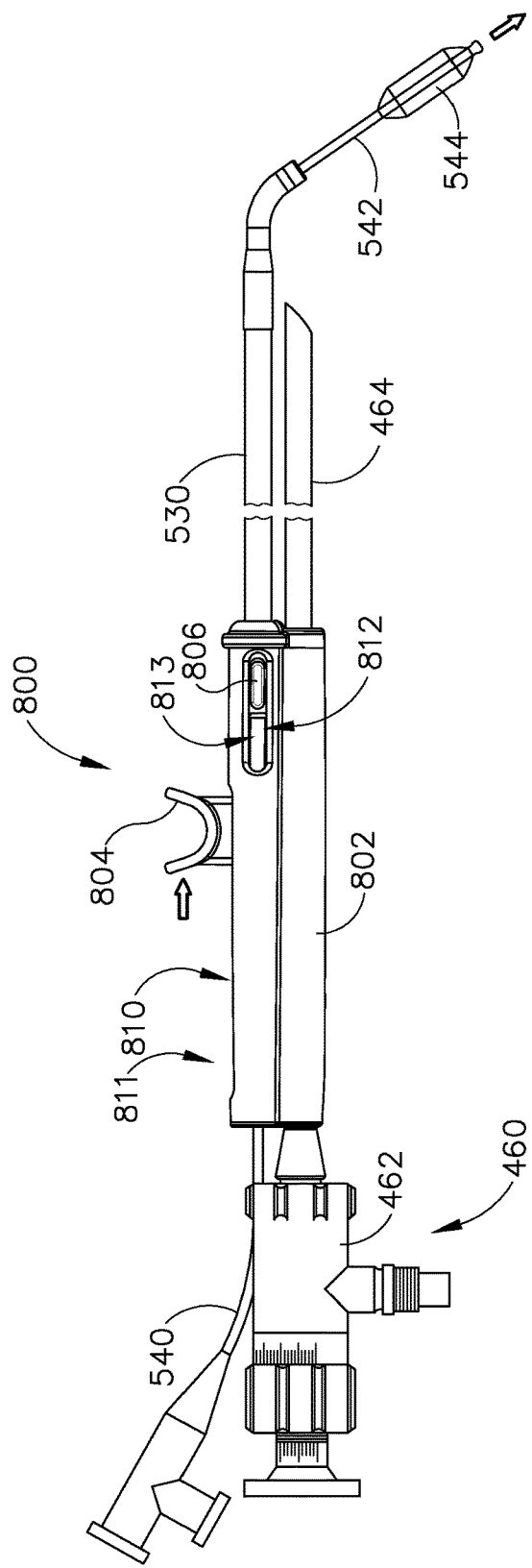
FIG. 47C depicts a side elevational view of the handle of FIG. 46, with the guide catheter of FIG. 7A, the balloon dilation catheter of FIG. 46, and the endoscope of FIG. 15 positioned therein, and with the balloon dilation catheter translated distally by distal translation of a second actuator of the handle.
Figure 48:
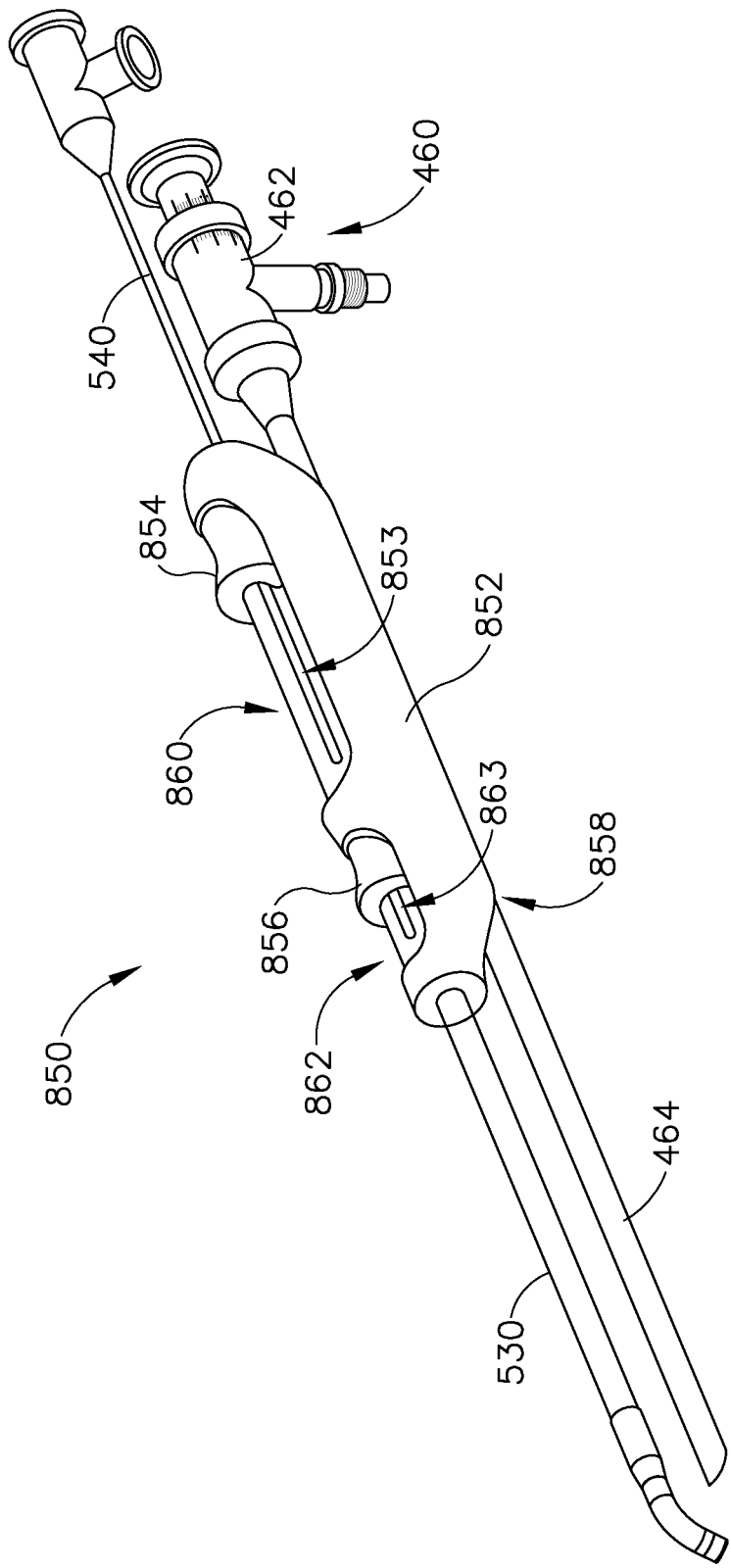
FIG. 48 depicts a perspective view of yet another exemplary handle suitable for use with the dilation catheter system of FIG. 12, with the guide catheter of FIG. 7A, an exemplary balloon dilation catheter, and the endoscope of FIG. 15 positioned therein.
Figure 49:
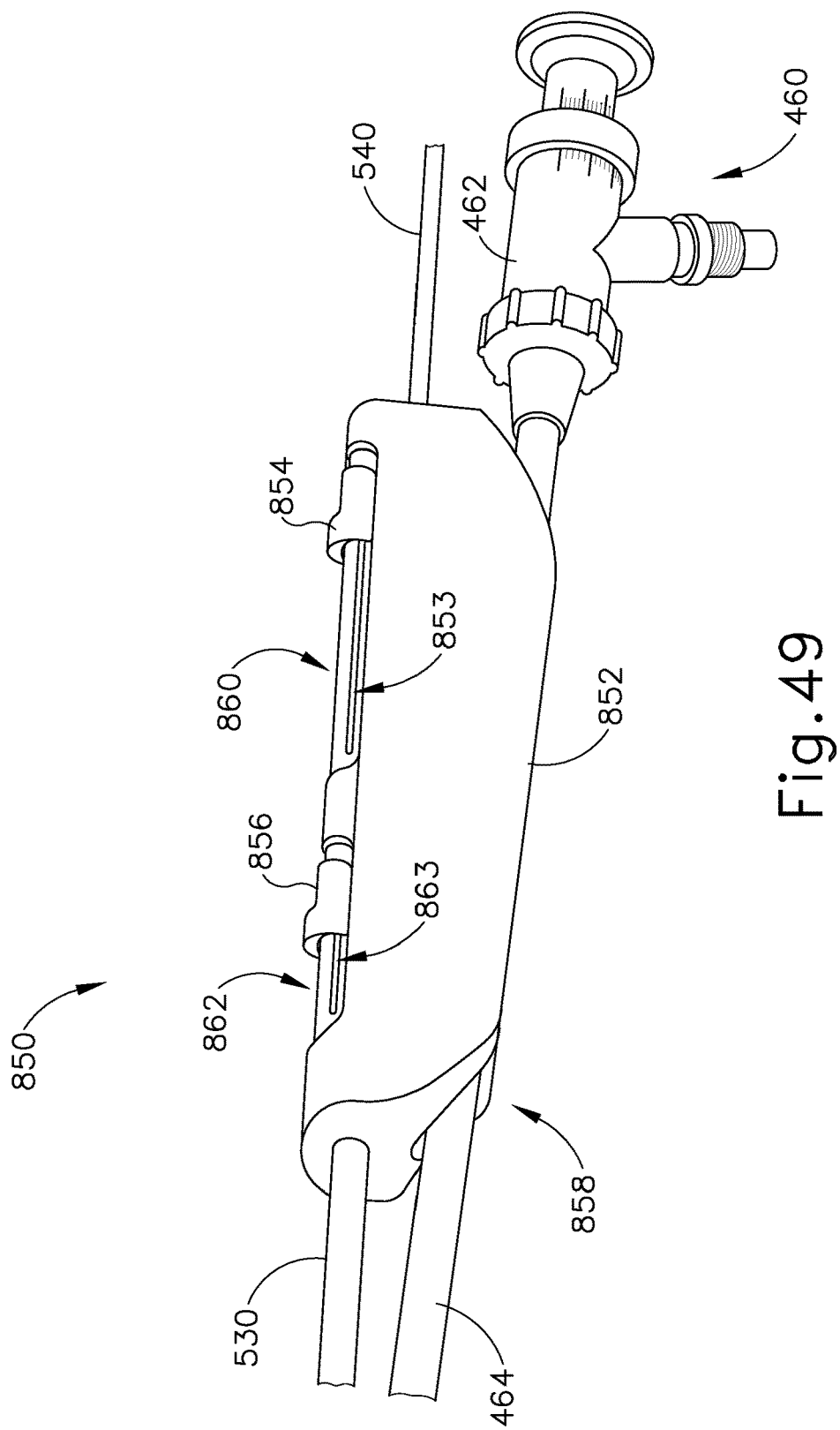
FIG. 49 depicts another perspective view of the handle of FIG. 48, with the guide catheter of FIG. 7A, the balloon dilation catheter of FIG. 48, and the endoscope of FIG. 15 positioned therein.
Figure 50:
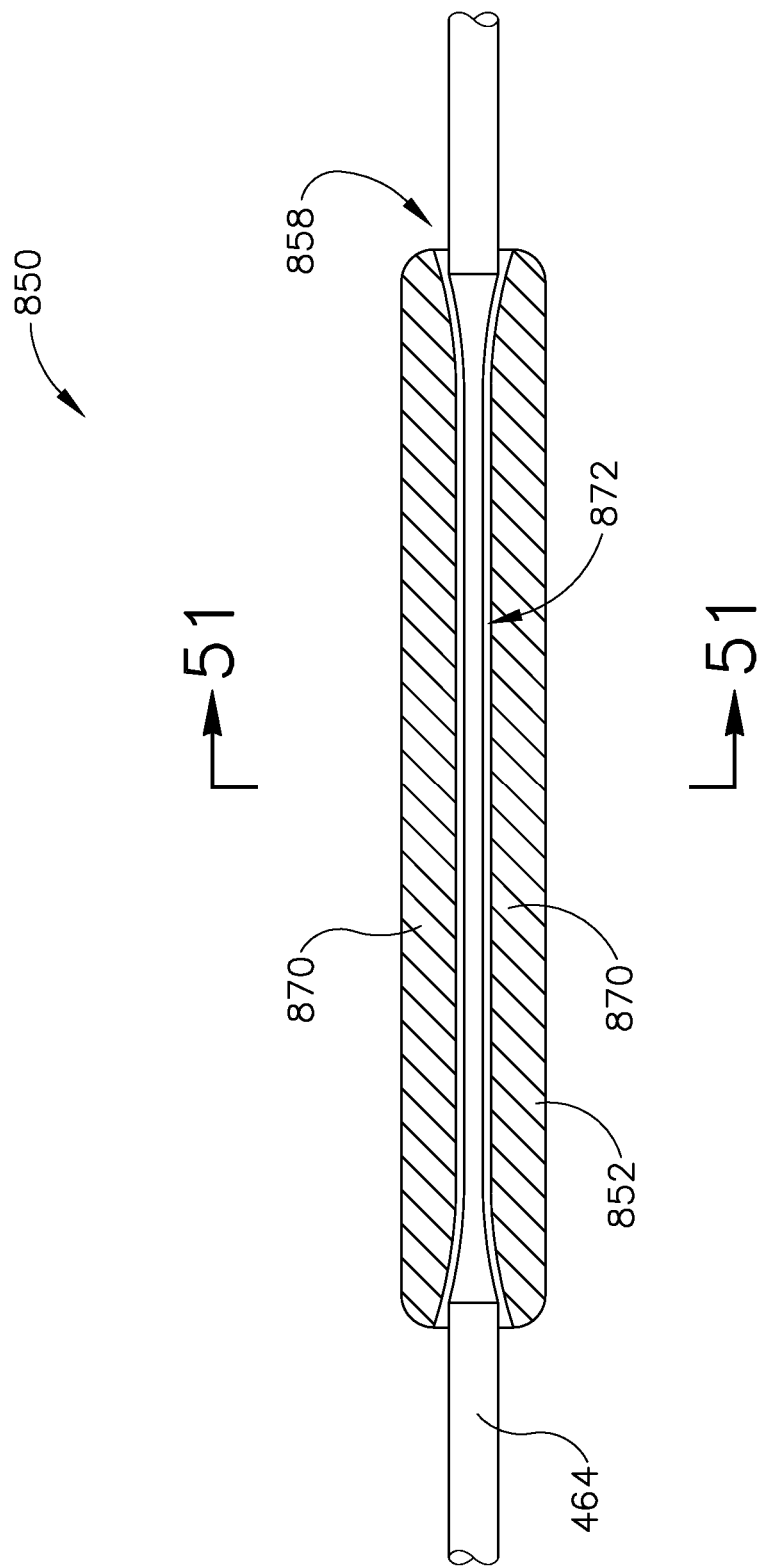
FIG. 50 depicts a bottom plan view of the handle of FIG. 48, with the guide catheter of FIG. 7A, the balloon dilation catheter of FIG. 48, and the endoscope of FIG. 15 positioned therein.

FIGS. 46-47C show another exemplary single-hand-use handle (800). As will be described in more detail below, handle (800) is operable to combine guide catheter (530), balloon dilation catheter (540), and endoscope (460) in such a manner as to allow a user to maneuver and operate each element using only a single hand. Handle (800) of the present example comprises a body (802), a balloon dilation catheter actuator (804), and a guide catheter actuator (806). Body (802) includes a through-bore (808) formed in a lower portion of body (802). Through-bore (808) extends the length of body (802). Through-bore (808) is operable to receive and selectively retain shaft (464) of endoscope (460). Body (802) further includes a channel (810) formed in an upper portion of body (802). Channel (810) extends partially the length of body (802). An elongate opening (811) formed in a bottom surface of body (802) extends substantially the length of channel (810) and provides external access to channel (810). Balloon dilation catheter actuator (804) is slidably coupled within channel (810) of body (802) via elongate opening (811) such that balloon dilation catheter actuator (804) may translate within channel (810) between a proximal longitudinal position and a distal longitudinal position along a length of channel (810). Balloon dilation catheter actuator (804) is coupled with balloon dilation catheter (540) such that translation of balloon dilation catheter actuator (804) within channel (810) causes concurrent translation of balloon dilation catheter (540) relative to body (802) as shown in FIG. 47C. As best seen in FIGS. 47A-47C, an exterior surface of balloon dilation catheter actuator (804) is saddle-shaped. This saddle-shaped exterior surface allows a user to easily locate and maneuver balloon dilation catheter actuator (804) with only a single finger or thumb while holding handle (800).

Body (802) further includes a channel (812) formed in a side portion of body (802) distally of channel (810). Channel (812) extends partially the length of body (802). An elongate opening (813) formed in a side surface of body (802) extends substantially the length of channel (812) and provides external access to channel (812). Guide catheter actuator (806) is slidably coupled within channel (812) of body (802) via elongate opening (813) such that guide catheter actuator (806) may translate within channel (812) between a proximal longitudinal position and a distal longitudinal position along a length of channel (812). Guide catheter actuator (806) is coupled with guide catheter (530) such that translation of guide catheter actuator (806) within channel (812) causes concurrent translation of guide catheter (530) relative to body (802) as shown in FIG. 47B.

It should be appreciated from the discussion above that handle (800) may be grasped and maneuvered, and actuators (804, 806) may be translated, all using a single hand. For instance, while grasping handle (800), the user may use his or her index finger or thumb to translate actuators (804, 806).

FIGS. 48-51 show an exemplary variation of handle (800), handle (850). As will be described in more detail below, handle (850) is operable to combine guide catheter (530), balloon dilation catheter (540), and endoscope (460) in such a manner as to allow a user to maneuver and operate each element using only a single hand. Handle (850) of the present example comprises a body (852), a balloon dilation catheter actuator (854), and a guide catheter actuator (856). Body (852) includes a through-bore (858) formed in a lower portion of body (852). Through-bore (858) extends the length of body (852). As will be described in more detail below, through-bore (858) is operable to receive and selectively retain shaft (464) of endoscope (460). Body (852) further includes an elongate recess (860) formed in a top surface of body (852). Recess (860) extends partially the length of body (852). Balloon dilation catheter actuator (854) is slidably coupled within recess (860) of body (852) via a pair of tracks (853) such that balloon dilation catheter actuator (854) may translate within recess (860) between a proximal longitudinal position and a distal longitudinal position along a length of recess (860). Balloon dilation catheter actuator (854) is coupled with balloon dilation catheter (540) such that translation of balloon dilation catheter actuator (854) within recess (860) causes concurrent translation of balloon dilation catheter (540) relative to body (852). An exterior surface of balloon dilation catheter actuator (854) is saddle-shaped. This saddle-shaped exterior surface allows a user to easily locate and maneuver balloon dilation catheter actuator (854) with only a single finger or thumb while holding handle (850).

Body (852) further includes an elongate recess (862) formed in the top surface of body (852) distally of recess (860). Recess (862) extends partially the length of body (852). Guide catheter actuator (856) is slidably coupled within recess (862) of body (852) via a pair of tracks (863) such that guide catheter actuator (856) may translate within recess (862) between a proximal longitudinal position and a distal longitudinal position along a length of recess (862). Guide catheter actuator (856) is coupled with guide catheter (530) such that translation of guide catheter actuator (856) within recess (862) causes concurrent translation of guide catheter (530) relative to body (852). An exterior surface of guide catheter actuator (856) is saddle-shaped. This saddle-shaped exterior surface allows a user to easily locate and maneuver guide catheter actuator (856) with only a single finger or thumb while holding handle (850).

Figure 51:
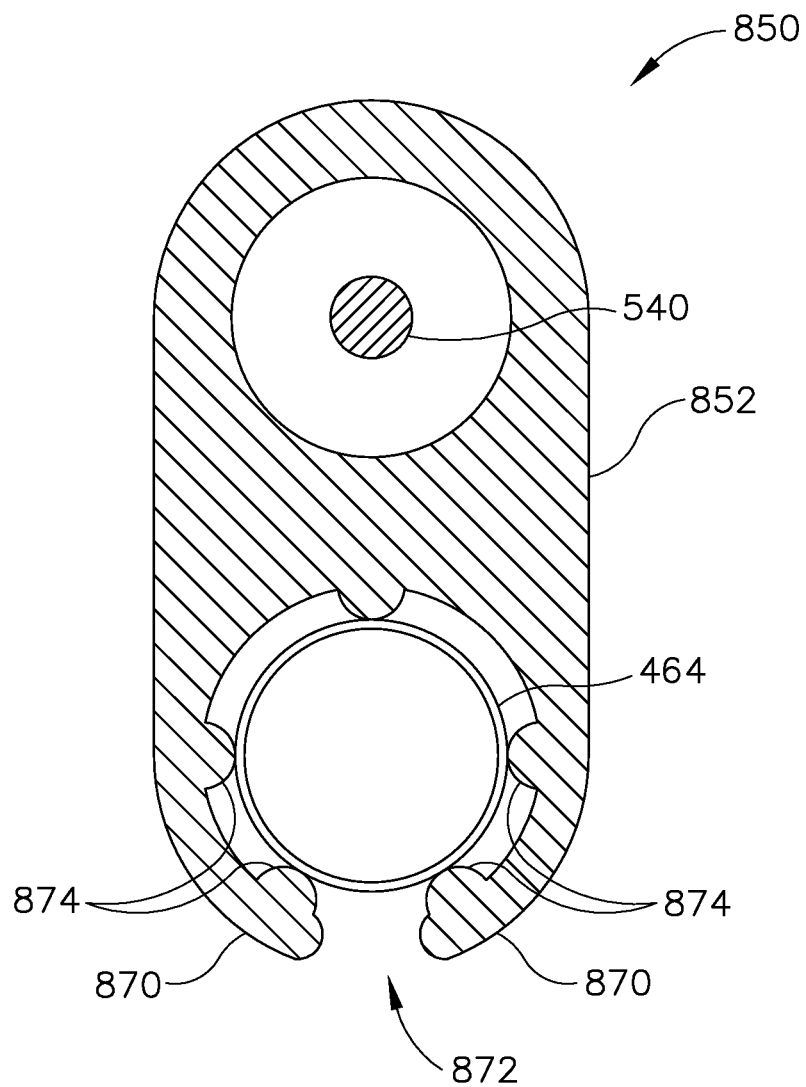
FIG. 51 depicts a cross-sectional rear view of the handle of FIG. 48 taken along line 51-51 of FIG. 50, with the guide catheter of FIG. 7A, the balloon dilation catheter of FIG. 48, and the endoscope of FIG. 15 positioned therein.

As mentioned above, body (852) includes a through-bore (858) formed in a lower portion of body (852). Body (852) includes a pair of resilient semi-circular flanges (870) that envelop and define through-bore (858) as best seen in FIG. 51. A gap (872) is defined between interior surfaces of flanges (870) such that flanges (870) may flex inwardly and outwardly toward and away from one another. In particular, flanges (870) are biased toward the position shown in FIG. 51, but may flex outwardly to accommodate insertion of shaft (464) of endoscope (460) into through-bore (858). Thus, it should be understood that shaft (464) of endoscope (460) may be positioned within through-bore (858) by coaxially aligning shaft (464) with through-bore (858) and inserting shaft (464) into through-bore (858) via an end of through-bore (858); or by aligning shaft (464) with gap (872) and upwardly inserting shaft (464) into through-bore (858) via gap (872) by causing flanges (870) to flex outwardly. Through-bore (858) includes a plurality of elongate ribs (874) extending inwardly from an interior surface of through-bore (858) and flanges (870). With endoscope (460) positioned within through-bore (858), ribs (874) are configured to bear against an exterior surface of endoscope (460) to thereby lock endoscope (460) within through-bore (858). It should be appreciated that the force exerted upon shaft (464) of endoscope (460) by ribs (874) may be great enough to effectively prevent all movement of endoscope (460) or only so great so as to prohibit inadvertent movement of endoscope (460) but at the same time allowing intentional movement of endoscope (460).

It should be appreciated from the discussion above that handle (850) may be grasped and maneuvered, and actuators (854, 856) may be translated, all using a single hand. For instance, while grasping handle (850), the user may use his or her index finger or thumb to translate actuators (854, 856).

IV. Exemplary Integral Pump

It may be desirable to provide a system for dilation of the Eustachian tube (26) that would include an integral pump operable to expand a balloon (544) of balloon dilation catheter (540). For instance, it may be desirable to provide a handle with an integral pump to allow a user while single-handedly operating dilation catheter system (410) described above, to further expand balloon (544) with the same single hand. In particular, and as will be described in more detail below, such an integral pump may be provided as an integral element of handle, balloon dilation catheter (540), or any other appropriate element of dilation catheter system (410) described herein. Various examples of such integral pumps will be described in greater detail below; while other examples will be apparent to those of ordinary skill in the art in view of the teachings herein. While the following examples are provided in the context of dilating a Eustachian tube (26) it should be understood that the same examples may be readily applied to the context of dilating ostia of paranasal sinuses, the frontal recess, and/or other anatomical passageways associated with the ear, nose, and throat.

A. Exemplary Catheter with Integral Pump

Figure 52:
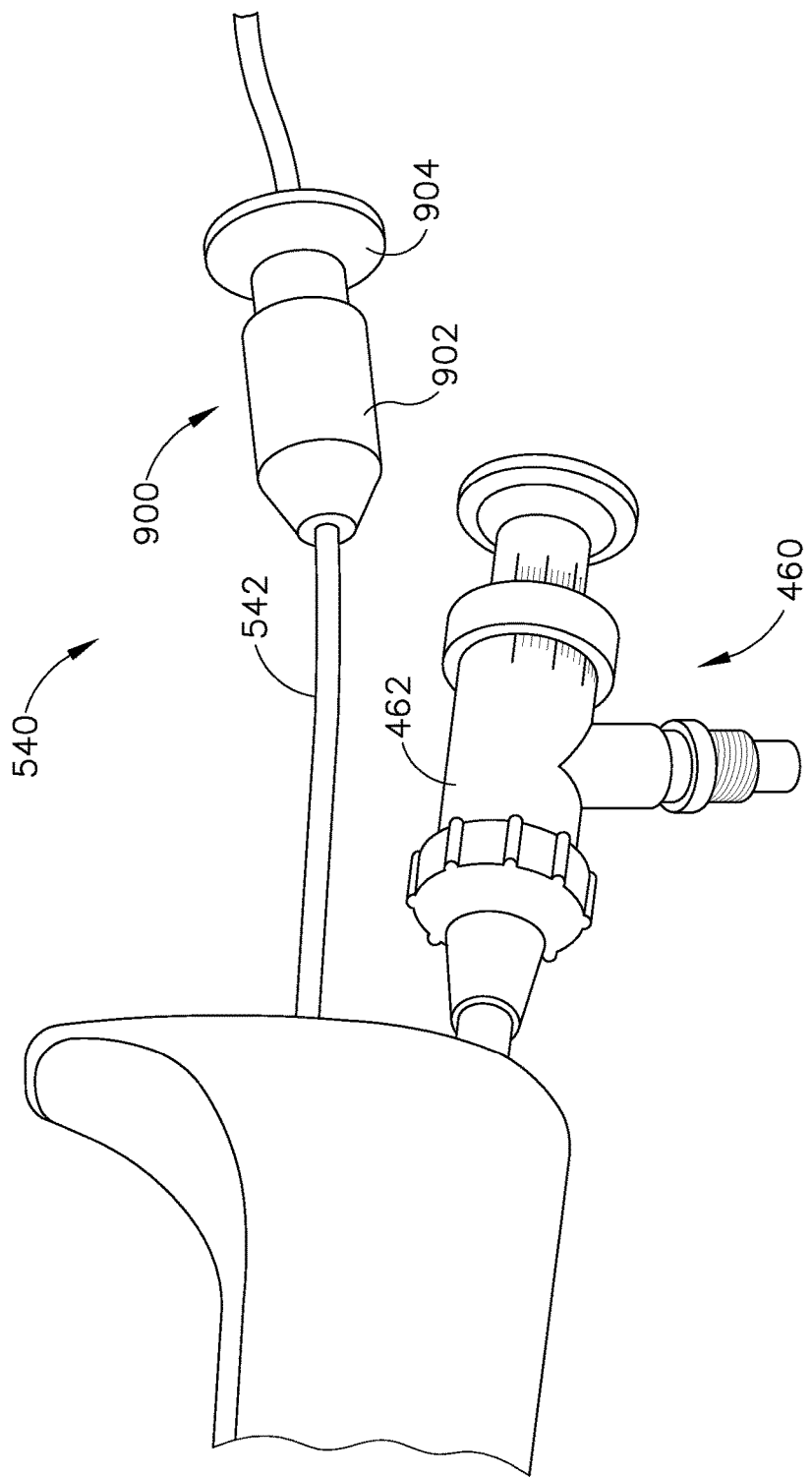
FIG. 52 depicts a perspective view of an exemplary in-line balloon dilation catheter pump.
Figure 53A:
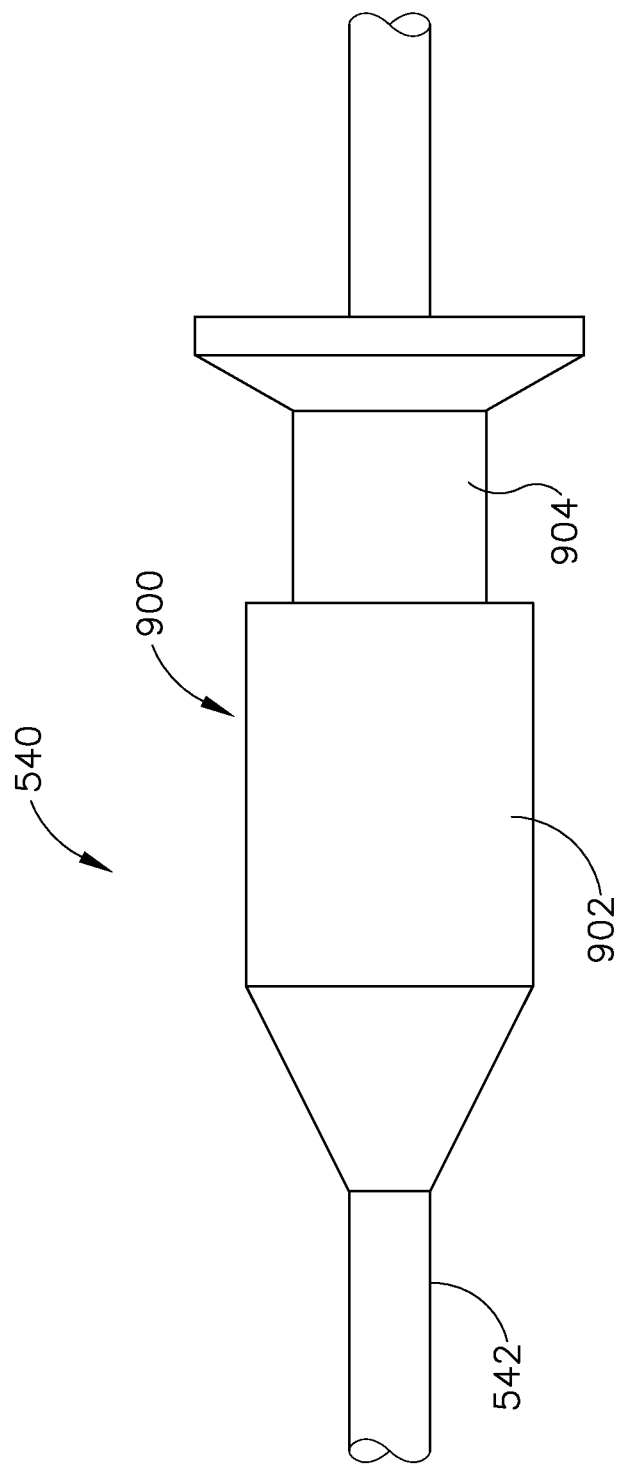
FIG. 53A depicts a side elevational view of the pump of FIG. 52, with an actuator of the pump in a first position.
Figure 53B:
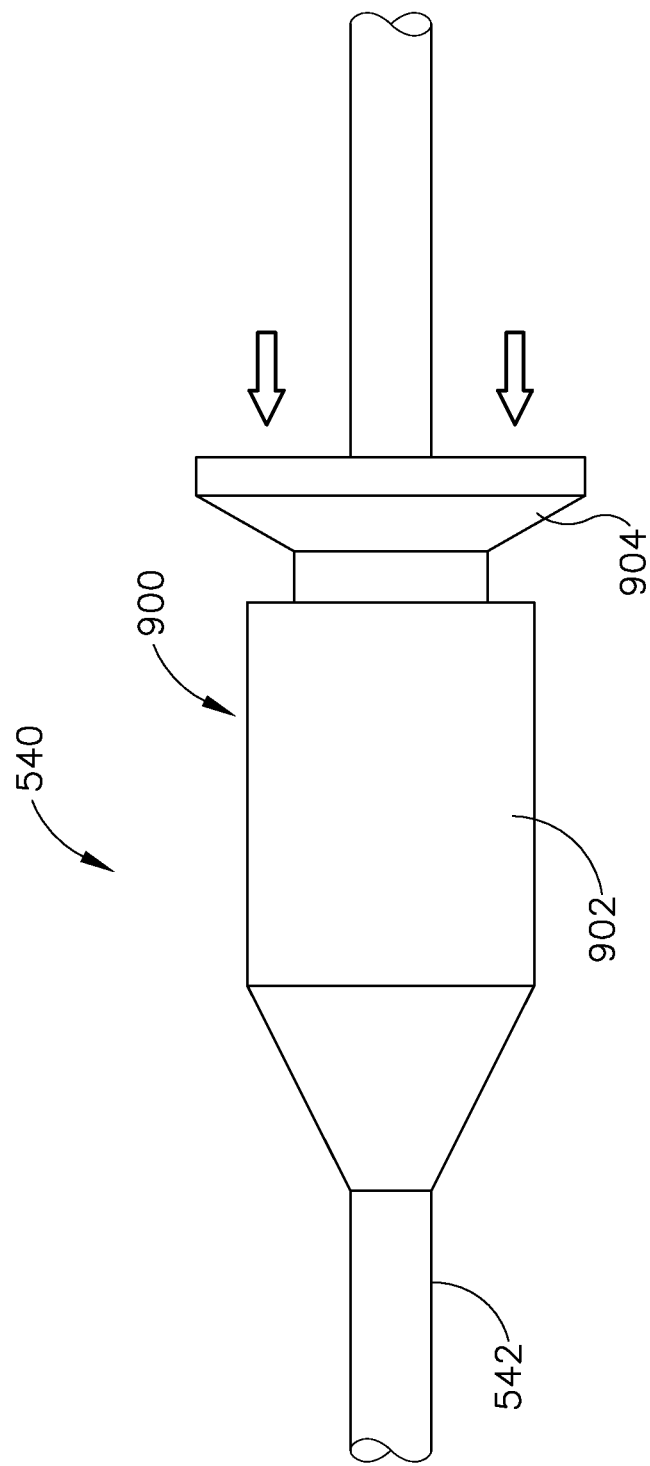
FIG. 53B depicts a side elevational view of the pump of FIG. 52, with the actuator of FIG. 53A moved into a second position.

FIGS. 52-53B show an exemplary integral pump (900). Pump (900) is configured as an integral element of balloon dilation catheter (540). In particular, pump (900) is configured as being in-line with an elongate shaft (542) of balloon dilation catheter (540). Pump (900) includes a body (902) and an actuator (904). Body (902) is positioned about elongate shaft (542) such that elongate shaft (542) passes through a hollow interior of body (902). Actuator (904) is slidably disposed within the hollow interior of body (902) and about elongate shaft (542) such that actuator (904) is operable to translate within body (902) and along elongate shaft (542) relative to body (902) and elongate shaft (542). A fluid seal exists between an exterior surface of actuator (904) and an interior surface of body (902) such that distal translation of actuator (904) into body (902), as shown in FIG. 53B, compresses fluid within the hollow interior of body (902). The hollow interior of body (902) is in fluid communication with a hollow interior of elongate shaft (542) such that this compressed fluid is communicated into the interior of elongate shaft (542). This compressed fluid within elongate shaft (542) is then communicated to balloon (544) to thereby expand balloon (544).

To deflate balloon (544), actuator (904) may be translated proximally to thereby draw fluid from within balloon (544) back into the hollow interior of body (902). In some versions, actuator (904) is resiliently biased proximally (e.g., by a spring positioned within the hollow interior of body (902)), such that simply releasing actuator (904) causes actuator (904) to retract proximally, thereby drawing fluid from within balloon (544) back into the hollow interior of body (902). In such versions of pump (900), it should be understood that actuator (904) may be pressed and released repeatedly to thereby cause repeated expansion and deflation of balloon (544). In some other versions, actuator (904) must be pulled proximally by the operator in order to draw fluid from within balloon (544) back into the hollow interior of body (902). In some such versions, actuator (904) includes a thumb ring or other feature facilitating manual proximal movement of actuator (904). Other suitable configurations, features, and operabilities will be apparent to those of ordinary skill in the art in view of the teachings herein.

B. Exemplary Handle with Integral Pump

Figure 54:
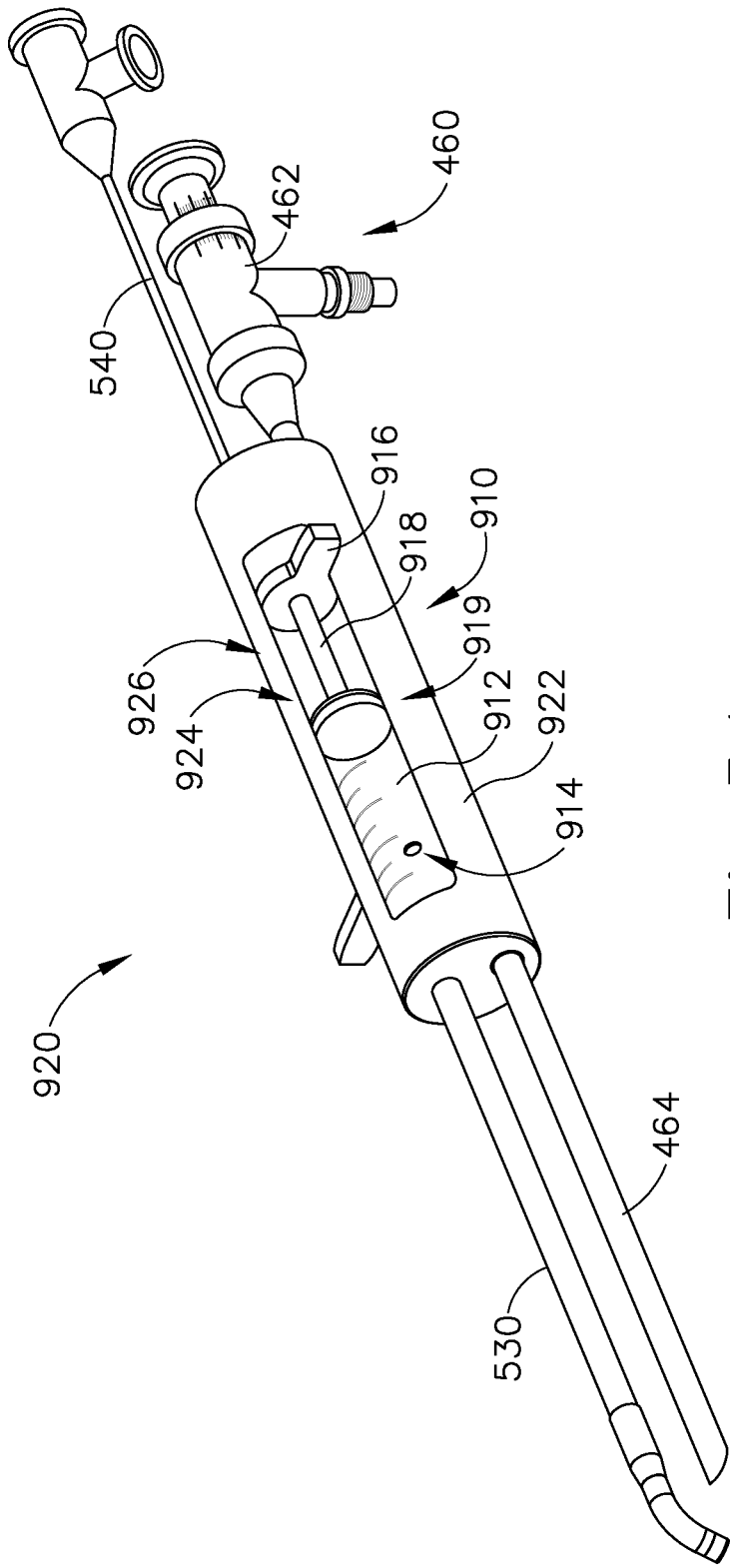
FIG. 54 depicts a perspective view of yet another exemplary handle suitable for use with the dilation catheter system of FIG. 12, with the guide catheter of FIG. 7A, an exemplary balloon dilation catheter, and the endoscope of FIG. 15 positioned therein.

FIG. 54 shows another exemplary integral pump (910). Pump (910) is configured as an integral element of a handle (920). Handle (920) includes a body (922). Body (922) includes a channel (924) formed in a side portion of body (922). Channel (924) extends partially the length of body (922). An elongate opening (926) formed in a side surface of body (922) extends substantially the length of channel (924) and provides external access to channel (924). A syringe-barrel-like tube (912) is positioned within a distal portion of channel (924). Tube (912) is in fluid communication with the hollow interior of elongate shaft (542) via an opening (914) formed in a sidewall of tube (912). Pump (910) includes an actuator (916). Actuator (916) is slidably coupled within channel (924) of body (922) via elongate opening (926) such that actuator (916) may translate within channel (924) between a proximal longitudinal position and a distal longitudinal position along a length of channel (924). Actuator (916) includes a plunger (918) extending from a distal end of actuator (916). A distal portion (919) of plunger (918) is slidably disposed within the hollow interior of tube (912) such that plunger (918) is operable to translate within tube (912) relative to tube (912). A fluid seal exists between an exterior surface of distal portion (919) of plunger (918) and an interior surface of tube (912) such that translation of plunger (918) into tube (912) is operable to compress fluid within the hollow interior of tube (912). Thus, it should be understood that as actuator (916) is translated distally within channel (924), plunger (918) is operable to compress fluid within the hollow interior of tube (912). In other words, pump (910) of the present example is configured like a syringe integral with body (922). As mentioned above, the hollow interior of tube (912) is in fluid communication with the hollow interior of elongate shaft (542) such that compressed fluid within tube (912) is communicated into the interior of elongate shaft (542). This compressed fluid within elongate shaft (542) is then communicated to balloon (544) to thereby expand balloon (544).

To deflate balloon (544), plunger (918) may be translated proximally within channel (924) to thereby draw fluid from within balloon (544) back into the hollow interior of tube (912). In some versions, plunger (918) is resiliently biased proximally (e.g., by a spring, etc.) such that simply releasing plunger (918) causes plunger (918) to retract proximally, thereby drawing fluid from within balloon (544) back into the hollow interior of tube (912). In such versions of pump (910), it should be understood that plunger (918) may be pressed and released repeatedly to thereby cause repeated expansion and deflation of balloon (544). In some other versions, plunger (918) must be pulled proximally by the operator in order to draw fluid from within balloon (544) back into the hollow interior tube (912). In some such versions, plunger (918) includes a thumb ring or other feature facilitating manual proximal movement of plunger (918). Other suitable configurations, features, and operabilities will be apparent to those of ordinary skill in the art in view of the teachings herein.

C. Exemplary Actuator with Integral Fluid Fitting

Figure 55:
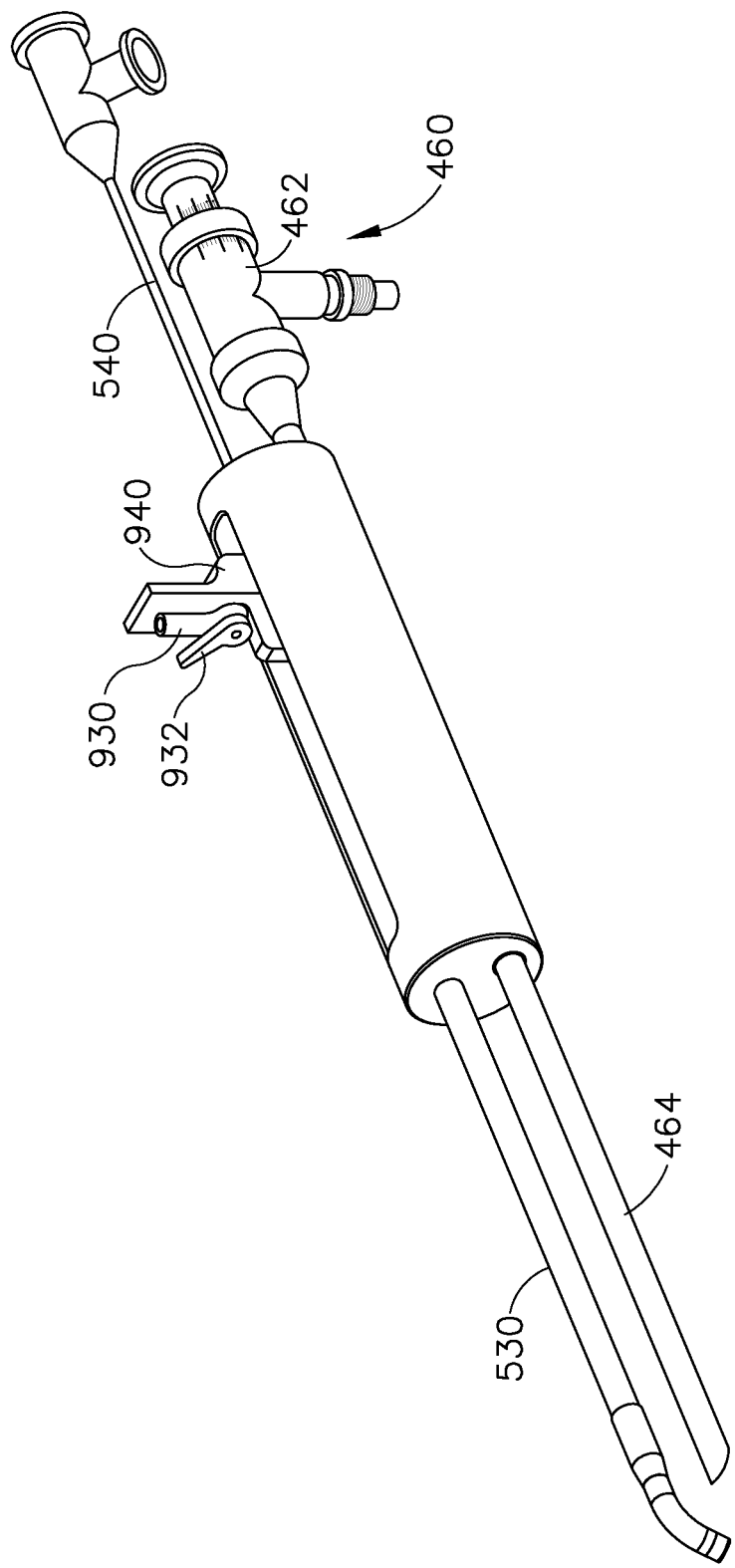
FIG. 55 depicts a perspective view of yet another exemplary handle suitable for use with the dilation catheter system of FIG. 12, with the guide catheter of FIG. 7A, an exemplary balloon dilation catheter, and the endoscope of FIG. 15 positioned therein.
Figure 56:
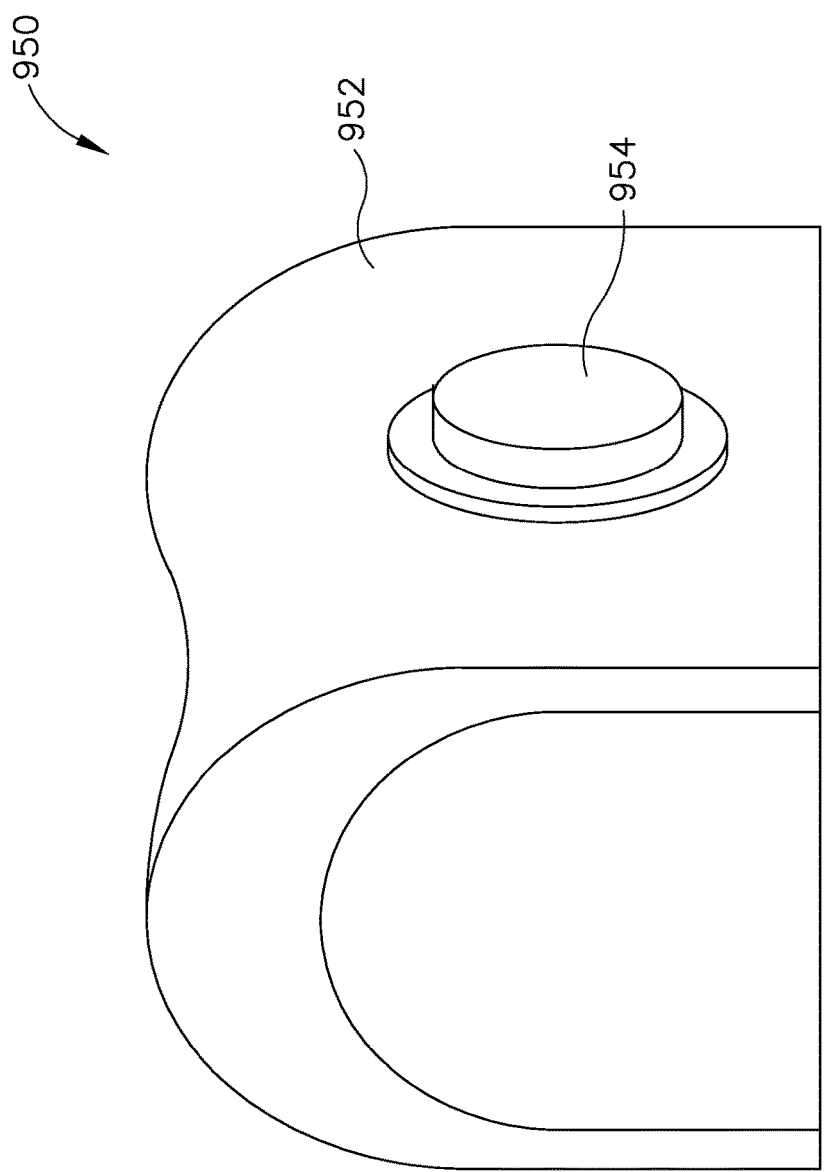
FIG. 56 depicts a perspective view of an exemplary actuator suitable for use with any of the handles described herein.
Figure 57:
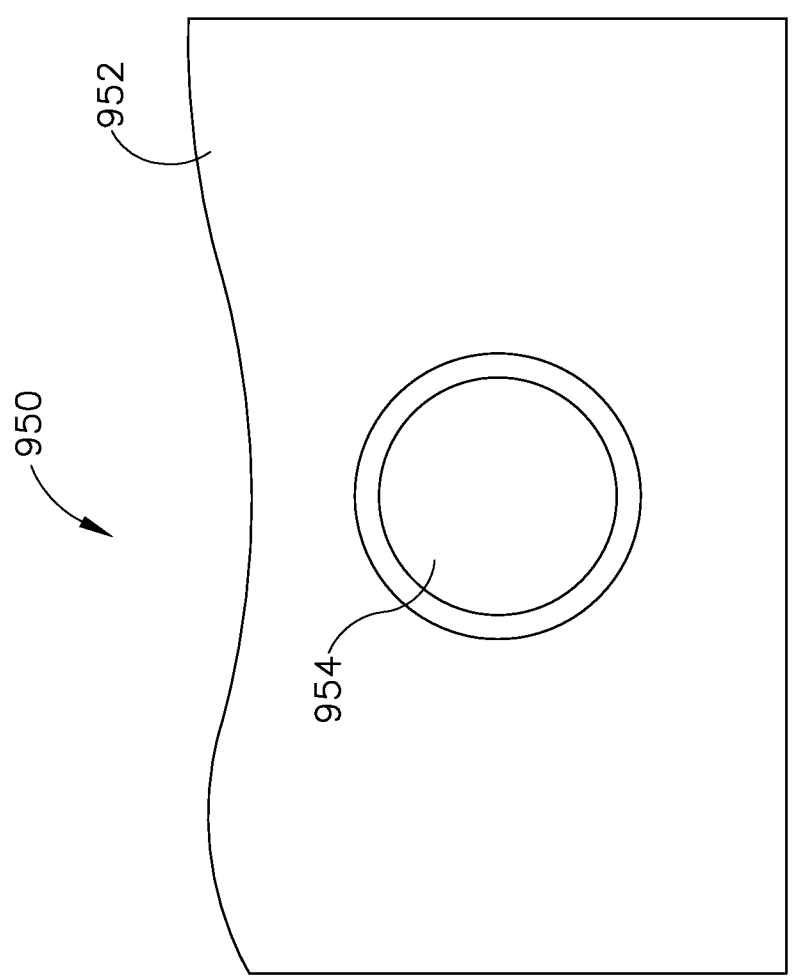
FIG. 57 depicts a side elevational view of the actuator of FIG. 56.

FIG. 55 shows an exemplary integral fluid fitting (930). Fluid fitting (930) of the present example is configured as an integral element of an actuator (940). Actuator (940) may be coupled with balloon dilation catheter (540) and/or endoscope (460) such that translation of actuator (940) causes concurrent translation of balloon dilation catheter (540) and/or endoscope (460). Fluid fitting (930) is in fluid communication with the hollow interior of elongate shaft (542) such that compressed fluid may be passed through fluid fitting (930) and into the interior of elongate shaft (542). This compressed fluid within elongate shaft (542) is then communicated to balloon (544) to thereby expand balloon (544). Fluid fitting (930) includes a handle (932) configured to control the flow of fluid through fluid fitting (930).

V. Exemplary Selective Coupling Actuators

It may be desirable to provide any of the actuators (306, 504, 554, 604, 654, 704, 754, 804, 806, 854, 856, 904, 916, 940) described above with features that allow a user to selectively couple such actuators (306, 504, 554, 604, 654, 704, 754, 804, 806, 854, 856, 904, 916, 940) with balloon dilation catheter (540) and/or guide catheter (530) such that translation of such actuators (306, 504, 554, 604, 654, 704, 754, 804, 806, 854, 856, 904, 916, 940) is only communicated to balloon dilation catheter (540) and/or guide catheter (530) when desired. In some such versions, movement of such actuators will not be communicated to balloon dilation catheter (540) and/or guide catheter (530) when such communication is not desired. Various examples of such actuators will be described in greater detail below; while other examples will be apparent to those of ordinary skill in the art in view of the teachings herein. While the following examples are provided in the context of dilating a Eustachian tube (26) it should be understood that the same examples may be readily applied to the context of dilating ostia of paranasal sinuses, the frontal recess, and/or other anatomical passageways associated with the ear, nose, and throat.

A. Exemplary Alternative Actuator with Sliding Buttons

Figure 58A:
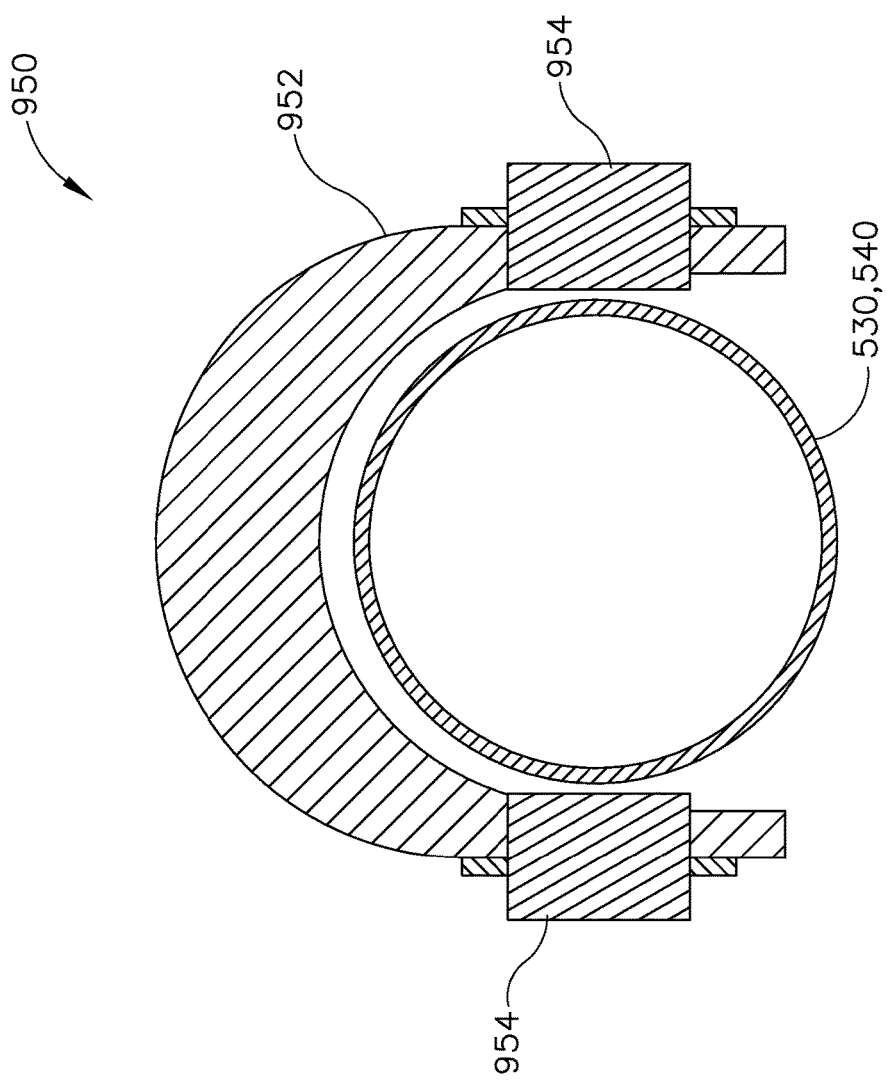
FIG. 58A depicts a cross-sectional front view of the actuator of FIG. 56, with a pair of buttons of the actuator in a first position.
Figure 58B:
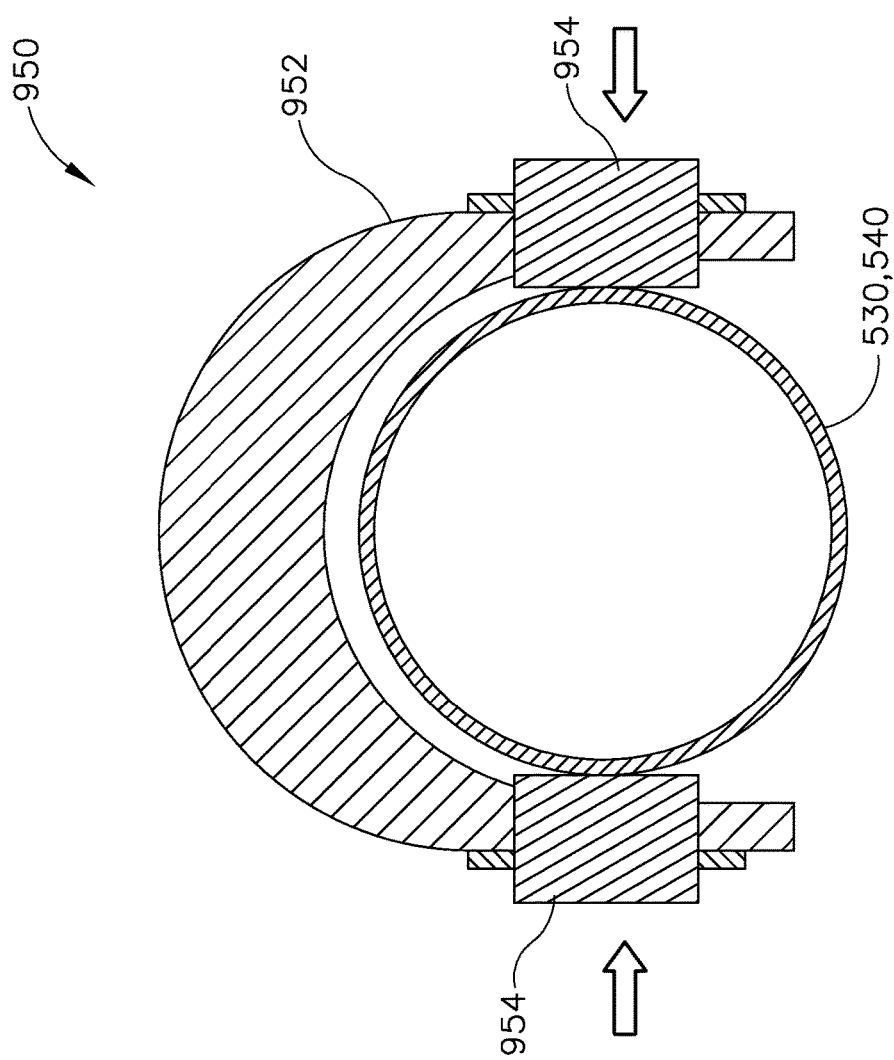
FIG. 58B depicts a cross-sectional front view of the actuator of FIG. 56, with the pair of buttons of FIG. 58A moved into a second position.
Figure 59:
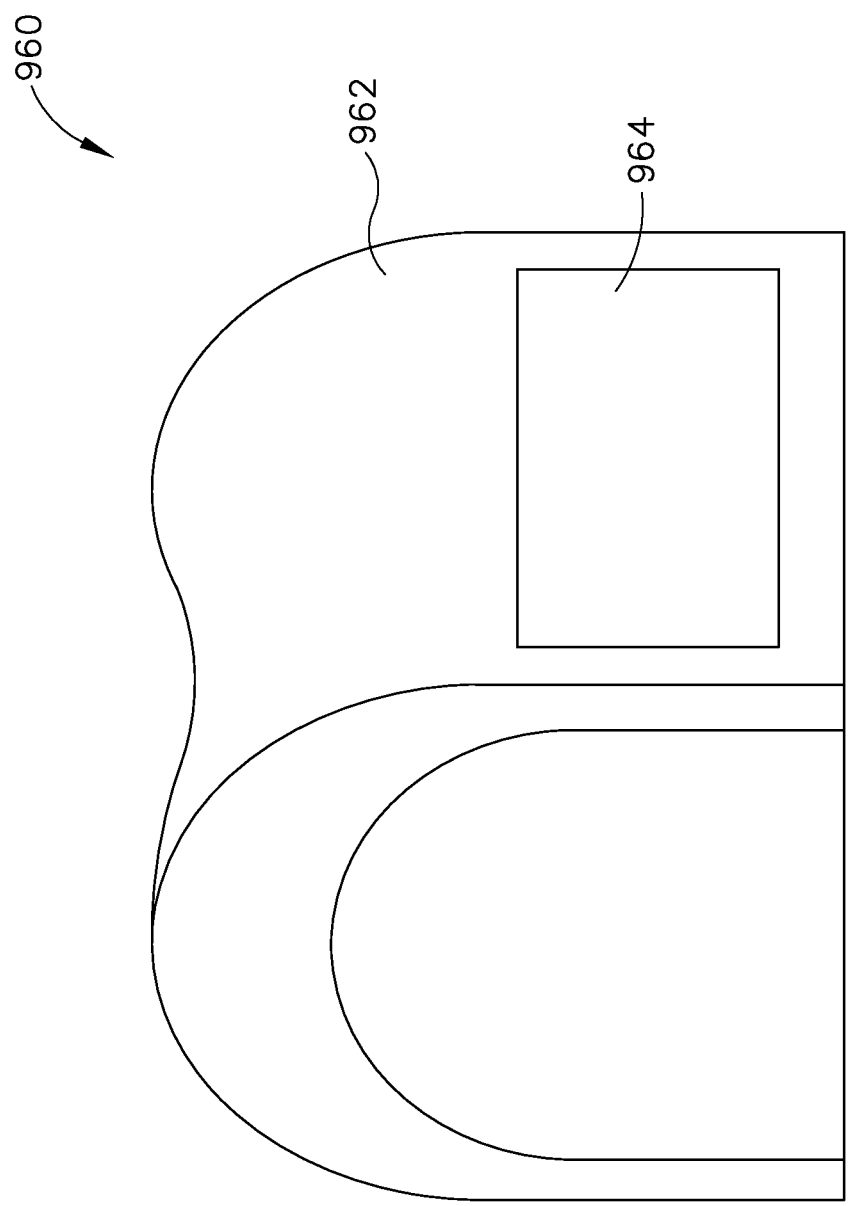
FIG. 59 depicts a perspective view of another exemplary actuator suitable for use with any of the handles described herein.
Figure 60:
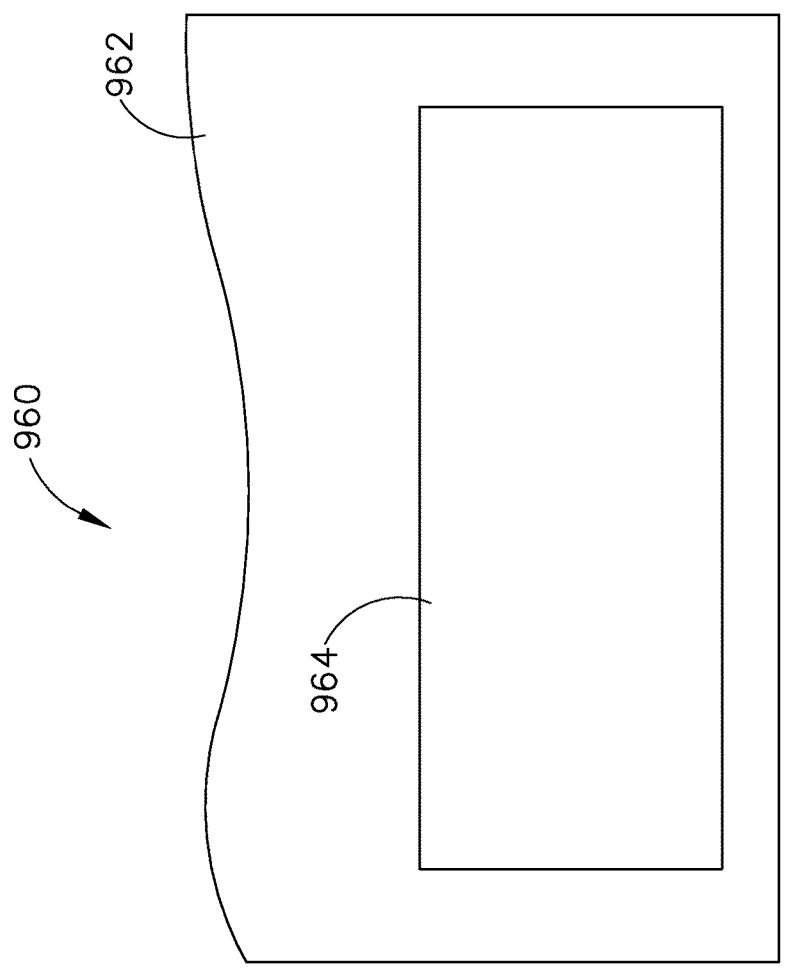
FIG. 60 depicts a side elevational view of the actuator of FIG. 59.

FIGS. 56-58B show an exemplary actuator (950). Actuator (950) comprises a body (952) having a hollow interior configured to slidably receive balloon dilation catheter (540) and/or guide catheter (530). Actuator (950) further comprises a pair of buttons (954) slidably disposed within opposite sidewalls of body (952). Buttons (954) extend from an interior surface of body (952) into the hollow interior of body (952). Buttons (954) are reseiliently biased toward a first position (e.g., by one or more springs, etc.) as shown in FIG. 58A; but are configured to translate inwardly in response to an inwardly directed force being exerted upon exterior surfaces of buttons (954) as shown in FIG. 58B. In the first position (FIG. 58A), a space exists between an interior surface of buttons (954) and an exterior surface of balloon dilation catheter (540) and/or guide catheter (530) such that translation of actuator (950) will not be communicated to balloon dilation catheter (540) and/or guide catheter (530). A user may exert an inwardly directed force upon the exterior surfaces of buttons (954) as shown in FIG. 58B such that the interior surface of buttons (954) engage the exterior surface of balloon dilation catheter (540) and/or guide catheter (530), thereby imposing friction on the exterior surface of balloon dilation catheter (540) and/or guide catheter (530), such that translation of actuator (950) will be communicated to balloon dilation catheter (540) and/or guide catheter (530). Thus, it should be understood that a user may selectively depress buttons (954) to thereby selectively communicate translation of actuator (950) to balloon dilation catheter (540) and/or guide catheter (530).

B. Exemplary Alternative Actuator with Deformable Members

Figure 61A:
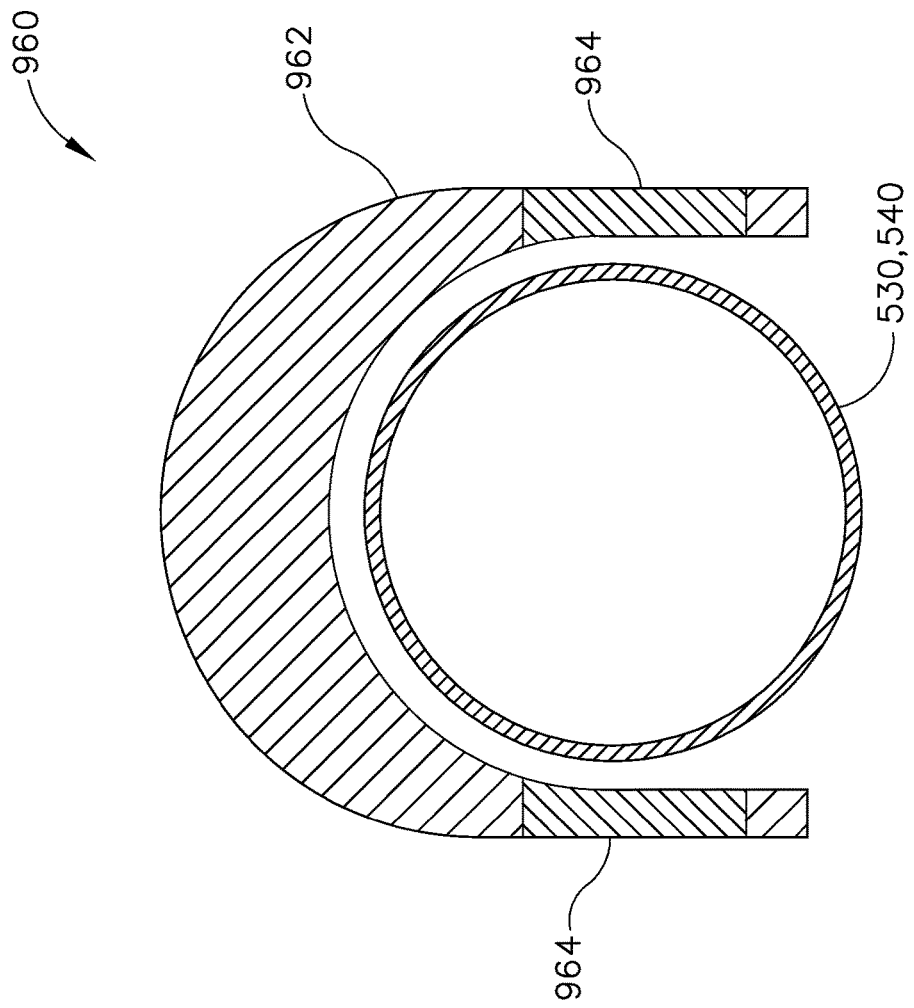
FIG. 61A depicts a cross-sectional front view of the actuator of FIG. 59, with a pair of buttons of the actuator in a first position.
Figure 61B:
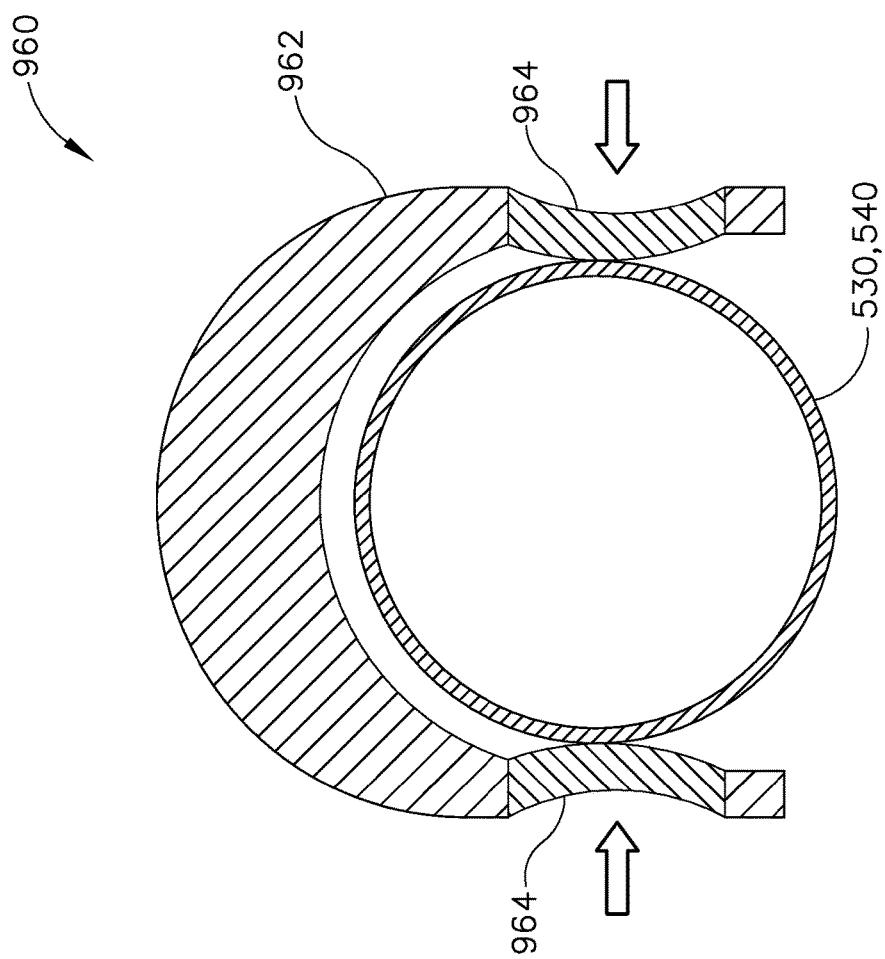
FIG. 61B depicts a cross-sectional front view of the actuator of FIG. 59, with the pair of buttons of FIG. 61A moved into a second position.

FIGS. 59-61B show another exemplary actuator (960). Actuator (960) comprises a body (962) having a hollow interior configured to slidably receive balloon dilation catheter (540) and/or guide catheter (530). Actuator (960) further comprises a pair of rectangular-shaped elastomeric membranes (964) disposed within opposite sidewalls of body (962). Membranes (964) extend between an exterior surface of body (962) and an interior surface of body (962). Membranes (964) are biased toward a first position as shown in FIG. 61A, but are configured to flex inwardly in response to an inwardly directed force being exerted upon an exterior surface of membranes (964) as shown in FIG. 61B. In the first position (FIG. 61A), a space exists between an interior surface of membranes (964) and an exterior surface of balloon dilation catheter (540) and/or guide catheter (530) such that translation of actuator (960) will not be communicated to balloon dilation catheter (540) and/or guide catheter (530). A user may exert an inwardly directed force upon the exterior surfaces of membranes (964) as shown in FIG. 61B such that the interior surface of membranes (964) engage the exterior surface of balloon dilation catheter (540) and/or guide catheter (530), thereby imposing friction on the exterior surface of balloon dilation catheter (540) and/or guide catheter (530), such that translation of actuator (960) will be communicated to balloon dilation catheter (540) and/or guide catheter (530). Thus, it should be understood that a user may selectively deform membranes (964) to thereby selectively communicate translation of actuator (960) to balloon dilation catheter (540) and/or guide catheter (530).

VI. Exemplary Handle Bodies

Figure 62:
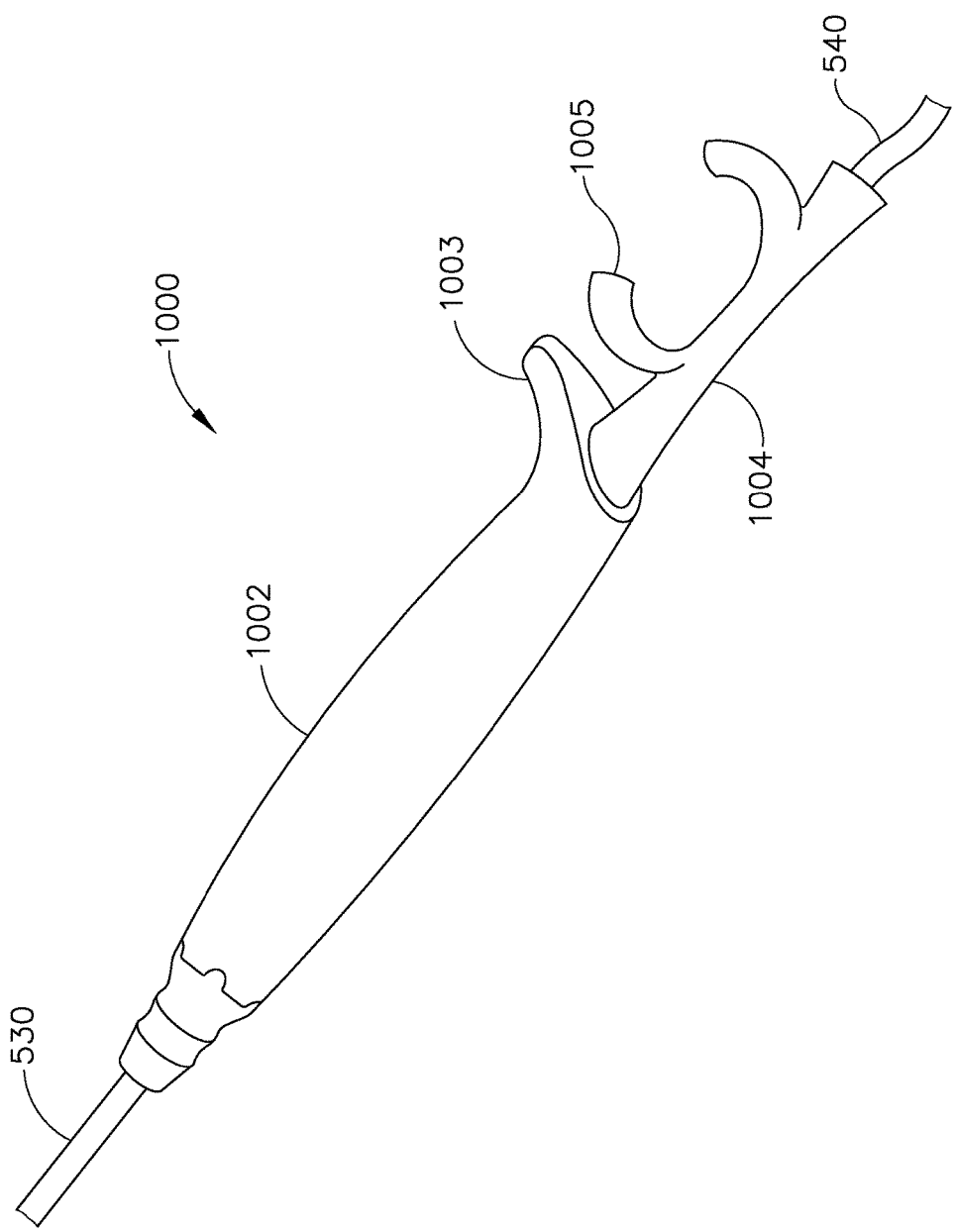
FIG. 62 depicts a perspective view of another exemplary handle suitable for use with the dilation catheter system of FIG. 12, with the guide catheter of FIG. 7A, an exemplary balloon dilation catheter, and the endoscope of FIG. 15 positioned therein.
Figure 63:
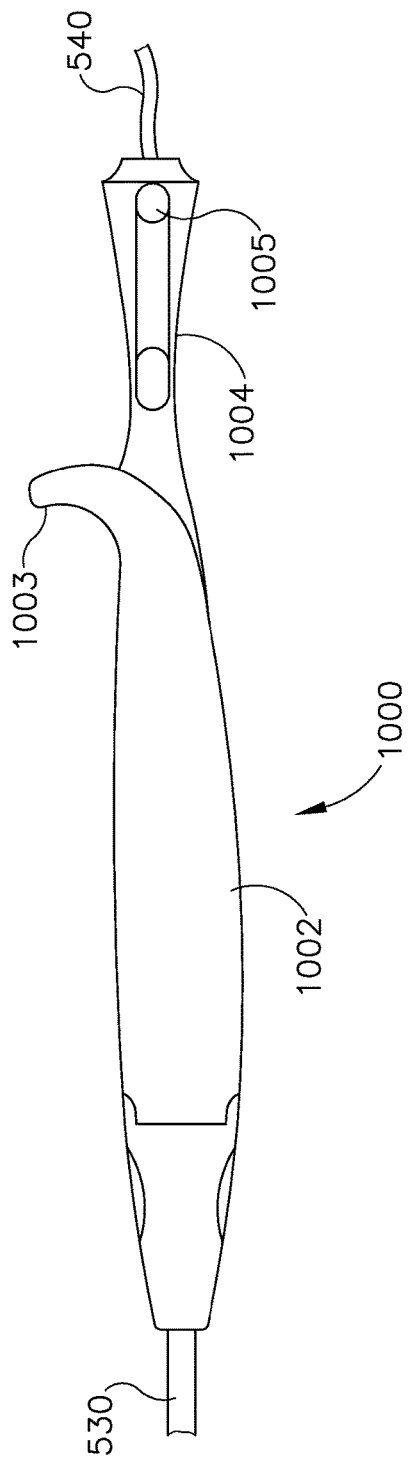
FIG. 63 depicts a top plan view of the handle of FIG. 62, with the guide catheter of FIG. 7A, the balloon dilation catheter of FIG. 62, and the endoscope of FIG. 15 positioned therein.
Figure 64:
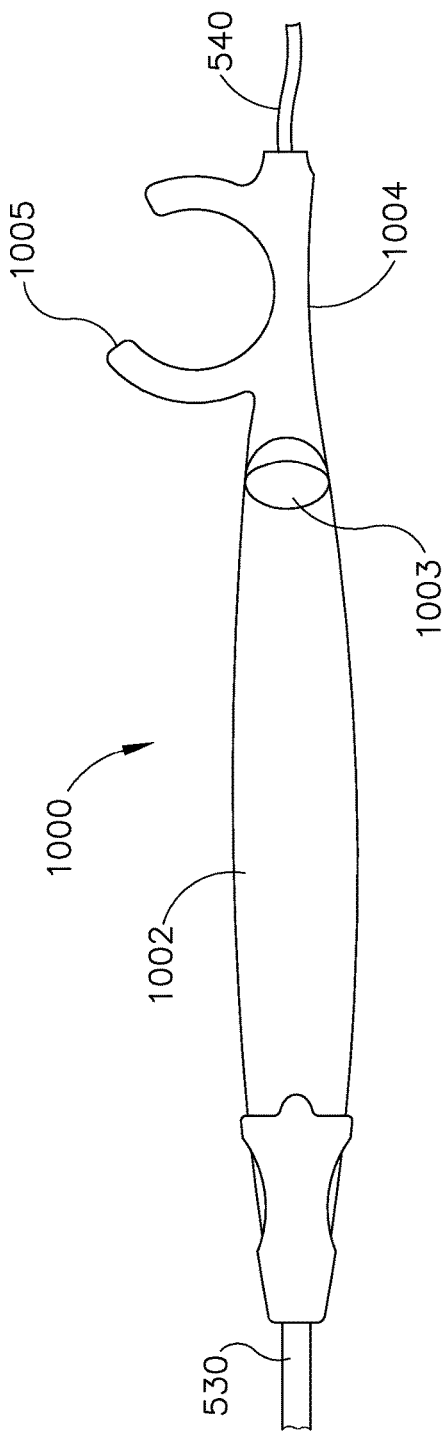
FIG. 64 depicts a side elevational view of the handle of FIG. 62, with the guide catheter of FIG. 7A, the balloon dilation catheter of FIG. 62, and the endoscope of FIG. 15 positioned therein.

FIGS. 62-69 show a series of exemplary bodies (1000, 1010, 1020, 1030, 1040, 1050) operable for incorporation in whole or in part with any of the handles (500, 550, 600, 650, 700, 750, 800, 850, 920) described above. FIGS. 62-64 shows an exemplary body (1000) that may be incorporated in whole or in part with any of the handles (500, 550, 600, 650, 700, 750, 800, 850, 920) described above. Body (1000) includes an elongated-oval-shaped handle portion (1002) and an actuator (1004). Actuator (1004) is slidably and rotatably disposed within a proximal end of handle portion (1002) such that actuator (1004) is operable to translate and/or rotate relative to handle portion (1002). Actuator (1004) is coupled with balloon dilation catheter (540) such that translation and/or rotation of actuator (1004) relative to handle portion (1002) causes concurrent translation of balloon dilation catheter (540). Actuator (1004) includes a semi-circular protrusion (1005) extending outwardly therefrom. A distal end of handle portion (1002) is configured to receive and selectively retain guide catheter (530) such that guide catheter (530) may be coupled with the distal end of body (1002) and extend distally therefrom. Handle portion (1002) includes a pommel (1003) formed in the proximal end of handle portion (1002) and extends outwardly therefrom. In the present example, protrusion (1005) and pommel (1003) are angularly offset from each other such that protrusion (1005) and pommel (1003) are oriented along respective planes that are separated by approximately 90° about the longitudinal axis of body (1000). Of course, protrusion (1005) and pommel (1003) may have any other suitable angular relationship.

It should be appreciated that handle portion (1002) may be gripped by a user such that the user's fingers and/or thumb rest adjacent pommel (1003). It should further be appreciated that as handle portion (1002) is being gripped, a user may user his or her finger or thumb to rotate and/or translate actuator (1004) relative to handle portion (1002) by engaging protrusion (1005) with their finger or thumb while gripping handle portion (1002) with the same hand.

Figure 65:
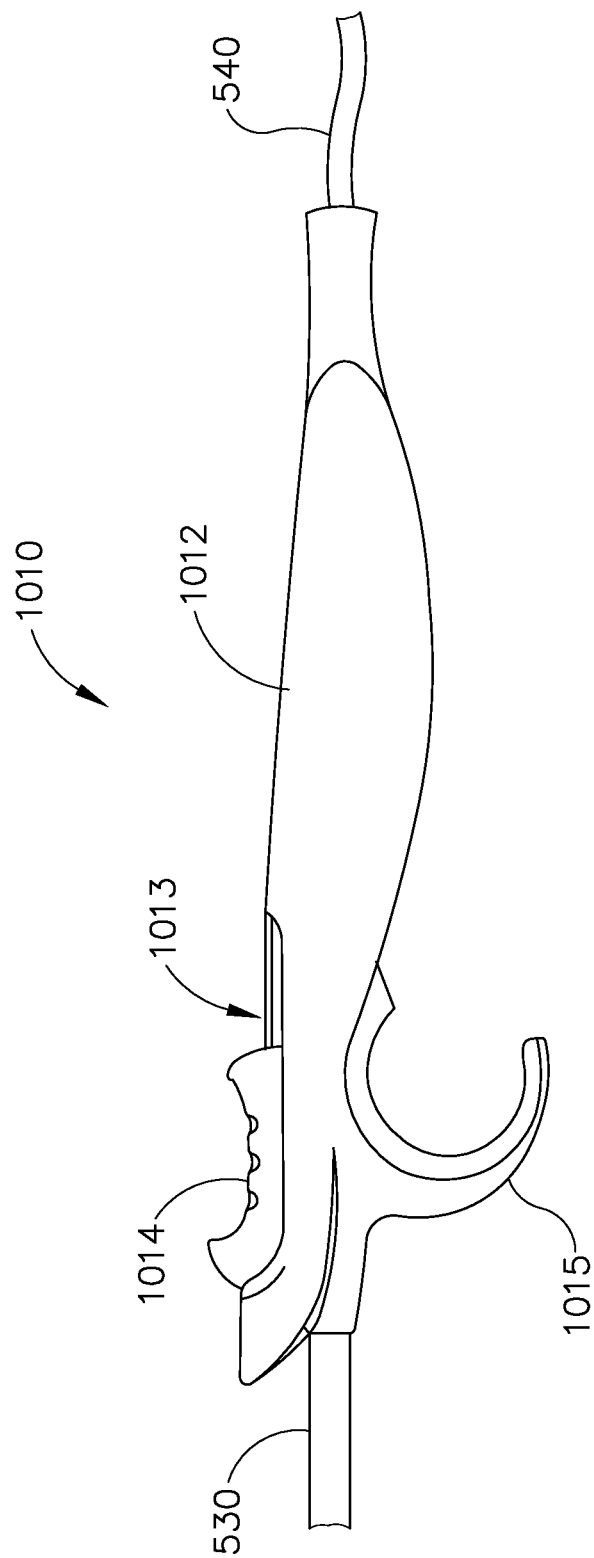
FIG. 65 depicts a side elevational view of another exemplary handle suitable for use with the dilation catheter system of FIG. 12, with the guide catheter of FIG. 7A, an exemplary balloon dilation catheter, and the endoscope of FIG. 15 positioned therein.

FIG. 65 shows another exemplary body (1010) operable for incorporation in whole or in part with any of the handles (500, 550, 600, 650, 700, 750, 800, 850, 920) described above. Body (1010) includes an elongated handle portion (1012) and an actuator (1014). Actuator (1014) is slidably disposed within an elongate recess (1013) formed in a top surface of handle portion (1012) such that actuator (1014) is operable to translate relative to handle portion (1012) within elongate recess (1013). Actuator (1014) is coupled with balloon dilation catheter (540) such that translation of actuator (1014) relative to handle portion (1012) causes concurrent translation of balloon dilation catheter (540). An exterior surface of actuator (1014) is saddle-shaped and includes a series of spaced-apart grooves. This saddle-shaped exterior surface and these groves allow a user to easily locate and translate actuator (1014) with only a single finger or thumb while holding body (1010). A distal end of handle portion (1012) is configured to receive and selectively retain guide catheter (530) such that guide catheter (530) may be coupled with the distal end of body (1010) and extend distally therefrom. Handle portion (1012) further includes a semi-circular pommel (1015) extending outwardly from a bottom surface of the distal end of handle portion (1012) opposite of actuator (1014). It should be appreciated that handle portion (1012) may be gripped by a user such that the user's fingers and/or thumb rest adjacent pommel (1015). It should further be appreciated that as handle portion (1012) is being gripped, a user may user his or her finger or thumb to translate actuator (1014) relative to handle portion (1012).

Figure 66:
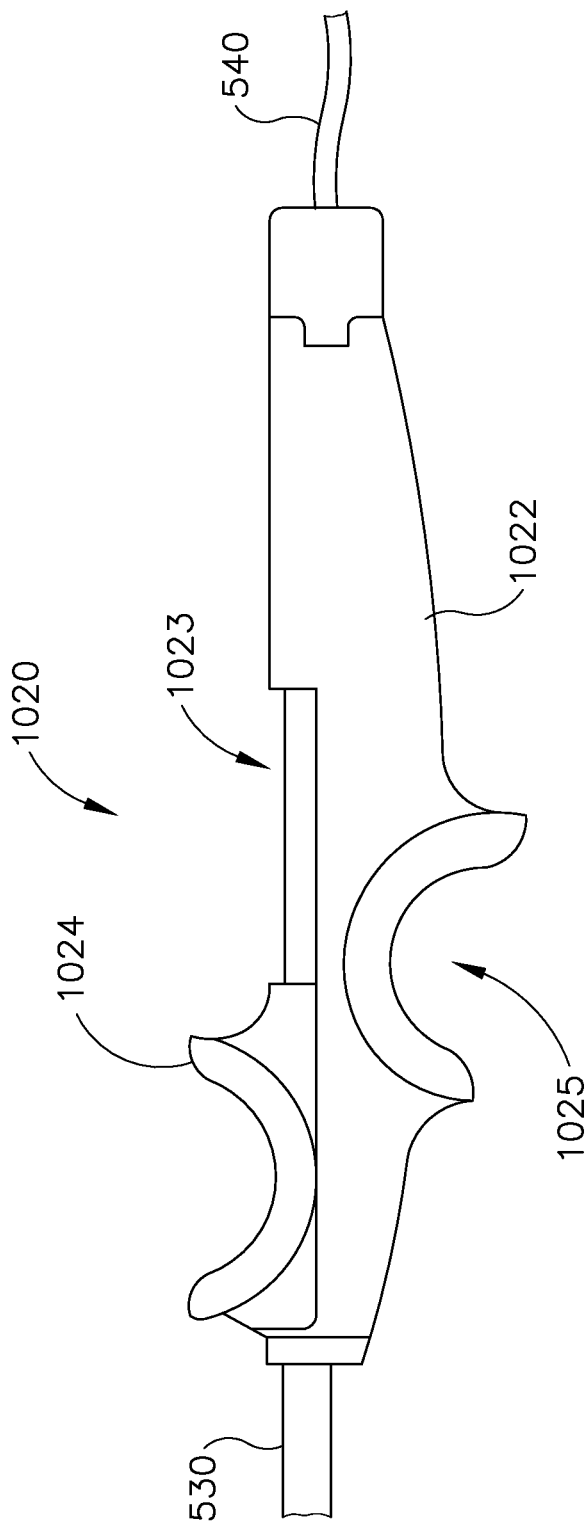
FIG. 66 depicts a side elevational view of another exemplary handle suitable for use with the dilation catheter system of FIG. 12, with the guide catheter of FIG. 7A, an exemplary balloon dilation catheter, and the endoscope of FIG. 15 positioned therein.

FIG. 66 shows yet another exemplary body (1020) operable for incorporation in whole or in part with any of the handles (500, 550, 600, 650, 700, 750, 800, 850, 920) described above. Body (1020) includes an elongated handle portion (1022) and an actuator (1024). Actuator (1024) is slidably disposed within an elongate recess (1023) formed in a top surface of handle portion (1022) such that actuator (1024) is operable to translate relative to handle portion (1022) within elongate recess (1023). Actuator (1024) is coupled with balloon dilation catheter (540) such that translation of actuator (1024) relative to handle portion (1022) causes concurrent translation of balloon dilation catheter (540). An exterior surface of actuator (1024) is saddle-shaped. This saddle-shaped exterior surface allows a user to easily locate and translate actuator (1024) with only a single finger or thumb while holding body (1020). A distal end of handle portion (1022) is configured to receive and selectively retain guide catheter (530) such that guide catheter (530) may be coupled with the distal end of body (1020) and extend distally therefrom. Handle portion (1022) further includes a semi-circular recess (1025) formed in a bottom surface of the distal end of handle portion (1022) opposite of actuator (1024). It should be appreciated that handle portion (1022) may be gripped by a user such that the user's fingers and/or thumb rest within recess (1025). It should further be appreciated that as handle portion (1022) is being gripped, a user may user his or her finger or thumb to translate actuator (1024) relative to handle portion (1022).

Figure 67:
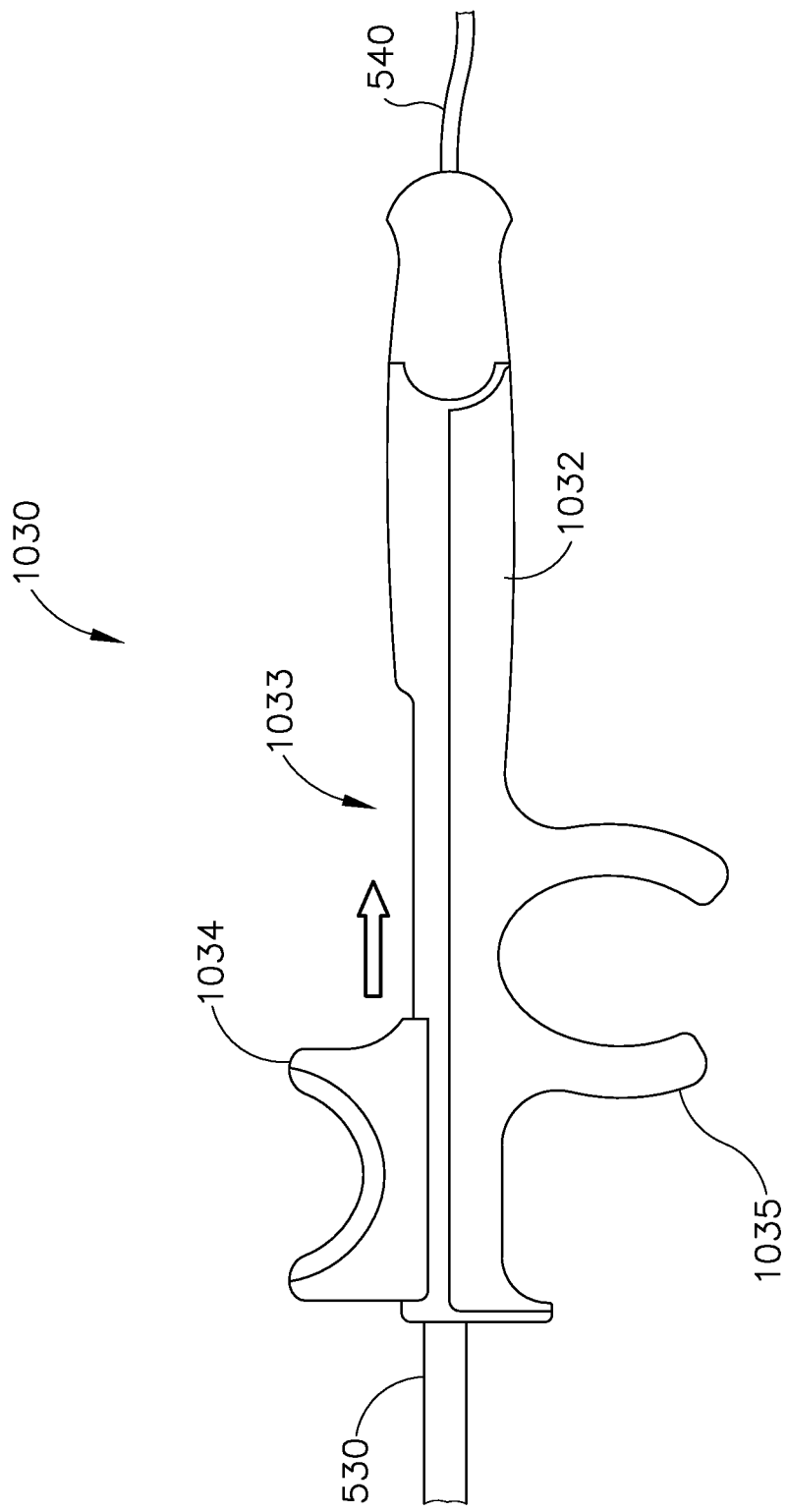
FIG. 67 depicts a side elevational view of another exemplary handle suitable for use with the dilation catheter system of FIG. 12, with the guide catheter of FIG. 7A, an exemplary balloon dilation catheter, and the endoscope of FIG. 15 positioned therein.

FIG. 67 shows yet another exemplary body (1030) operable for incorporation in whole or in part with any of the handles (500, 550, 600, 650, 700, 750, 800, 850, 920) described above. Body (1030) includes an elongated handle portion (1032) and an actuator (1034). Actuator (1034) is slidably disposed within an elongate recess (1033) formed in a top surface of handle portion (1032) such that actuator (1034) is operable to translate relative to handle portion (1032) within elongate recess (1033). Actuator (1034) is coupled with balloon dilation catheter (540) such that translation of actuator (1034) relative to handle portion (1032) causes concurrent translation of balloon dilation catheter (540). An exterior surface of actuator (1034) is saddle-shaped. This saddle-shaped exterior surface allows a user to easily locate and translate actuator (1034) with only a single finger or thumb while holding body (1030). A distal end of handle portion (1032) is configured to receive and selectively retain guide catheter (530) such that guide catheter (530) may be coupled with the distal end of body (1030) and extend distally therefrom. Handle portion (1032) includes a semi-circular protrusion (1035) extending from a bottom surface of the distal end of handle portion (1032) opposite of actuator (1034). It should be appreciated that handle portion (1032) may be gripped by a user such that the user's fingers and/or thumb rest within protrusion (1035). It should further be appreciated that as handle portion (1032) is being gripped, a user may user his or her finger or thumb to translate actuator (1034) relative to handle portion (1032).

Figure 68:
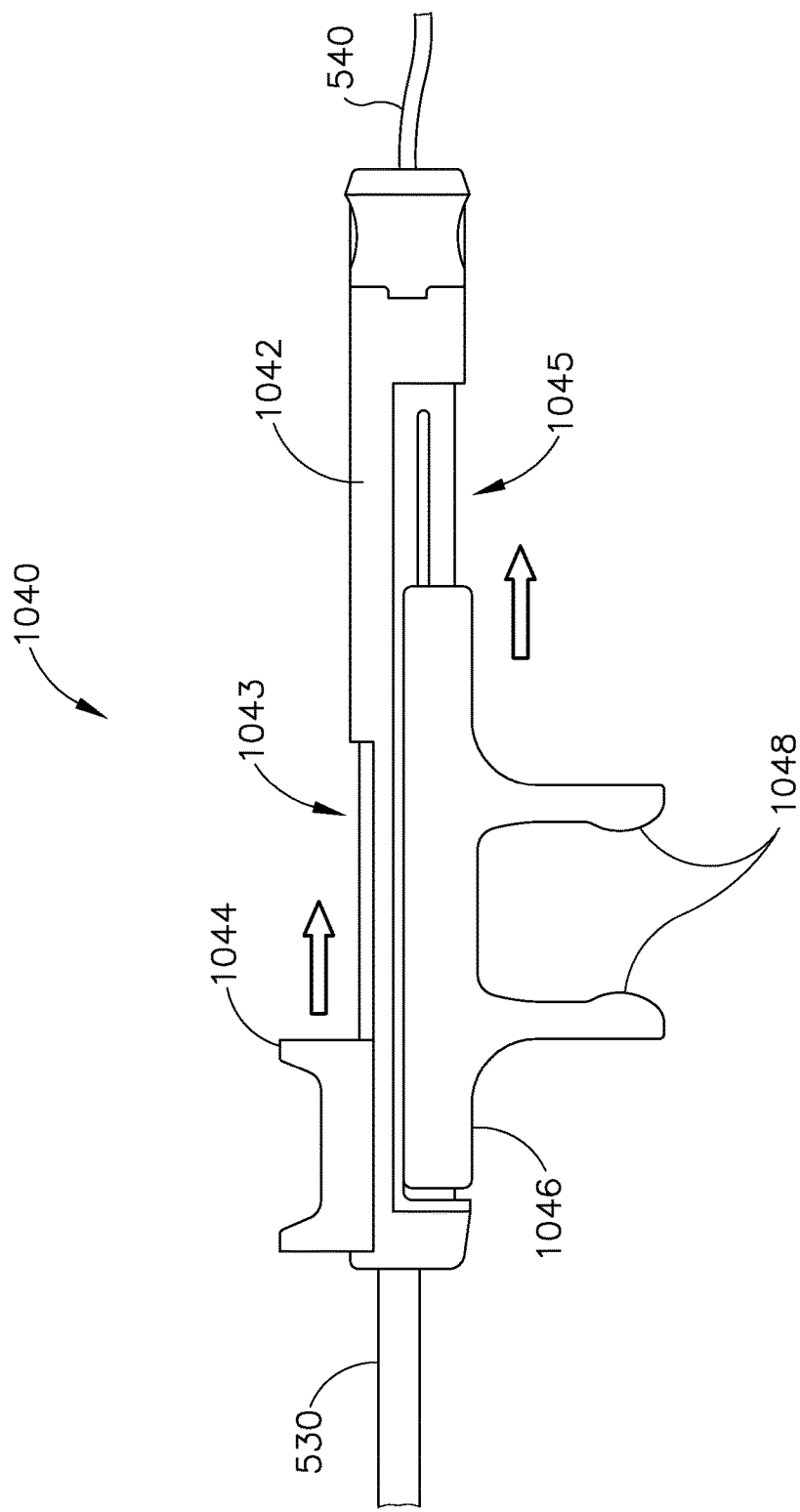
FIG. 68 depicts a side elevational view of another exemplary handle suitable for use with the dilation catheter system of FIG. 12, with the guide catheter of FIG. 7A, an exemplary balloon dilation catheter, and the endoscope of FIG. 15 positioned therein.

FIG. 68 shows yet another exemplary body (1040) operable for incorporation in whole or in part with any of the handles (500, 550, 600, 650, 700, 750, 800, 850, 920) described above. Body (1040) includes an elongated handle portion (1042), a balloon dilation catheter actuator (1044), and a guide catheter actuator (1046). Balloon dilation catheter actuator (1044) is slidably disposed within an elongate recess (1043) formed in a top surface of handle portion (1042) such that balloon dilation catheter actuator (1044) is operable to translate relative to handle portion (1042) within elongate recess (1043). Balloon dilation catheter actuator (1044) is coupled with balloon dilation catheter (540) such that translation of balloon dilation catheter actuator (1044) relative to handle portion (1042) causes concurrent translation of balloon dilation catheter (540). An exterior surface of balloon dilation catheter actuator (1044) is saddle-shaped. This saddle-shaped exterior surface allows a user to easily locate and translate balloon dilation catheter actuator (1044) with only a single finger or thumb while holding body (1040). Guide catheter actuator (1046) is slidably disposed within an elongate recess (1045) formed in a bottom surface of handle portion (1042) opposite balloon dilation catheter actuator (1044) such that guide catheter actuator (1046) is operable to translate relative to handle portion (1042) within elongate recess (1045). Guide catheter actuator (1046) is coupled with guide catheter (530) such that translation of guide catheter actuator (1046) relative to handle portion (1042) causes concurrent translation of guide catheter (530). Guide catheter actuator (1046) includes a pair of posts (1048) extending from a bottom surface of guide catheter actuator (1046). These posts allow a user to easily locate and translate guide catheter actuator (1046) with only a single finger or thumb while holding body (1040). It should be appreciated that handle portion (1042) may be gripped by a user such that the user's fingers and/or thumb rest within and/or adjacent posts (1048) of guide catheter actuator (1046). It should further be appreciated that as handle portion (1042) is being gripped, a user may user his or her finger or thumb to translate actuators (1044, 1046) relative to handle portion (1042).

FIG. 69 shows yet another exemplary body (1050) configured for use in whole or in part with any of the handles (500, 550, 600, 650, 700, 750, 800, 850, 920) described above. Body (1050) includes an elongated handle portion (1052) and an actuator (1054). Actuator (1054) is slidably disposed within an elongate recess (1053) formed in a top surface of handle portion (1052) such that actuator (1054) is operable to translate relative to handle portion (1052) within elongate recess (1053). Actuator (1054) is coupled with balloon dilation catheter (540) such that translation of actuator (1054) relative to handle portion (1052) causes concurrent translation of balloon dilation catheter (540). An exterior surface of actuator (1054) is saddle-shaped. This saddle-shaped exterior surface allows a user to easily locate and translate actuator (1054) with only a single finger or thumb while holding body (1050). Handle portion (1052) includes a pair of posts (1056) extending outwardly from a bottom surface of handle portion (1052) opposite actuator (1054). It should be appreciated that handle portion (1052) may be gripped by a user such that the user's fingers and/or thumb rest within and/or adjacent posts (1056) of handle portion (1052). It should further be appreciated that as handle portion (1052) is being gripped, a user may user his or her finger or thumb to translate actuator (1054) relative to handle portion (1052).

VII. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A dilation system, wherein the catheter system comprises: (a) a body, wherein the body comprises a distal end and a proximal end; (b) a guide member, wherein the guide member is coupled to the distal end of the body and extends distally therefrom; (c) a dilation member, wherein the dilation member comprises an expandable dilator, wherein the dilation member is configured to translate relative to the guide member; (d) an endoscope, wherein endoscope is disposed within the body and extends distally therefrom; and (e) an actuator, wherein the actuator is movably coupled with the body, wherein the actuator is coupled with the dilation member, wherein the actuator is configured to move relative to the body to thereby cause translation of the dilation member; wherein the body, the guide member, the dilation member, the endoscope, and the actuator are sized, arranged, and configured to be grasped and manipulated together by a single hand.

EXAMPLE 2

The dilation system of Example 1, wherein the actuator is configured to translate relative to the body to thereby cause concurrent translation of the dilation member.

EXAMPLE 3

The dilation system of any one or more of Examples 1 through 2, wherein the actuator is configured to rotate relative to the body to thereby cause translation of the dilation member.

EXAMPLE 4

The dilation system of any one or more of Examples 1 through 3, wherein the dilation system further comprises a rotation knob, wherein the rotation knob is coupled with the guide member, wherein the rotation knob is configured to rotate relative to the body to thereby cause concurrent rotation of the guide member.

EXAMPLE 5

The dilation system of any one or more of Examples 1 through 4, wherein the dilation system further comprises a housing, wherein the housing is configured receive and selectively retain the endoscope.

EXAMPLE 6

The dilation system of Example 5, wherein the housing is configured to translate relative to the body to thereby cause concurrent translation of the endoscope.

EXAMPLE 7

The dilation system of any one or more of Examples 5 through 6, wherein the housing is configured to rotate relative to the body to thereby cause concurrent rotation of the endoscope.

EXAMPLE 8

The dilation system of any one or more of Examples 5 through 7, wherein the housing comprises a locking feature, wherein the locking feature is configured to selectively lock the endoscope in position relative to the housing.

EXAMPLE 9

The dilation system of Example 8, wherein the locking feature comprises a lever arm pivotably coupled with the body, wherein the lever arm is configured to pivot between an unlocked position and a locked position, wherein the lever arm is configured to bear against the endoscope when in the locked position.

EXAMPLE 10

The dilation system of Example 9, wherein the locking feature comprises a pair of resilient flanges.

EXAMPLE 11

The dilation system of Example 10, wherein the locking feature further comprises a lever pivotably coupled with the body, wherein the lever is configured to rotate between an unlocked position and a locked position, wherein the lever is configured to bear against the resilient flanges when in the locked position so as to cause the resilient flanges to bear against the endoscope.

EXAMPLE 12

The dilation system of Example 8, wherein the locking feature comprises at least one friction ring.

EXAMPLE 13

The dilation system of Example 8, wherein the locking feature comprises a cover coupled with the body by a hinge, wherein the cover is configured to rotate between an unlocked position and a locked position, wherein the cover is configured to bear against the endoscope when in the locked position.

EXAMPLE 14

The dilation system of any one or more of Examples 1 through 13, wherein the actuator is configured to translate relative to the body to thereby cause concurrent translation of the dilation member, wherein a portion of the actuator is further configured to rotate relative to the body to thereby cause translation of the dilation member.

EXAMPLE 15

The dilation system of any one or more of Examples 1 through 14, wherein the actuator is configured to rotate relative to the body to thereby cause concurrent rotation of the dilation member.

EXAMPLE 16

The dilation system of any one or more of Examples 1 through 15, wherein the dilation system further comprises a guide member actuator, wherein the guide member actuator is coupled with the guide member, wherein the guide member actuator is configured to translate relative to the body to thereby cause concurrent translation of the guide member.

EXAMPLE 17

The dilation system of any one or more of Examples 1 through 16, wherein the guide member comprises a guide catheter, wherein the dilation member comprises a dilation catheter, wherein the expandable dilator comprises a balloon.

EXAMPLE 18

A dilation system, wherein the dilation system comprises: (a) a body, wherein the body comprises a distal end and a proximal end; (b) a guide member, wherein the guide member is coupled to the distal end of the body and extends distally therefrom; (c) a balloon dilation catheter, wherein the dilation catheter comprises an expandable balloon dilator, wherein the dilation catheter is configured to translate relative to the guide member; (d) an endoscope, wherein endoscope is disposed within the body and extends distally therefrom; and (e) a pump, wherein the pump is formed as an integral element of either the body or the balloon dilation member, wherein the integral pump is configured to actuate to thereby expand and deflate the balloon dilator.

EXAMPLE 19

The dilation system of Example 18, wherein the pump comprises a plunger and tube.

EXAMPLE 20

A dilation system, wherein the dilation system comprises: (a) a body, wherein the body comprises a distal end and a proximal end; (b) a guide member, wherein the guide member is coupled to the distal end of the body and extends distally therefrom; (c) a balloon dilation catheter, wherein the dilation catheter comprises an expandable balloon dilator, wherein the dilation catheter is configured to translate relative to the guide member; (d) an endoscope, wherein the endoscope is disposed within the body and extends distally therefrom; and (e) an actuator, wherein the actuator is movably coupled with the body, wherein the actuator comprises features configured selectively couple the actuator with the balloon dilation catheter, wherein the actuator is configured to move relative to the body to thereby cause translation of the balloon dilation catheter when the actuator is coupled with the balloon dilation catheter.

VIII. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A dilation system, wherein the dilation system comprises:
   (a) a body, wherein the body comprises a distal end and a proximal end;
   (b) a guide member, wherein the guide member is coupled to the distal end of the body and extends distally therefrom;
   (c) a dilation member, wherein the dilation member comprises an expandable dilator, wherein the dilation member is configured to translate relative to the guide member;
   (d) an endoscope, wherein the endoscope is disposed within the body and extends distally therefrom, wherein the body comprises a bore in a lower portion of the body, wherein the bore is sized and configured to receive the endoscope, wherein the bore comprises a sidewall configured to extend substantially from the distal end of the body to the proximal end of the body; and
   (e) an actuator, wherein the actuator is movably coupled with the body, wherein the actuator is coupled with the dilation member, wherein the actuator is configured to move relative to the body to thereby cause translation of the dilation member;
   wherein the body, the guide member, the dilation member, the endoscope, and the actuator are sized, arranged, and configured to be grasped and manipulated together by a single hand.

2. The dilation system of claim 1, wherein the actuator is configured to translate relative to the body to thereby cause concurrent translation of the dilation member.

3. The dilation system of claim 1, wherein the dilation system further comprises a rotation knob, wherein the rotation knob is coupled with the guide member, wherein the rotation knob is configured to rotate relative to the body to thereby cause concurrent rotation of the guide member.

4. The dilation system of claim 1, wherein the dilation system further comprises a housing, wherein the housing is configured receive and selectively retain the endoscope.

5. The dilation system of claim 1, wherein the guide member comprises a guide catheter, wherein the dilation member comprises a dilation catheter, wherein the expandable dilator comprises a balloon.

6. The dilation system of claim 1, wherein the endoscope comprises a shaft, wherein the distal end of the shaft includes a curved transparent window, wherein the shaft includes a plurality of rod lenses and light transmitting fibers extending along the length of the shaft.

7. The dilation system of claim 6, wherein the endoscope comprises a viewing range of approximately 180 degrees.

8. The dilation system of claim 6, wherein the endoscope comprises a light post, wherein the light post is in communication with the light transmitting fibers, wherein the light post is configured to couple with a light source to illuminate the site in the patient distal to the window.

9. The dilation system of claim 1, wherein the bore is configured to selectively retain the endoscope.

10. The dilation system of claim 1, wherein the actuator comprises a hollow oval-shaped structure.

11. The dilation system of claim 1, wherein actuator comprises a protrusion configured to selectively receive the dilation member.

12. The dilation system of claim 1, wherein the proximal end of the body comprises an edge fillet configured to receive the dilation member, wherein the edge fillet is configured to allow for transition of the dilation member into and out of the body at varying angles relative to the body.

13. The dilation system of claim 1, wherein the dilation member is configured to pass through the proximal and distal end of the body when the dilation member is translated past the distal end of the body.

14. The dilation system of claim 1, wherein the dilation member is configured to pass through the guide member.

15. The dilation system of claim 1, wherein the bore comprises a locking feature to secure the endoscope to the body.

16. The dilation system of claim 1, wherein the actuator is configured to be actuated with a single finger or thumb.

17. A dilation system, wherein the dilation system comprises:

(a) a body, wherein the body comprises a distal end and a proximal end;
(b) a guide member, wherein the guide member is coupled to the distal end of the body and extends distally therefrom;
(c) a balloon dilation catheter, wherein the dilation catheter comprises an expandable balloon dilator, wherein the dilation catheter is configured to translate relative to the guide member;
(d) an endoscope, wherein the endoscope is disposed within the body and extends distally therefrom; and
(e) an actuator, wherein the actuator is movably coupled with the body, wherein the actuator is configured to radially surround an outer diameter of the body, wherein the actuator comprises features configured to selectively couple the actuator with the balloon dilation catheter, wherein the actuator is configured to move relative to the body to thereby cause translation of the balloon dilation catheter when the actuator is coupled with the balloon dilation catheter.

18. A handheld assembly for dilating an anatomical passageway, wherein the handle assembly comprises:

(a) a body, wherein the body comprises a distal end and a proximal end; wherein the body comprises a first lumen and a second lumen, wherein the first lumen and the second lumen extend from the distal end to the proximal end, wherein the first lumen and second lumen are incommunicable;
(b) a guide member, wherein the guide member is configured to be substantially coaxially aligned with the first lumen;
(c) a dilation member, wherein the dilation member comprises an expandable dilator, wherein the dilation member is configured to be aligned by the guide member;
(d) an endoscope, wherein the endoscope is sized and configured to be positioned within the second lumen, wherein the endoscope is configured to illuminate and view the expandable dilator,
(e) an actuator, wherein the actuator is movably coupled with the body, wherein the actuator is coupled with the dilation member, wherein the actuator is configured to move relative to the body to thereby cause translation of the dilation member,
wherein the handheld assembly is sized, arranged, and configured to be grasped and manipulated by a single hand.

* * * * *